(12) United States Patent
Tanaka et al.

(10) Patent No.: US 8,475,888 B2
(45) Date of Patent: *Jul. 2, 2013

(54) FIVE-RING LIQUID CRYSTAL COMPOUND HAVING A NITROGEN-CONTAINING HETEROCYCLIC RING, LIQUID CRYSTAL COMPOSITION AND LIQUID CRYSTAL DISPLAY DEVICE

(75) Inventors: Hiroyuki Tanaka, Chiba (JP); Kouki Sagou, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/125,041

(22) PCT Filed: Oct. 14, 2009

(86) PCT No.: PCT/JP2009/067807
§ 371 (c)(1), (2), (4) Date: Apr. 19, 2011

(87) PCT Pub. No.: WO2010/047260
PCT Pub. Date: Apr. 29, 2010

(65) Prior Publication Data
US 2011/0193022 A1 Aug. 11, 2011

(30) Foreign Application Priority Data
Oct. 21, 2008 (JP) ................. 2008-270639

(51) Int. Cl.
C09K 19/34 (2006.01)
C09K 19/32 (2006.01)
C09K 19/30 (2006.01)
C09K 19/12 (2006.01)
C09K 19/20 (2006.01)
C07D 239/02 (2006.01)

(52) U.S. Cl.
USPC .................. 428/1.1; 252/299.61; 252/299.62; 252/299.63; 252/299.66; 252/299.67; 252/299.5; 544/298; 544/303; 544/318; 544/335

(58) Field of Classification Search
CPC .... C07D 239/24; C07D 239/30; C09K 19/345; C09K 19/3458
USPC .......... 428/1.1; 252/299.61, 299.63, 299.62, 252/299.66, 299.67, 299.5; 544/298, 318, 544/335, 303; 546/282, 302, 326, 330, 331, 546/339
See application file for complete search history.

(56) References Cited

U.S. PATENT DOCUMENTS 5,262,085 A 11/1993 Bartmann et al.
7,976,913 B2 * 7/2011 Hiraoka et al. ................. 428/1.1
8,012,547 B2 * 9/2011 Lietzau et al. ................. 428/1.1
8,071,182 B2 * 12/2011 Yanai et al. ..................... 428/1.1
8,147,929 B2 * 4/2012 Saito ............................. 428/1.1
8,221,854 B2 * 7/2012 Czanta et al. .................. 428/1.1
2005/0017216 A1 1/2005 Poetsch et al.
2005/0279968 A1 12/2005 Manabe et al.
2006/0061699 A1 3/2006 Kirsch et al.
2006/0210724 A1 9/2006 Heckmeier et al.
2006/0286308 A1 12/2006 Kirsch et al.
2008/0193682 A1 8/2008 Lietzau et al.
2010/0127213 A1 * 5/2010 Czanta et al. ............ 252/299.61
2011/0315925 A1 * 12/2011 Hiraoka et al. .......... 252/299.61

FOREIGN PATENT DOCUMENTS

DE 102008016053 A1 * 10/2008
DE 102008017025 A1 * 10/2008
EP 0786445 7/1997
EP 0844229 5/1998
GB 2229438 9/1990
JP 10-251186 9/1998
WO 2006125530 11/2006

* cited by examiner

Primary Examiner — Shean C Wu
(74) Attorney, Agent, or Firm — J.C. Patents

(57) ABSTRACT

Provided is a liquid crystal compound having general physical properties necessary for a compound, stability to heat, light or the like, a wide liquid crystal phase temperature range, a high clearing point, an excellent compatibility with other liquid crystal compounds, a large refractive index anisotropy and a large dielectric anisotropy. Provided are a liquid crystal composition including the liquid crystal compound, and a liquid crystal display device containing the liquid crystal composition.

The compound is represented by formula (1):

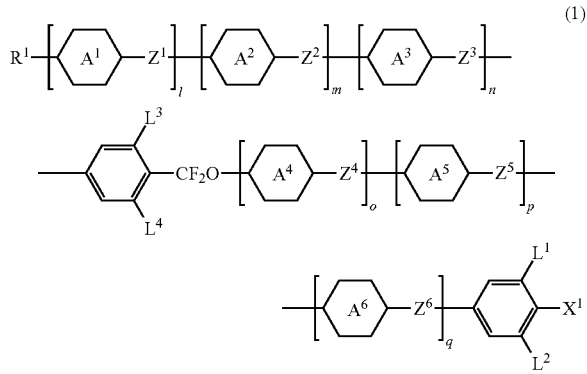

wherein, for example, $R^1$ is alkyl having 1 to 20 carbons; at least one of the rings $A^1$ to $A^6$ is pyrimidine-2,5-diyl or pyridine-2,5-diyl and the others are 1,4-cyclohexylene or 1,4-phenylene; $Z^1$ to $Z^6$ are a single bond; $L^1$ to $L^4$ is hydrogen or halogen; $X^1$ is hydrogen, halogen, —C≡N or alkyl having 1 to 10 carbons; and l, m, n, o, p and q are 0 or 1 and l+m+n+o+p+q=3.

16 Claims, No Drawings

FIVE-RING LIQUID CRYSTAL COMPOUND HAVING A NITROGEN-CONTAINING HETEROCYCLIC RING, LIQUID CRYSTAL COMPOSITION AND LIQUID CRYSTAL DISPLAY DEVICE

FIELD OF THE INVENTION

The invention relates to a new liquid crystal compound and a liquid crystal composition which are useful as a material for a display device. More specifically, the invention relates to a new liquid crystal compound that has a wide temperature range of a liquid crystal phase, a high clearing point, an excellent compatibility with other liquid crystal compounds, a large refractive index anisotropy and a large dielectric anisotropy, and when the compound is used for a liquid crystal display device, it is possible for the device to be used in a wide temperature range, to be driven at a low voltage, and to give steep electro-optic characteristics, and relates to a liquid crystal display device that contains a composition including the compound.

BACKGROUND OF THE INVENTION

A display device using a liquid crystal compound (in this application, the term "a liquid crystal compound" is used as a generic term for a compound having a liquid crystal phase and a compound having no liquid crystal phases but useful as a component of a liquid crystal composition) has been widely used for displays of watches, calculators, word processors and so forth. In this display device, the refractive index anisotropy, the dielectric anisotropy and so forth of the liquid crystal compound are utilized.

In a liquid crystal display device, a classification based on an operating mode for liquid crystals includes modes of phase change (PC), twisted nematic (TN), super twisted nematic (STN), bistable twisted nematic (BTN), electrically controlled birefringence (ECB), optically compensated bend (OCB), in-plane switching (IPS), vertical alignment (VA) and polymer sustained alignment (PSA). A classification based on a driving mode in the device includes a passive matrix (PM) and an active matrix (AM). The PM is further classified into static, multiplex and so forth, and the AM is classified into a thin film transistor (TFT), a metal-insulator-metal (MIM) and so forth.

These liquid crystal display devices contain a liquid crystal composition with suitable physical properties. It is desirable that the liquid crystal composition has suitable physical properties in order to improve the characteristics of the liquid crystal display device. General physical properties necessary for the liquid crystal compound that is a component of the liquid crystal composition are as follows.
(1) chemically stable and physically stable,
(2) a high clearing point (transition temperature between a liquid crystal phase and an isotropic phase),
(3) a low minimum temperature of a liquid crystal phase (a nematic phase, a smectic phase and so forth), especially a low minimum temperature of the nematic phase,
(4) an excellent compatibility with other liquid crystal compounds,
(5) a large dielectric anisotropy, and
(6) a large refractive index anisotropy.

A voltage holding ratio can be increased when a composition including a chemically and physically stable liquid crystal compound, as described in item (1), is used for a display device. The temperature range of a nematic phase can be increased in a composition that includes a liquid crystal compound having a high clearing point or a low minimum temperature of a liquid crystal phase as described in items (2) and (3), and thus the device can be used in a wide temperature range.

A liquid crystal compound is generally used in the form of a composition prepared by mixing it with many other liquid crystal compounds in order to exhibit characteristics that are difficult to be attained by a single compound. Accordingly, it is desirable that a liquid crystal compound used for a display device has an excellent compatibility with other liquid crystal compounds and so forth, as described in item (4).

Recently, a liquid crystal display device having a better quality especially of display performance such as characteristics of contrast, display capacity and response time is required. Moreover, a liquid crystal material suitable for a low driving voltage is required, that is to say, a liquid crystal compound that makes it possible to decrease the threshold voltage, and a liquid crystal composition that includes the compound and is suitable for a low driving voltage are required.

Threshold voltage ($V_{th}$) is expressed, as is well known, by the following equation; See H. J. Deuling, et al., Mol. Cryst. Liq. Cryst., 27 (1975) 81:

$$V_{th} = \pi (K/\epsilon_0 \Delta\epsilon)^{1/2}$$

where K is an elastic constant, $\epsilon_o$ is a dielectric constant in a vacuum. As the equation shows, there are two possible ways in order to decrease $V_{th}$: the value of $\Delta\epsilon$ (dielectric anisotropy) is increased or the value of K is decreased. Since it is still hard to control the value of K by use of the present technology, such demand is dealt with the use of a liquid crystal material having a large $\Delta\epsilon$ at present stage. Under the circumstances, a liquid crystal compound having a large dielectric anisotropy, as described in item (5), has been studied eagerly.

It is desirable for an excellent liquid crystal display that the value of the thickness of the liquid crystal display device and the refractive index anisotropy ($\Delta n$) of the liquid crystal material used is constant. See E. Jakeman, et al., Phys. Lett., 39A. 69 (1972). The response speed of the liquid crystal display device is inversely proportional to the square of the cell thickness. Then, a liquid crystal composition having large refractive index anisotropy should be used in order to produce a liquid crystal display device that is able to respond at high speed and thus can be applied to the display of moving images and so forth. Accordingly, a liquid crystal compound having a large refractive index anisotropy as is described in item (6) is desired.

A variety of liquid crystal compounds having a large dielectric anisotropy and refractive index anisotropy have been synthesized until now, and some of them have been used for practical purposes. For example, a four-ring compound having a bonding group $CF_2O$ is disclosed in the patent documents No. 1 to No. 6. However, since these compounds do not have sufficiently high clearing points, the temperature range of a display device containing the composition that includes the compound is not sufficiently wide.

The patent documents No. 7 to No. 10 discloses five-ring compounds having a tetrahydropyran ring and a bonding group $CF_2O$ [the compounds (S-1) to (S-3)]. The patent documents No. 11 and No. 12 disclose compounds having a tetrahydropyran ring and a dioxane ring [the compounds (S-4) and (S-5)]. However, these compounds do not have a sufficiently wide temperature range of a liquid crystal phase or a sufficiently large refractive index anisotropy and dielectric anisotropy.

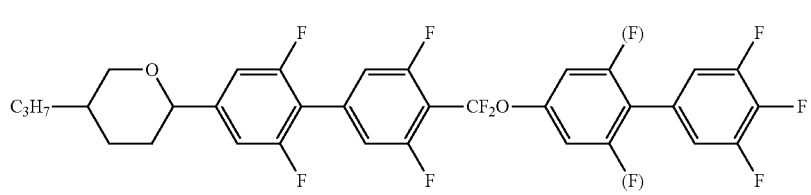

(S-1)

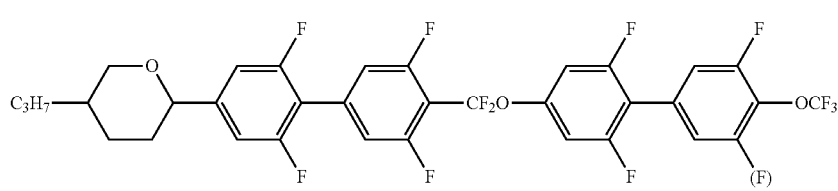

(S-2)

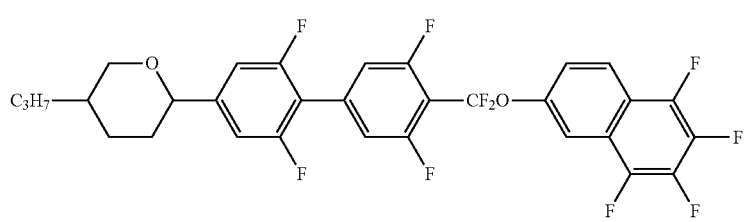

(S-3)

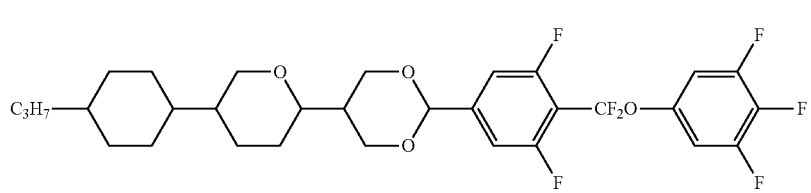

(S-4)

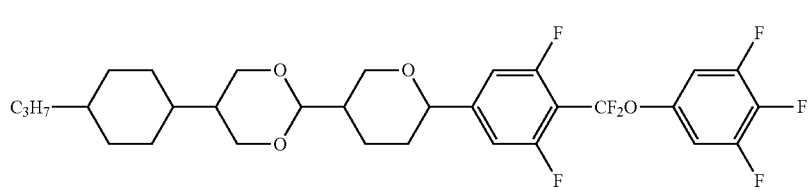

(S-5)

PRIOR ART

Patent Document

Patent document No. 1: WO 96-011897 A.
Patent document No. 2: JP H10-204016 A (1998).
Patent document No. 3: GB 2,229,438 A (1990).
Patent document No. 4: DE 4,023,106 A (1992).
Patent document No. 5: JP H10-251186 A (1998).
Patent document No. 6: WO 2004-035710 A.
Patent document No. 7: WO 2004-048501 A.
Patent document No. 8: JP 2004-352721 A.
Patent document No. 9: WO 2005-019378 A.
Patent document No. 10: WO 2005-019381 A.
Patent document No. 11: WO 2006-125511 A.
Patent document No. 12: WO 2006-125530 A.

OUTLINE OF THE INVENTION

Subject to be solved by the Invention

The first aim of the invention is to provide a liquid crystal compound having general physical properties necessary for a compound, stability to heat, light or the like, a wide temperature range of a liquid crystal phase, a high clearing point, an excellent compatibility with other liquid crystal compounds, a large optical anisotropy and a large dielectric anisotropy. The second aim is to provide a liquid crystal composition including this compound and having a wide temperature range of a liquid crystal phase, a small viscosity, a suitable refractive index anisotropy and a low threshold voltage. The third aim is to provide a liquid crystal display device containing this composition and having a wide operating temperature range, a short response time, small electric power consumption, a large contrast and a low driving voltage.

Means for solving the Subject

The invention provides the following liquid crystal compound, liquid crystal composition, liquid crystal display device containing the liquid crystal composition and so forth. The terminal group, the ring, the bonding group and so forth in the compound represented by formula (1) will be described below.

Item 1. A compound represented by formula (1).

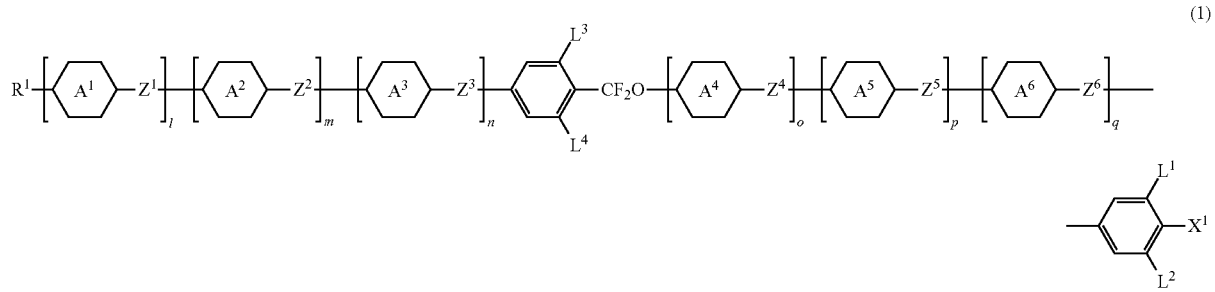

In formula (1), $R^1$ is alkyl having 1 to 20 carbons, and in the alkyl, arbitrary —$CH_2$— may be replaced by —O—, —S— or —CH=CH—; the ring $A^1$, the ring $A^2$, the ring $A^3$, the ring $A^4$, the ring $A^5$ and the ring $A^6$ are independently pyrimidine-2,5-diyl, pyridine-2,5-diyl, 1,4-cyclohexylene, 1,3-dioxane-2,5-diyl, 1,4-phenylene, or 1,4-phenylene in which arbitrary hydrogen is replaced by halogen, and at least one of the ring $A^1$, the ring $A^2$, the ring $A^3$, the ring $A^4$, the ring $A^5$ and the ring $A^6$ is pyrimidine-2,5-diyl or pyridine-2,5-diyl; $Z^1$, $Z^2$, $Z^3$, $Z^4$, $Z^5$ and $Z^6$ are independently a single bond, —$CH_2CH_2$—, —CH=CH—, —C≡C—, —COO—, —OCO—, —$CF_2O$—, —$OCF_2$—, —$CH_2O$—, —$OCH_2$—, —CF=CF—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH=CH—$(CH_2)_2$— or —$(CH_2)_2$—CH=CH—; $L^1$, $L^2$, $L^3$ and $L^4$ are independently hydrogen or halogen; $X^1$ is hydrogen, halogen, —C≡N, —N=C=S, —$SF_5$ or alkyl having 1 to 10 carbons, and in alkyl having 2 to 10 carbons, arbitrary —$CH_2$— may be replaced by —O—, —S— or —CH=CH—, where in these substituents, arbitrary hydrogen may be replaced by halogen; and l, m, n, o, p and q are independently 0 or 1, and l+m+n+o+p+q is 3.

Item 2. The compound according to item 1, wherein in formula (1), $R^1$ is alkyl having 1 to 20 carbons, alkenyl having 2 to 21 carbons, alkoxy having 1 to 19 carbons, alkenyloxy having 2 to 20 carbons or alkylthio having 1 to 19 carbons; and $X^1$ is hydrogen, halogen, —C≡N, —N=C=S, —$SF_5$, alkyl having 1 to 10 carbons, alkenyl having 2 to 11 carbons, alkoxy having 1 to 9 carbons, alkenyloxy having 2 to 10 carbons, alkylthio having 1 to 9 carbons, —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, —$(CF_2)_5$—F, —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3F$, —$OCF_2CHFCF_3$, —$OCHFCF_2CF_3$, —$O(CH_2)_4$—F, —O—$(CF_2)_4$—F, —O—$(CH_2)_5$—F, —O—$(CF_2)_5$—F, —CH=CHF, —CH=$CF_2$, —CF=CHF, —CH=$CHCH_2F$, —CH=$CHCF_3$, —$(CH_2)_2$—CH=$CF_2$—$CH_2CH$=$CHCF_3$ or —CH=$CHCF_2CF_3$.

Item 3. The compound according to item 1 or 2, wherein in formula (1), $Z^1$, $Z^2$, $Z^3$, $Z^4$, $Z^5$ and $Z^6$ are independently a single bond, —$CH_2CH_2$—, —CH=CH—, —C≡C—, —COO—, —$CF_2O$—, —$CH_2O$— or —$OCH_2$—.

Item 4. The compound according to item 1, wherein the compound is represented by any one of formulas (1-1) to (1-3):

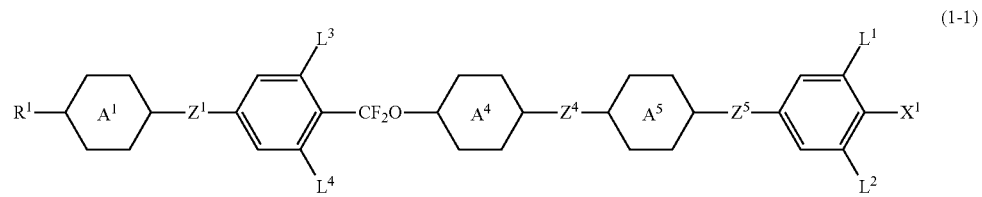

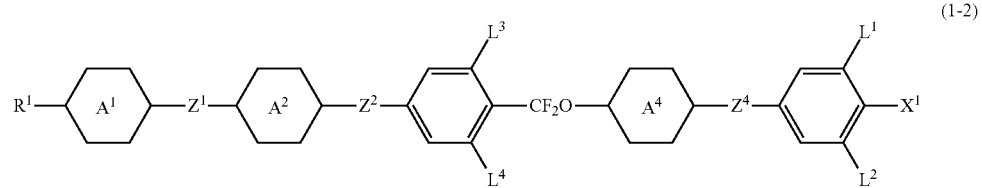

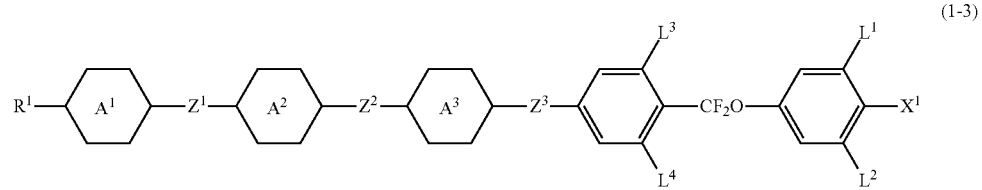

In these formulas, $R^1$ is alkyl having 1 to 15 carbons, alkenyl having 2 to 15 carbons, alkoxy having 1 to 15 carbons or alkenyloxy having 2 to 15 carbons; the ring $A^1$, the ring $A^2$, the ring $A^3$, the ring $A^4$ and the ring $A^5$ are independently pyrimidine-2,5-diyl, pyridine-2,5-diyl, 1,4-cyclohexylene, 1,3-dioxane-2,5-diyl, 1,4-phenylene, or 1,4-phenylene in which arbitrary hydrogen is replaced by halogen, and at least one of the ring $A^1$, the ring $A^2$, the ring $A^3$, the ring $A^4$ and the ring $A^5$ is pyrimidine-2,5-diyl or pyridine-2,5-diyl in each formula; $Z^1$, $Z^2$, $Z^3$, $Z^4$ and $Z^5$ are independently a single bond, —$CH_2CH_2$—, —CH=CH—, —C≡C—, —COO—, —$CF_2O$—, —$CH_2O$— or —$OCH_2$—; $L^1$, $L^2$, $L^3$ and $L^4$ are independently hydrogen or fluorine; and $X^1$ is fluorine, chlorine, —C≡N, —$CF_3$, —$CHF_2$, —$CH_2F$, —$OCF_3$, —$OCHF_2$ or —$OCH_2F$.

Item 5. The compound according to item 1, wherein the compound is represented by any one of formulas (1-4) to (1-6).

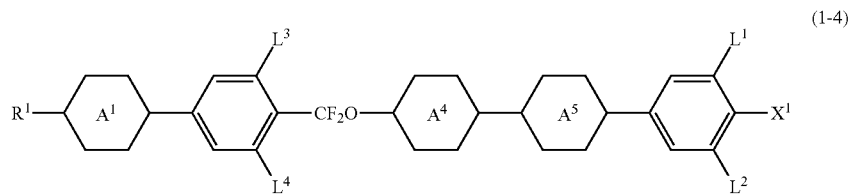

(1-4)

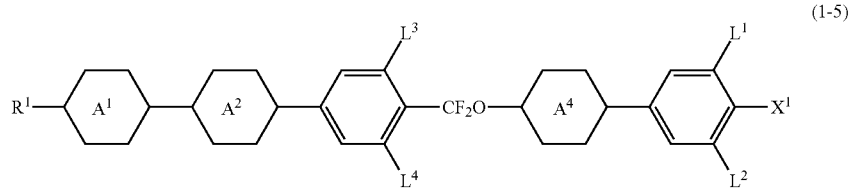

(1-5)

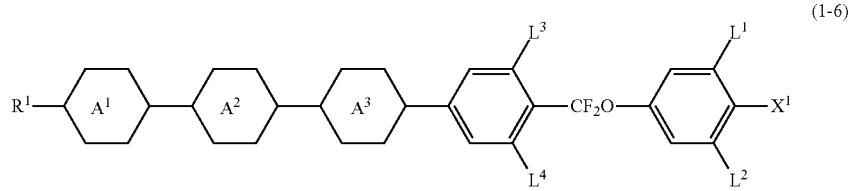

(1-6)

In these formulas, $R^1$ is alkyl having 1 to 15 carbons or alkenyl having 2 to 15 carbons; the ring $A^1$, the ring $A^2$, the ring $A^3$, the ring $A^4$ and the ring $A^5$ are independently pyrimidine-2,5-diyl, pyridine-2,5-diyl, 1,4-cyclohexylene, 1,3-dioxane-2,5-diyl, 1,4-phenylene, or 1,4-phenylene in which arbitrary hydrogen is replaced by halogen, and at least one of the ring $A^1$, the ring $A^2$, the ring $A^3$, the ring $A^4$ and the ring $A^5$ is pyrimidine-2,5-diyl or pyridine-2,5-diyl in each formula; $L^1$, $L^2$, $L^3$ and $L^4$ are independently hydrogen or fluorine; and $X^1$ is fluorine, chlorine, —C≡N, —$CF_3$, —$CHF_2$, —$CH_2F$, —$OCF_3$, —$OCHF_2$ or —$OCH_2F$.

Item 6. The compound according to item 1, wherein the compound is represented by any one of formulas (1-7) to (1-16).

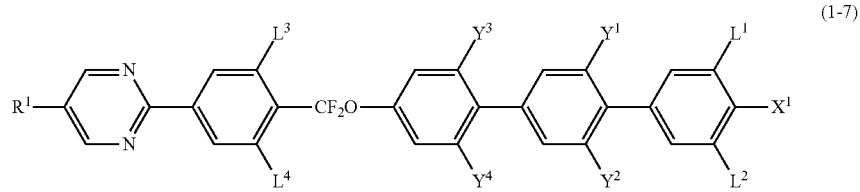

(1-7)

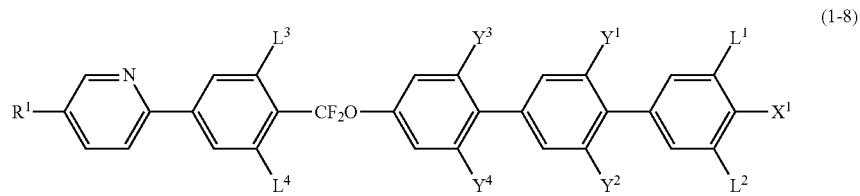

(1-8)

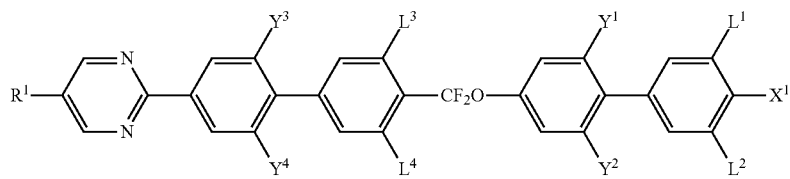
(1-9)
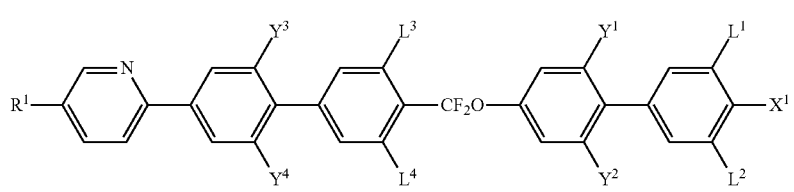
(1-10)
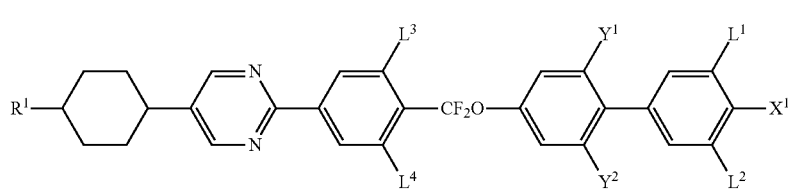
(1-11)
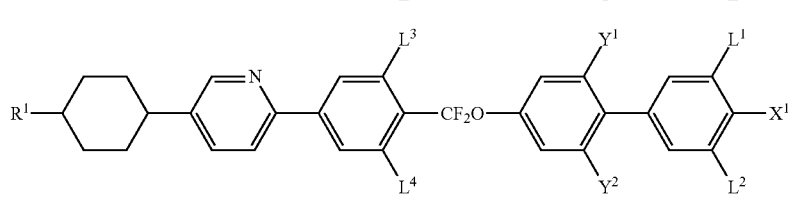
(1-12)
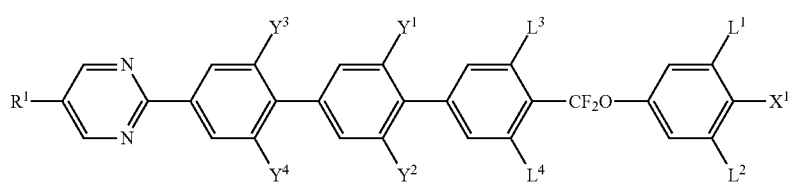
(1-13)
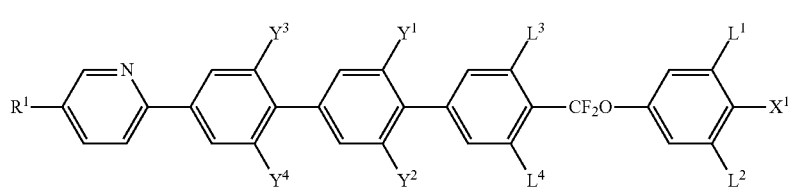
(1-14)
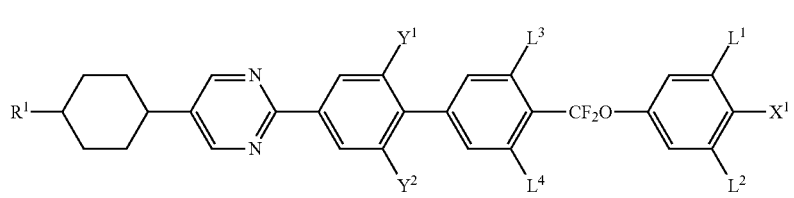
(1-15)
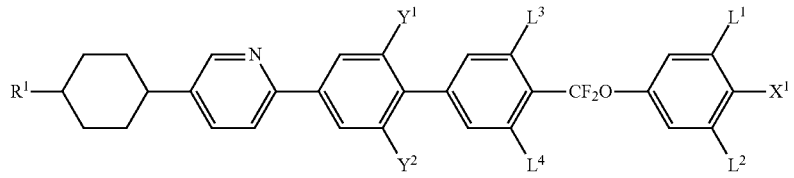
(1-16)
In these formulas, $R^1$ is alkyl having 1 to 15 carbons; $L^1$, $L^2$, $L^3$, $L^4$, $Y^1$, $Y^2$, $Y^3$ and $Y^4$ are independently hydrogen or fluorine; and $X^1$ is fluorine or —$OCF_3$.
Item 7. The compound according to item 1, wherein the compound is represented by any one of formulas (I-17) to (1-21).

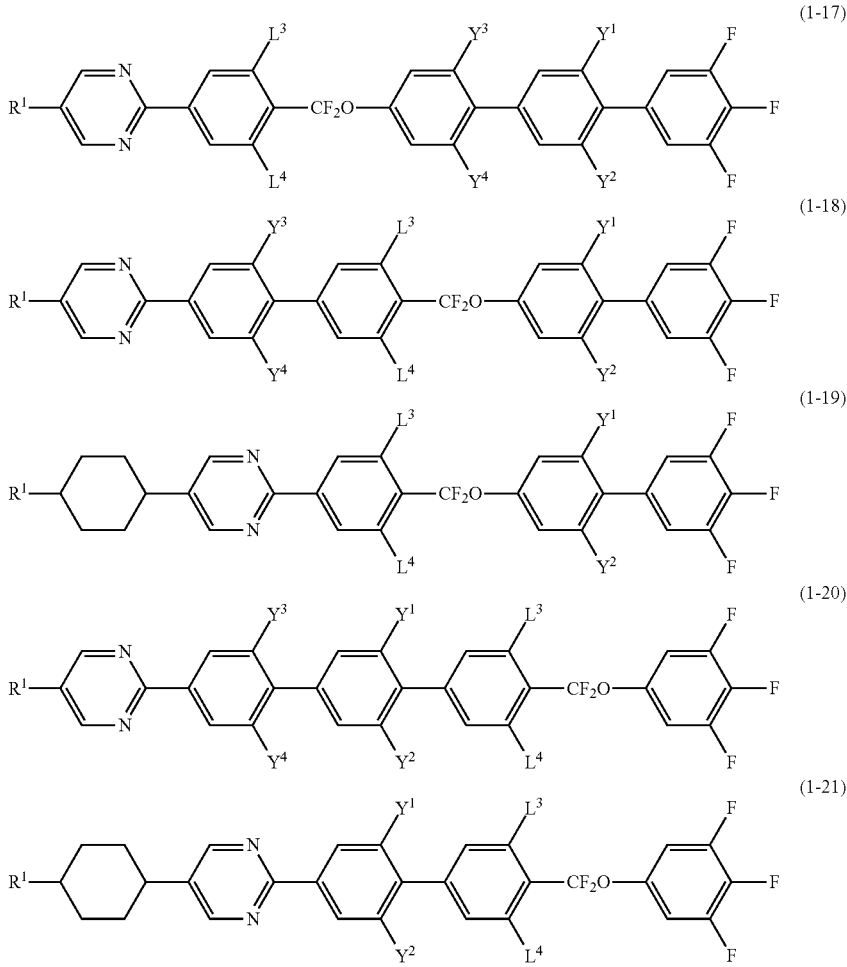

In these formulas, $R^1$ is alkyl having 1 to 15 carbons; and $L^3$, $L^4$, $Y^1$, $Y^2$, $Y^3$ and $Y^4$ are independently hydrogen or fluorine.

Item 8. A liquid crystal composition including two or more components, wherein one component is at least one compound according to any one of items 1 to 7 as one component.

Item 9. The liquid crystal composition according to item 8, including at least one compound selected from the group of compounds represented by the general formulas (2), (3) and (4) as one component.

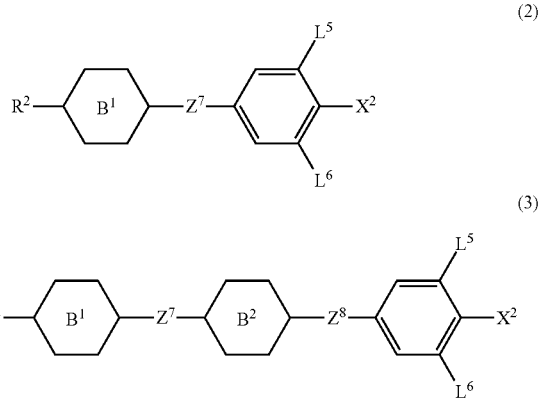

-continued

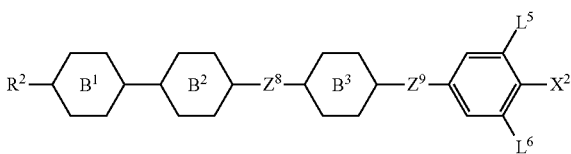

In these formulas, $R^2$ is alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—; $X^2$ is fluorine, chlorine, —$OCF_3$, —$OCHF_2$, —$CF_3$, —$CHF_2$, —$CH_2F$, —$OCF_2CHF_2$ or —$OCF_2CHFCF_3$; the ring $B^1$, the ring $B^2$ and the ring $B^3$ are independently 1,4-cyclohexylene, 1,3-dioxane-2,5-diyl, pyrimidine-2,5-diyl, tetrahydropyran-2,5-diyl, 1,4-phenylene, or 1,4-phenylene in which arbitrary hydrogen is replaced by fluorine; $Z^7$, $Z^8$ and $Z^9$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^5$ and $L^6$ are independently hydrogen or fluorine.

Item 10. The liquid crystal composition according to item 8, including at least one compound selected from the group of compounds represented by the general formula (5) as one component.

(5)

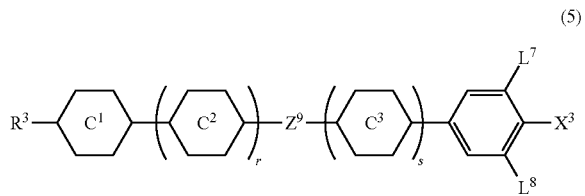

In these formulas, $R^3$ is alkyl having 1 to 10 carbons or alkenyl having 2 to 10 carbons, and in the alkyl and the alkenyl, arbitrary hydrogen may be replaced by fluorine, arbitrary —$CH_2$— may be replaced by —O—; $X^3$ is —C≡N or —C≡C—C≡N; the ring $C^1$, the ring $C^2$ and the ring $C^3$ are independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl or pyrimidine-2,5-diyl; $Z^9$ is —$(CH_2)_2$—COO—, —$CF_2$O—, —$OCF_2$—, —C≡C—, —$CH_2$O— or a single bond; $L^7$ and $L^8$ are independently hydrogen or fluorine; and r is 0 or 1, s is 0 or 1, and r+s is 0, 1 or 2.

Item 11. The liquid crystal composition according to item 8, including at least one compound selected from the group of compounds represented by the general formulas (6), (7), (8), (9) and (10) as one component.

(11)

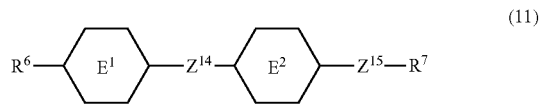

(12)

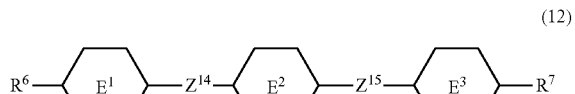

(13)

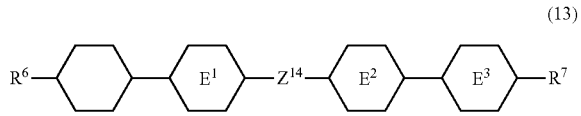

In these formulas, $R^6$ and $R^7$ are independently alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—; the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{14}$ and $Z^{15}$ are independently —C≡C—, —COO—, —$(CH_2)_2$—, —CH═CH— or a single bond.

(6)

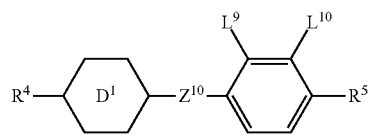

(7)

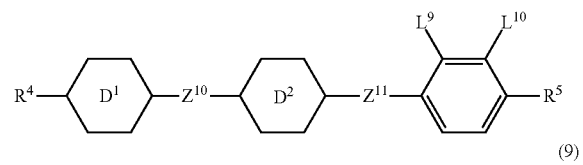

(8)

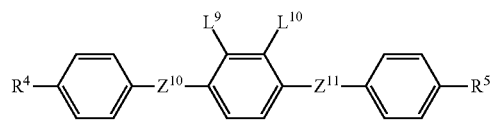

(9)

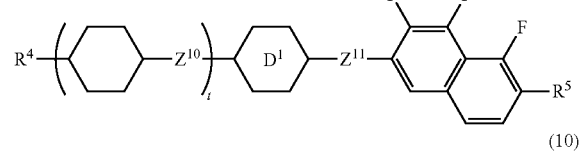

(10)

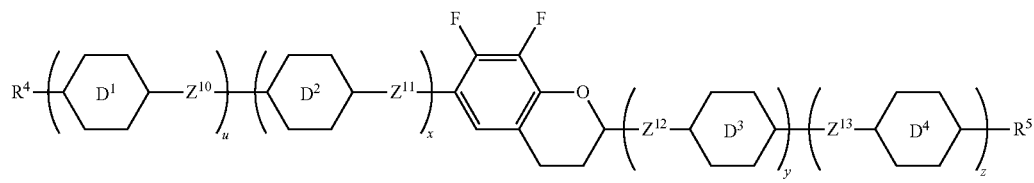

In these formulas, $R^4$ and $R^5$ are independently alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—; the ring $D^1$, the ring $D^2$, the ring $D^3$ and the ring $D^4$ are independently 1,4-cyclohexylene, 1,4-cyclohexenylene, 1,4-phenylene, 1,4-phenylene in which arbitrary hydrogen is replaced by fluorine, tetrahydropyran-2,5-diyl or decahydronaphthalene-2,6-diyl; $Z^{10}$, $Z^{11}$, $Z^{12}$ and $Z^{13}$ are independently —$(CH_2)_2$—, —COO—, —$CH_2$O—, —$OCF_2$—, —$OCF_2$—$(CH_2)_2$— or a single bond; $L^9$ and $L^{10}$ are independently fluorine or chlorine; and t, u, x, y and z are independently 0 or 1, and u+x+y+z is 1 or 2.

Item 12. The liquid crystal composition according to item 8, including at least one compound selected from the group of compounds represented by the general formulas (11), (12) and (13) as one component.

Item 13. The liquid crystal composition according to item 9, further including at least one compound selected from the group of compounds represented by the general formula (5) described in item 10.

Item 14. The liquid crystal composition according to item 9, further including at least one compound selected from the group of compounds represented by the general formulas (11), (12) and (13) described in item 12.

Item 15. The liquid crystal composition according to item 10, further including at least one compound selected from the group of compounds represented by the general formulas (11), (12) and (13) described in item 12.

Item 16. The liquid crystal composition according to item 11, further including at least one compound selected from the group of compounds represented by the general formulas (11), (12) and (13) described in item 12.

Item 17. The liquid crystal composition according to any one of items 8 to 16, further including at least one optically active compound.
Item 18. The liquid crystal composition according to any one of items 8 to 17, including at least one antioxidant and/or ultraviolet light absorber.
Item 19. A liquid crystal display device containing the liquid crystal composition according to any one of items 8 to 18.

Usage of the terms in this specification is as follows. A liquid crystal compound is a generic term for a compound having a liquid crystal phase such as a nematic phase or a smectic phase, and also for a compound having no liquid crystal phases but useful as a component for a liquid crystal composition. The terms, a liquid crystal compound, a liquid crystal composition and a liquid crystal display device may be abbreviated to a compound, a composition and a device, respectively. A liquid crystal display device is a generic term for a liquid crystal display panel and a liquid crystal display module. A maximum temperature of a nematic phase is the phase transition temperature between a nematic phase and an isotropic phase, and may simply be abbreviated to a clearing point or the maximum temperature. A minimum temperature of the nematic phase may simply be abbreviated to the minimum temperature. The compound represented by formula (1) may be abbreviated to the compound (1). This abbreviation may apply to the compound represented by formula (2) or the like. In formula (1) to formula (13), the symbol B, D, E or the like which is surrounded by a hexagonal shape corresponds to the ring B, the ring D, the ring E or the like, respectively. The amount of a compound that is expressed as a percentage means a weight percentage (% by weight) based on the total weight of the composition. A plurality of a symbol such as the $A^1, Y^1$, B or the like are used in the same or different formulas, where arbitrary two of these symbols may mean the same or different groups.

"Arbitrary" is used not only in cases where the position is arbitrary but also in cases where the number is arbitrary. However, it is not used in cases where the number is 0 (zero). The expression "arbitrary A may be replaced by B, C or D" includes cases where arbitrary A is replaced by B, and arbitrary A is replaced by C, and arbitrary A is replaced by D, and also cases where a plurality of A are replaced by at least two of B, C and/or D. For example, the expression "alkyl in which arbitrary —$CH_2$— may be replaced by —O— or —CH=CH—" includes alkyl, alkenyl, alkoxy, alkoxyalkyl, alkoxyalkenyl and alkenyloxyalkyl. Incidentally, it is undesirable in the invention that two successive —$CH_2$— are replaced by —O— to give —O—O—. It is also undesirable that terminal —$CH_2$— in the alkyl is replaced by —O—. The invention will be further explained below.

Effect of the Invention

The compounds of the invention have general physical properties necessary for a compound, stability to heat, light or the like, a wide temperature range of a liquid crystal phase, a high clearing point, an excellent compatibility with other liquid crystal compounds, a large refractive index anisotropy and a large dielectric anisotropy. The liquid crystal composition of the invention includes at least one of these compounds and has a high maximum temperature of a nematic phase, a low minimum temperature of a nematic phase, a small viscosity, a suitable refractive index anisotropy and a low threshold voltage. The liquid crystal display device of the invention contains this composition and has a wide operating temperature range, a short response time, small electric power consumption, a large contrast ratio and a low driving voltage.

EMBODIMENT TO CARRY OUT THE INVENTION 1-1. The Compound of the Invention

The first aspect of the invention is concerned with a compound represented by formula (1).

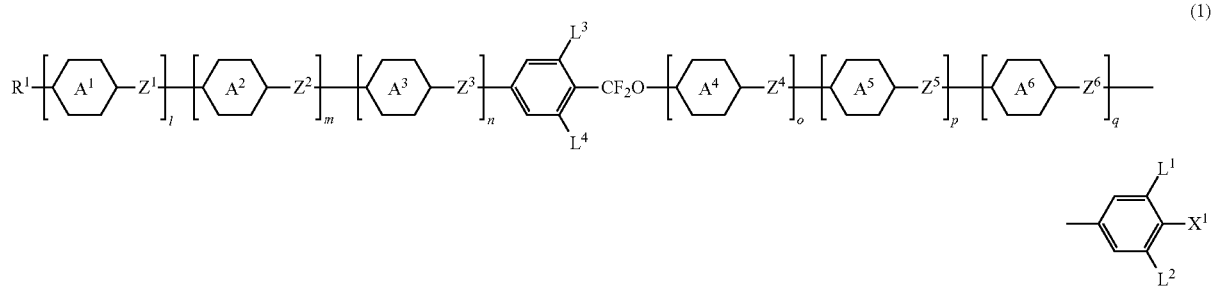

(1)

In formula (1), $R^1$ is alkyl having 1 to 20 carbons, and in alkyl having 2 to 20 carbons, arbitrary —$CH_2$— may be replaced by —O—, —S— or —CH=CH—. For example, examples of a group in which arbitrary —$CH_2$— in $CH_3$—$(CH_2)_3$— is replaced by —O—, —S— or —CH=CH— include $CH_3$—$(CH_2)_2$—O—, $CH_3O$—$(CH_2)_2$—$CH_3OCH_2O$—, $CH_3$—$(CH_2)_2$—S—, $CH_3S$—$(CH_2)_2$—, $CH_3SCH_2S$—, $CH_2$=CH—$(CH_2)_3$—, $CH_3CH$=CH—$(CH_2)_2$— and $CH_3CH$=$CHCH_2O$—.

Examples of such $R^1$ include alkyl, alkoxy, alkoxyalkyl, alkoxyalkoxy, thioalkyl, thioalkylalkoxy, alkenyl, alkenyloxy, alkenyloxyalkyl and alkoxyalkenyl. In these groups, a straight chain is preferable to a branched chain. The branched-chain group is desirable even when $R^1$ is optically active. A desirable configuration of —CH=CH— in the alkenyl depends on the position of the double bond. The trans-configuration is preferable in the alkenyl having the double bond in the odd positions, such as —CH=$CHCH_3$, —CH=$CHC_2H_5$, —CH=$CHC_3H_7$, —CH=$CHC_4H_9$, —$C_2H_4$CH=$CHCH_3$ and —$C_2H_4$CH=$CHC_2H_5$. The cis-configuration is preferable in the alkenyl having the double bond in the even positions, such as —$CH_2$CH=$CHCH_3$, —$CH_2$CH=$CHC_2H_5$ and —$CH_2$CH=$CHC_3H_7$. An alkenyl compound having a desirable configuration has a high maximum temperature or a wide temperature range of a liquid crystal phase. For detailed explanation, see Mol. Cryst. Liq. Cryst., 1985, 131, 109 and Mol. Cryst. Liq. Cryst., 1985, 131, 327.

The alkyl may be straight chain or branched chain and specific examples of the alkyl are —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

The alkoxy may be straight chain or branched chain and specific examples of the alkoxy are —CH$_3$, —C$_2$H$_5$, —C$_3$H$_7$, —C$_4$H$_9$, —C$_5$H$_{11}$, —C$_6$H$_{13}$ and —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$ and —C$_{14}$H$_{29}$, and —C$_{15}$H$_{31}$.

The alkoxyalkyl may be straight chain or branched chain and specific examples of alkoxyalkyl are —OCH$_2$OCH$_3$, —CH$_2$OC$_2$H$_5$, —CH$_2$OC$_3$H$_7$, —(CH$_2$)$_2$, —OCH$_3$, —(CH$_2$)$_2$OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

The alkenyl may be straight chain or branched chain and specific examples of alkenyl are —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$, —CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$, —CH=CH$_2$.

The alkenyloxy may be straight chain or branched chain and specific examples of alkenyloxy are —OCH$_2$CH=CH$_2$, —OCH$_2$CH=CHCH$_3$ and —OCH$_2$CH=CHC$_2$H$_5$.

Desirable R$^1$ is alkyl having 1 to 15 carbons or alkenyl having 2 to 15 carbons. Most desirable examples of R$^1$ are —CH$_3$, —C$_2$H$_5$, —C$_3$H$_7$, C$_4$H$_9$, C$_5$H$_{11}$, —C$_6$H$_{13}$, —C$_8$H$_{17}$, —C$_9$H$_{19}$, —C$_{10}$H$_{21}$—C$_{11}$H$_{23}$, —C$_{12}$H$_{25}$, —C$_{13}$H$_{27}$, —C$_{14}$H$_{29}$, —C$_{15}$H$_{31}$, —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

In formula (1), the ring A$^1$, the ring A$^2$, the ring A$^3$, the ring A$^4$, the ring A$^5$ and the ring A$^6$ are independently pyrimidine-2,5-diyl (14-1), pyridine-2,5-diyl (14-2), 1,4-cyclohexylene (14-3), 1,3-dioxane-2,5-diyl (14-4), 1,4-phenylene (14-5) or 1,4-phenylene in which arbitrary hydrogen is replaced by halogen, and at least one of the ring A$^1$, the ring A$^2$, the ring A$^3$, the ring A$^4$, the ring A$^5$ and the ring A$^6$ is pyrimidine-2,5-diyl or pyridine-2,5-diyl. Examples of 1,4-phenylene in which arbitrary hydrogen is replaced by halogen are formulas (14-6) to (14-22). Desirable examples are the groups represented by formulas (14-6) to (14-11).

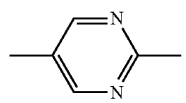 (14-1)

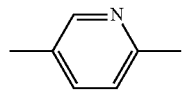 (14-2)

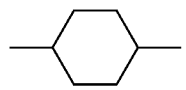 (14-3)

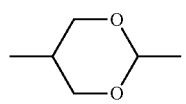 (14-4)

 (14-5)

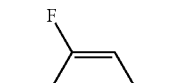 (14-6)

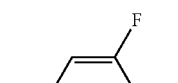 (14-7)

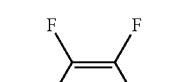 (14-8)

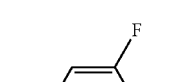 (14-9)

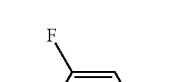 (14-10)

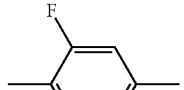 (14-11)

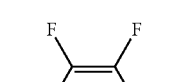 (14-12)

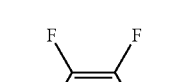 (14-13)

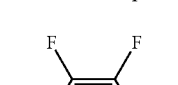 (14-14)

-continued (14-15) 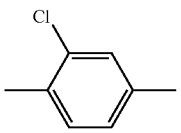

(14-16) 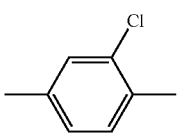

(14-17) 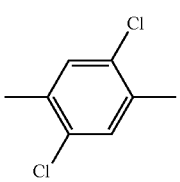

(14-18) 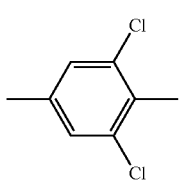

(14-19) 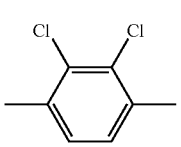

(14-20) 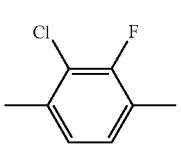

(14-21) 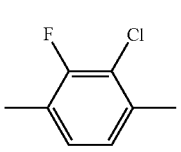

(14-22) 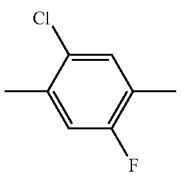

Desirable examples of the ring $A^1$, the ring $A^2$, the ring $A^3$, the ring $A^4$, the ring $A^5$ and the ring $A^6$ are pyrimidine-2,5-diyl (14-1), pyridine-2,5-diyl (14-2), 1,4-cyclohexylene (14-3), 1,3-dioxane-2,5-diyl (14-4), 1,4-phenylene (14-5), 2-fluoro-1,4-phenylene (14-6 and 14-7), 2,3-difluoro-1,4-phenylene (14-8), 2,5-difluoro-1,4-phenylene (14-10) and 2,6-difluoro-1,4-phenylene (14-9 and 14-11).

Most desirable examples of the ring $A^1$, the ring $A^2$, the ring $A^3$, the ring $A^4$, the ring $A^5$ and the ring $A^6$ are pyrimidine-2,5-diyl, pyridine-2,5-diyl, 1,4-cyclohexylene, 1,3-dioxane-2,5-diyl, 1,4-phenylene, 2-fluoro-1,4-phenylene and 2,6-difluoro-1,4-phenylene.

In formula (1), $Z^1$, $Z^2$, $Z^3$, $Z^4$, $Z^5$ and $Z^6$ are independently a single bond, —CH$_2$CH$_2$—, —CH=CH—, —C≡C—, —COO—, —COO—, —CF$_2$O—, —OCF$_2$—, —CH$_2$O—, —OCH$_2$—, —CF=CF—, —(CH$_2$)$_4$—, —(CH$_2$)$_2$CF$_2$O—, —(CH$_2$)$_2$—OCF$_2$—, —CF$_2$O—(CH$_2$)$_2$—, —OCF$_2$—(CH$_2$)$_2$—, —CH=CH—(CH$_2$)$_2$— or —(CH$_2$)$_2$—CH=CH—.

Desirable examples of $Z^1$, $Z^2$, $Z^3Z^4$, $Z^5$ and $Z^6$ are a single bond, —CH$_2$CH$_2$—, —CH=CH—, —C≡C—, —COO—, —CF$_2$O—, —CH$_2$O— or —OCH$_2$—. In these bonds, trans is preferable to cis in the configuration of the double bond with regard to bonding groups such as —CH=CH—, —CF=CF—, —CH=CH—(CH$_2$)$_2$— and —(CH$_2$)$_2$—CH=CH—. Most desirable $Z^1$, $Z^2$, $Z^3$, $Z^4$, $Z^5$ and $Z^6$ are single bonds.

In formula (1), $L^1$, $L^2$, $L^3$ and $L^4$ are independently hydrogen or halogen. Desirable $L^1$, $L^2$, $L^3$ and $L^4$ are independently hydrogen or fluorine.

In formula (1), $X^1$ is hydrogen, halogen, —C≡N, —N=C=S, —SF$_5$ or alkyl having 1 to 10 carbons; and in alkyl having 2 to 10 carbons, arbitrary —CH$_2$— may be replaced by —O—, —S— or —CH=CH—; and in alkyl having 1 to 10 carbons or alkyl having 2 to 10 carbons in which arbitrary —CH$_2$— is replaced by —O—, —S— or —CH=CH—, arbitrary hydrogen may be replaced by halogen.

Specific examples of alkyl in which arbitrary hydrogen is replaced by halogen are —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F and —(CF$_2$)$_5$—F.

Specific examples of alkoxy in which arbitrary hydrogen is replaced by halogen are —OCH$_2$F, —OCHF$_2$, —OCF$_3$, —O—(CH$_2$)$_2$—F, —OCF$_2$CH$_2$F, —OCF$_2$CHF$_2$—OCH$_2$CF$_3$, —O—(CH$_2$)$_3$—F, —O—(CF$_2$)$_3$—F, —OCF$_2$CHFCF$_3$, —OCHFCF$_2$CF$_3$, —O—(CH$_2$)$_4$—F, —O—(CF$_2$)$_4$—F, —O—(CH$_2$)$_5$—F and —O—(CF$_2$)$_5$—F.

Specific examples of alkenyl in which arbitrary hydrogen is replaced by halogen are —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$ and —CH=CHCF$_2$CF$_3$.

Specific examples of $X^1$ are hydrogen, fluorine, chlorine, —C≡N, —N=C=S, —SF$_5$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —CH$_2$F, —CHF$_2$, —CF$_3$, —(CH$_2$)$_2$—F, —CF$_2$CH$_2$F, —CF$_2$CHF$_2$—CH$_2$CF$_3$, —CF$_2$CF$_3$, —(CH$_2$)$_3$—F, —(CF$_2$)$_3$—CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —OCH$_3$, —OC$_2$H$_5$, —OC$_3$H$_7$, —OC$_4$H$_9$, —OC$_5$H$_{11}$, —OCH$_2$F, —OCHF$_2$, —OCF$_3$, —O—(CH$_2$)$_2$, —F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$, —(CH$_2$)$_3$—CH=CH$_2$, —CH=CHF, —CH=CF$_2$, —CF=CHF, —CH=CHCH$_2$F, —CH=CHCF$_3$, —(CH$_2$)$_2$—CH=CF$_2$—CH$_2$CH=CHCF$_3$ and —CH=CHCF$_2$CF$_3$.

Examples of desirable $X^1$ are fluorine, chlorine, —CF$_3$, —CHF$_2$, —CH$_2$F, —OCF$_3$—OCHF$_2$ and —OCH$_2$F. Examples of most desirable $X^1$ is fluorine.

In formula (1), l, m, n, o, p and q are independently 0 or 1, and l+m+n+o+p+q is 3. A desirable combination of l, m, n, o, p and q is (l=o=p=1 and m=n=q=0) such as in formula (1-1), ($l=m=o=1$ and $n=p=q=0$) such as in formula (1-2), and ($l=m=n=1$ and $o=p=q=0$) such as in formula (1-3).

1-2. Physical Properties of the Compound of the Invention and Methods for Their Adjustment The compound (1) of the invention will be further explained in detail. The compound (1) is a five-ring liquid crystal compound having a nitrogen-containing heterocyclic ring. The compound is physically and chemically very stable under the conditions that the device is usually used, and has an excellent compatibility with other liquid crystal compounds. The composition including this compound is stable under the conditions that the device is usually used. This compound does not deposit its crystals (or its smectic phase) even when the composition is kept in storage at a low temperature. This compound has a five-ring, a wide temperature range of a liquid crystal phase and a high clearing point. Accordingly, the temperature range of a nematic phase in the composition can be increased and the display device can be used in a wide temperature range. This compound has a large refractive index anisotropy. Hence, a composition that has refractive index anisotropy suitable for the cell thickness of a liquid crystal display device can be provided, and thus the compound is suitable for producing a liquid crystal display device with high display performance. Moreover, this compound is useful as a component for decreasing the threshold voltage of a composition since it has a large dielectric anisotropy.

Physical properties of the compound (1) such as the clearing point, the refractive index anisotropy and the dielectric anisotropy can be adjusted arbitrarily by a suitable selection of the combination of l, m, n, o, p and q, the kinds of the ring $A^1$ to $A^6$, the left-terminal group $R^1$, the substituent on the benzene ring located at the right end position, the position of substitution ($L^1$, $L^2$ and $X^1$) and the bonding group $Z^1$ to $Z^6$. The effect of the combination of l, m, n, o, p and q and the kinds of the rings $A^1$ to $A^6$, the left-terminal group $R^1$, the right-terminal group $X^1$, the bonding group $Z^1$ to $Z^6$, $L^1$ and $L^2$, on the physical properties of the compound (1) will be explained below.

When the combination of l, m, n, o, p and q is ($l=m=n=1$ and $o=p=q=0$) such as in formula (1-3), the temperature range of a liquid crystal phase is wide, the clearing point is high, and the refractive index anisotropy is large. When the combination is ($l=m=o=1$ and $n=p=q=0$) such as in formula (1-2), the compatibility with other compounds is high and the dielectric anisotropy is large. When the combination is ($l=o=p=1$ and $m=n=q=0$) such as in formula (1-1), the dielectric anisotropy is large.

The compatibility with other compounds is high, the refractive index anisotropy is large, and the dielectric anisotropy is large, when the ring $A^1$ is pyrimidine-2,5-diyl, the ring $A^2$ and the ring $A^4$ are 1,4-phenylene, or 1,4-phenylene in which arbitrary hydrogen is replaced by halogen, and the combination is ($l=m=o=1$ and $n=p=q=0$) such as in formula (1-2). The clearing point is high, the refractive index anisotropy is large, the dielectric anisotropy is large, when the ring $A^1$ is pyrimidine-2,5-diyl, the ring $A^2$ and the ring $A^3$ are 1,4-phenylene, or 1,4-phenylene in which arbitrary hydrogen is replaced by halogen, the combination is ($l=m=n=1$ and $o=p=q=0$) such as in formula (1-3). The dielectric anisotropy is large, when the ring $A^1$ is pyrimidine-2,5-diyl, the ring $A^4$ and the ring $A^5$ are 1,4-phenylene, or 1,4-phenylene in which arbitrary hydrogen is replaced by halogen, and the combination is ($l=o=p=1$ and $m=n=q=0$) such as in formula (1-1). The clearing point is high and the compatibility with other compounds is high, when the ring $A^1$ is 1,4-cyclohexylene, the ring $A^2$ is pyrimidine-2,5-diyl, the ring $A^3$ is 1,4-phenylene, or 1,4-phenylene in which arbitrary hydrogen is replaced by halogen, and the combination is ($l=m=n=1$ and $o=p=q=0$) such as in formula (1-3). The compatibility with other compounds is high, when the ring $A^1$ is pyridine-2,5-diyl, the ring $A^2$ and the ring $A^4$ are 1,4-phenylene, or 1,4-phenylene in which arbitrary hydrogen is replaced by halogen, and the combination is ($l=m=o=1$ and $n=p=q=0$) such as in formula (1-2).

The temperature range of a liquid crystal phase is wide and the viscosity is small, when $R^1$ is straight chain. The compatibility with other liquid crystal compounds is excellent, when $R^1$ is branched chain. The compound is useful as a chiral dopant, when $R^1$ is an optically active group. Reverse twisted domain that will be formed in a device can be prevented by the addition of this compound to a composition. The compound where $R^1$ is not optically active is useful as a component of a composition. A desirable configuration depends on the position of the double bond, When $R^1$ is alkenyl. An alkenyl compound that has a desirable configuration has a high maximum temperature or a wide temperature range of a liquid crystal phase.

The viscosity is small, when the bonding group $Z^1$, $Z^2$, $Z^3$, $Z^4$, $Z^5$ and $Z^6$ are a single bond, —$CH_2CH_2$—, —CH═CH—, —$CF_2O$—, —$OCF_2$—, —$CH_2O$—, —$OCH_2$—, —CF═CF—, —$(CH_2)_3$—O—, —O—$(CH_2)_3$—, —$(CH_2)_2$—$CF_2O$—, —$OCF_2$—$(CH_2)_2$— or —$(CH_2)_4$—. The viscosity is smaller, when the bonding group is a single bond, —$(CH_2)_2$—, —$CF_2O$—, —$OCF_2$— or —CH═CH—. The temperature range of a liquid crystal phase is wide and the ratio of the elastic constants $K_{33}/K_{11}$ ($K_{33}$: bend elastic constant, $K_{11}$: splay elastic constant) is large, when the bonding group is —CH═CH—. The optical anisotropy is large, when the bonding group is —C≡C—. The compound is relatively stable chemically and is relatively hard to be deteriorated, when $Z^1$, $Z^2$, $Z^3$, $Z^4$, $Z^5$ and $Z^6$ are a single bond, —$(CH_2)_2$—, —$CH_2O$—, —$CF_2O$—, —$OCF_2$— or —$(CH_2)_4$—.

The dielectric anisotropy is large, when the right-terminal group $X^1$ is fluorine, chlorine, —C≡N, —N═C═S, —$SF_5$, —$CF_3$, —$CHF_2$, —$CH_2F$, —$OCF_3$, —$OCHF_2$ or —$OCH_2F$. The optical anisotropy is large, when $X^1$ is —C≡N, —N═C═S or alkenyl. The compound is chemically stable, when $X^1$ is fluorine, —$OCF_3$ or alkyl.

The dielectric anisotropy is large, when both $L^1$ and $L^2$ are fluorine and $X^1$ is fluorine, chlorine, —C≡N, —N═C═S, —$SF_5$, —$CF_3$, —$CHF_2$, —$CH_2F$, —$OCF_3$, —$OCHF_2$ or —$OCH_2F$. The dielectric anisotropy is large and the temperature range of a liquid crystal phase is wide, and further the compound is chemically stable and is relatively hard to be deteriorated, when $L^1$ is fluorine and $X^1$ is —$OCF_3$, or when both $L^1$ and $L^2$ are fluorine and $X^1$ is —$OCF_3$, or when all of $L^1$, $L^2$ and $X^1$ are fluorine.

As is described above, a compound having desired physical properties can be obtained by the suitable selection of the kinds of the ring structure, the terminal group, the bonding group and so forth. Thus, the compound (1) is useful for a component of a composition that will be used for a device having PC, TN, STN, ECB, OCB, IPS, VA or the like.

1-3. Specific Examples of the Compound (1)

Desirable examples of the compound (1) are formulas (1-4) to (1-6). More desirable examples are formulas (1-7) to (1-16). Further desirable examples are formulas (1-17) to (1-21).

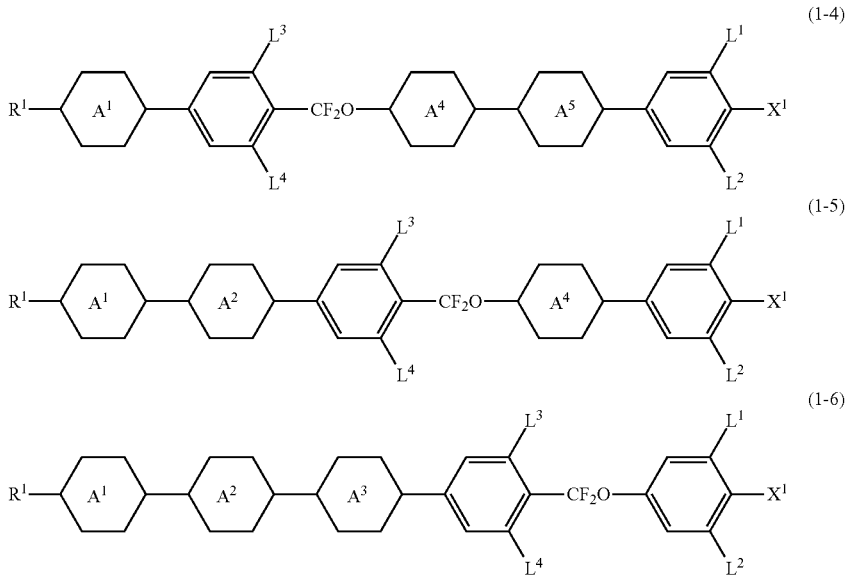

In these formulas, $R^1$ is alkyl having 1 to 15 carbons or alkenyl having 2 to 15 carbons; the ring $A^1$, the ring $A^2$, the ring $A^3$, the ring $A^4$ and the ring $A^5$ are independently pyrimidine-2,5-diyl, pyridine-2,5-diyl, 1,4-cyclohexylene, 1,3-dioxane-2,5-diyl, 1,4-phenylene, or 1,4-phenylene in which arbitrary hydrogen is replaced by halogen, and at least one of the ring $A^1$, the ring $A^2$, the ring $A^3$, the ring $A^4$ and the ring $A^5$ is pyrimidine-2,5-diyl or pyridine-2,5-diyl in each formula; $L^1$, $L^2$, $L^3$ and $L^4$ are independently hydrogen or fluorine; and X' is fluorine, chlorine, —C≡N, —$CF_3$, —$CHF_2$, —$CH_2F$, —$OCF_3$, —$OCHF_2$ or —$OCH_2F$.

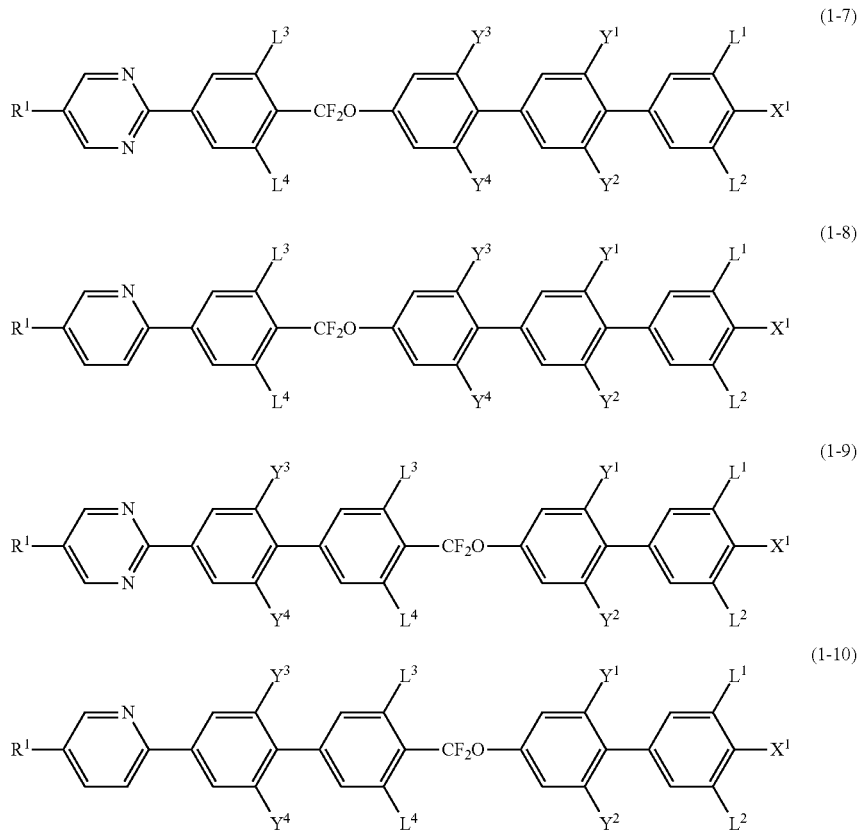

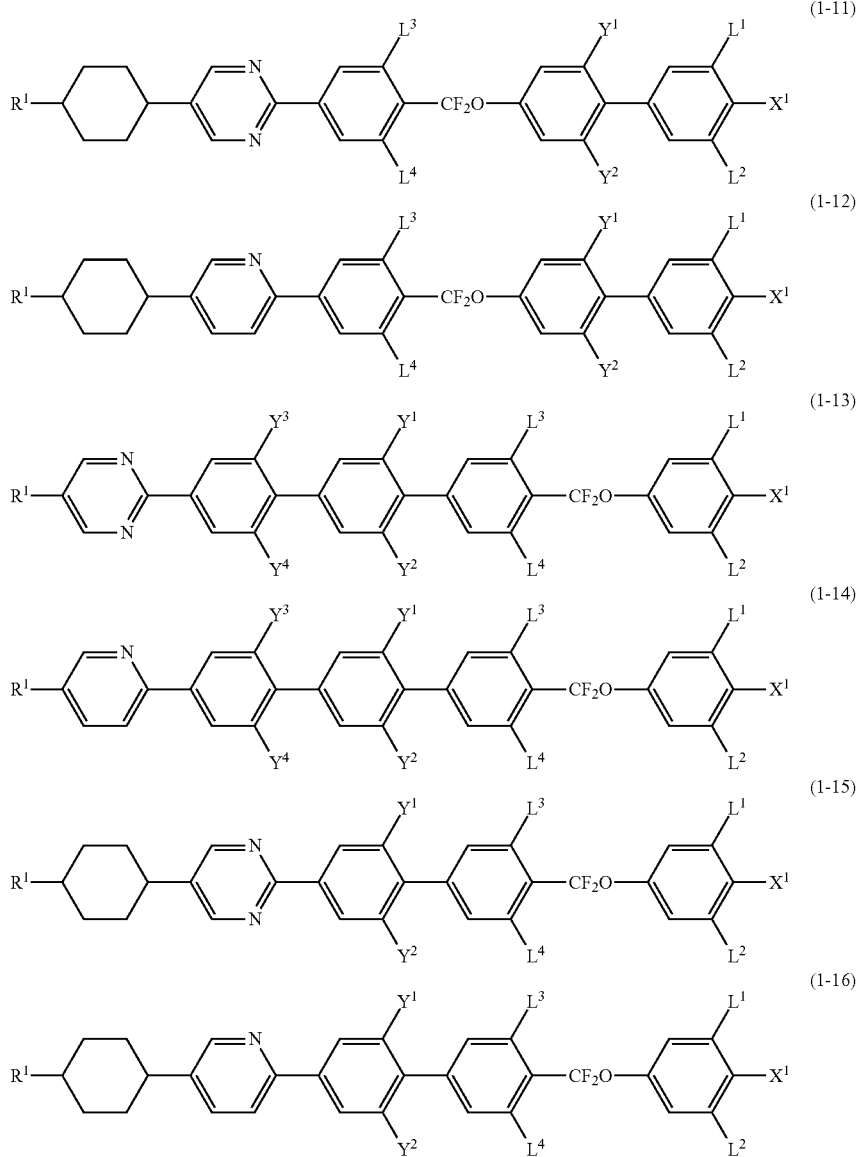
In these formulas, $R^1$ is alkyl having 1 to 15 carbons; $L^1$, $L^2$, $L^3$, $L^4$, $Y^1$, $Y^2$, $Y^3$ and $Y^4$ are independently hydrogen or fluorine; and $X^1$ is fluorine or —$OCF_3$.
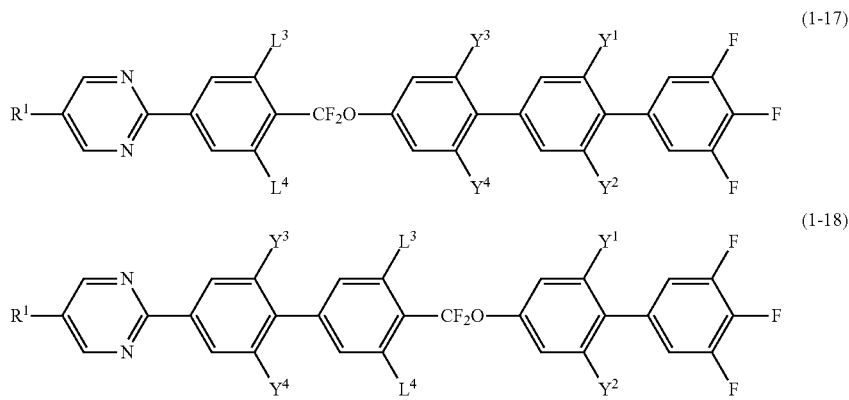

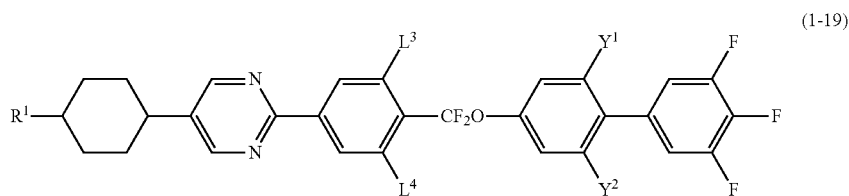

(1-19)

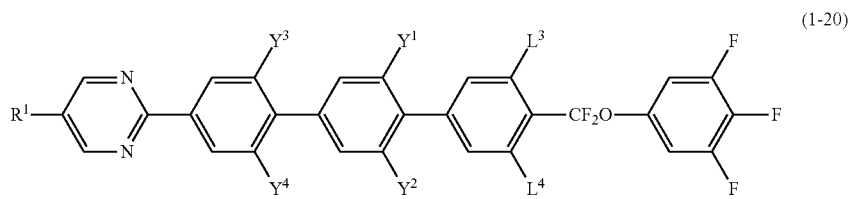

(1-20)

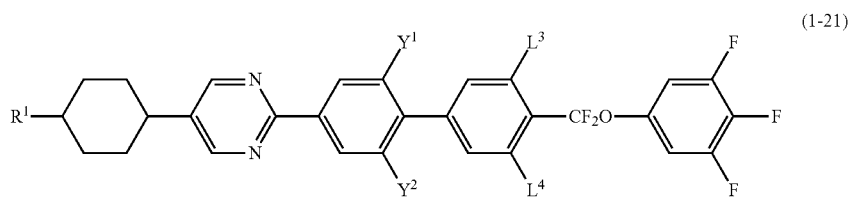

(1-21)

In these formulas, $R^1$ is alkyl having 1 to 15 carbons; and $L^3$, $L^4$, $Y^1$, $Y^2$, $Y^3$ and $Y^4$ are independently hydrogen or fluorine.

1-4. Preparation the Compound (1)

Next, the preparation of the compound (1) will be explained. The compound (1) can be prepared by a suitable combination of techniques in synthetic organic chemistry. Methods of introducing objective terminal groups, rings and bonding groups into starting materials are described in books such as Organic Syntheses (John Wiley & Sons, Inc), Organic Reactions (John Wiley & Sons, Inc), Comprehensive Organic Synthesis (Pergamon Press) and New Experimental Chemistry Course (Shin Jikken Kagaku Kouza, in Japanese) (Maruzen Co., Ltd.).

1-4-1. Method for Forming the Bonding Groups $Z^1$ to $Z^6$

One example of methods for forming the bonding group $Z^1$ to $Z^6$ of the compound (1) is shown in the following schemes. In the schemes, $MSG^1$ or $MSG^2$ is a monovalent organic group having at least one ring. A plurality of the $MSG^1$ (or $MSG^2$) used in the schemes may be the same or different organic groups. The compounds (1A) to (1J) correspond to the compound (1).

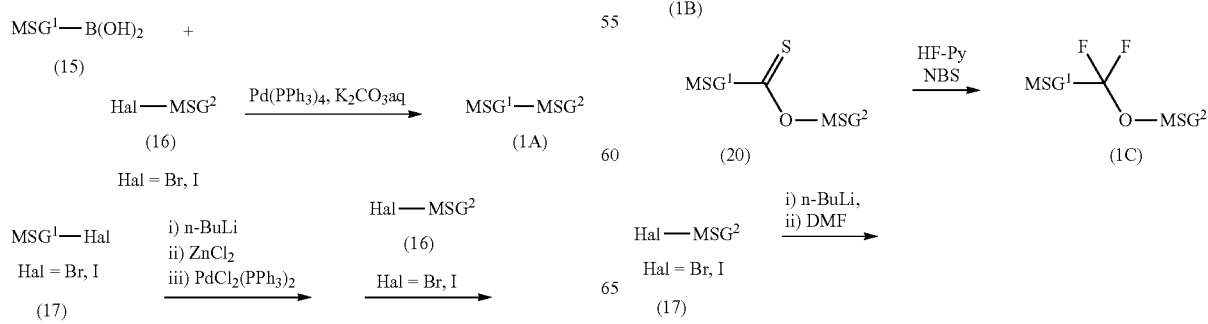

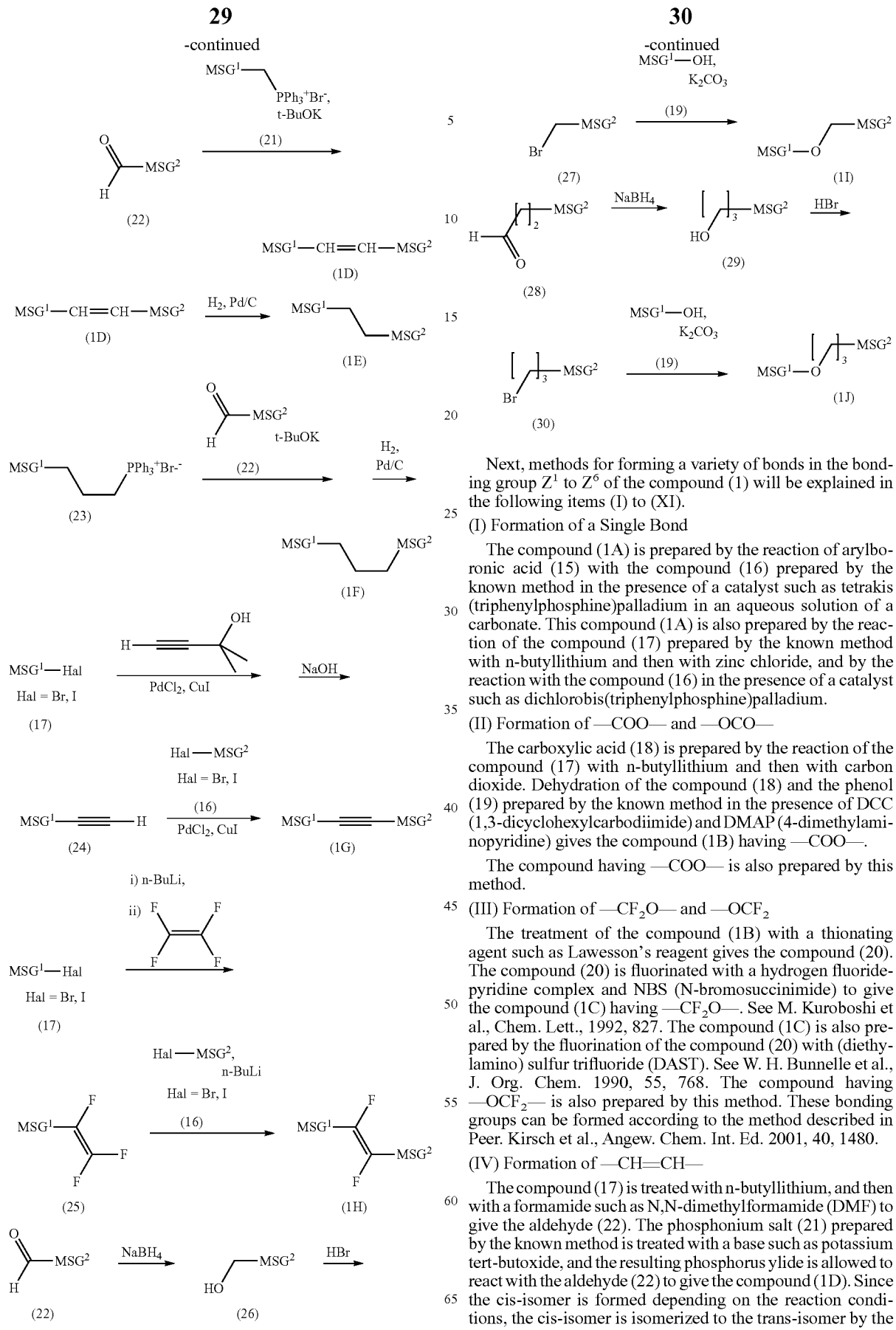

Next, methods for forming a variety of bonds in the bonding group $Z^1$ to $Z^6$ of the compound (1) will be explained in the following items (I) to (XI).

(I) Formation of a Single Bond

The compound (1A) is prepared by the reaction of arylboronic acid (15) with the compound (16) prepared by the known method in the presence of a catalyst such as tetrakis(triphenylphosphine)palladium in an aqueous solution of a carbonate. This compound (1A) is also prepared by the reaction of the compound (17) prepared by the known method with n-butyllithium and then with zinc chloride, and by the reaction with the compound (16) in the presence of a catalyst such as dichlorobis(triphenylphosphine)palladium.

(II) Formation of —COO— and —OCO—

The carboxylic acid (18) is prepared by the reaction of the compound (17) with n-butyllithium and then with carbon dioxide. Dehydration of the compound (18) and the phenol (19) prepared by the known method in the presence of DCC (1,3-dicyclohexylcarbodiimide) and DMAP (4-dimethylaminopyridine) gives the compound (1B) having —COO—.

The compound having —COO— is also prepared by this method.

(III) Formation of —CF$_2$O— and —OCF$_2$

The treatment of the compound (1B) with a thionating agent such as Lawesson's reagent gives the compound (20). The compound (20) is fluorinated with a hydrogen fluoride-pyridine complex and NBS (N-bromosuccinimide) to give the compound (1C) having —CF$_2$O—. See M. Kuroboshi et al., Chem. Lett., 1992, 827. The compound (1C) is also prepared by the fluorination of the compound (20) with (diethylamino) sulfur trifluoride (DAST). See W. H. Bunnelle et al., J. Org. Chem. 1990, 55, 768. The compound having —OCF$_2$— is also prepared by this method. These bonding groups can be formed according to the method described in Peer. Kirsch et al., Angew. Chem. Int. Ed. 2001, 40, 1480.

(IV) Formation of —CH=CH—

The compound (17) is treated with n-butyllithium, and then with a formamide such as N,N-dimethylformamide (DMF) to give the aldehyde (22). The phosphonium salt (21) prepared by the known method is treated with a base such as potassium tert-butoxide, and the resulting phosphorus ylide is allowed to react with the aldehyde (22) to give the compound (1D). Since the cis-isomer is formed depending on the reaction conditions, the cis-isomer is isomerized to the trans-isomer by the known method as requested.

(V) Formation of —(CH$_2$)$_2$—

The compound (1E) is prepared by the hydrogenation of the compound (1D) in the presence of a catalyst such as palladium on carbon.

(VI) Formation of —(CH$_2$)$_4$—

A compound having —(CH$_2$)$_2$—CH=CH— is prepared according to the method described in item (IV), using the phosphonium salt (23) instead of the phosphonium salt (21). The catalytic hydrogenation of the resulting compound gives the compound (1F).

(VII) Formation of —C≡C—

The compound (17) is allowed to react with 2-methyl-3-butyn-2-ol in the presence of a catalyst of dichloropalladium and a copper halide, and the product is deprotected under basic conditions to give the compound (24). The compound (24) is allowed to react with the compound (16) in the presence of a catalyst of dichlorobis(triphenylphosphine)palladium and a copper halide to give the compound (1G).

(VIII) Formation of —CF=CF—

The compound (17) is treated with n-butyllithium, and then allowed to react with tetrafluoroethylene to give the compound (25). The compound (16) is treated with n-butyllithium, and then allowed to react with the compound (25) to give the compound (1H).

(IX) Formation of —CH$_2$O— or —OCH$_2$—

The compound (22) is reduced with a reducing agent such as sodium borohydride to give the compound (26). The compound (26) is halogenated with hydrobromic acid or the like, giving the compound (27). The compound (27) is allowed to react with the compound (19) in the presence of potassium carbonate or the like, giving the compound (II).

(X) Formation of —(CH$_2$)$_3$O— or —O(CH$_2$)$_3$—

The compound (1J) is prepared according to the method described in the preceding item (IX), using the compound (28) instead of the compound (22).

1-4-2. Method for Forming the Rings A$^1$, A$^2$, A$^3$, A$^4$, A$^5$ and A$^6$

For the formation of rings such as pyrimidine-2,5-diyl, pyridine-2,5-diyl, 1,4-cyclohexylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene and 2,3,5,6-tetrafluoro-1,4-phenylene, starting materials are commercially available or methods for forming the rings are well-known.

1-4-3-1. Method for Preparing the Compound (1)

There are a plurality of methods for preparing the compound represented by formula (1), and examples will be shown here. The dehydrating condensation of the carboxylic acid derivative (31) with the alcohol derivative (32) in the presence of DCC, DMAP and so forth gives the ester derivative (33). The ester derivative (33) is treated with a thionating agent such as Lawesson's reagent to give the thion-O-ester derivative (34), which is then fluorinated with a hydrogen fluoride-pyridine complex and NBS to give the compound (1).

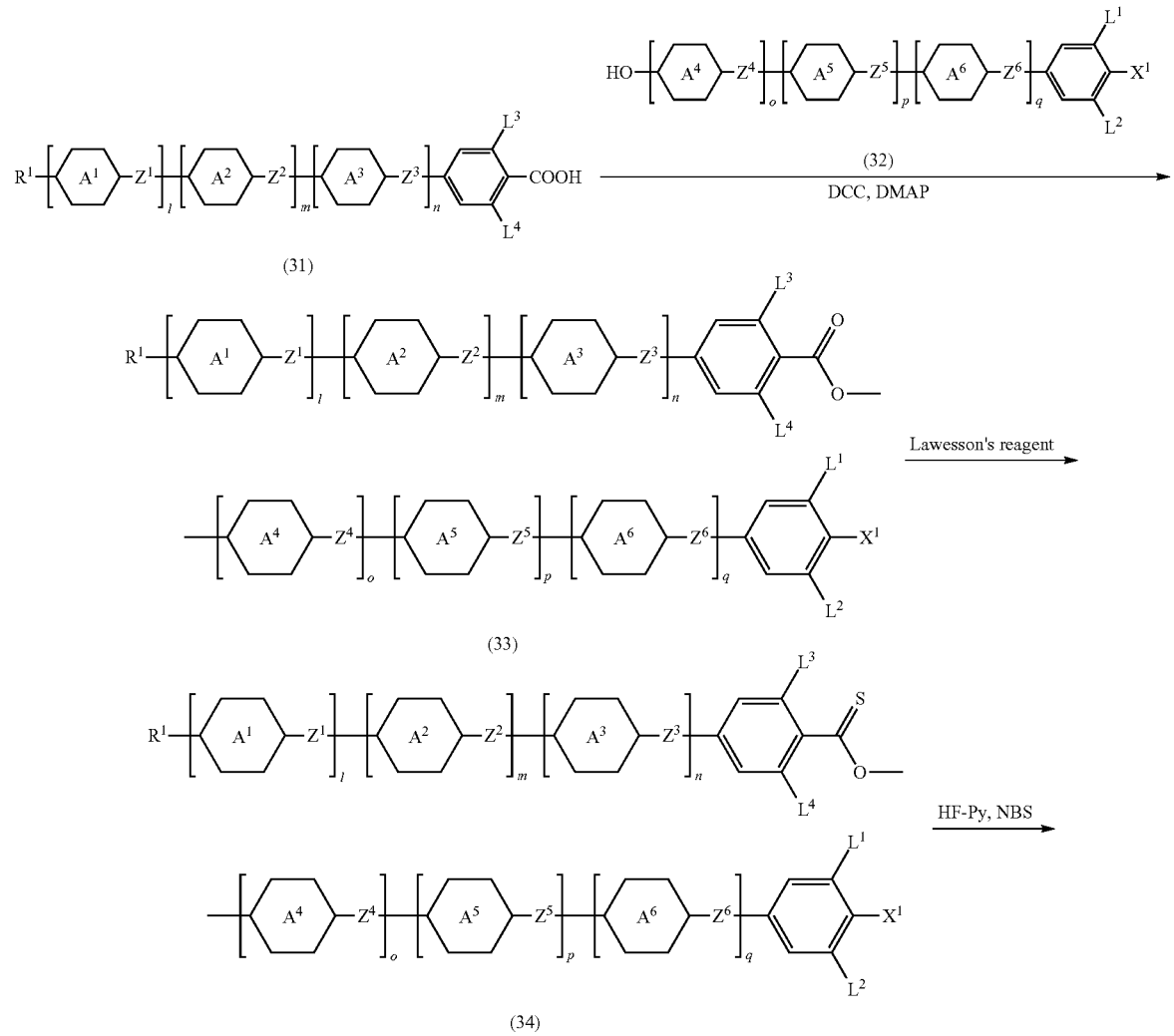

-continued

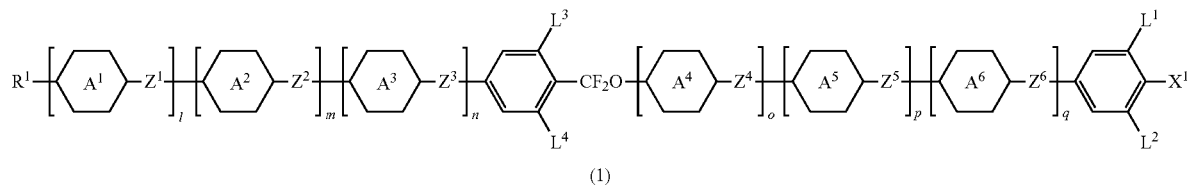

(1)

In these formulas, the definition of the rings $A^1$ to $A^6$, $Z^1$ to $Z^6$, $L^1$ to $L^4$, $R^1$, $X^1$, l, m, n, o, p and q is the same with that described in item 1.

In formula (1), when the ring $A^1$ is pyrimidine-2,5-diyl and $Z^1$ is a single bond, the compound can be prepared by the following method. The compound represented by formula (35) is allowed to react with the urea (36) under acidic conditions, and the resulting product is allowed to react with a chlorinating reagent such as phosphorus oxychloride to give the 2-chloropyrimidine derivative (37). The compound (37) where $R^1$ is an alkyl group is commercially available, although the availability depends on the alkyl chain-length. The carboxylic acid derivative (38) is allowed to react with 1,3-propanedithiol and trifluoromethanesulfonic acid to give the dithianylium salt (39), according to the method described in P. Kirsch et al., Angew. Chem. Int. Ed., 2001, 40, 1480. The compound (39) is added dropwise to a mixture of the alcohol derivative (40) and triethylamine, and is allowed to react with triethylamine trihydrofluoride at low temperature, and then with bromine to give the compound (41). The reaction of the compound (41) with bis(pinacolato)diboron (42) in the presence of a catalyst such as tetrakis(triphenylphosphine) gives the compound (43), which is then reacted with 2-chloropyrimidine derivative (37) in the presence of a catalyst such as tetrakis(triphenylphosphine) palladium, giving the compound (1-22).

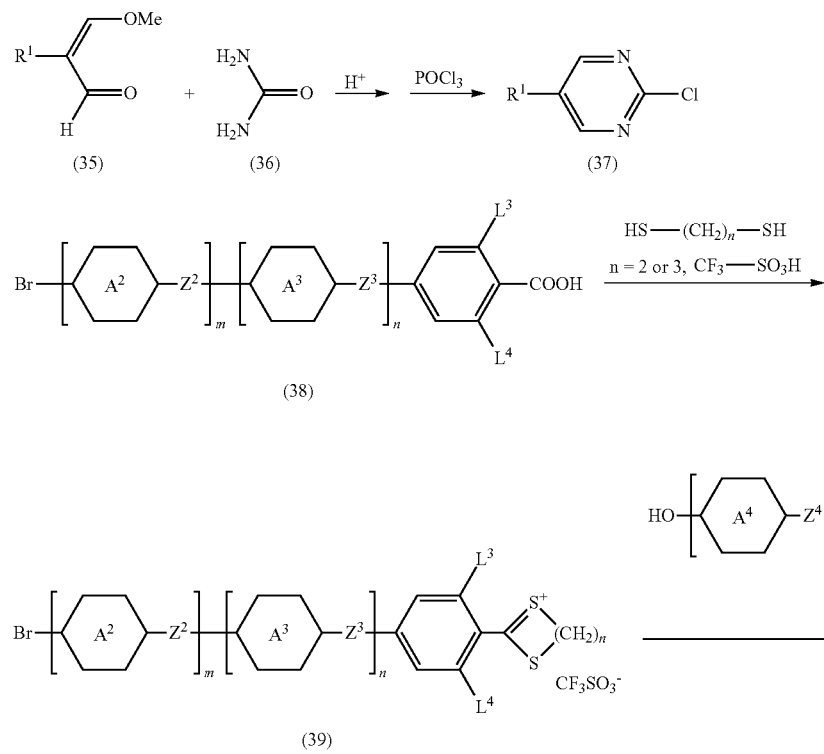

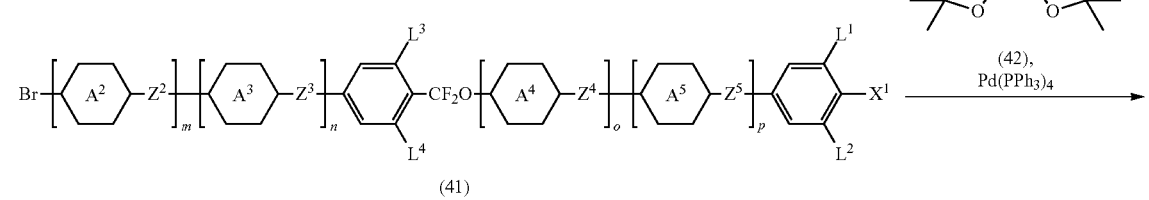

(41)

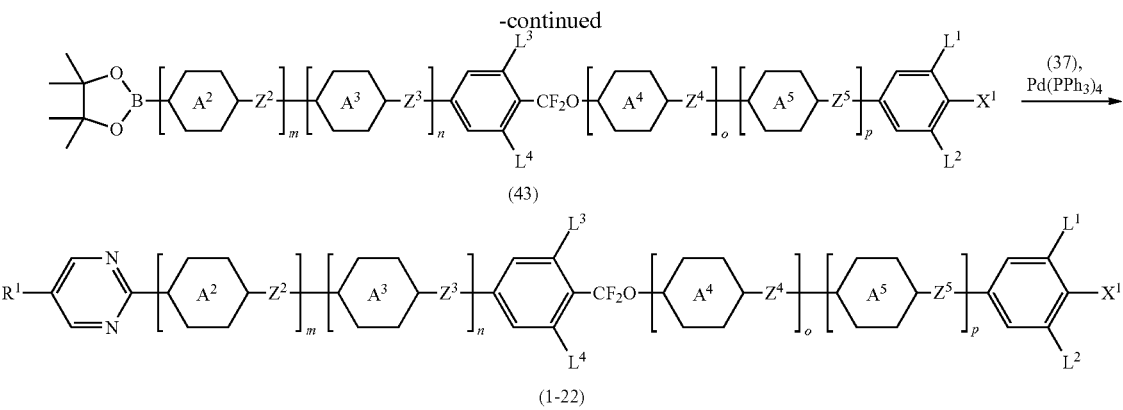

In these formulas, the definition of the rings $A^2$ to $A^5$, $Z^2$ to $Z^5$, $L^1$ to $L^4$, $R^1$, $X^1$ is the same with that described in item 1; and m, n, o and p are independently 0 or 1 and m+n+o+p is 2.

In formula (1), when the ring $A^1$ is pyridine-2,5-diyl and $Z^1$ is a single bond, the compound can be prepared by the following method. Phosphorus oxychloride is mixed with DMF to give the Vilsmeier reagent, which is allowed to react with N-benzylacetamide derivative (44) to give the 2-chloropyridine derivative (45). The reaction of the compound (43) with the compound (45) in the presence of a catalyst such as tetrakis(triphenylphosphine)palladium gives the compound (1-23).

In formula (1), when the ring $A^1$ is pyridine-2,5-diyl, $Z^1$ is a single bond, and $R^1$ is alkyl, the compound can be prepared by the following method. 5-Bromo-2-chloropyridine (46) is allowed to react with n-butyllithium, and then with formylpiperidine to give the formylpyridine derivative (47), which is reacted with the corresponding Wittig reagent to give the alkenylpyridine derivative (48). The reaction of the compound (43) with the compound (48) gives the compound (49), which is catalytically hydrogenated to the compound (1-24).

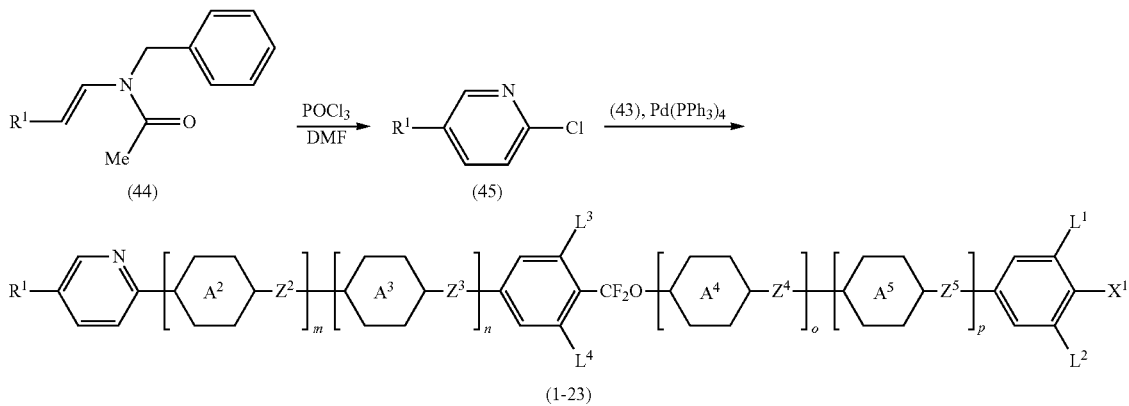

In these formulas, the definition of the rings $A^2$ to $A^6$, $Z^2$ to $Z^6$, $L^1$ to $L^4$, $R^1$, X is the same with that described in item 1; and m, n, o and p are independently 0 or 1 and m+n+o+p is 2.

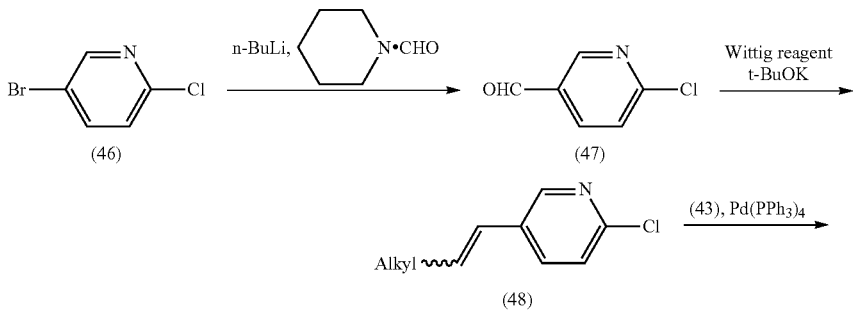

-continued

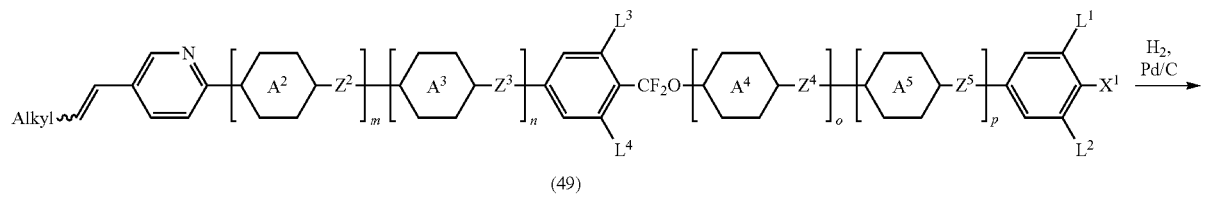

(49)

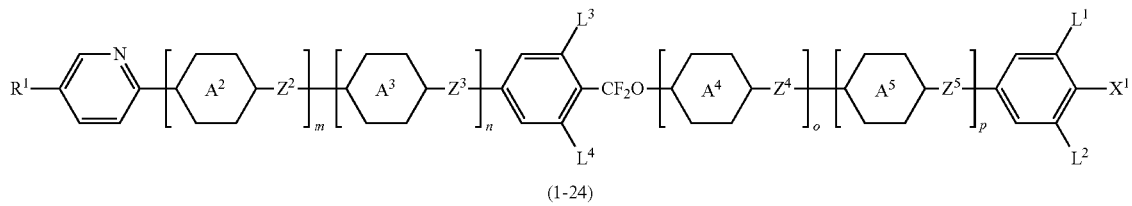

(1-24)

In these formulas, the definition of the rings $A^2$ to $A^5$, $Z^2$ to $Z^6$, $L^1$ to $L^4$, $X^1$ is the same with that described in item 1; $R^1$ is alkyl having 1 to 20 carbons; and m, n, o and p are independently 0 or 1, and m+n+o+p is 2.

In formula (1), when the ring $A^2$ is pyrimidine-2,5-diyl, $Z^2$ is a single bond and l=1, the compound can be prepared by the following method. The compound (50) is allowed to react with the urea (36) under acidic conditions, and the resulting product is allowed to react with a chlorinating agent such as phosphorus oxychloride to give 2-chloropyrimidine derivative (51). The compound (52), which is prepared according to a method similar to the preparation of the compound (43) described above, is allowed to react with the compound (51) to give the compound (1-25).

hydrogen is replaced by fluorine, $Z^1$ is a single bond, and both $L^3$ and $L^4$ are fluorine, the compound can be prepared by the following method. The alcohol derivative (53) is allowed to react with chlorotriisopropylsilane or the like, giving the compound (54). According to the method described in U.S. Pat. No. 6,231,785 B1, the compound (54) is allowed to react with n-butyllithium, and then with dibromodifluoromethane to give the bromodifluoromethane derivative (55), which is reacted with the phenol derivative (56) in the presence of a base such as potassium carbonate to give the compound (57). The compound (57) is deprotected with the action of tetrabutylammonium fluoride or the like to give the alcohol derivative (58), which is allowed to react with trifluoromethanesulfonic acid anhydride in the presence of

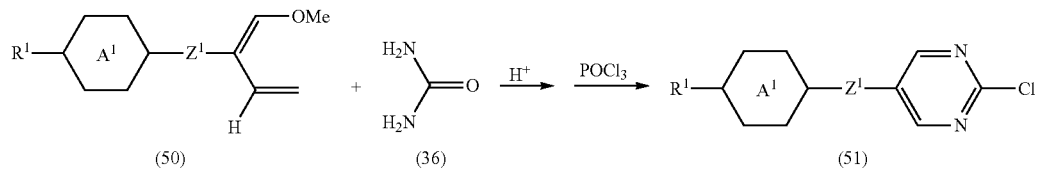

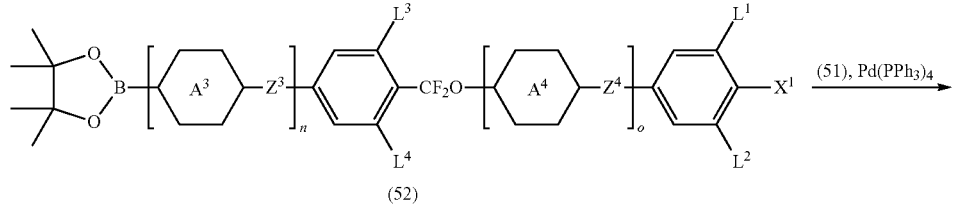

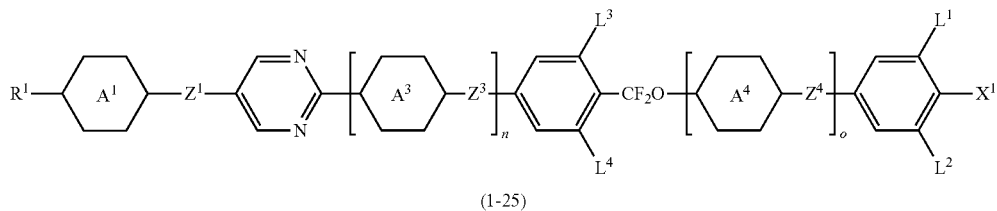

(1-25)

In these formulas, the definition of the ring $A^1$, the ring $A^3$, the ring $A^4$, $Z^1$, $Z^3$, $Z^4$, $L^1$ to $L^4$, $R^1$ and $X^1$ is the same with that described in item 1; and n and o are independently 0 or 1 and n+o=1.

In formula (1), when the ring $A^1$ is pyrimidine-2,5-diyl, the ring $A^4$ is 1,4-phenylene, or 1,4-phenylene in which arbitrary dimethylaminopyridine and pyridine to give the compound (59). The reaction of the compound (59) with bis(pinacolato) diboron (42) in the presence of a catalyst such as dichlorobisdiphenylphosphinoferrocenepalladium gives the compound (60), which is reacted with 2-chloropyrimidine derivative (37) in the presence of a catalyst such as tetrakis (triphenylphosphine)palladium to give the compound (1-26).

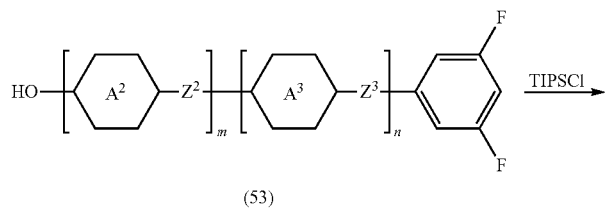
(53)
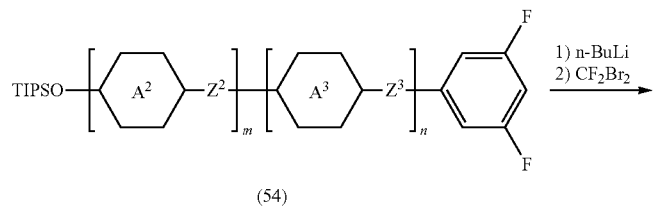
(54)
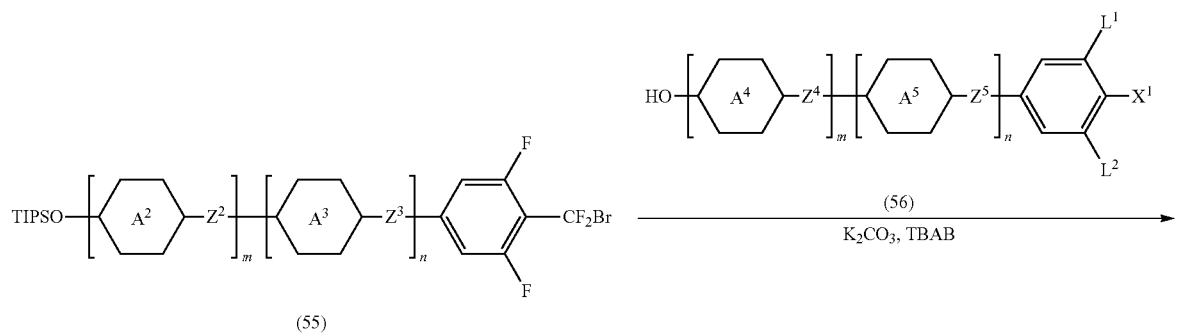
(55) (56)
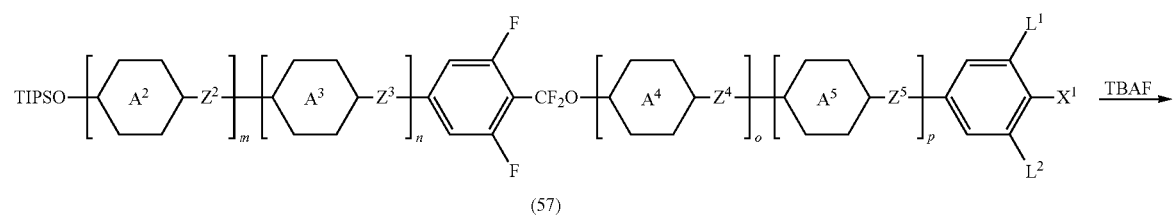
(57)
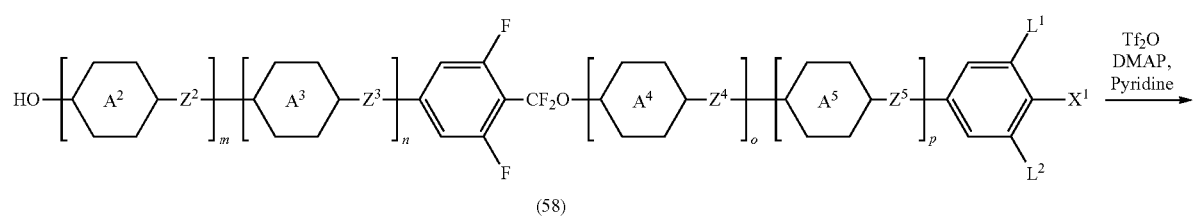
(58)
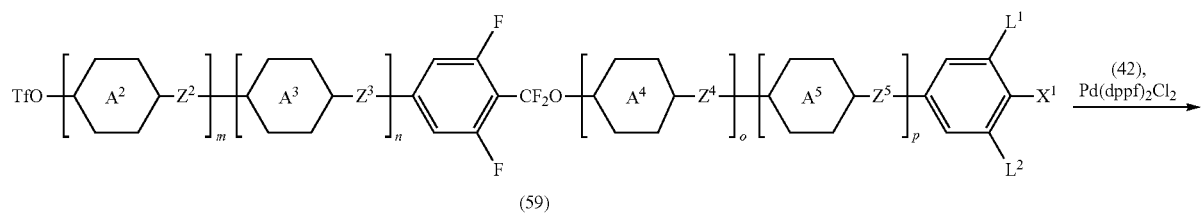
(59)
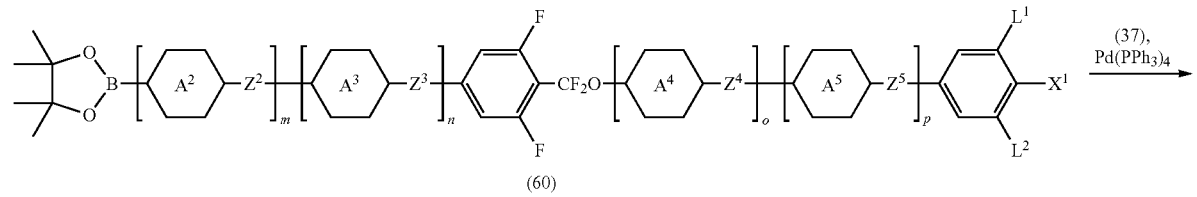
(60)

-continued

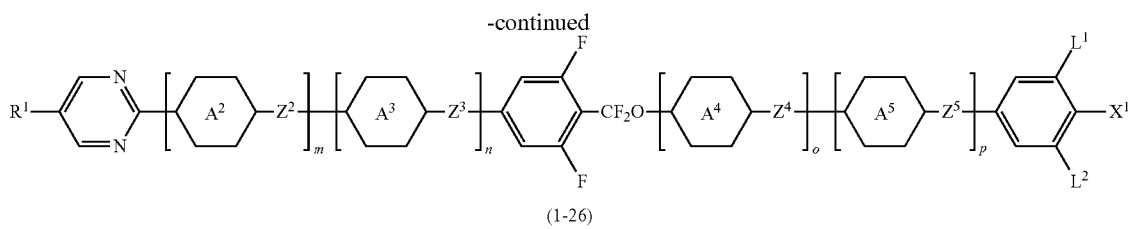

(1-26)

In these formulas, the ring $A^4$ is 1,4-phenylene, or 1,4-phenylene in which arbitrary hydrogen is replaced by fluorine; the definition of the ring $A^2$ to $A^3$, the ring $A^5$, $Z^2$ to $Z^5$, $L^1, L^2, R^1, X^1$ is the same with that described in item 1; and m, n, o and p are independently 0 or 1, and m+n+o+p is 2.

1-4-3-3. Method for Preparing the Phenol Derivative (56) Which is a Starting Material The phenol derivative (56) which is a starting material for the compound (1) is prepared by, for example, the following method. In formula (56), when both o and p are 0, a Grignard reagent prepared from the bromobenzene derivative (61) is allowed to react with trialkyl borate to give the boronic acid ester derivative, which is oxidized with peracetic acid (See R. L. Kidwellet et. al., Organic Syntheses, Vol. 5, Page 918 (1973)), or the boronic acid derivative (62) obtained easily by acid-catalyzed hydrolysis of a boronic acid ester is oxidized with peracetic acid, easily giving the desired phenol derivative (56-1).

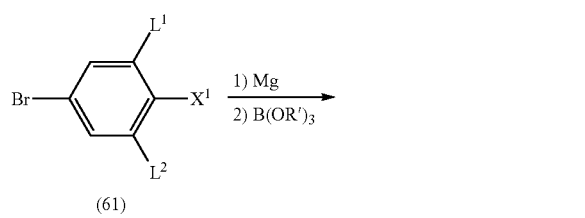

In this formula, the definition of $L^1$, $L^2$ and $X^1$ is the same with that described in item 1.

In formula (56), when both $Z^4$ and $Z^5$ are a single bond, o is 1, and p is 0 (or both o and p are 1), for example, the boronic acid derivative (62) is allowed to react with the anisole derivative (63) in the presence of a catalyst of tetrakis(triphenylphosphine)palladium under basic conditions to give the coupling products, the compound (64). See Akira Suzuki, et. al., Journal of Synthetic Organic Chemistry, Japan, Vol. 46, No. 9, page 848 (1988). Then, demethylation by the action with boron tribromide gives the desired phenol derivative (56-2).

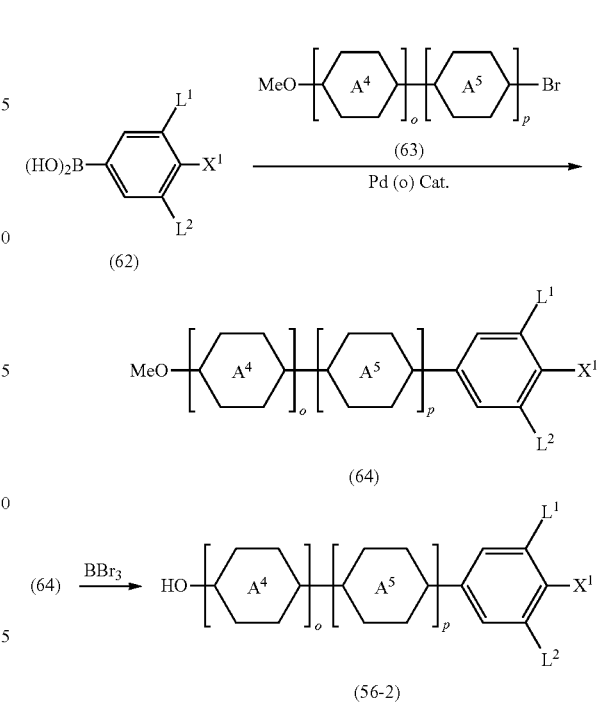

In this formula, the ring $A^4$ is 1,4-phenylene, or 1,4-phenylene in which arbitrary hydrogen is replaced by fluorine, and the definition of the ring $A^5$, $L^1$, $L^2$, o, p and $X^1$ is the same with that described in item 1.

In formula (56), when both o and p are 0, the compound can also be prepared by the following method. The benzylether derivative (65) is treated with n- or sec-butyllithium in THF at −70° C. or lower, and then reacted with trialkyl borate to give a boric acid ester derivative. The resulting boric acid derivative or its acid-catalyzed hydrolysate, a boronic acid derivative, is oxidized with peracetic acid to give the phenol derivative (66). The phenol derivative (66) is converted to phenolate by the reaction with sodium hydride, and the product is etherified by the action of fluoroalkyl bromide and then deprotected by reductive catalytic hydrogenation to give the desired phenol derivative (56-3).

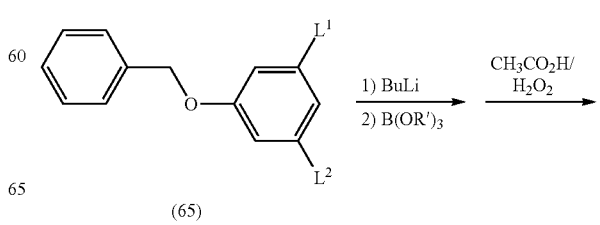

-continued

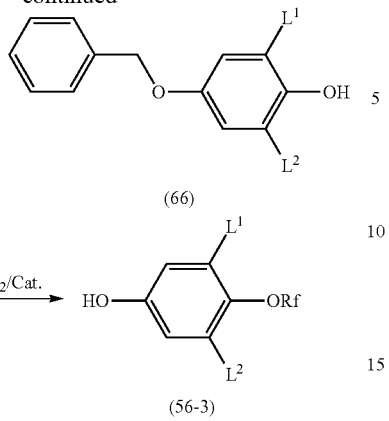
(66)

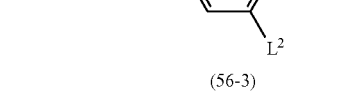
(56-3)

In formulas above, the definition of $L^1$ and $L^2$ is the same with that described in item 1, and Rf shows a fluoroalkyl group excluding a trifluoromethyl group.

2. The Composition of the Invention

The second aspect of the invention is a composition including the compound represented by formula (1), and is preferably a liquid crystal composition which can be used as a liquid crystal material. The liquid crystal composition of the invention should include the compound represented by formula (1) described above as the component A. There may be the composition (a) including the component A and the other components whose names are not written in this specification. Liquid crystal compositions having a variety of characteristics are also provided by the addition of a component selected from the components B, C and D, which will be shown below, to the component A.

As a component that will be added to the component A, the component B that is at least one compound selected from the group of formulas (2), (3) and (4) described above, or the component C that is at least one compound selected from the group of formula (5) described above, or the component D that is at least one compound selected from the group of formulas (6), (7), (8), (9) and (10) described above is desirable. Furthermore, the threshold voltage, the temperature range of a liquid crystal phase, the optical anisotropy, the dielectric anisotropy, the viscosity and so forth can be adjusted by the addition of the component E that is at least one compound selected from the group of formulas (11), (12) and (13).

In each component of the liquid crystal composition used for the invention, there are not major differences in physical properties even if the component is an analogue composed of isotopes of each element.

Among the component B described above, desirable examples of the compound represented by formula (2) include formulas (2-1) to (2-16), desirable examples of the compound represented by formula (3) include formulas (3-1) to (3-112), and desirable examples of the compound represented by formula (4) include formulas (4-1) to (4-52).

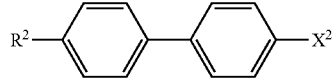
(2-1)

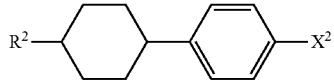
(2-2)

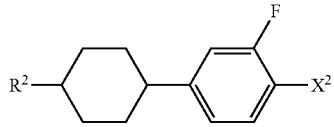
(2-3)

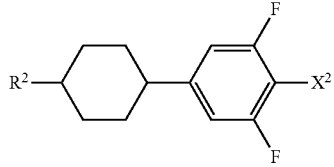
(2-4)

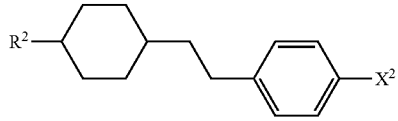
(2-5)

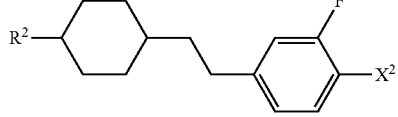
(2-6)

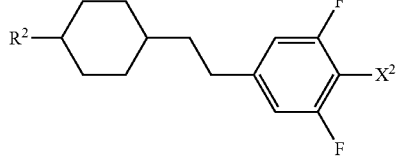
(2-7)

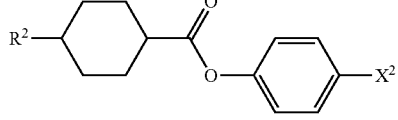
(2-8)

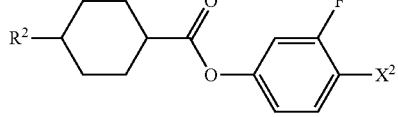
(2-9)

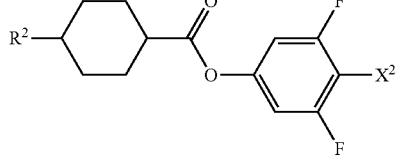
(2-10)

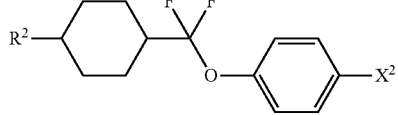
(2-11)

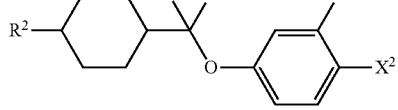
(2-12)

(2-13) 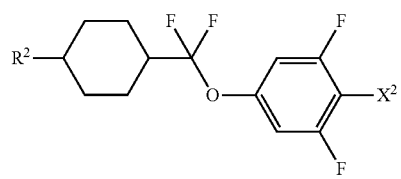
(2-14) 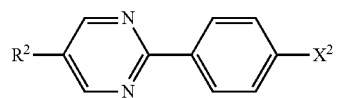
(2-15) 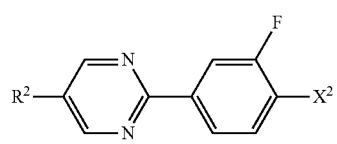
(2-16) 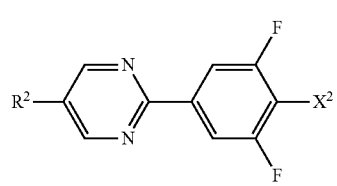
(3-1) 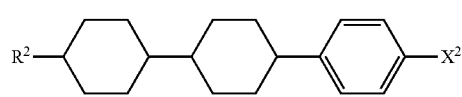
(3-2) 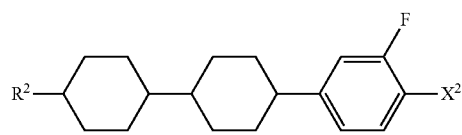
(3-3) 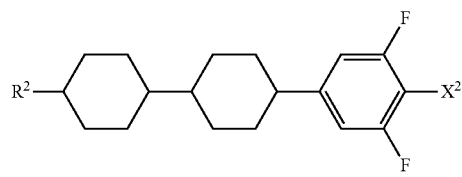
(3-4) 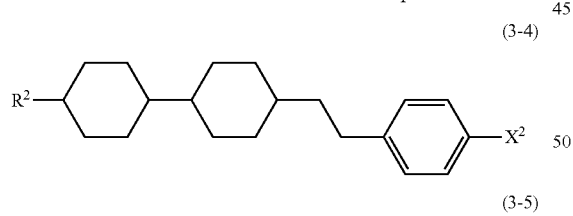
(3-5) 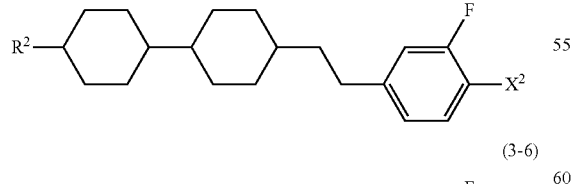
(3-6) 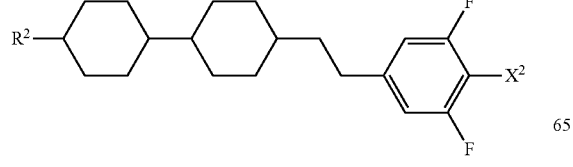
(3-7) 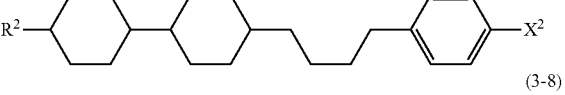
(3-8) 
(3-9) 
(3-10) 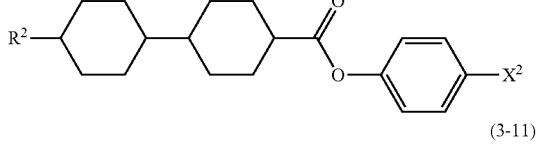
(3-11) 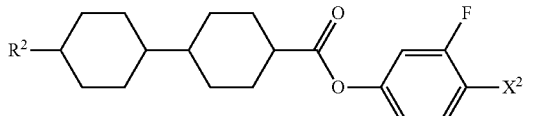
(3-12) 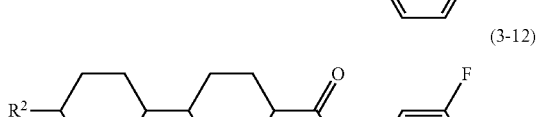
(3-13) 
(3-14) 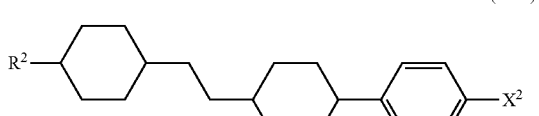
(3-15) 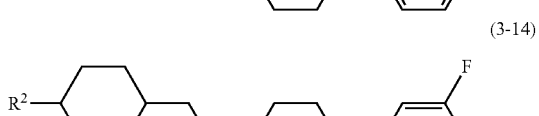
(316) 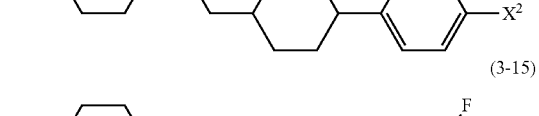
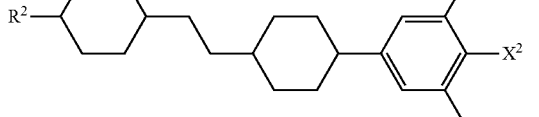
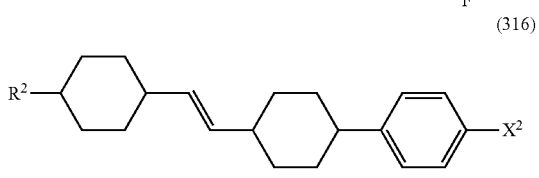

(3-17)
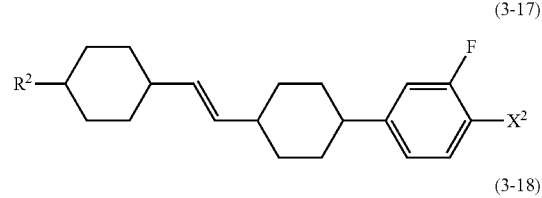
(3-18)
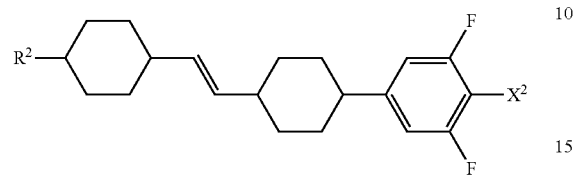
(3-19)
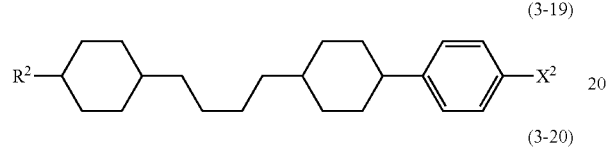
(3-20)
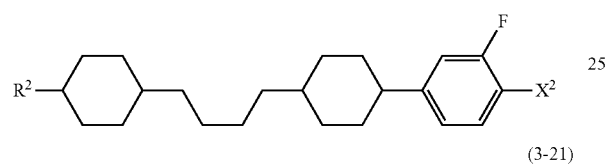
(3-21)
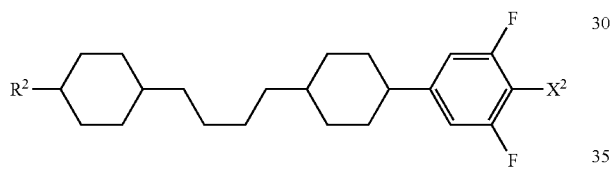
(3-22)
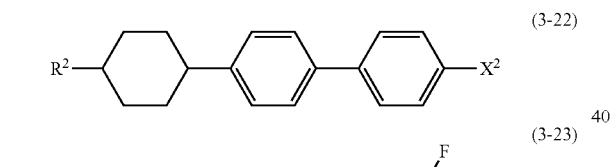
(3-23)
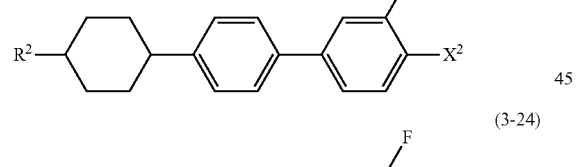
(3-24)
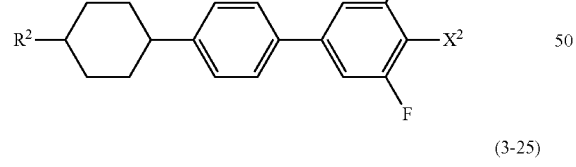
(3-25)
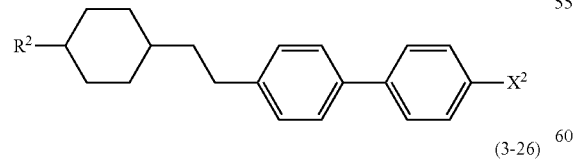
(3-26)
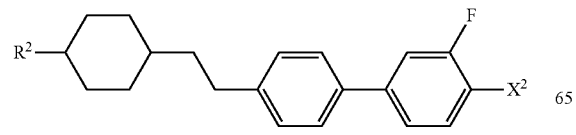
(3-27)
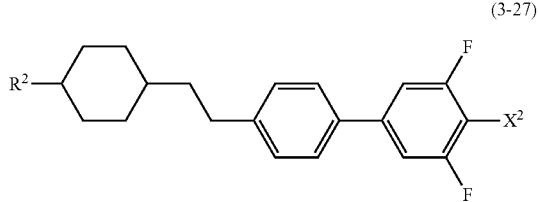
(3-28)
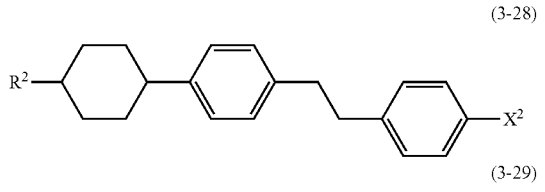
(3-29)
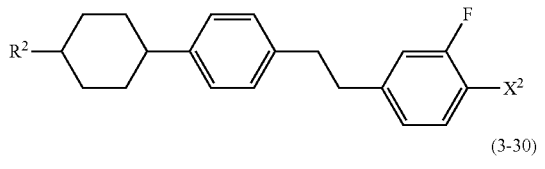
(3-30)
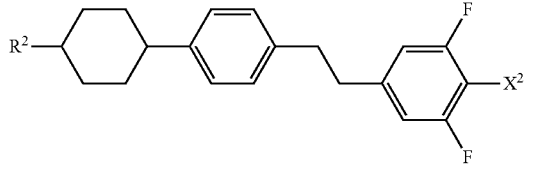
(3-31)
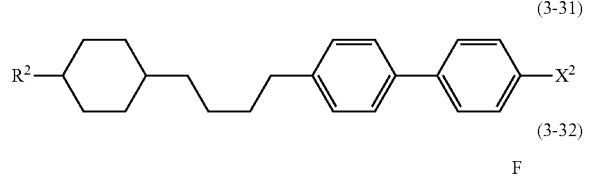
(3-32)
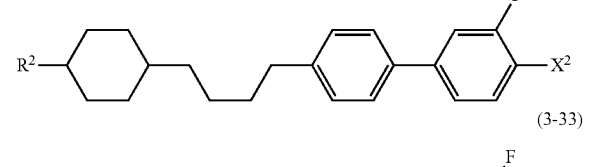
(3-33)
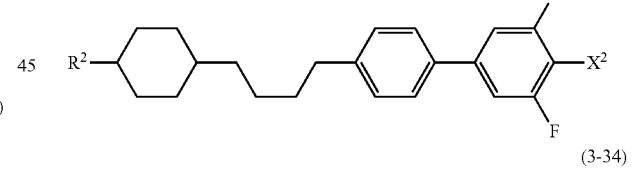
(3-34)
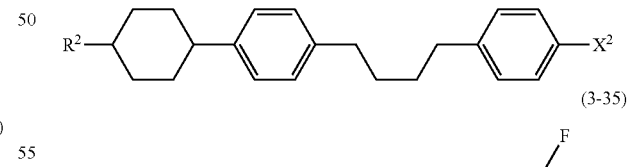
(3-35)
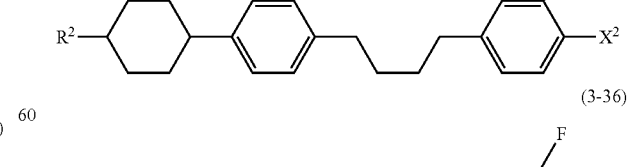
(3-36)
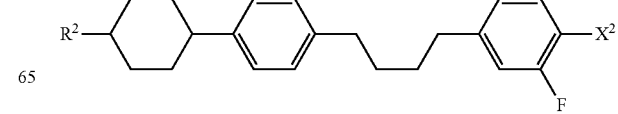

(3-37)
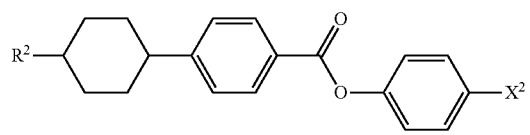
(3-38)
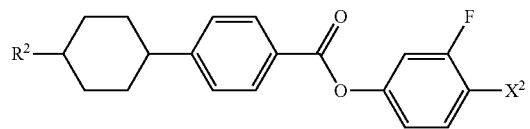
(3-39)
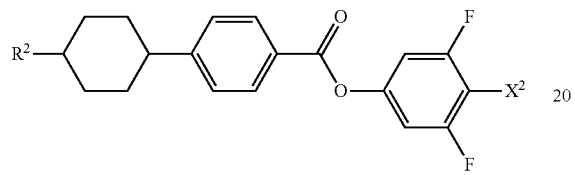
(3-40)
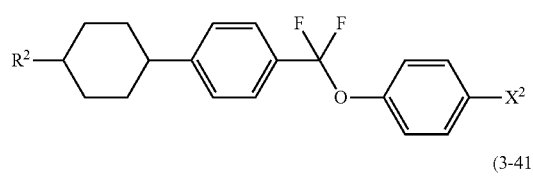
(3-41)
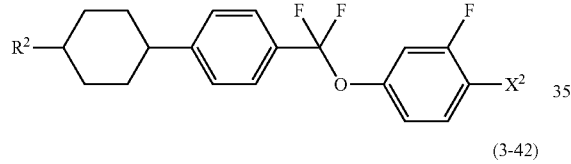
(3-42)
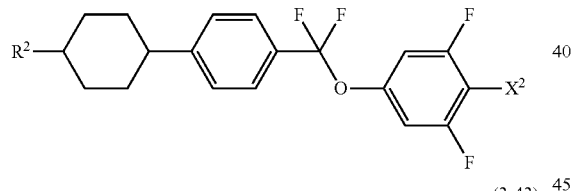
(3-43)
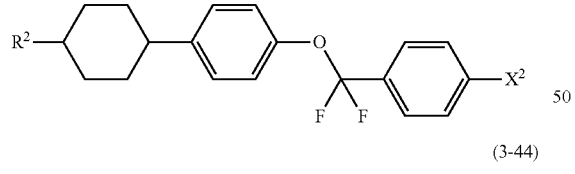
(3-44)
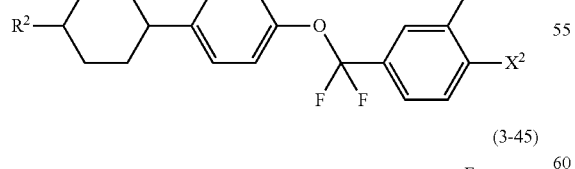
(3-45)
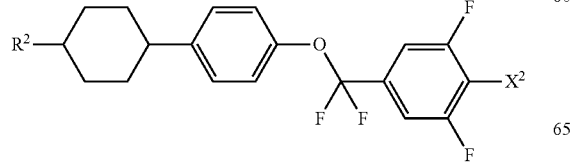
(3-46)
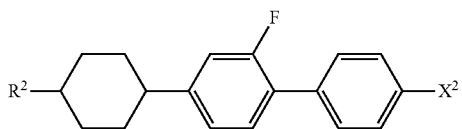
(3-47)
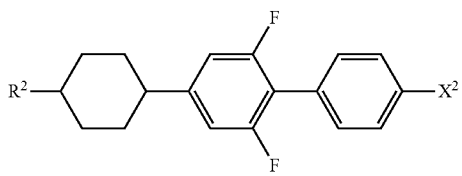
(3-48)
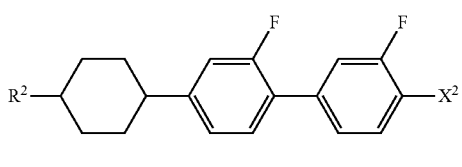
(3-49)
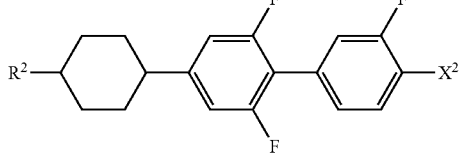
(3-50)
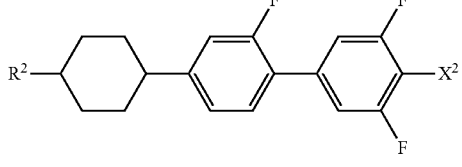
(3-51)
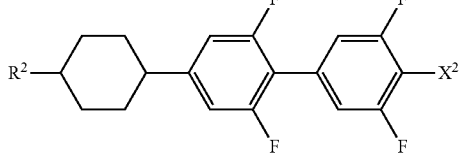
(3-52)
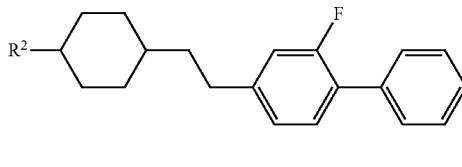
(3-53)
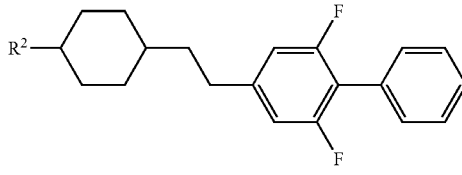
(3-54)
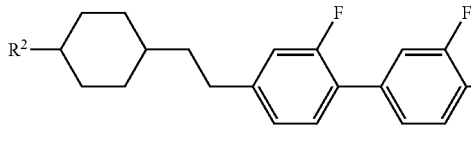

(3-55)
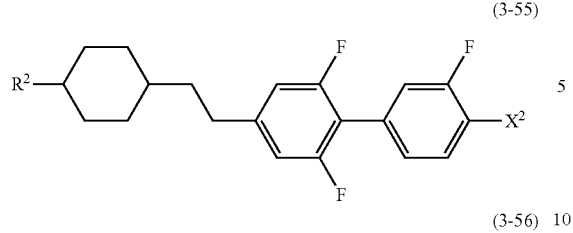
(3-56)
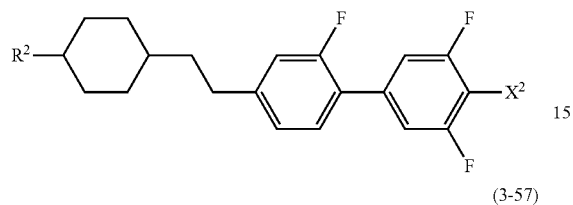
(3-57)
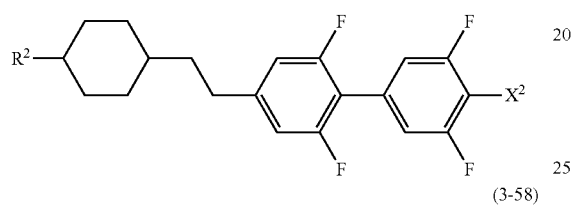
(3-58)
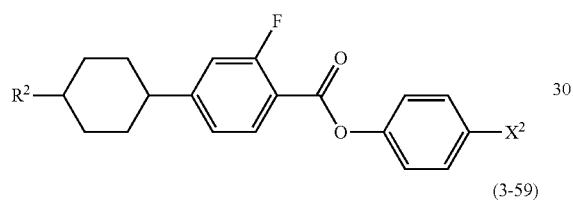
(3-59)
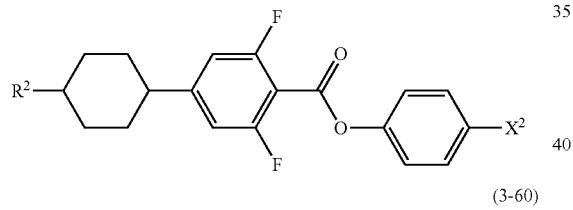
(3-60)
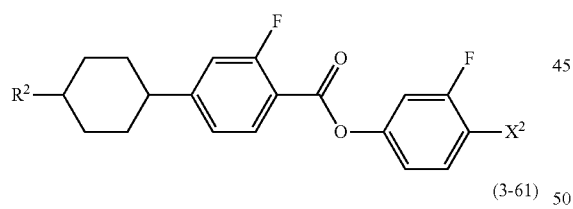
(3-61)
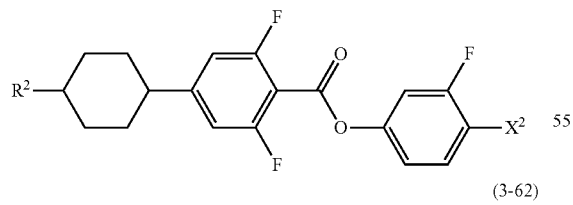
(3-62)
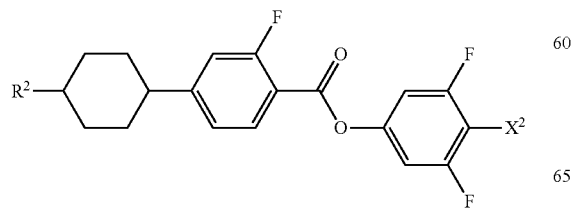
(3-63)
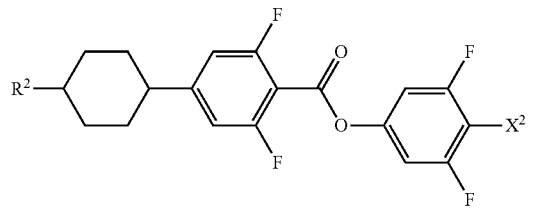
(3-64)
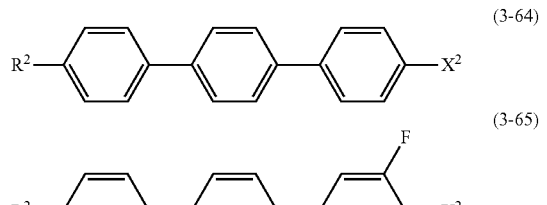
(3-65)
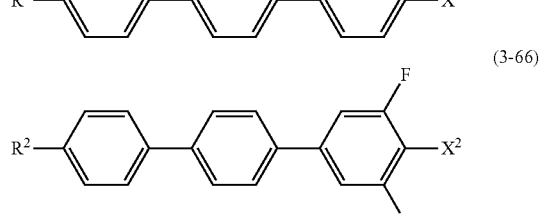
(3-66)
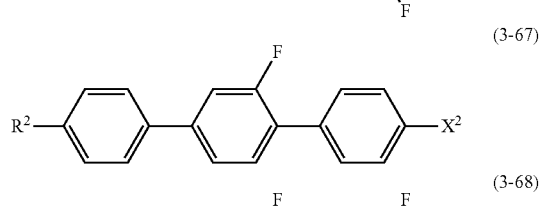
(3-67)
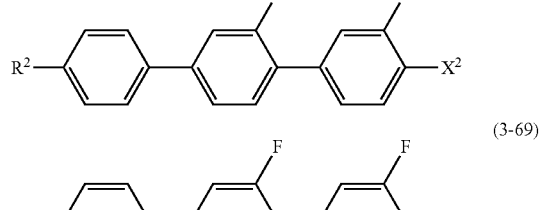
(3-68)
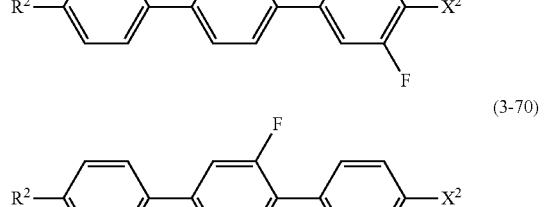
(3-69)
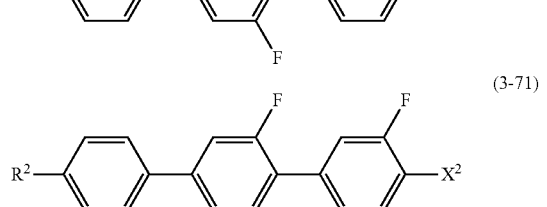
(3-70)
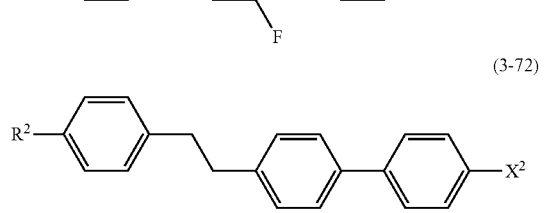
(3-71)
(3-72)

(3-73) 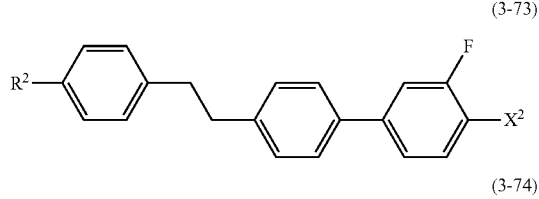
(3-74) 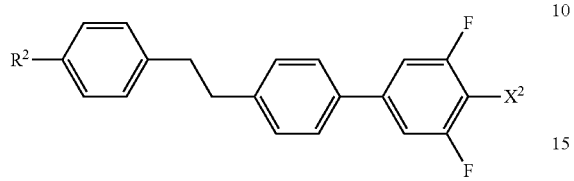
(3-75) 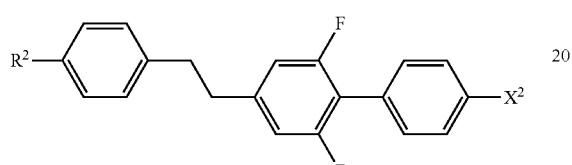
(3-76) 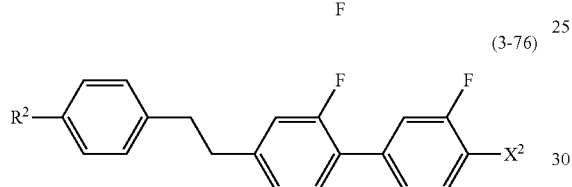
(3-77) 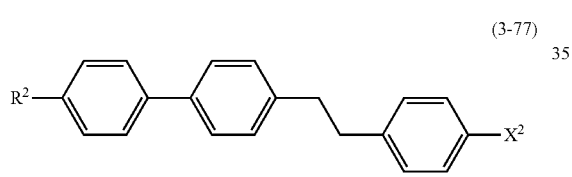
(3-78) 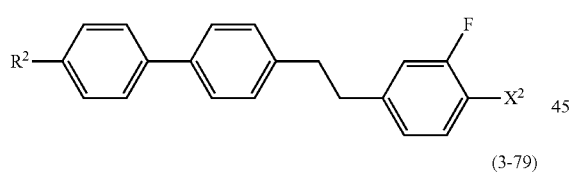
(3-79) 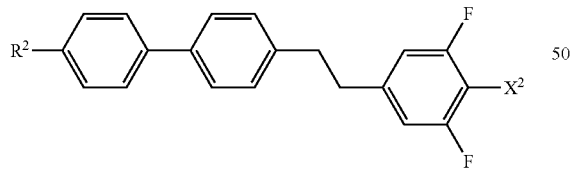
(3-80) 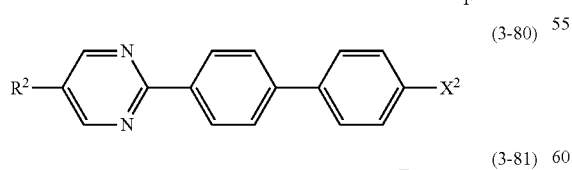
(3-81) 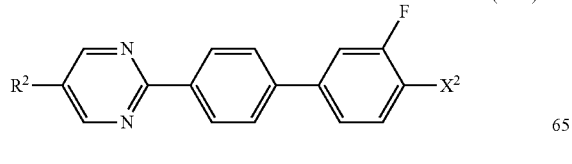
(3-82) 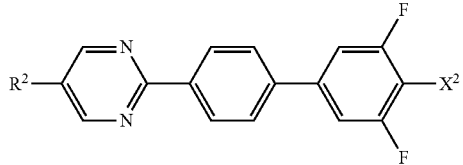
(3-83) 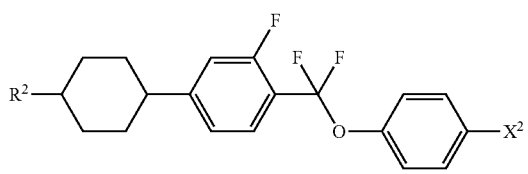
(3-84) 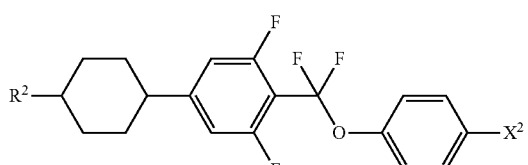
(3-85) 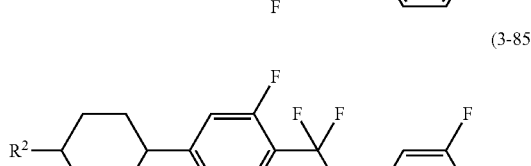
(3-86) 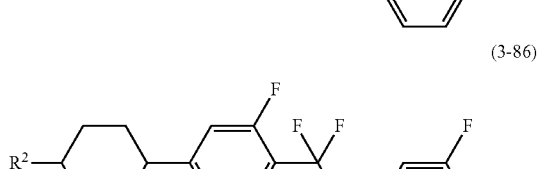
(3-87) 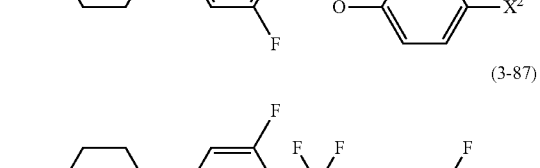
(3-88) 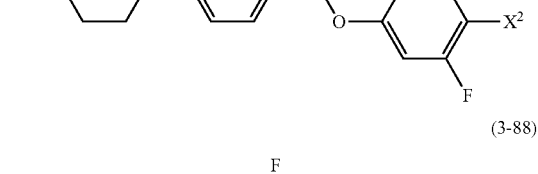
(3-89) 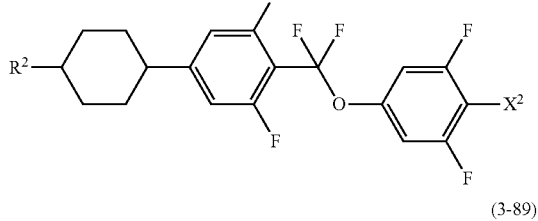

(3-90)
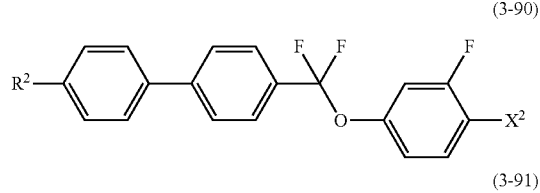
(3-91)
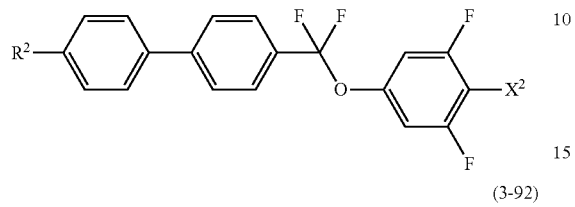
(3-92)
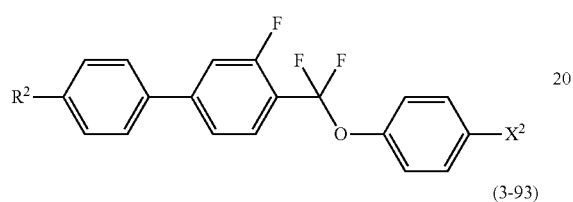
(3-93)
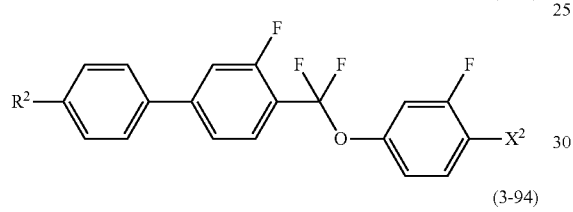
(3-94)
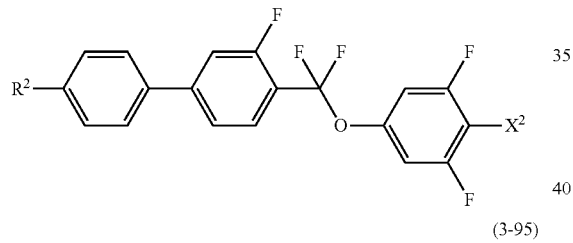
(3-95)
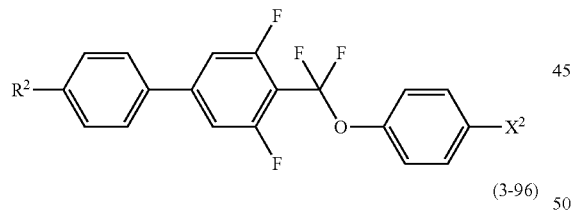
(3-96)
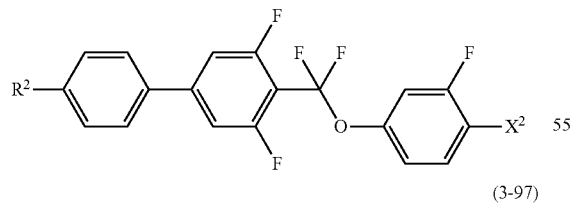
(3-97)
(3-98)
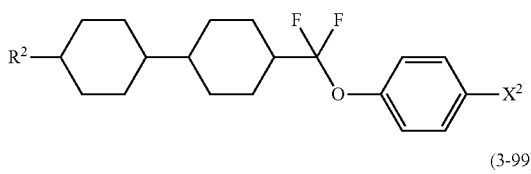
(3-99)
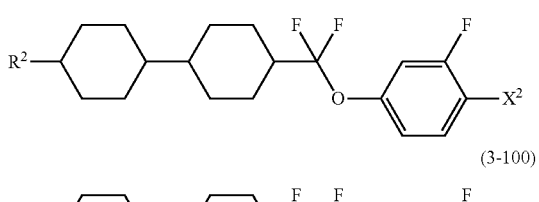
(3-100)
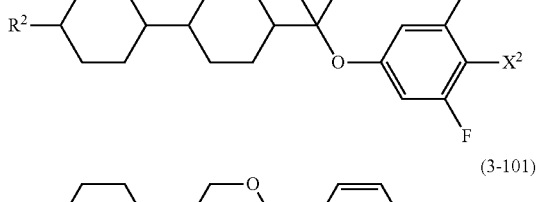
(3-101)
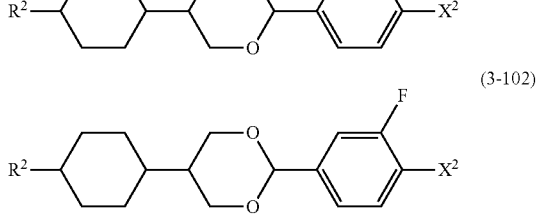
(3-102)
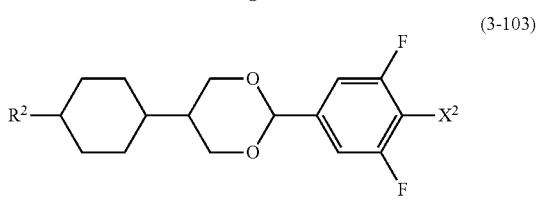
(3-103)
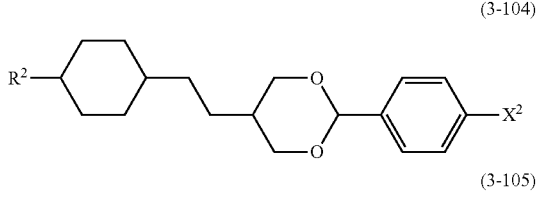
(3-104)
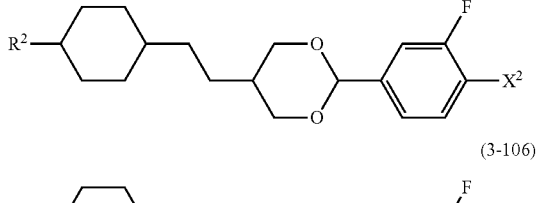
(3-105)
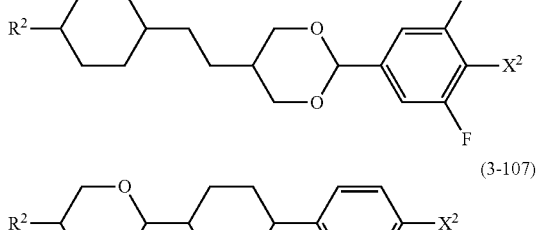
(3-106)
(3-107)

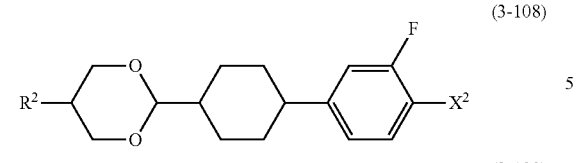 (3-108)
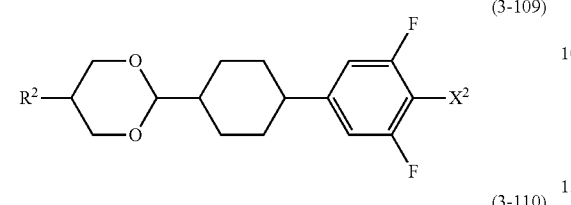 (3-109)
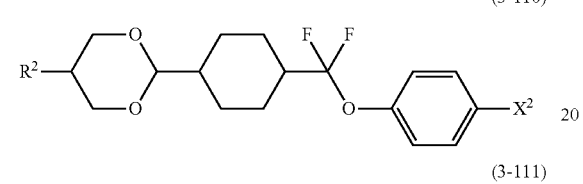 (3-110)
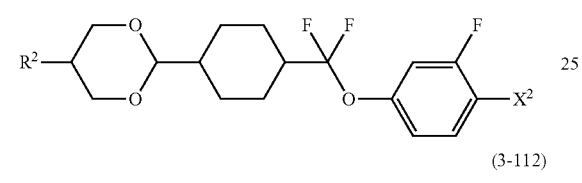 (3-111)
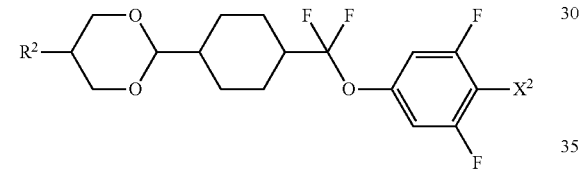 (3-112)
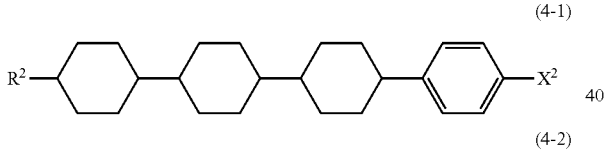 (4-1)
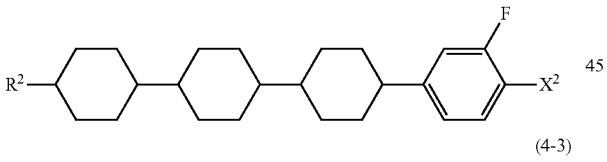 (4-2)
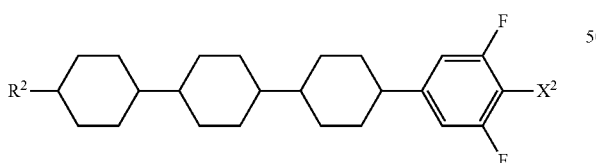 (4-3)
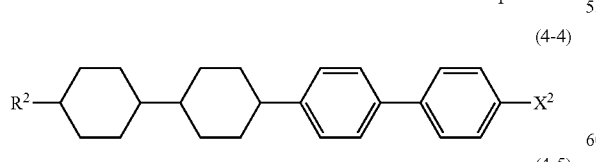 (4-4)
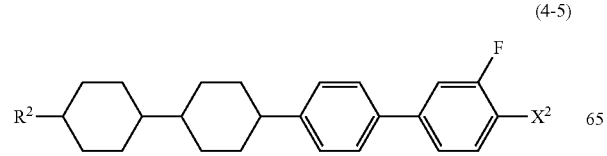 (4-5)
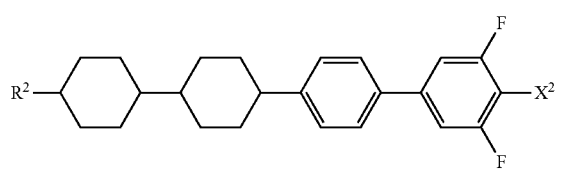 (4-6)
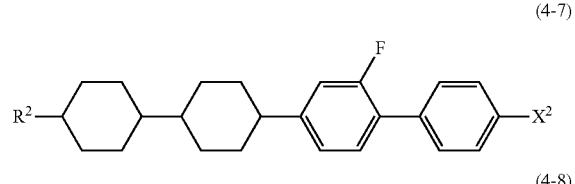 (4-7)
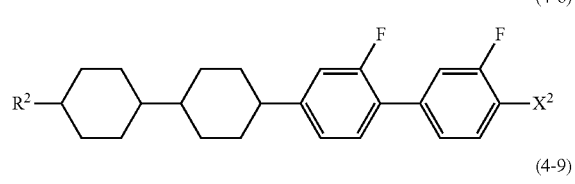 (4-8)
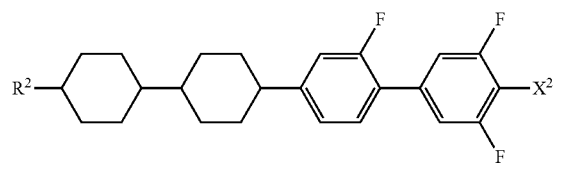 (4-9)
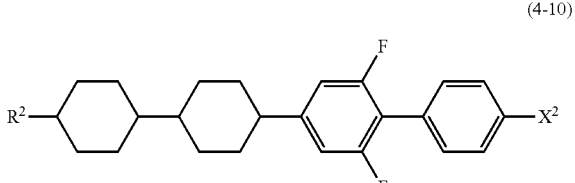 (4-10)
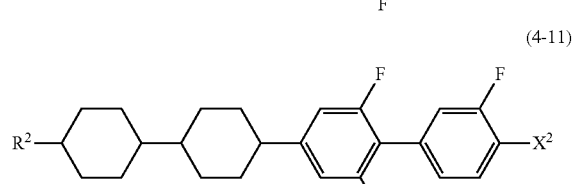 (4-11)
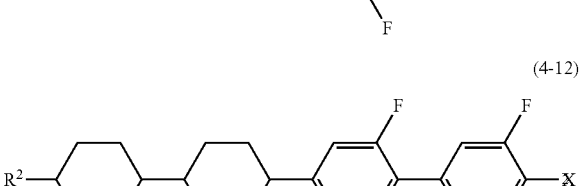 (4-12)
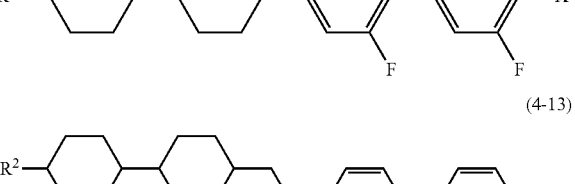 (4-13)
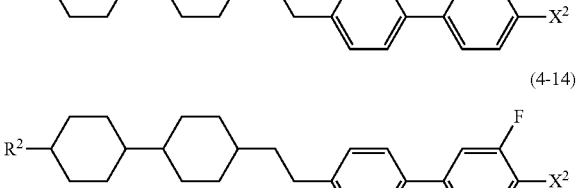 (4-14)

(4-15)
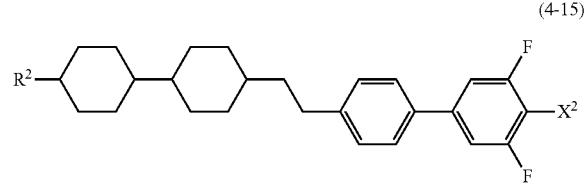
(4-16)
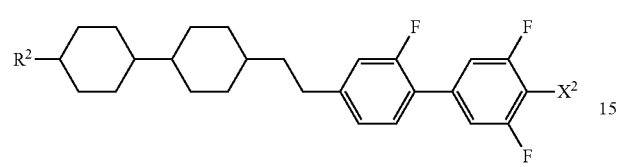
(4-17)
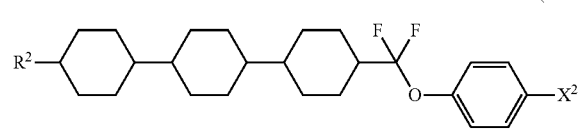
(4-18)
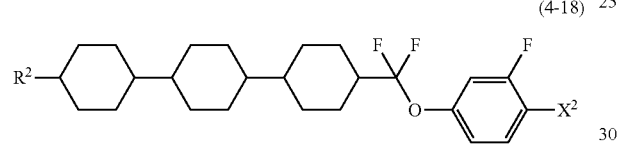
(4-19)
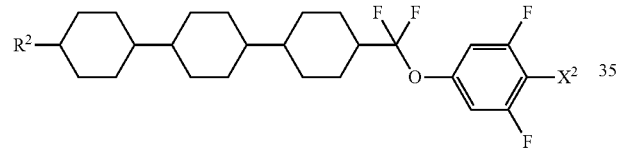
(4-20)
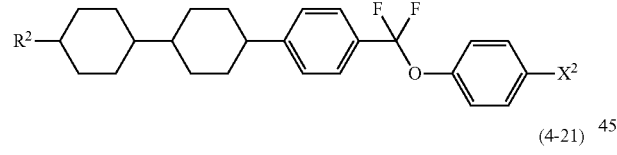
(4-21)
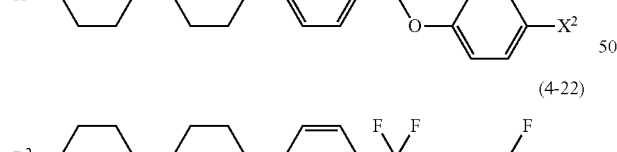
(4-22)
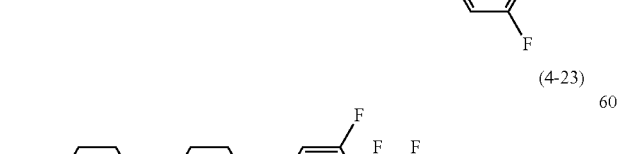
(4-23)
(4-24)
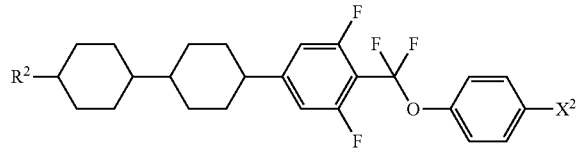
(4-25)
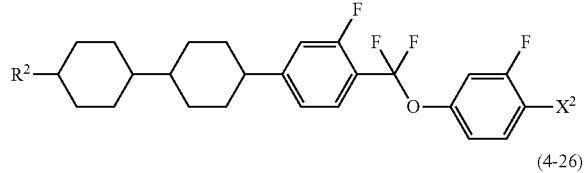
(4-26)
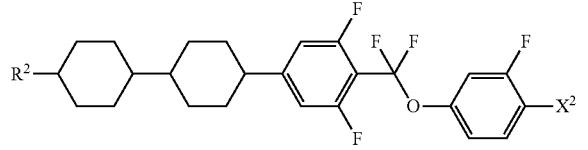
(4-27)
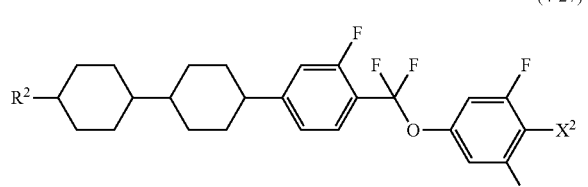
(4-28)
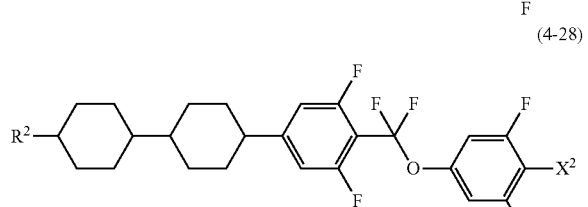
(4-29)
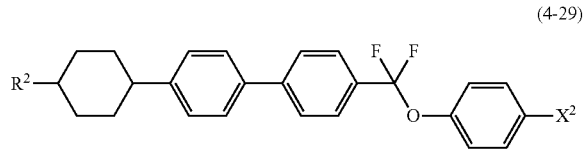
(4-30)
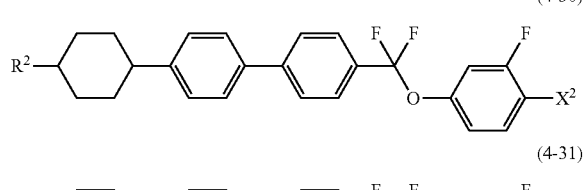
(4-31)
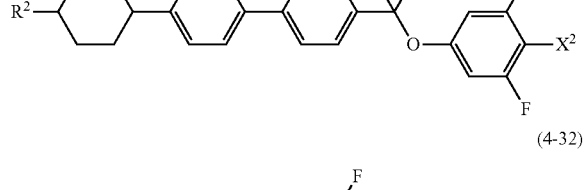
(4-32)
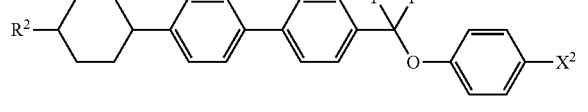

(4-33) 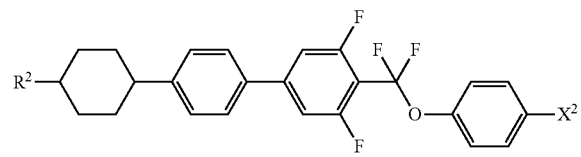
(4-34) 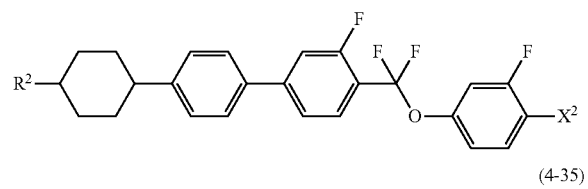
(4-35) 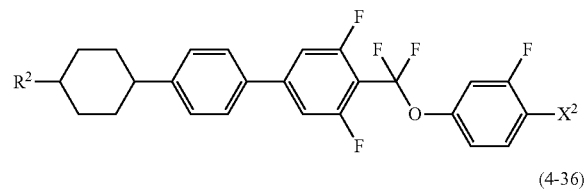
(4-36) 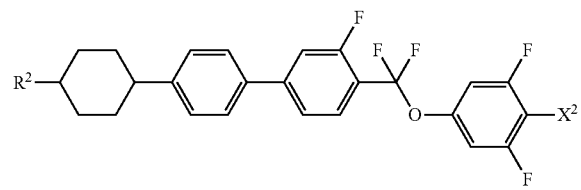
(4-37) 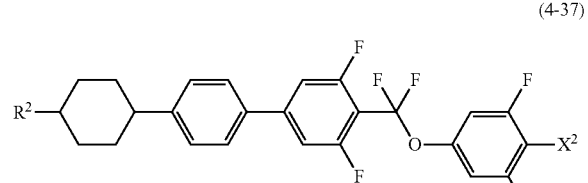
(4-38) 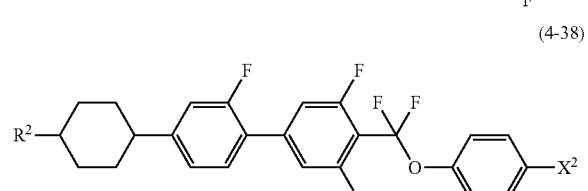
(4-39) 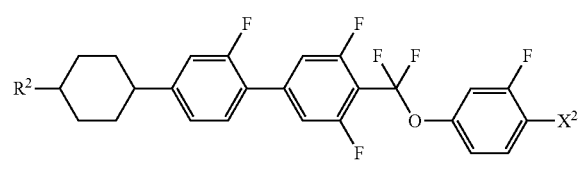
(4-40) 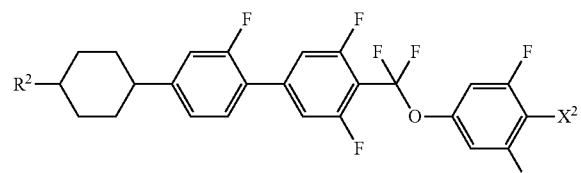
(4-41) 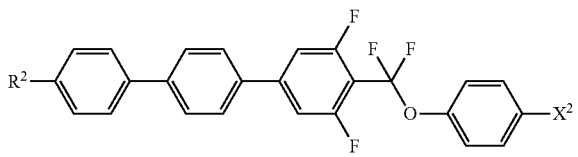
(4-42) 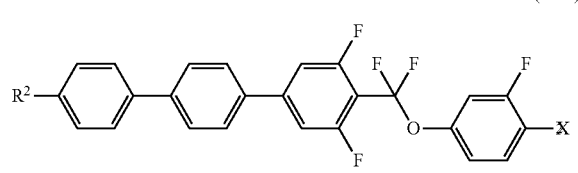
(4-43) 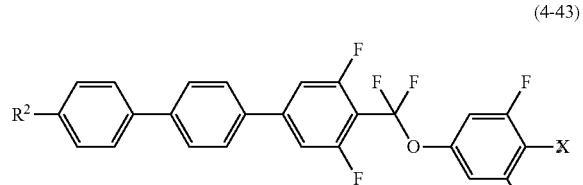
(4-44) 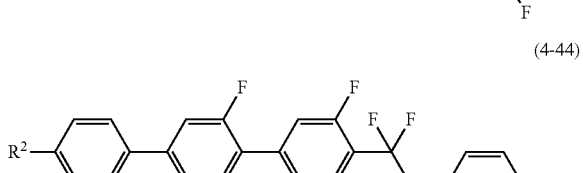
(4-45) 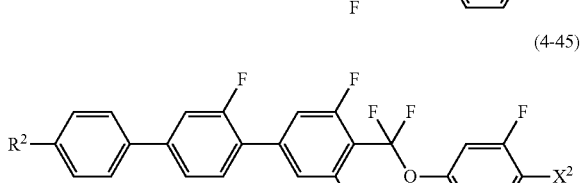
(4-46) 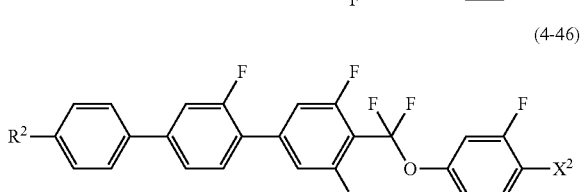
(4-47) 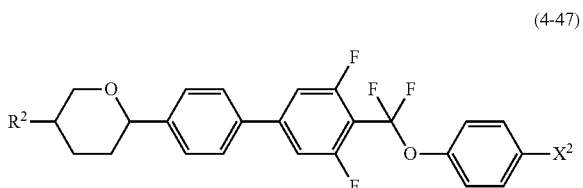
(4-48) 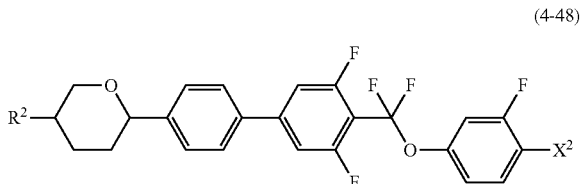

(4-49)
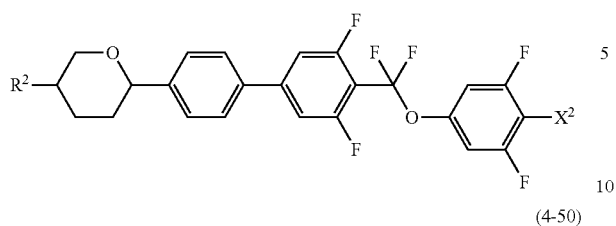

(4-50)
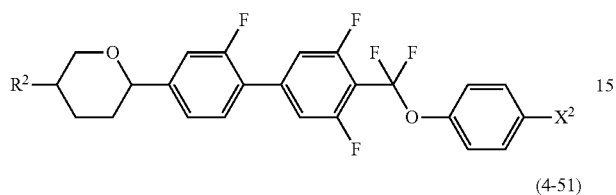

(4-51)
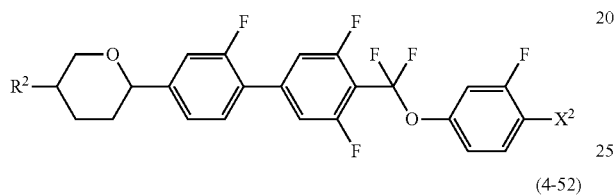

(4-52)
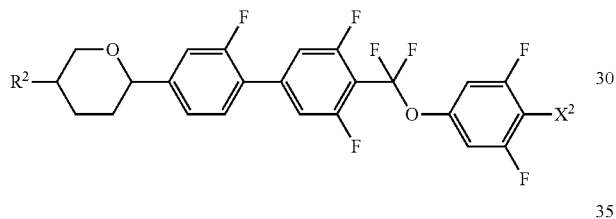

In formulas above, the definition of $R^2$ and $X^2$ is described previously.

The compounds represented by these formulas (2) to (4), namely the component B, are used for preparing a liquid crystal composition utilized for TFT, since the dielectric anisotropy is positive, and the thermal stability and the chemical stability are quite excellent. The content of the component B in the liquid crystal composition of the invention is suitably in the range of 1 to 99% by weight, preferably in the range of 10 to 97% by weight, and more preferably in the range of 40 to 95% by weight based on the total weight of the liquid crystal composition. The viscosity can be adjusted by further addition of the compound represented by formulas (11) to (13), namely the component E.

Desirable examples of the compound represented by formula (5) described above, namely the component C, include formulas (5-1) to (5-62).

(5-1)
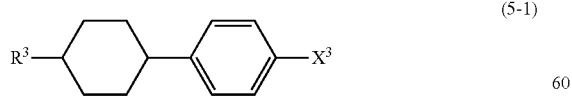

(5-2)
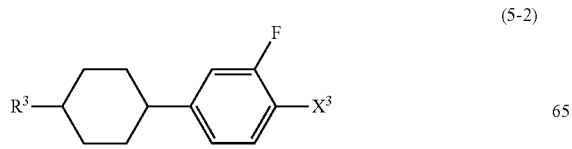

(5-3)
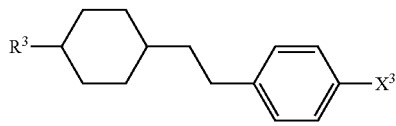

(5-4)
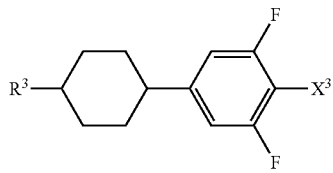

(5-5)
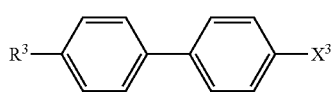

(5-6)
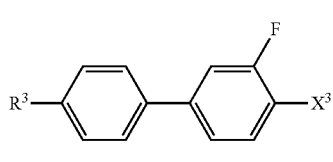

(5-7)
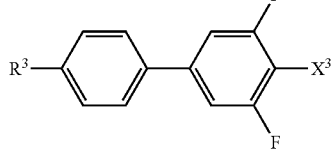

(5-8)
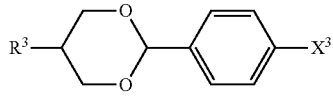

(5-9)
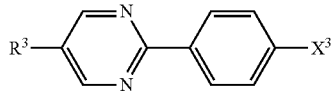

(5-10)
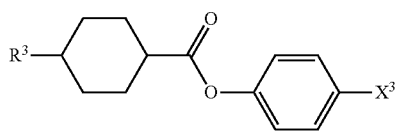

(5-11)
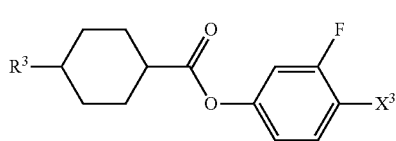

(5-12)
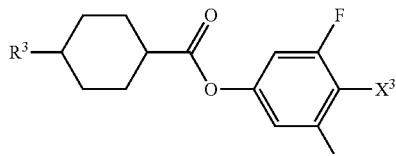

(5-13)
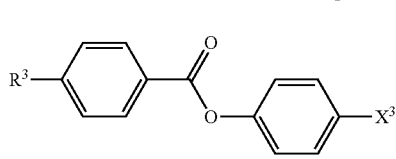

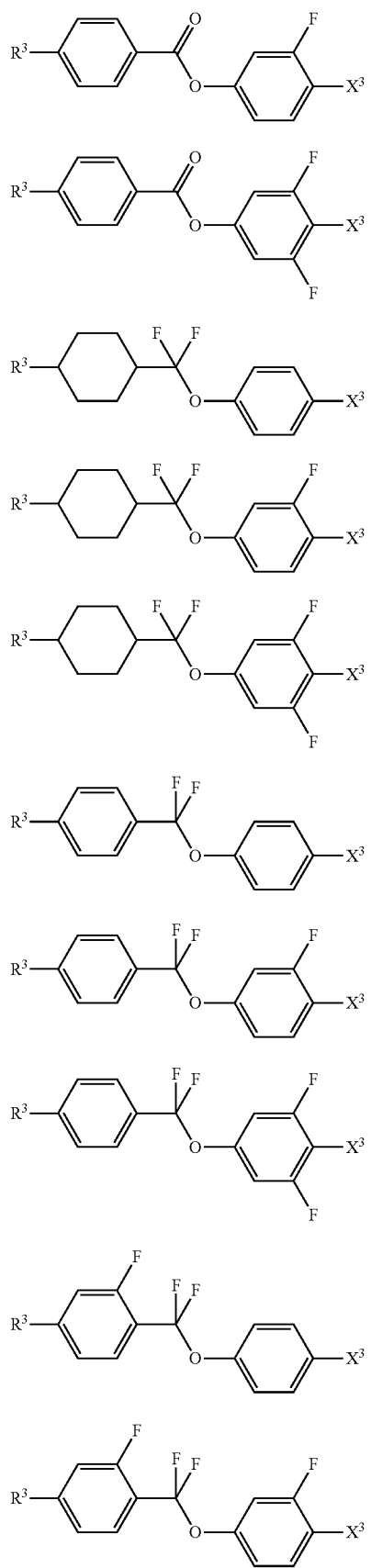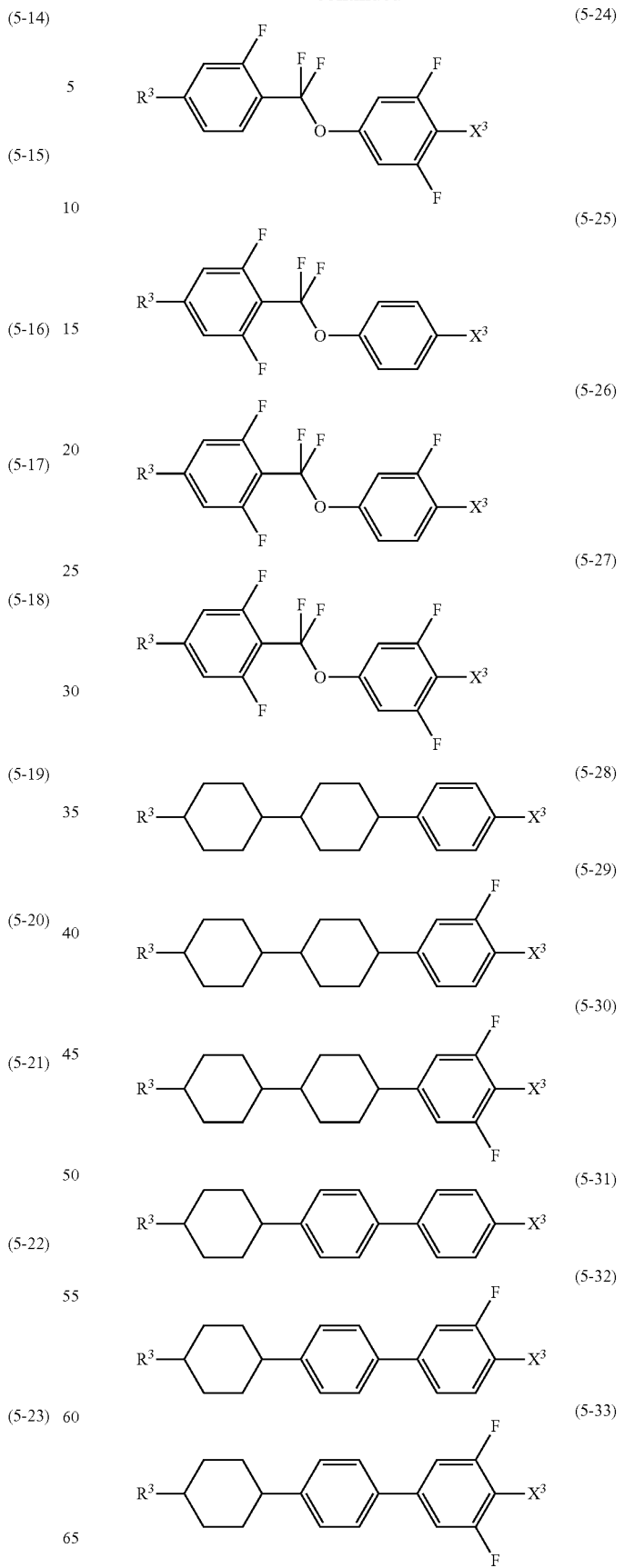

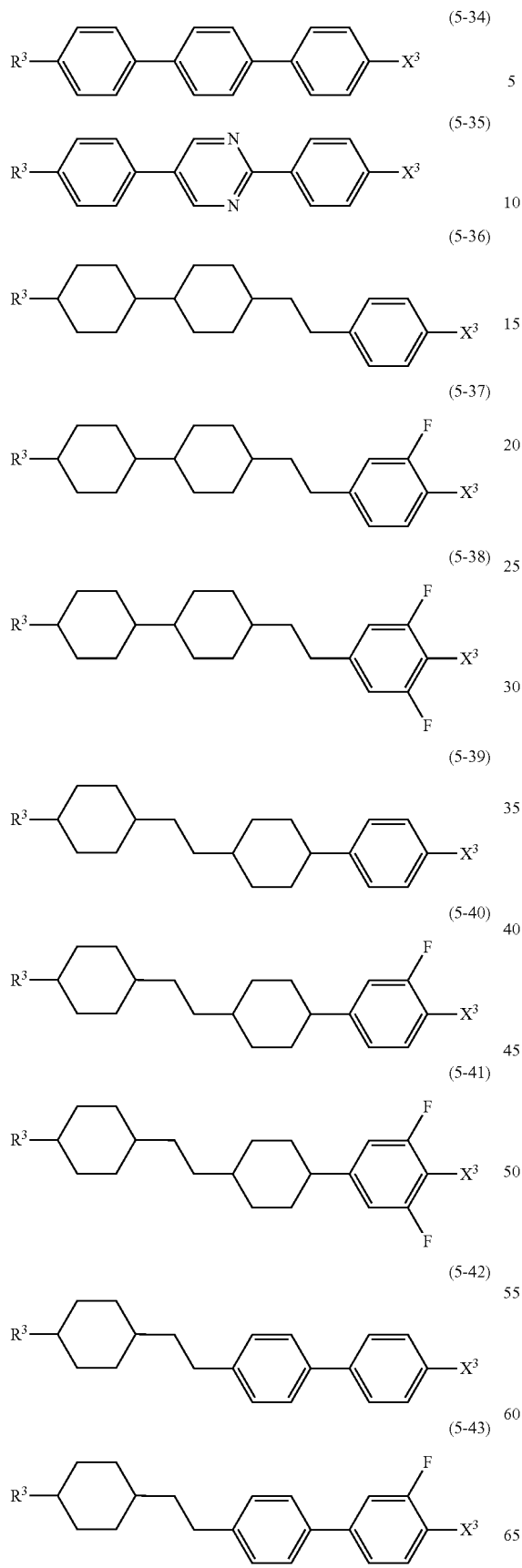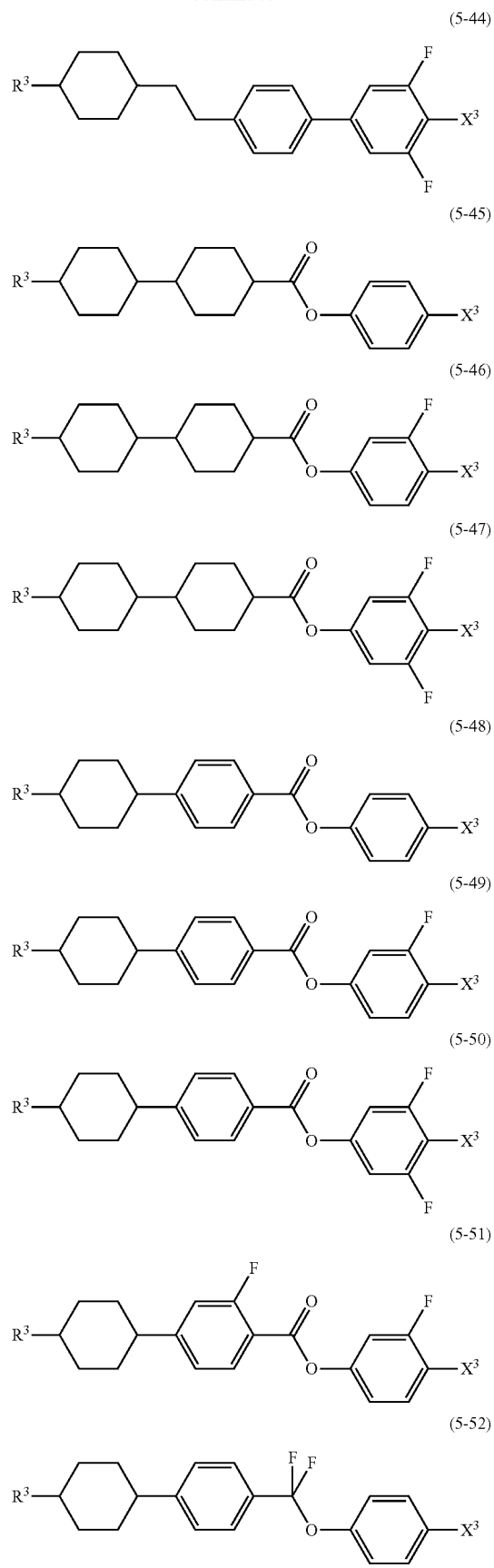

(5-53)
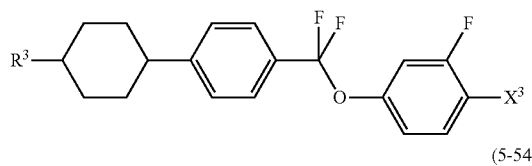

(5-54)
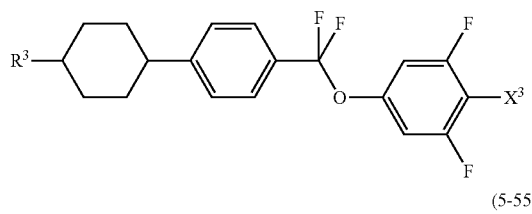

(5-55)

(5-56)
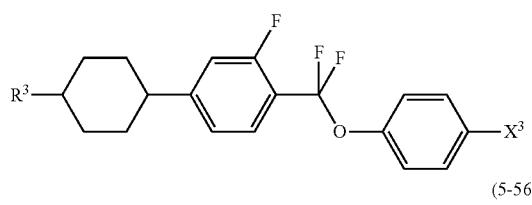

(5-57)
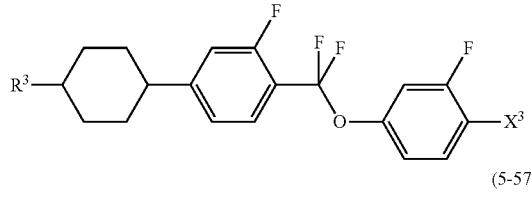

(5-58)
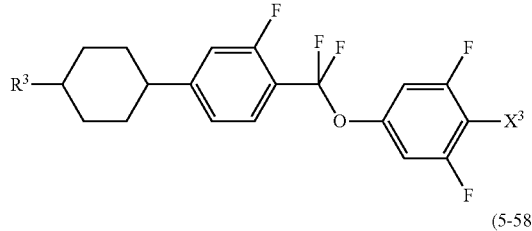

(5-59)
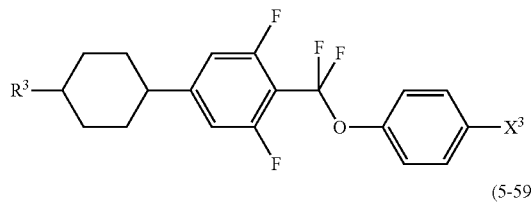

(5-60)
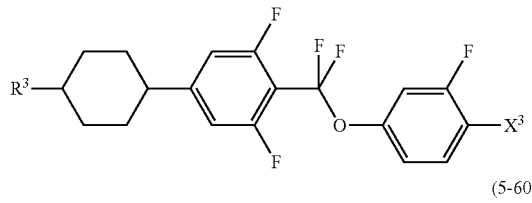

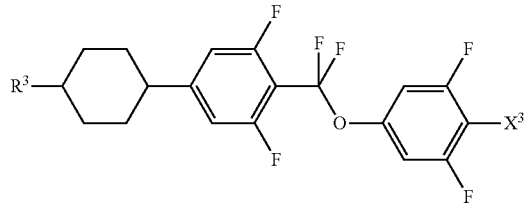

(5-61)
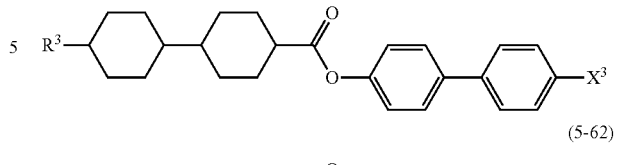

(5-62)
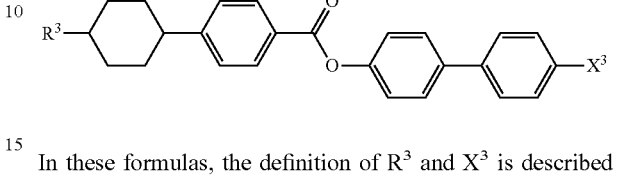

In these formulas, the definition of $R^3$ and $X^3$ is described previously.

The compound represented by formula (5), namely component C, is mainly used to prepare a liquid crystal composition utilized for STN and TN since the dielectric anisotropy is positive and its value is quite large. The threshold voltage of the composition can be decreased by the addition of the component C. The viscosity and the optical anisotropy can be adjusted, and the temperature range of a liquid crystal phase can be increased. Furthermore, the component C can be utilized for an improvement of the steepness.

The content of the component C is preferably in the range of 0.1 to 99.9% by weight, more preferably 10 to 97% by weight, and further preferably in the range of 40 to 95% by weight based on the total weight of the composition, when a liquid crystal composition utilized for STN or TN is prepared. The threshold voltage, the temperature range of a liquid crystal phase, the optical anisotropy, the dielectric anisotropy, the viscosity and so forth can be adjusted by the addition of a component that will be described later.

The component D that is at leas one compound selected from the group of formulas (6) to (8) and formula (10) is desirable when a liquid crystal composition having negative dielectric anisotropy of the invention, which is utilized for a vertical alignment mode (a VA mode) and so forth, is prepared.

Desirable example of the compounds represented by formulas (6) to (8) and formula (10), namely the component D, include formulas (6-1) to (6-5), formulas (7-1) to (7-11), formula (8-1) and formulas (10-1) to (10-11), respectively.

(6-1)
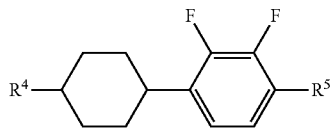

(6-2)
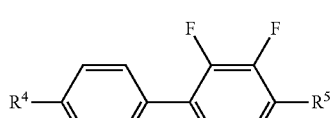

(6-3)
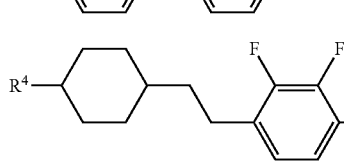

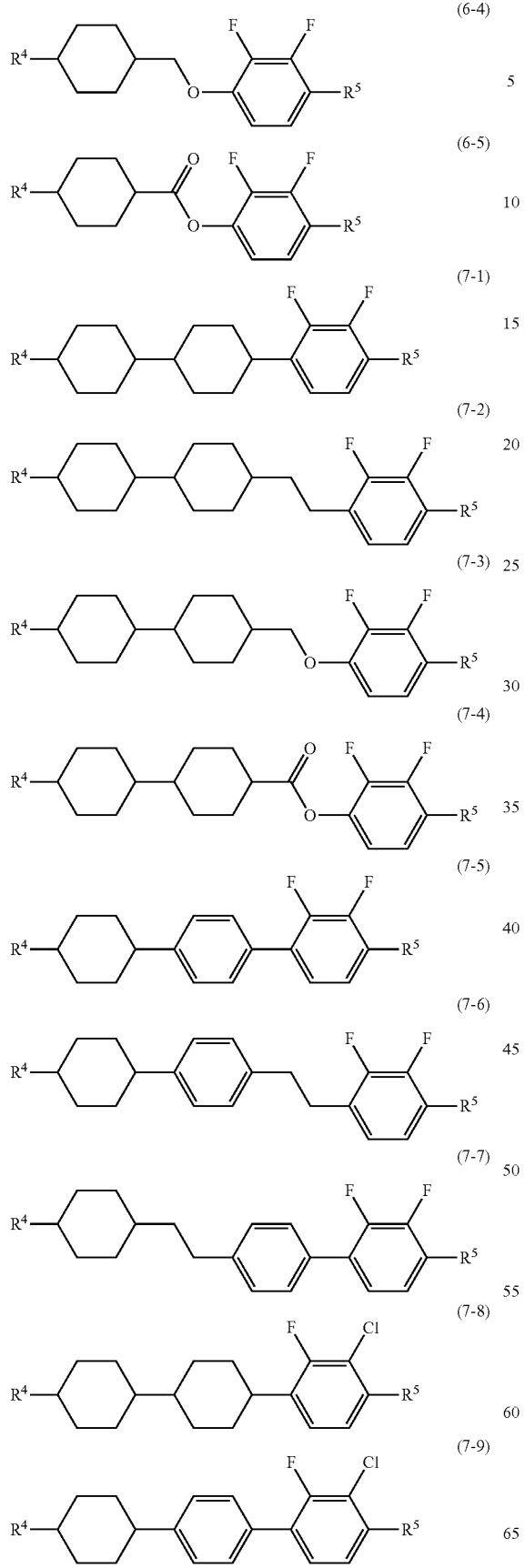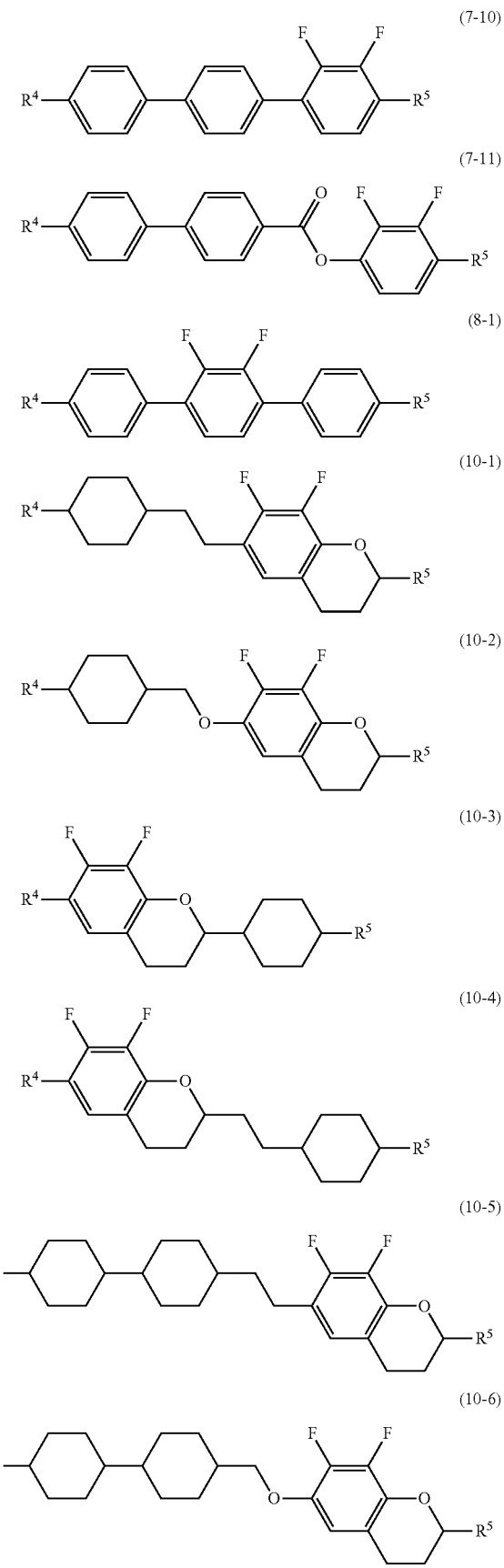

-continued

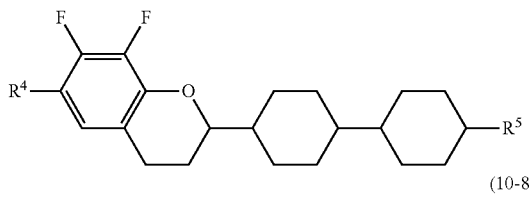
(10-7)

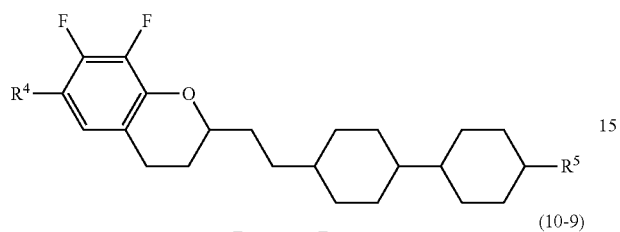
(10-8)

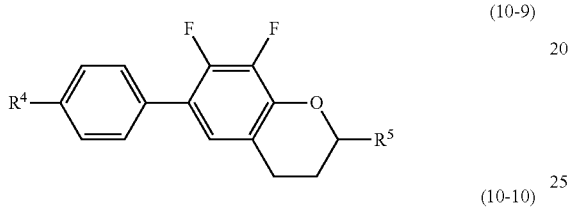
(10-9)

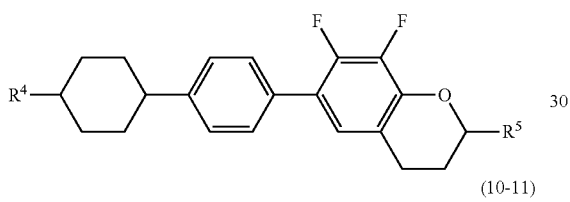
(10-10)

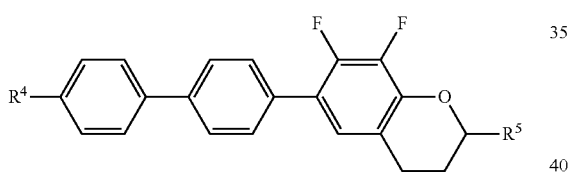
(10-11)

In formulas above, the definition of $R^4$ and $R^5$ is described previously.

These compounds of the component D is mainly used for a liquid crystal composition having negative dielectric anisotropy which is utilized for a VA mode. When the content increases, the threshold voltage of the composition is decreased, but the viscosity is increased. Accordingly, the content is preferably smaller if the desired value of the threshold value is satisfied. However, there are cases where the content of less than 40% by weight may not allowed for the voltage-driving, since the absolute value of the dielectric anisotropy is about 5.

The compound represented by formula (6) among the component D is effective mainly in adjusting the threshold voltage, adjusting the viscosity, and adjusting the refractive index anisotropy, since it is a two-ring compound. The compound represented by formulas (7) and (8) are effective in increasing the clearing point, increasing the temperature range of a nematic phase, decreasing the threshold voltage or increasing the optical anisotropy for instance, since it is a three-ring compound.

The content of the component D is preferably 40% by weight or higher, and more preferably in the range of 50 to 95% by weight based on the total weight of the composition when a composition utilized for a VA mode is prepared. The elastic constant can be adjusted and the voltage-transmission curve of the composition can be adjusted by the addition of the component D. The content of the component D is preferably 30% by weight or lower based on the total weight of the composition when the component D is mixed with a composition having positive dielectric anisotropy.

Desirable examples of the compound represented by formulas (11), (12) and (13), namely the component E, include formulas (11-1) to (11-11), formulas (12-1) to (12-18) and formulas (13-1) to (13-6), respectively.

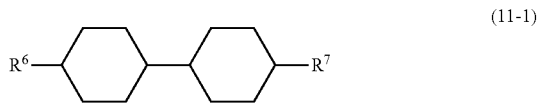
(11-1)

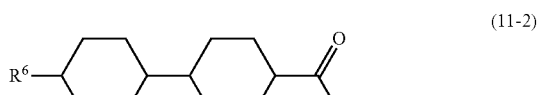
(11-2)

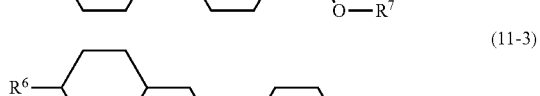
(11-3)

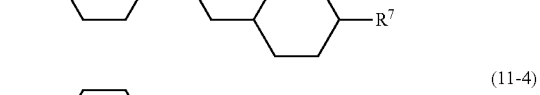
(11-4)

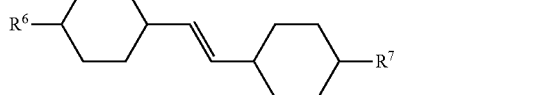
(11-5)

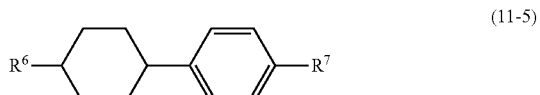
(11-6)

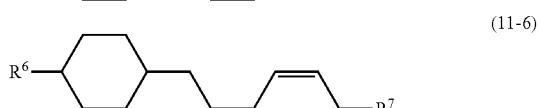
(11-7)

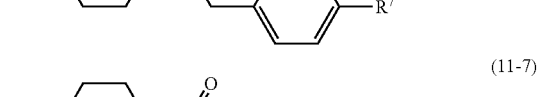
(11-8)

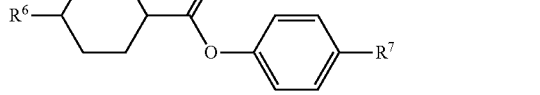
(11-9)

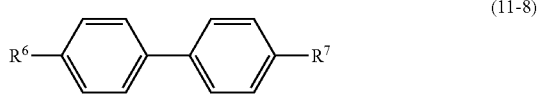
(11-10)

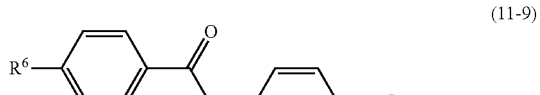
(11-11)

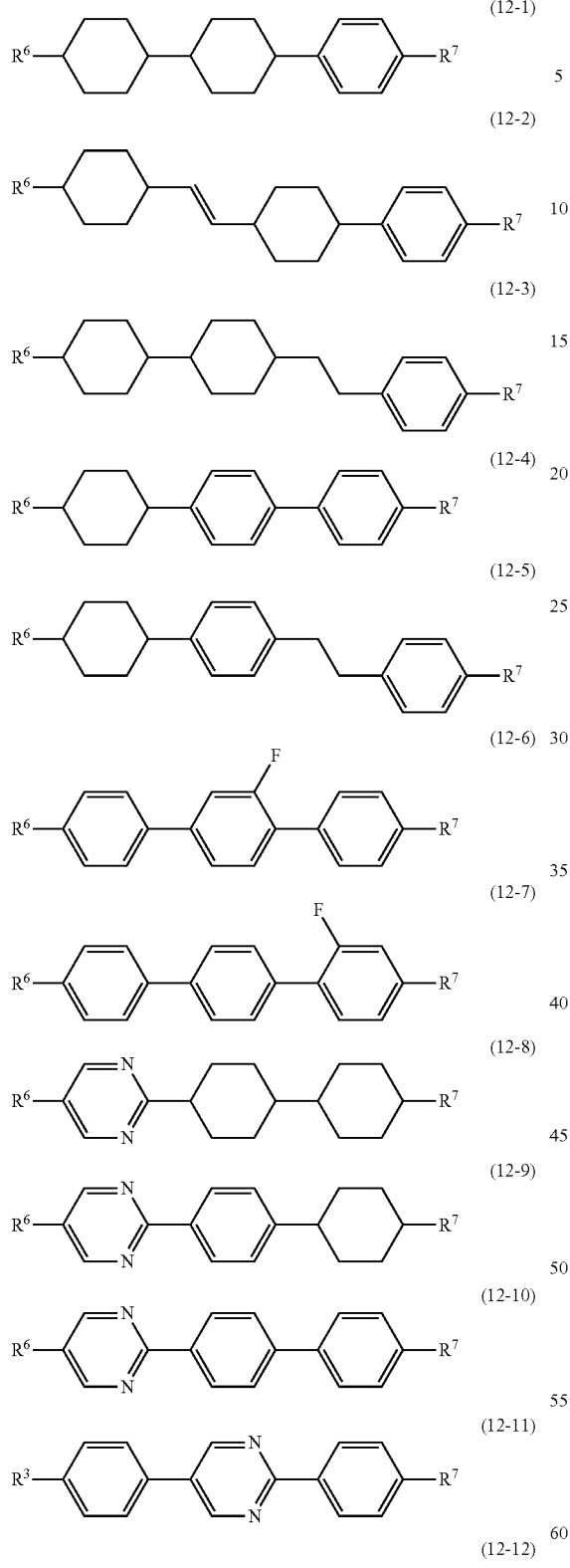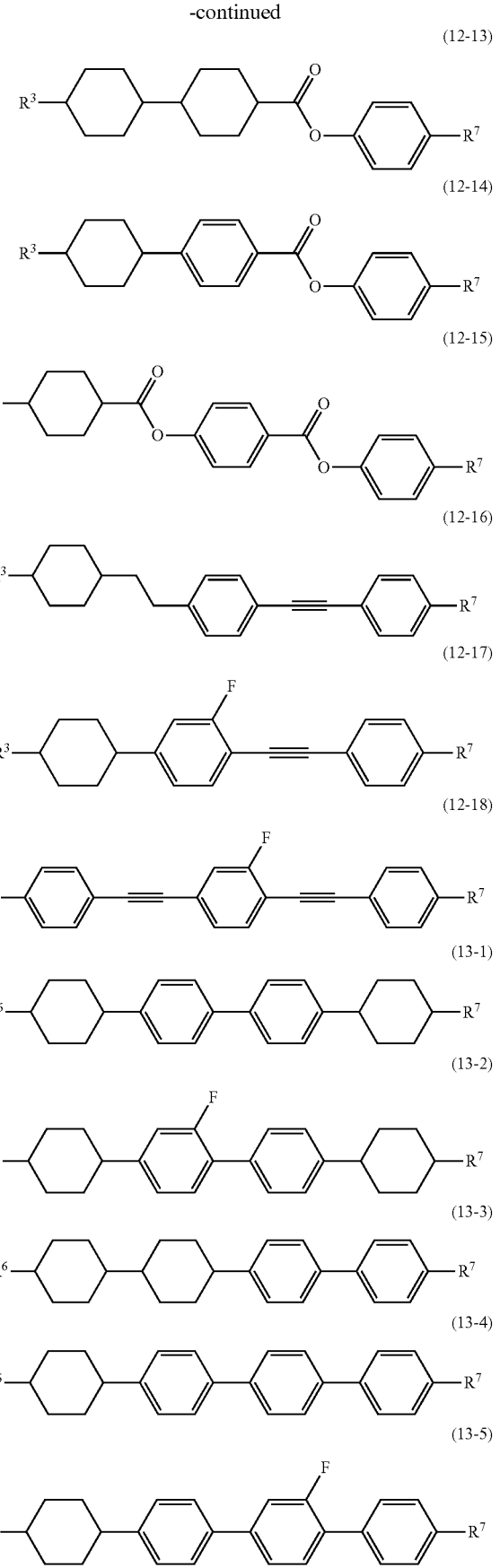

-continued

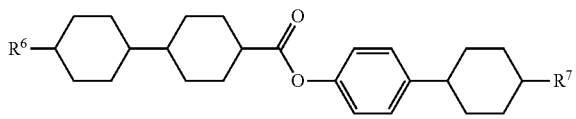
(13-6)

In formulas above, the definition of $R^6$ and $R^7$ is described previously.

The compound represented by formulas (11) to (13), namely the component E, in which the absolute value of the dielectric anisotropy is small, is close to neutral. The compound represented by formula (11) is effective mainly in adjusting the viscosity or adjusting the optical anisotropy, and the compound represented by formulas (12) and (13) are effective in increasing the temperature range of a nematic phase that is caused by an increase of the clearing point for instance, or in adjusting the optical anisotropy.

When the content of the compound represented by the component E increases, the threshold voltage of the liquid crystal composition is increased and the viscosity is decreased. Accordingly, it is desirable that the content is increased as long as a desired value of the threshold voltage of the liquid crystal composition is satisfied. The content of the component E is preferably 30% by weight or higher, and more preferably 50% by weight or higher based on the total weight of the composition when a liquid crystal composition utilized for TFT is prepared. The content of the component E is preferably 30% by weight or higher, and more preferably 40% by weight or higher based on the total weight of the composition when a liquid crystal composition utilized for STN or TN is prepared.

It is desirable that the liquid crystal composition of the invention includes at least one of the compounds represented by formula (1) in the range of 0.1% to 99% by weight for exhibiting excellent characteristics.

The liquid crystal composition of the invention is generally prepared according to any known method such as the mutual dissolution of necessary components at a high temperature. An additive that is well-known to a person skilled in the art may be added to the composition depending on its intended use. For example, the liquid crystal composition (e) including an optically active compound which will be described below, or a liquid crystal composition utilized for a GH mode, to which a dye is added, can be prepared. The additive is generally well known to a person skilled in the art, and is described in the literature and so forth in detail.

The liquid crystal composition (e) of the invention includes at least one optically active compound, in addition to the liquid crystal composition of the invention described above. A known chiral dopant is added as an optically active compound. The chiral dopant is effective in inducing a helical structure in liquid crystals, adjusting a necessary twist angle and thus preventing a reverse twist. Examples of the chiral dopant include the following optically active compounds (Op-1) to (Op-13).

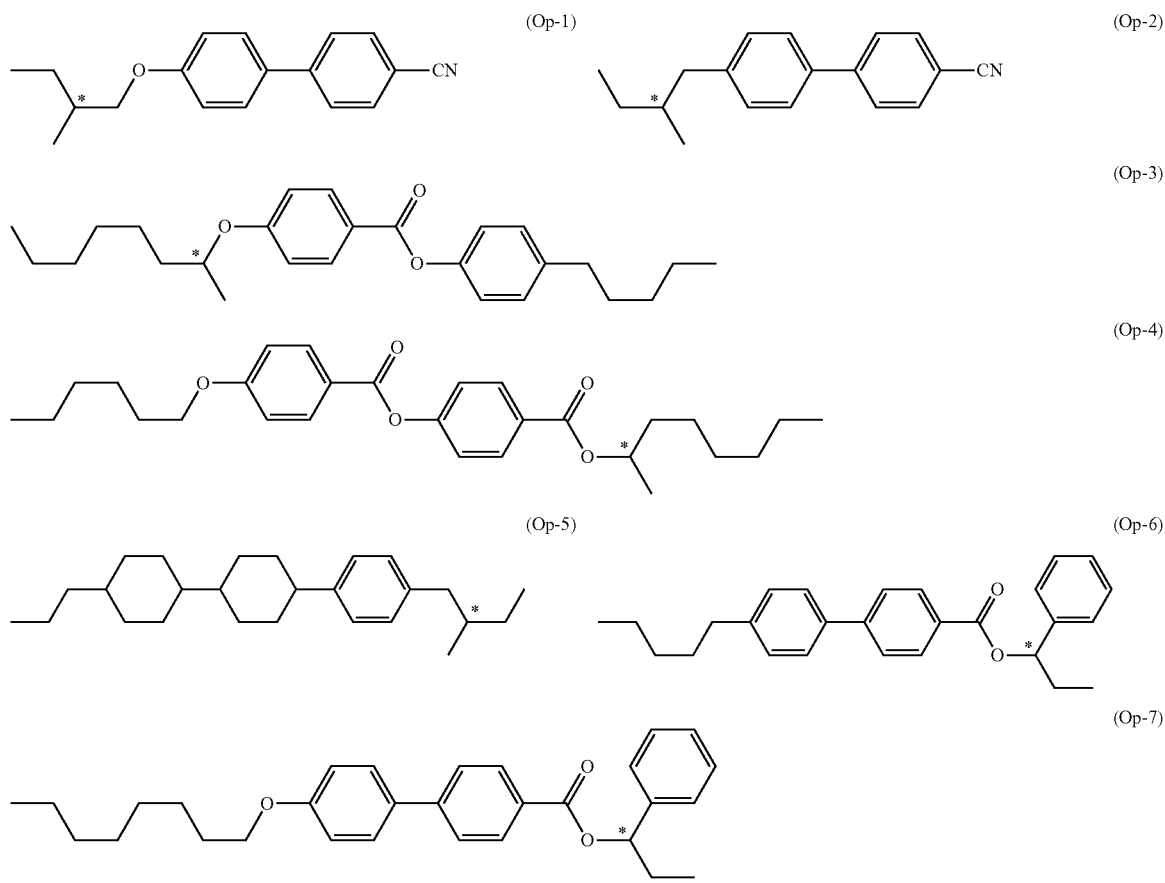

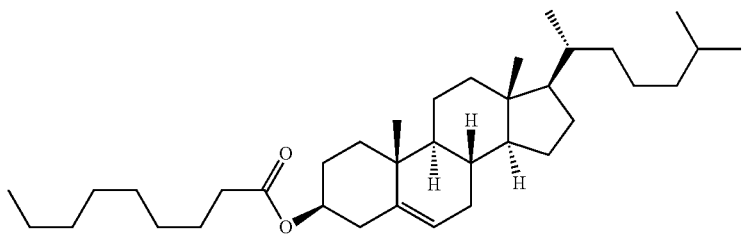
(Op-8)

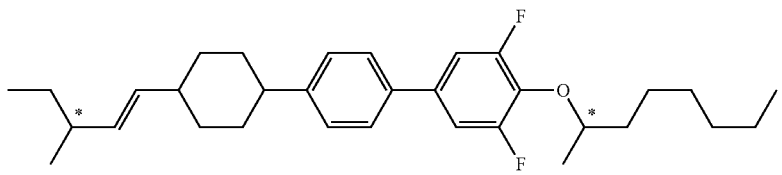
(Op-9)

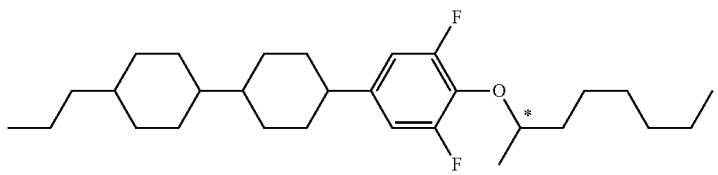
(Op-10)

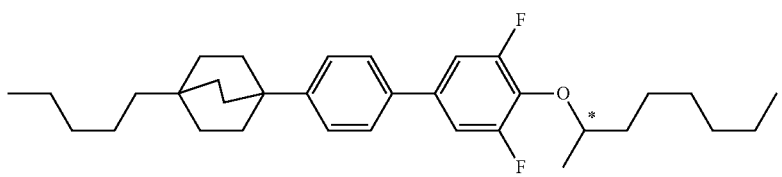
(Op-11)

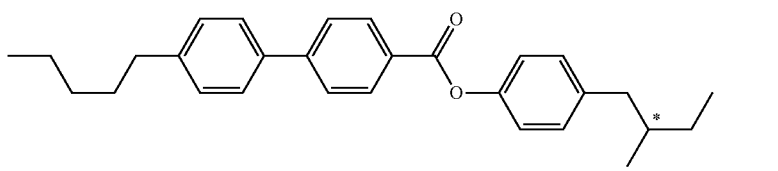
(Op-12)

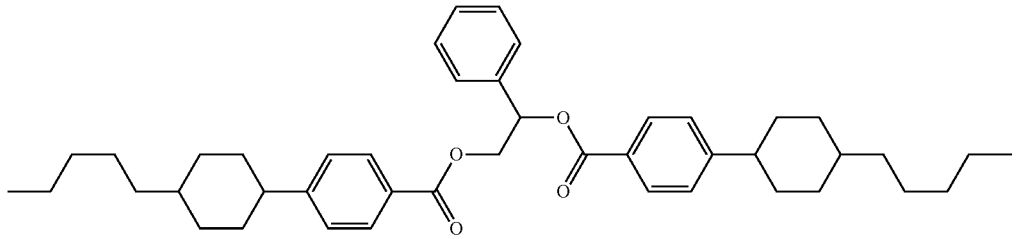
(Op-13)

A helical pitch is usually adjusted by the addition of this optically active compound to the liquid crystal composition of the invention. It is desirable to adjust the helical pitch to the range of 40 to 200 micrometers in a liquid crystal composition for TFT and TN modes. It is desirable to adjust the helical pitch to the range of 6 to 20 micrometers in a liquid crystal composition for a STN mode. It is desirable to adjust the helical pitch to the range of 1.5 to 4 micrometers in a liquid crystal composition for a bistable TN mode. Two or more optically active compounds may be added for the purpose of adjusting the temperature dependence of the helical pitch.

The liquid crystal composition of the invention can be used for a GH mode by the addition of a dichroic dye such as a merocyanine, stylyl, azo, azomethine, azoxy, quinophthalone, anthraquinone or tetrazine compound.

The liquid crystal composition of the invention can be used for NCAP prepared by micro-encapsulating nematic liquid crystals, and for a polymer-distributed liquid crystal display device (PDLCD) prepared by forming a three-dimensional network polymer in liquid crystals, such as a polymer network liquid crystal display device (PNLCD), and also for a double refraction control (ECB) mode or a DS mode.

EXAMPLES

The invention will be explained below in more detail based on examples. However, the invention is not limited to the examples. The term "%" means "% by weight," unless otherwise noted.

Analytical methods will be explained first, since the resulting compounds herein were identified on the basis of nuclear magnetic resonance spectra obtained by means of $^1$H-NMR analysis, gas chromatograms obtained by means of gas chromatography (GC) analysis and so forth.

$^1$H-NMR Analysis:

A model DRX-500 apparatus (made by Bruker BioSpin Corporation) was used for measurement. Samples prepared in the examples and so forth were dissolved in deuterated solvents such as $CDCl_3$ in which the samples were soluble, and the measurement was carried out under the conditions of room temperature, twenty-four times of accumulation and 500 MHz. In the explanation of the resulting nuclear magnetic resonance spectra, the symbols s, d, t, q and m stand for a singlet, a doublet, a triplet, a quartet and a multiplet, respectively. Tetramethylsilane (TMS) was used as the standard reference material for the zero point of the chemical shift (5 values).

GC Analysis

A Gas Chromatograph Model GC-14B made by Shimadzu Corporation was used for measurement. A capillary column CBP1-M25-025 (length 25 m, bore 0.22 mm, film thickness 0.25 micrometer; dimethylpolysiloxane as a stationary liquid phase; non-polar) made by Shimadzu Corporation was used. Helium was used as a carrier gas, and its flow rate was adjusted to 1 ml per minute. The temperature of the sample injector was set at 300° C. and the temperature of the detector (FID) was set at 300° C.

A sample was dissolved in toluene to give a 1% by weight solution, and then 1 microliter of the solution obtained was injected into the sample injector.

Chromatopac Model C—R6A made by Shimadzu Corporation or its equivalent was used as a recorder. The obtained gas chromatogram showed the retention time of the peaks and the values of the peak areas corresponding to the component compounds.

Chloroform or hexane, for example, may also be used as a solvent for diluting the sample. The following capillary columns may also be used: DB-1 (length 30 m, bore 0.32 mm, film thickness 0.25 micrometer) made by Agilent Technologies Inc., HP-1 (length 30 m, bore 0.32 mm, film thickness 0.25 micrometer) made by Agilent Technologies Inc., Rtx-1 (length 30 m, bore 0.32 mm, film thickness 0.25 micrometer) made by Restek Corporation, BP-1 (length 30 m, bore 0.32 mm, film thickness 0.25 micrometer) made by SGE International Pty. Ltd, and so forth.

The ratio of the peak areas in the gas chromatogram corresponds to the ratio of component compounds. In general, the percentage by weight of each component compound in an analytical sample is not completely the same as the percentage of each peak area in the analytical sample. In the invention, however, the percentage by weight of the component compound in the analytical sample corresponds substantially to the percentage of the peak area in the analytical sample, because the correction coefficient is essentially 1 (one) when the columns described above are used. This is because there is no significant difference among the correction coefficients of the liquid crystal compounds as components. An internal standard method using gas chromatograms is used in order to determine the composition ratio of the liquid crystal compounds in the liquid crystal composition more accurately by means of the gas chromatograms. The component of liquid crystal compounds (test-component) weighed accurately in a fixed amount and a liquid crystal compound serving as a standard (standard reference material) are analyzed simultaneously by means of gas chromatography, and the relative intensity is calculated in advance from the ratio of the peak area of the test-component to that of the standard reference material. Then, the composition ratio of the liquid crystal compounds in the liquid crystal composition can be determined more accurately by means of the gas-chromatographic analysis using the correction method based on the relative intensity of the peak area of each component to that of the standard reference material.

Samples for the Measurement of Physical Properties of a Liquid Crystal Compound and so Forth Two kinds of samples are used for measuring physical properties of a liquid crystal compound: one is the compound itself, and the other is a mixture of the compound and mother liquid crystals.

In the latter case using a sample in which the compound is mixed with mother liquid crystals, the measurement is carried out according to the following method. First, the sample is prepared by mixing 15% by weight of the liquid crystal compound obtained and 85% by weight of the mother liquid crystals. Then, extrapolated values are calculated from the measured values of the resulting sample by means of an extrapolation method based on the following formula. The extrapolated values are regarded as physical properties of this compound.

[Extrapolated value]=(100×[Measured value of sample]−[% by weight of mother liquid crystals]×[Measured value of mother liquid crystals])/[% by weight of liquid crystal compound]

When a smectic phase or crystals deposited even at this ratio of the compound to the mother liquid crystals at 25° C., the ratio of the liquid crystal compound to the mother liquid crystals was changed in the order of (10% by weight: 90% by weight), (5% by weight: 95% by weight) and (1% by weight: 99% by weight). Physical properties of the sample were measured at the ratio in which the smectic phase or the crystals did not deposit at 25° C. Extrapolated values were determined according to the above equation, and regarded as physical properties of the liquid crystal compound.

There are a variety of mother liquid crystals used for measurement and, for example, each component (% by weight) of the mother liquid crystals (A) is shown below. Mother Liquid Crystals A:

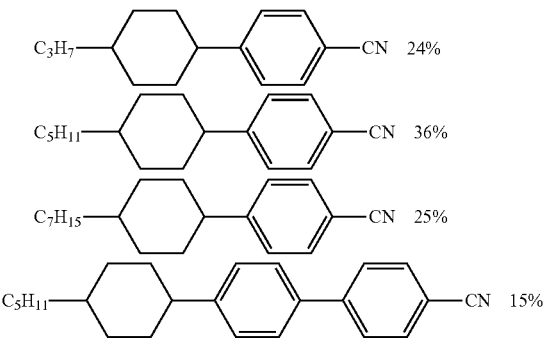

Methods for Measurement of Physical Properties of a Liquid Crystal Compound and so Forth Physical properties of compounds were measured according to the following methods. Most of the measurement methods are those described in the Standard of Electronic Industries Association of Japan, EIAJ•ED-2521A, or those with some modifications. No TFT was attached to a TN device used for measurement.

When a liquid crystal compound itself was employed as a sample, measured values was described here as experimental data. When a sample was prepared by mixing the liquid crystal compound with mother liquid crystals, values calculated from measured values according to the extrapolation method was described here as experimental data.

Phase Structure and Transition Temperature (° C.)

Measurements were carried out according to the following methods (1) and (2).

(1) A compound was placed on a hot plate of a melting point apparatus (Hot Stage Model FP-52 made by Mettler Toledo International Inc.) equipped with a polarizing microscope, and the phase conditions and their changes were observed with the polarizing microscope, specifying the kind of liquid crystal phase while the compound was heated at the rate of 3° C. per minute.

(2) A sample was heated and then cooled at a rate of 3° C. per minute using a Perkin-Elmer differential scanning calorimeter, a DSC-7 System or a Diamond DSC System. The starting point of an endothermic peak or an exothermic peak caused by a phase change of the sample was obtained by means of the extrapolation, and thus the phase transition temperature was determined.

Hereinafter, the symbol C stood for crystals, which were expressed by $C_1$ or $C_2$ when the kinds of the crystals were distinguishable. The symbols S and N stood for a smectic phase and a nematic phase, respectively. The symbol I stood for a liquid (isotropic). When a smectic A phase, a smectic B phase, a smectic C phase or a smectic F phase were distinguishable in the smectic phases, they were expressed as $S_A$, $S_B$, $S_C$ or $S_F$, respectively. Phase-transition temperatures were expressed as, for example, "C 50.0 N 100.0 I", which means that the phase-transition temperature from crystals to a nematic phase (CN) is 50.0° C., and the phase-transition temperature from the nematic phase to a liquid (NI) is 100.0° C. The same applied to the other transition temperatures.

Maximum Temperature of a Nematic Phase ($T_{NI}$; ° C.)

A sample (a mixture of a liquid crystal compound and mother liquid crystals) was placed on a hot plate of a melting point apparatus (Hot Stage Model FP-52 made by Mettler Toledo International Inc.) equipped with a polarizing microscope, and was observed with the polarizing microscope while being heated at the rate of 1° C. per minute. A maximum temperature was expressed as a temperature measured when part of the sample began to change from a nematic phase to an isotropic liquid. Hereinafter, the maximum temperature of a nematic phase may simply be abbreviated to "maximum temperature."

Compatibility at Low Temperature

Samples were prepared by mixing a liquid crystal compound with mother liquid crystals so that the amount of the liquid crystal compound became 20% by weight, 15% by weight, 10% by weight, 5% by weight, 3% by weight and 1% by weight, and placed in glass vials. After these glass vials had been kept in a freezer at −10° C. or −20° C. for a certain period of time, they were observed as to whether or not crystals or a smectic phase had been deposited.

Viscosity (Bulk Viscosity; η; Measured at 20° C.; mPa·s)

A mixture of a liquid crystal compound and mother liquid crystals was measured by use of an E-type viscometer was used for measurement.

Refractive Index Anisotropy (Δn)

Measurement was carried out using an Abbe refractometer with a polarizing plate attached to the ocular, on irradiation with light at a wavelength of 589 nm at 25° C. The surface of the main prism was rubbed in one direction, and then a sample (a mixture of a liquid crystal compound and mother liquid crystals) was dropped onto the main prism. A refractive index (n∥) was measured when the direction of the polarized light was parallel to that of the rubbing. A refractive index (n⊥) was measured when the direction of polarized light was perpendicular to that of the rubbing. The value of the refractive index anisotropy (Δn) was calculated from the equation: Δn=n∥−n⊥.

Dielectric Anisotropy (Δ∈; measured at 25° C.)

A sample (a mixture of a liquid crystal compound and mother liquid crystals) was poured into a liquid crystal cell in which the distance between two glass substrates (the cell gap) was about 9 micrometers and the twist angle was 80 degrees. A voltage of 20 volts was applied to this cell, and a dielectric constant (∈∥) in the major axis direction of liquid crystal molecules was measured. A voltage of 0.5 volt was applied to the device and a dielectric constant (∈⊥) in the minor axis direction of the liquid crystal molecules was measured. The value of dielectric anisotropy was calculated from the equation: Δ∈=∈∥−∈⊥.

Example 1

Preparation of 4-[difluoro[(2,3',4',5'-tetrafluoro[1,1'-biphenyl]-4-yl)oxy]methyl]-4'-(5-pentylpyrimidine-2-yl)-2',3,5-trifluoro-1,1'-biphenyl (Compound No. 1-2-5)

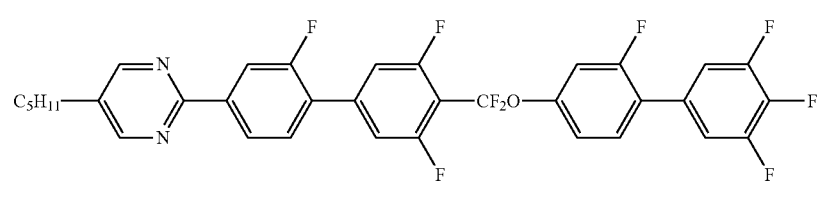

C 83.8 SA 124 N 237 I

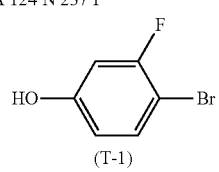

(T-1)

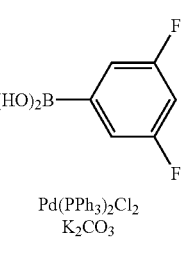

Pd(PPh$_3$)$_2$Cl$_2$
K$_2$CO$_3$

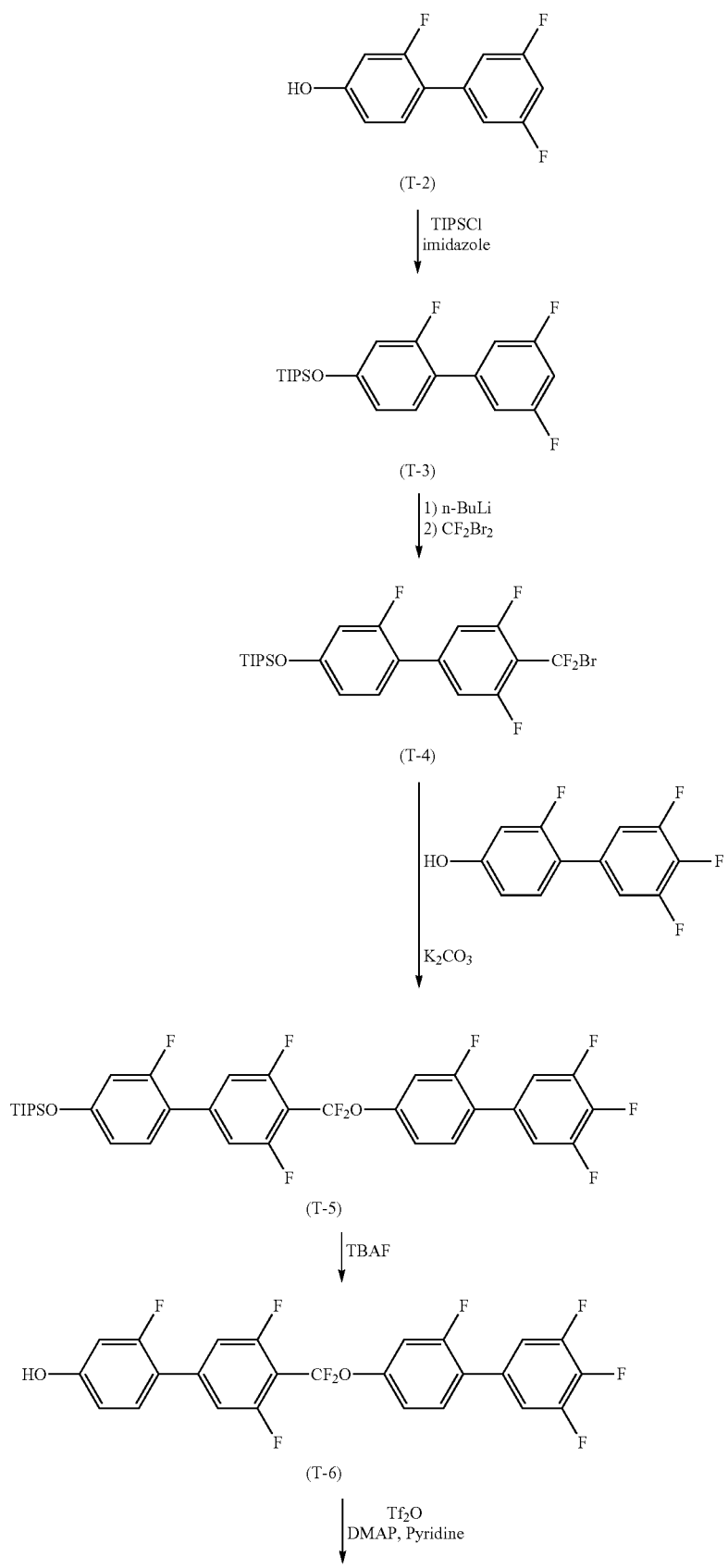

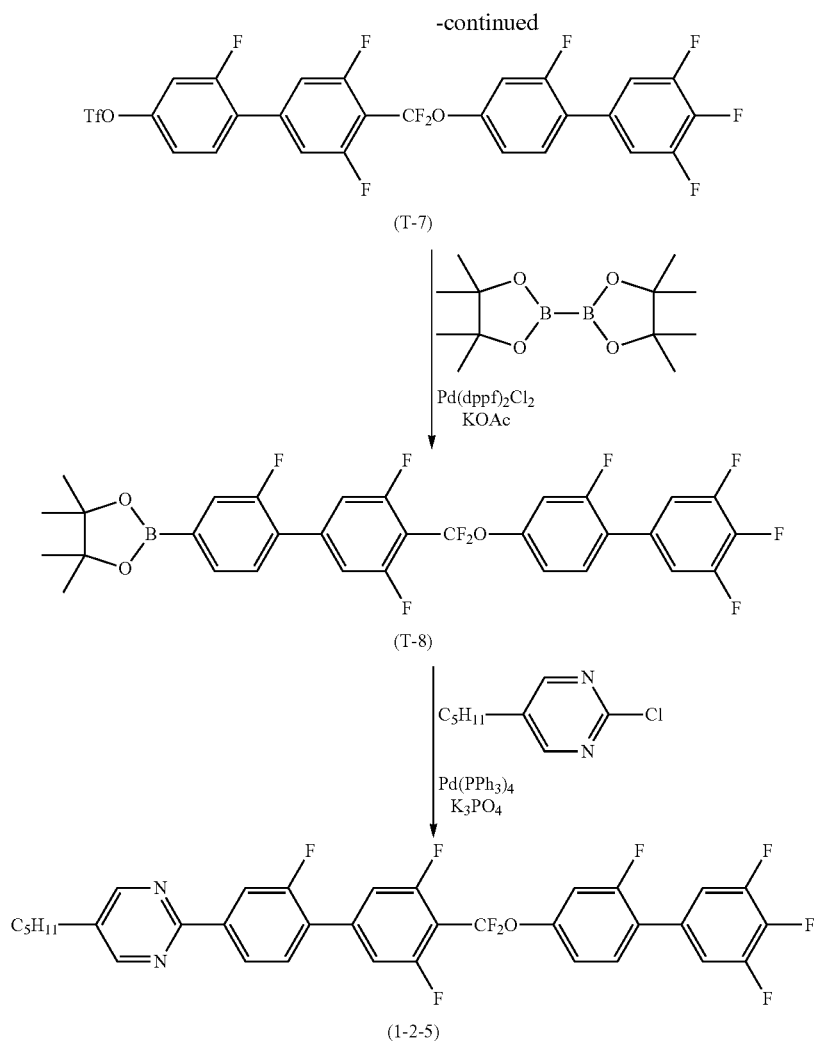

(T-7)

(T-8)

(1-2-5)

Preparation of the Compound (T-2)

4-Bromo-3-fluorophenol (T-1) (50.0 g), 3,5-difluorophenylboronic acid (45.5 g), potassium carbonate (72.4 g), Pd(Ph$_3$P)$_2$Cl$_2$ (5.52 g) and 2-propanol (500 ml) were put in a reaction vessel and heated to reflux for 5 hours under an atmosphere of nitrogen. After the reaction solution had been cooled to 25° C., it was poured into water (500 ml) and mixed with it. Toluene (500 ml) was added to the solution to separate organic and aqueous phases, and extraction was carried out. The combined organic phase was washed with water and dried over anhydrous magnesium sulfate. The resulting solution was concentrated under reduced pressure and the residue was purified with a fractional operation by means of column chromatography (silica gel; toluene). The product was further purified by recrystallization from a mixed solvent of heptane/Solmix A-11 and dried, giving 4-hydroxy-2,3',5'-trifluoro-1,1'-biphenyl (T-2) (43.4 g). The yield based on the compound (T-1) was 74%.

Preparation of the Compound (T-3)

The compound (T-2) (13.7 g), imidazole (10.4 g) and dichloromethane (70.0 ml) were put in a reaction vessel and cooled to 0° C. under an atmosphere of nitrogen. Chlorotriisopropylsilane (12.9 g) in a dichloromethane (15.0 ml) solution was slowly added dropwise, and the stirring was continued for another 4 hours. The resulting reaction mixture was washed with water and dried over anhydrous magnesium sulfate. The resulting solution was concentrated under reduced pressure and the residue was purified with a fractional operation by means of column chromatography (silica gel; heptane). The solvent was distilled off and the product was dried, giving 4-triisopropylsilyloxy-2,3',5'-trifluoro-1,1'-biphenyl (T-3) (22.8 g). The yield based on the compound (T-2) was 98%.

Preparation of the Compound (T-4)

The compound (T-3) (22.8 g) and THF (350 ml) were put in a reaction vessel and cooled to −74° C. under an atmosphere of nitrogen. n-Butyllithium (1.60M in n-hexane; 38.7 ml) was added dropwise in the temperature range of −74° C. to −70° C., and the stirring was continued for another 60 minutes. Then, dibromodifluoromethane (15.1 g) in a THF (60.0 ml) solution was added dropwise in the temperature range of −75° C. to −70° C., and the stirring was continued for another 60 minutes while the mixture was allowed to return to 25° C. The resultant reaction mixture was poured into ice-water (400 ml) and mixed with it. Toluene (200 ml) was added to the solution to separate organic and aqueous phases, and extraction was carried out. The combined organic phase was washed with water and dried over anhydrous magnesium sulfate. The resulting solution was concentrated under reduced pressure and the residue was purified with a fractional operation by means of column chromatography (silica gel; heptane). The solvent was distilled off and the product was dried, giving 4-bromodifluoromethyl-4'-triisopropylsilyloxy-2',3,5-trifluoro-1,1'-biphenyl (T-4) (26.3 g). The yield based on the compound (T-3) was 86%.

Preparation of the Compound (T-5)

The compound (T-4) (10.0 g) prepared in the above step, 4-hydroxy-2,3',4',5'-tetrafluoro-1,1'-biphenyl (4.62 g), potassium carbonate (1.76 g), heptane (10.0 ml) and water (100 ml) were put in a reaction vessel and heated to reflux for 5 hours under an atmosphere of nitrogen. After the reaction mixture had been returned to 25° C., toluene (100 ml) was added to the solution to separate organic and aqueous phases, and extraction was carried out. The combined organic phase was washed successively with a saturated aqueous solution of sodium hydrogencarbonate, an aqueous 0.5 N-sodium hydroxide solution, brine, and dried over anhydrous magnesium sulfate. The resulting solution was concentrated under reduced pressure and the residue was purified with a fractional operation by means of column chromatography (silica gel; heptane) and dried, giving 4-[difluoro[(2,3',4',5'-tetrafluoro[1,1'-biphenyl]-4-yl)oxy]methyl]-4'-triisopropylsilyloxy-2',3,5-trifluoro-1,1'-biphenyl (T-5) (7.49 g). The yield based on the compound (T-4) was 70%.

Preparation of the Compound (T-6)

The compound (T-5) (7.49 g), THF (150 ml) were put in a reaction vessel and cooled to 0° C. under an atmosphere of nitrogen. Tetrabutylammonium fluoride (TBAF; 1.00 M THF solution; 13.4 ml) was slowly added dropwise, and the stirring was continued for another 120 minutes while the mixture was allowed to return to 25° C. The resulting reaction mixture was poured into ice-water (200 ml) and mixed with it. Toluene (200 ml) was added to the solution to separate organic and aqueous phases, and extraction was carried out. The combined organic phase was washed with water and dried over anhydrous magnesium sulfate. The resulting solution was concentrated under reduced pressure and the residue was purified with a fractional operation by means of column chromatography (silica gel; toluene/ethyl acetate=5:1 by volume). The solvent was distilled off, giving 4-[difluoro[(2,3',4',5'-tetrafluoro[1,1'-biphenyl]-4-yl)oxy]methyl]-4'-hydroxy-2',3,5-trifluoro-1,1'-biphenyl (T-6) (5.68 g). The yield based on the compound (T-5) was 99%.

Preparation of the Compound (T-7)

The compound (T-6) (5.68 g), dimethylaminopyridine (2.02 g) and dichloromethane (60.0 ml) were put in a reaction vessel and cooled to −30° C. under an atmosphere of nitrogen. Pyridine (1.50 ml) and then trifluoromethanesulfonic acid anhydride (3.74 g) were slowly added dropwise, and the stirring was continued for another 2 hours. The resulting reaction mixture was washed with water and dried over anhydrous magnesium sulfate. The resulting solution was concentrated under reduced pressure and the residue was purified with a fractional operation by means of column chromatography (silica gel; heptane/ethyl acetate=10:1 by volume) and dried, giving 4-[difluoro[(2,3',4',5'-tetrafluoro[1,1'-biphenyl]-4-yl)oxy]methyl]-4'-trifluoromethanesulfonyloxy-2',3,5-trifluoro-1,1'-biphenyl (T-7) (4.23 g). The yield based on the compound (T-6) was 59%.

Preparation of the Compound (T-8)

The compound (T-7) (4.23 g), bis(pinacolato)diboron (1.83 g), potassium acetate (1.93 g), dichlorobis(diphenylphosphino)ferrocenepalladium (0.160 g) and dioxane (50.0 ml) were put in a reaction vessel and heated to reflux for 2 hours under an atmosphere of nitrogen. After the reaction solution had been cooled to 25° C., it was poured into water (100 ml) and mixed with it. Toluene (100 ml) was added to the solution to separate organic and aqueous phases, and extraction was carried out. The combined organic phase was washed with water and dried over anhydrous magnesium sulfate. The resulting solution was concentrated under reduced pressure and the residue was purified with a fractional operation by means of column chromatography (silica gel; heptane/toluene=1:1 by volume) and dried, giving the pinacol borate ester (T-8) (3.11 g). The yield based on the compound (T-7) was 66%.

Preparation of the Compound (No. 1-2-5)

The compound (T-8) (3.11 g), 2-chloro-5-pentylpyrimidine (1.01 g), potassium phosphate (2.11 g), Pd(PPh$_3$)$_4$ (0.0575 g), toluene (30.0 ml) and ethanol (30.0 ml) were put in a reaction vessel and heated to reflux for 2 hours under an atmosphere of nitrogen. After the reaction solution had been cooled to 25° C., it was poured into water (100 ml) and mixed with it. Toluene (100 ml) was added to the solution to separate organic and aqueous phases, and extraction was carried out. The combined organic phase was washed with water and dried over anhydrous magnesium sulfate. The resulting solution was concentrated under reduced pressure and the residue was purified with a fractional operation by means of column chromatography (silica gel; heptane/ethyl acetate=5:1 by volume). The product was further purified by recrystallization from a mixed solvent of ethyl acetate/Solmix A-11 and dried, giving 4-[difluoro[(2,3',4',5'-tetrafluoro[1,1'-biphenyl]-4-yl)oxy]methyl]-4'-(5-pentylpyrimidine-2-yl)-2',3,5-trifluoro-1,1'-biphenyl (No. 1-2-5) (1.31 g). The yield based on the compound (T-8) was 42%.

The chemical shift (δ, ppm) in $^1$H-NMR analysis was described below, and the compound obtained was identified as 4-[difluoro[(2,3',4',5'-tetrafluoro[1,1'-biphenyl]-4-yl)oxy]methyl]-4'-(5-pentylpyrimidine-2-yl)-2',3,5-trifluoro-1,1'-biphenyl. The solvent for measurement was CDCl$_3$.

Chemical shift δ (ppm); 8.66 (s, 2H), 8.33 (dd, J=8.10 Hz, J=1.30 Hz, 1H), 8.28 (dd, J=12.1 Hz, 1.50 Hz, 1H), 7.56 (dd, J=8.00 Hz, J=8.00 Hz, 1H), 7.39 (dd, J=8.40 Hz, J=8.40 Hz, 1H), 7.31 (d, J=10.6 Hz, 2H), 7.23-7.14 (m, 4H), 2.66 (t, J=7.75 Hz, 2H), 1.73-1.64 (m, 2H), 1.43-1.34 (m, 4H) and 0.92 (t, 6.80 Hz, 3H).

The phase transition temperature of the resulting compound (No. 1-2-5) was as follows.

Phase transition temperature: C 83.8 S$_A$ 124 N 237 I.

Example 2

Physical Properties of the Liquid Crystal Compound (No. 1-2-5)

The four compounds for the mother liquid crystals A described above were mixed to give the mother liquid crystals A having a nematic phase. The physical properties of the mother liquid crystals A were as follows.

Maximum temperature (T$_{NI}$)=71.7° C.; refractive index anisotropy (Δn)=0.137; dielectric anisotropy (Δ∈)=11.0.

The liquid crystal composition B consisting of the mother liquid crystals A (85% by weight) and 4-[difluoro[(2,3',4',5'-tetrafluoro[1,1'-biphenyl]-4-yl)oxy]methyl]-4'-(5-pentylpyrimidine-2-yl)-2',3,5-trifluoro-1,1'-biphenyl (No. 1-2-5) (15% by weight) prepared in Example 1 was prepared. The physical properties of the resulting liquid crystal composition B were measured, and the extrapolated values of the physical properties of the liquid crystal compound (No. 1-2-5) were calculated. The values were as follows.

Maximum temperature (T$_{NI}$)=154° C.; refractive index anisotropy (Δn)=0.237; dielectric anisotropy (Δ∈)=56.6.

From these results, it was found that the liquid crystal compound (No. 1-2-5) had a wide temperature range of a liquid crystal phase, an especially high maximum temperature ($T_{NI}$), a large refractive index anisotropy and an especially high dielectric anisotropy.

Example 3

Preparation of 4-[difluoro[(2,3',4',5'-tetrafluoro[1,1'-biphenyl]-4-yl)oxy]methyl]-4'-(5-pentylpyridine-2-yl)-2',3,5-trifluoro-1,1'-biphenyl (Compound No. 1-2-85)

to −70° C., formylpiperidine (9.70 g) was added dropwise in the temperature range of −70° C. to −65° C., and the stirring was continued for another 60 minutes while the mixture was allowed to return to room temperature. The resulting reaction mixture was poured into ice-water (500 ml) and mixed with it. Diethyl ether (200 ml) was added to the solution to separate organic and aqueous phases, and extraction was carried out. The combined organic phase was washed with water and dried over anhydrous magnesium sulfate. The resulting solution was concentrated under reduced pressure and the residue was purified with a fractional operation by means of column chromatography (silica gel; toluene). The product was further

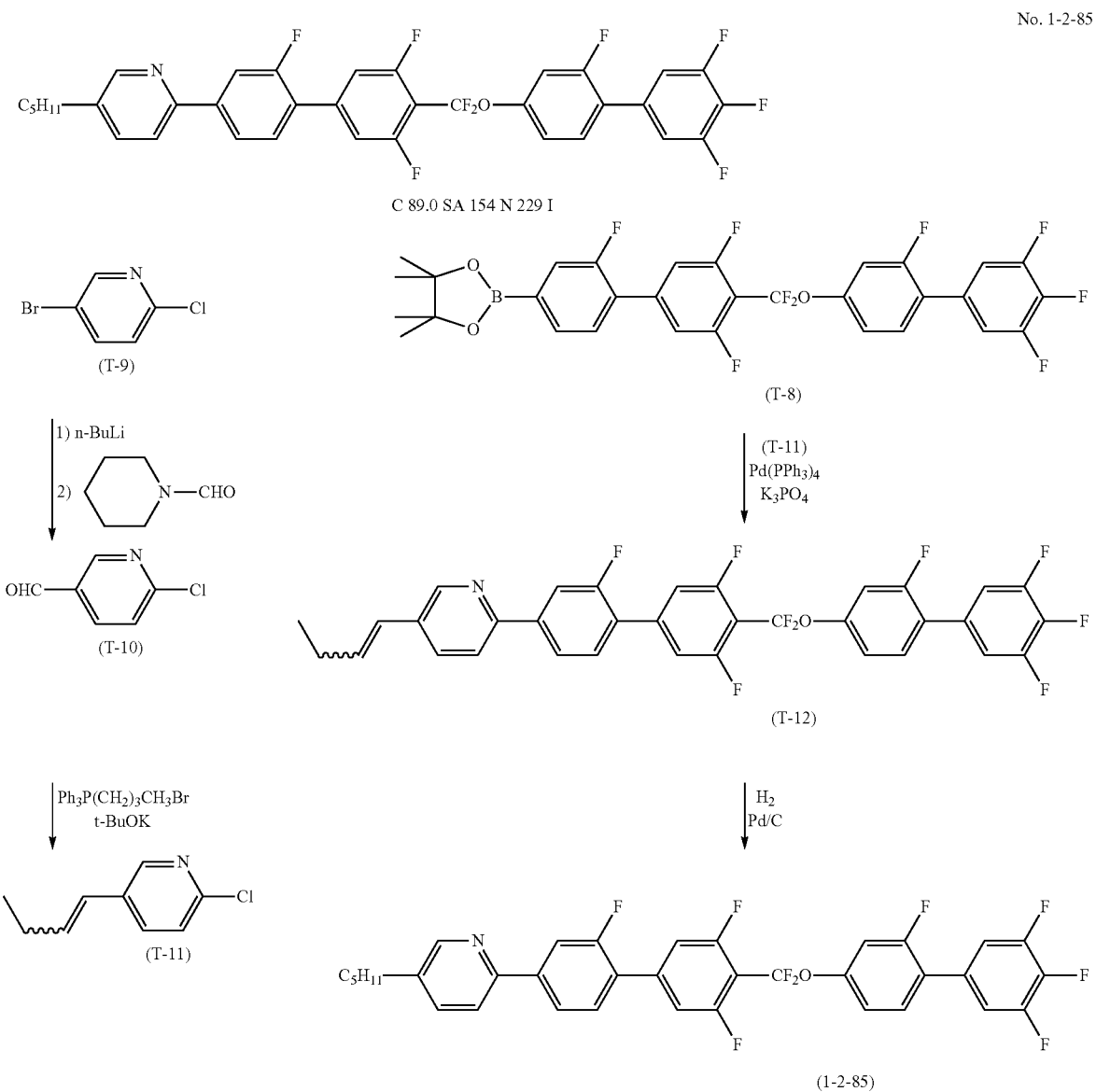

Preparation of the Compound (T-10)

5-Bromo-2-chloropyridine (T-9) (15.0 g) and diethyl ether (450 ml) were put in a reaction vessel and cooled to −50° C. under an atmosphere of nitrogen. n-Butyllithium (1.57 M in n-hexane; 54.6 ml) was added dropwise in the temperature range of −50° C. to −45° C., and the stirring was continued for another 90 minutes. After the reaction vessel had been cooled purified by recrystallization from heptane. The solvent was distilled off and the product was dried, giving 2-chloro-5-formylpyridine (T-10) (7.01 g). The yield based on the compound (T-9) was 68%.

Preparation of the Compound (T-11)

Butyltriphenylphosphonium bromide (21.1 g) and THF (90.0 ml) were put in a reaction vessel and cooled to −30° C.

under an atmosphere of nitrogen. Potassium t-butoxide (5.68 g) was added slowly, and the stirring was continued for another 30 minutes. Then, the compound (T-10) (5.98 g) in a THF (50.0 ml) solution was added dropwise in the temperature range of −30° C. to −25° C., and the stirring was continued for another 2 hours while the reaction mixture was allowed to return to room temperature. The resulting reaction mixture was poured into ice-water (200 ml) and mixed with it. Toluene (200 ml) was added to the solution to separate organic and aqueous phases, and extraction was carried out. The combined organic phase was washed successively with water, 1N-hydrochloric acid, a saturated aqueous solution of sodium hydrogencarbonate and water, and dried over anhydrous magnesium sulfate. The resulting solution was concentrated under reduced pressure and the residue was purified with a fractional operation by means of column chromatography (silica gel; heptane/ethyl acetate=10:1 by volume) to give 2-chloro-5-(1-pentenyl)pyridine (T-11) (6.96 g). The yield based on the compound (T-11) was 99%.

Preparation of the Compound (T-12)

The compound (T-8) (2.77 g), the compound (T-11) (0.887 g), potassium phosphate (1.89 g), Pd(PPh$_3$)$_4$ (0.0513 g), toluene (25.0 ml) and ethanol (25.0 ml) were put in a reaction vessel and heated to reflux for 1 hours under an atmosphere of nitrogen. After the reaction solution had been cooled to room temperature, it was poured into water (50.0 ml) and mixed with it. Toluene (50 ml) was added to the solution to separate organic and aqueous phases, and extraction was carried out. The combined organic phase was washed with water and dried over anhydrous magnesium sulfate. The resulting solution was concentrated under reduced pressure and the residue was purified with a fractional operation by means of column chromatography (silica gel; heptane/ethyl acetate=5:1 by volume) and dried, giving 4-[difluoro[(2,3',4',5'-tetrafluoro[1,1'-biphenyl]-4-yl)oxy]methyl]-4'-[5-(1-pentenyl)pyridine-2-yl]-2',3,5-trifluoro-1,1'-biphenyl (T-12) (2.77 g). The yield based on the compound (T-8) was 97%.

Preparation of the Compound (No. 1-2-85)

The compound (T-12) (2.77 g), a palladium on carbon catalyst (5% Pd/C; NX type; 50%-wet; N. E. Chemcat Corporation; 0.139 g), toluene (25.0 ml) and IPA (25.0 ml) were put in a reaction vessel under an atmosphere of nitrogen and stirred under a hydrogen atmosphere at room temperature for 8 hours. After the catalyst had been removed by filtration, the filtrate was concentrated under reduced pressure and the residue was purified with a fractional operation by means of column chromatography (silica gel; heptane/ethyl acetate=5:1 by volume). The product was further purified by recrystallization from a mixed solvent of ethyl acetate/Solmix A-11 to give 4-[difluoro[(2,3',4',5'-tetrafluoro [1,1'-biphenyl]-4-yl)oxy]methyl]-4'-(5-pentylpyridine-2-yl)-2',3,5-trifluoro-1,1'-biphenyl (Compound No. 1-2-85) (2.00 g). The yield based on the compound (T-12) was 72%.

The chemical shift (δ, ppm) in $^1$H-NMR analysis was described below, and the compound obtained was identified as 4-[difluoro[(2,3',4',5'-tetrafluoro [1,1'-biphenyl]-4-yl)oxy]methyl]-4'-(5-pentylpyridine-2-yl)-2',3,5-trifluoro-1,1'-biphenyl. The solvent for measurement was CDCl$_3$.

Chemical shift δ (ppm); 8.55 (d, J=1.85 Hz, 1H), 7.92-7.84 (m, 2H), 7.70 (d, J=8.10 Hz, 1H), 7.62 (dd, J=8.05 Hz, J=2.15 Hz, 1H), 7.54 (dd, J=8.30 Hz, J=8.30 Hz, 1H), 7.39 (dd, J=8.50 Hz, 8.50 Hz, 1H), 7.29 (d, J=10.6 Hz, 2H), 7.24-7.14 (m, 4H), 2.67 (t, J=7.80 Hz, 2H), 1.73-1.64 (m, 2H), 1.43-1.31 (m, 4H) and 0.91 (t, 6.90 Hz, 3H).

The phase transition temperature of the resulting compound (No. 1-2-85) was as follows.

Phase transition temperature: C 89.0 S$_A$ 154 N 229 I.

Example 4

Physical Properties of the Liquid Crystal Compound (No. 1-2-85)

The liquid crystal composition C consisting of the mother liquid crystals A (85% by weight) and 4-[difluoro[(2,3',4',5'-tetrafluoro[1,1'-biphenyl]-4-yl)oxy]methyl]-4'-(5-pentylpyridine-2-yl)-2',3,5-trifluoro-1,1'-biphenyl (No. 1-2-85) (15% by weight) prepared in Example 3 was prepared. The physical properties of the resulting liquid crystal composition C were measured, and the extrapolated values of the physical properties of the liquid crystal compound (No. 1-2-85) were calculated. The values were as follows.

Maximum temperature (T$_{NI}$)=148° C.; refractive index anisotropy (Δn)=0.237; dielectric anisotropy (Δ∈)=48.6.

From these results, it was found that the liquid crystal compound (No. 1-2-85) had a wide temperature range of a liquid crystal phase, an especially high maximum temperature (T$_{NI}$), a large refractive index anisotropy and an especially high dielectric anisotropy.

Example 5

Preparation of 4-[difluoro(3,4,5-trifluorophenoxy) methyl]-4"-(5-pentylpyrimidine-2-yl)-2',2",3,5-tetrafluoro-1,1',4',1"-terphenyl (Compound No. 1-3-5)

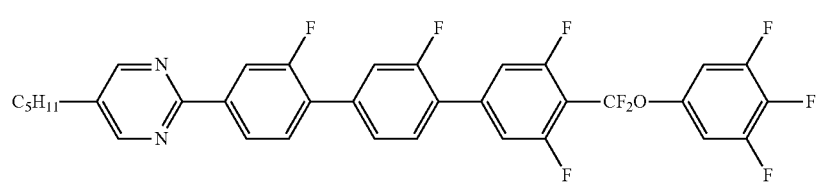

No. 1-3-5

C 123 SA 250 N 266 I

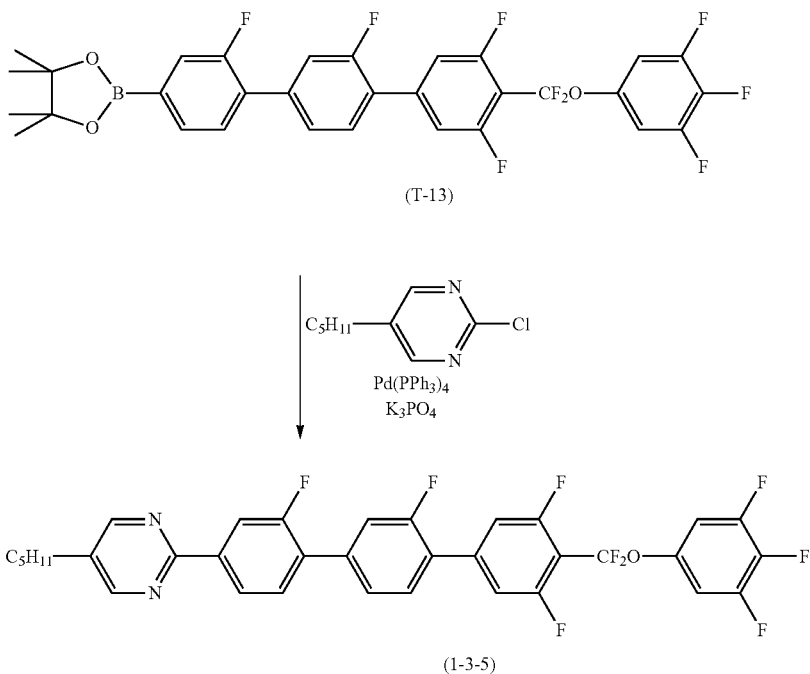

(T-13)

(1-3-5)

Preparation of the Compound (No. 1-3-5)

2-Chloro-5-pentylpyrimidine (0.275 g), potassium phosphate (0.573 g), Pd(PPh$_3$)$_4$ (0.0156 g), toluene (20.0 ml), ethanol (20.0 ml) and the compound (T-13) (0.845 g) prepared by a method similar to the preparation of the compound (T-8) were put in a reaction vessel and heated to reflux for 5 hours under an atmosphere of nitrogen. After the reaction solution had been cooled to 25° C., it was poured into water (50 ml) and mixed with it. Toluene (50 ml) was added to the solution to separate organic and aqueous phases, and extraction was carried out. The combined organic phase was washed with water and dried over anhydrous magnesium sulfate. The resulting solution was concentrated under reduced pressure and the residue was purified with a fractional operation by means of column chromatography (silica gel; toluene). The product was further purified by recrystallization from a mixed solvent of ethyl acetate/Solmix A-11 and dried, giving 4-[difluoro(3,4,5-trifluorophenoxy)methyl]-4"-(5-pentylpyrimidine-2-yl)-2',2",3,5-tetrafluoro-1,1',4',1"-terphe nyl (No. 1-3-5) (0.679 g). The yield based on the compound (T-13) was 78%.

The chemical shift (δ, ppm) in $^1$H-NMR analysis was described below, and the compound obtained was identified as 4-[difluoro(3,4,5-trifluorophenoxy)methyl]-4"-(5-pentylpyrimidine-2-yl)-2',2",3,5-tetrafluoro-1,1',4',1"-terphenyl. The solvent for measurement was CDCl$_3$.

Chemical shift δ (ppm); 8.66 (s, 2H), 8.32 (dd, J=8.15 Hz, J=1.70 Hz, 1H), 8.27 (dd, J=12.1 Hz, 1.60 Hz, 1H), 7.60 (dd, J=8.05 Hz, J=8.05 Hz, 1H), 7.58-7.48 (m, 3H), 7.29 (d, J=10.7 Hz, 2H), 7.05-6.97 (m, 2H), 2.66 (t, J=7.85 Hz, 2H), 1.73-1.64 (m, 2H), 1.44-1.33 (m, 4H) and 0.92 (t, 6.80 Hz, 3H).

The phase transition temperature of the resulting compound (No. 1-3-5) was as follows.

Phase transition temperature: C 123 S$_A$ 250 N 266 I.

Example 6

Physical Properties of the Liquid Crystal Compound (No. 1-3-5)

The liquid crystal composition D consisting of the mother liquid crystals A (95% by weight) and 4-[difluoro(3,4,5-trifluorophenoxy)methyl]-4"-(5-pentylpyrimidine-2-yl)-2',2", 3,5-tetrafluoro-1,1',4',1"-terphenyl (No. 1-3-5) (5% by weight) prepared in Example 5 was prepared. The physical properties of the resulting liquid crystal composition D were measured, and the extrapolated values of the physical properties of the liquid crystal compound (No. 1-3-5) were calculated. The values were as follows.

Maximum temperature (T$_{NI}$)=172° C.; refractive index anisotropy (Δn)=0.257; dielectric anisotropy (Δ∈)=49.9.

From these results, it was found that the liquid crystal compound (No. 1-3-5) had a wide temperature range of a liquid crystal phase, an especially high maximum temperature (T$_{NI}$), a large refractive index anisotropy and a large dielectric anisotropy.

Example 7

The following compounds (No. 1-1-1) to (No. 1-1-136), (No. 1-2-1) to (No. 1-2-152) and (No. 1-3-1) to (No. 1-3-235) can be prepared based on Example 1 and synthetic methods described here. Data attached to the compound are values obtained according to the methods described above. The phase transition temperature is expressed in terms of a measured value of a compound itself. The maximum temperature (T$_{NI}$), the dielectric anisotropy (Δ∈) and the refractive index anisotropy (Δn) are expressed in terms of extrapolated values, which are calculated according to the extrapolation method from measured values of a sample in which a compound is mixed with the mother liquid crystals (A) as is described in Examples 2, 4 and 6.

| No. | |
|---|---|
| 1-1-1 | 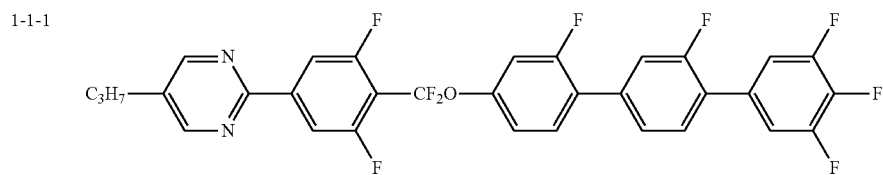 |
| 1-1-2 | 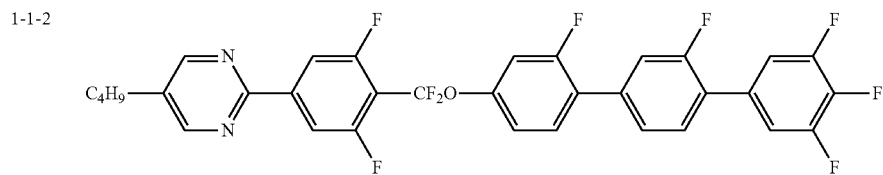 |
| 1-1-3 | 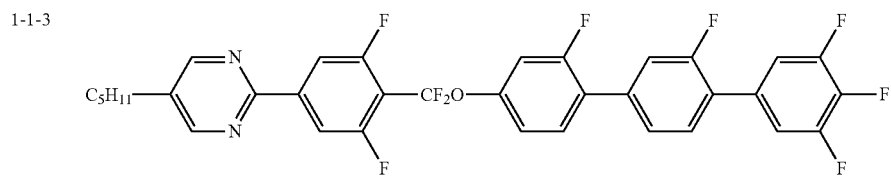 |
| 1-1-4 | 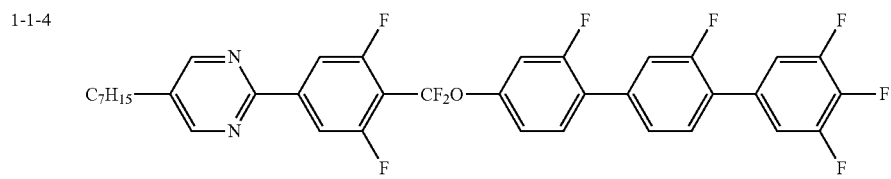 |
| 1-1-5 | 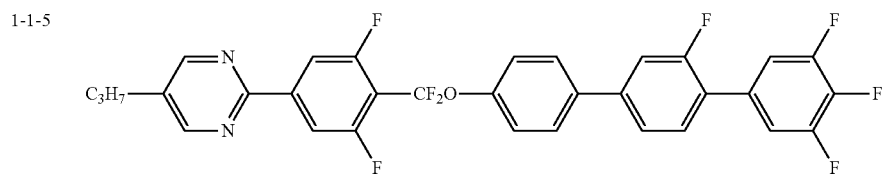 |
| 1-1-6 | 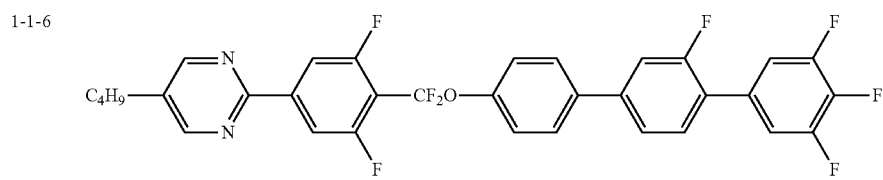 |
| 1-1-7 | 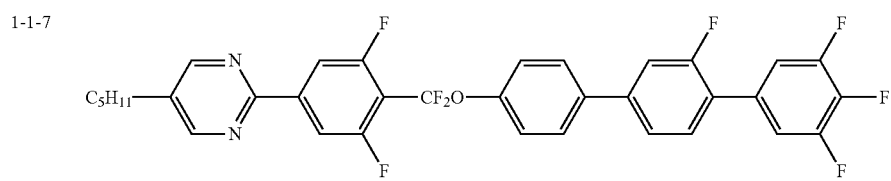 |
| 1-1-8 | 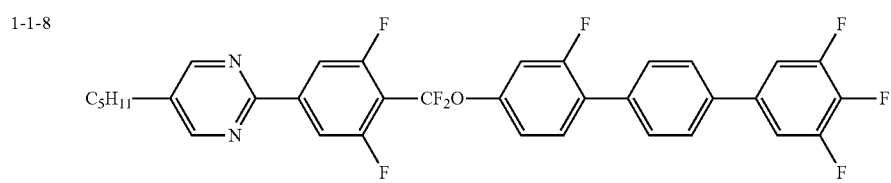 |

-continued
| No. | |
|---|---|
| 1-1-9 | 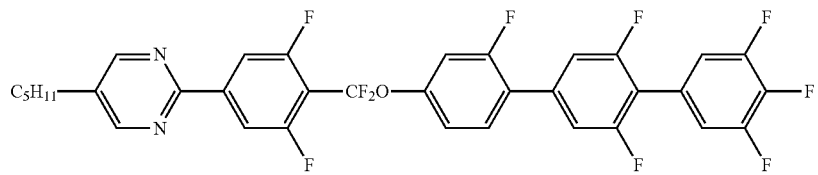 |
| 1-1-10 | 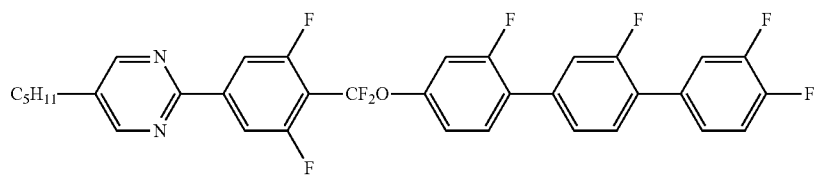 |
| 1-1-11 | 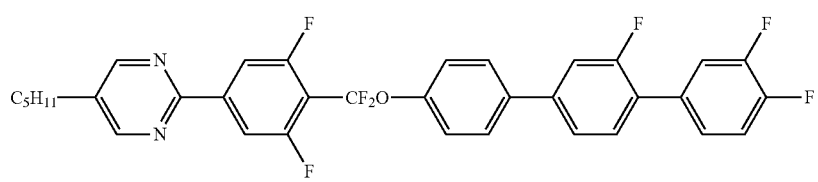 |
| 1-1-12 | 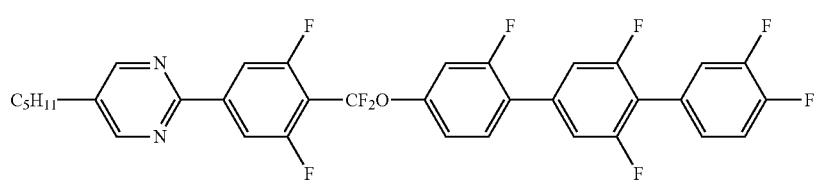 |
| 1-1-13 | 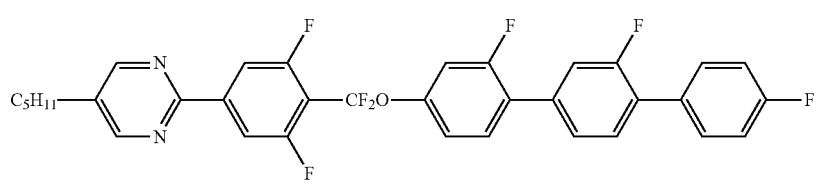 |
| 1-1-14 | 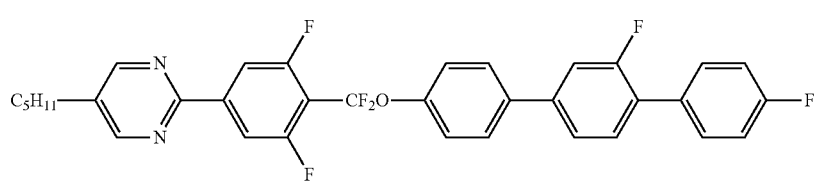 |
| 1-1-15 | 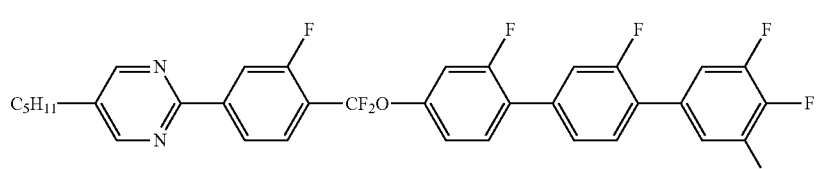 |
| 1-1-16 | 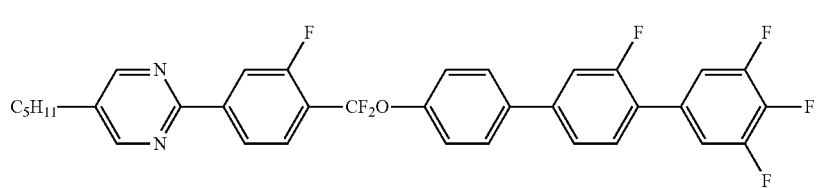 |

-continued
| No. |
|---|
1-1-17 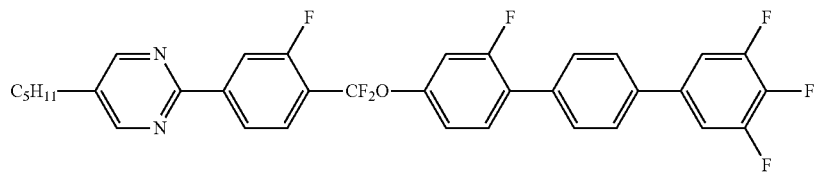
1-1-18 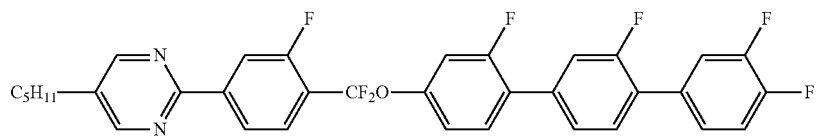
1-1-19 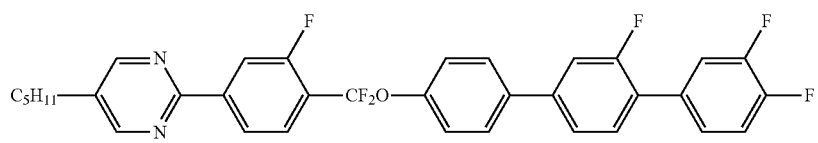
1-1-20 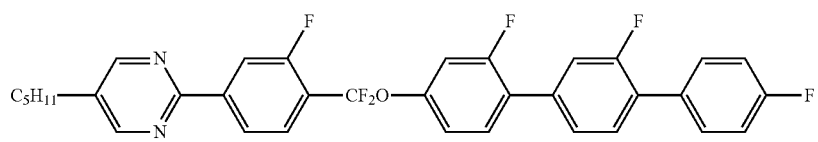
1-1-21 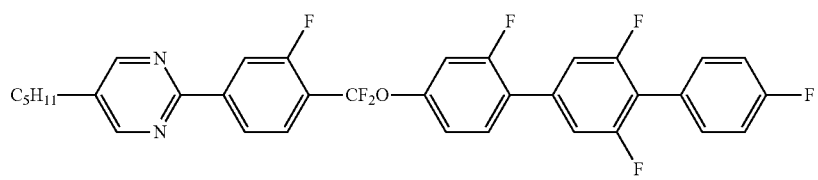
1-1-22 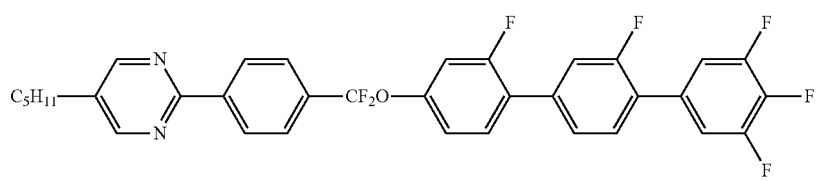
1-1-23 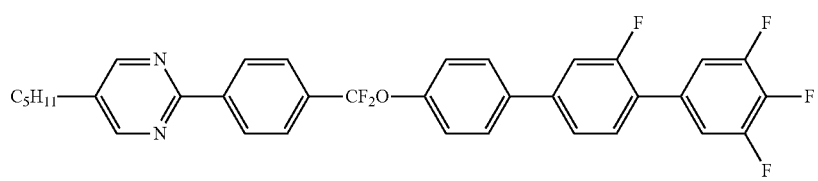
1-1-24 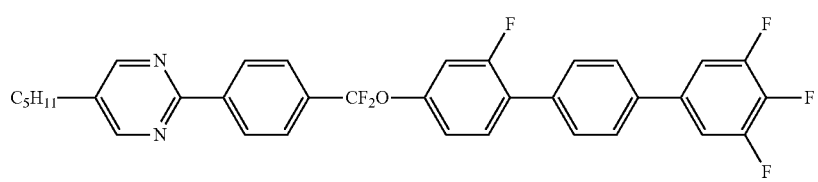
1-1-25 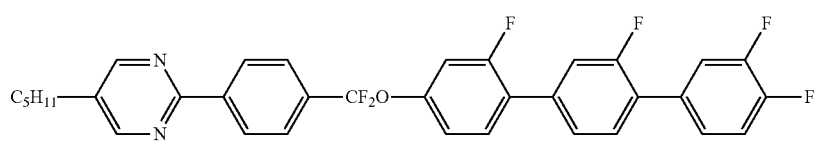

-continued
| No. | |
|---|---|
| 1-1-26 | 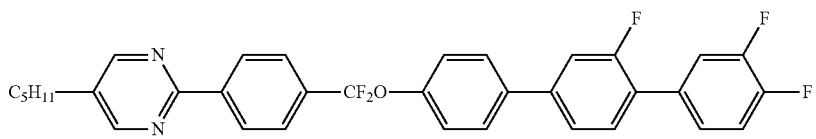 |
| 1-1-27 | 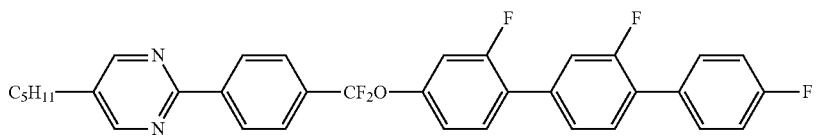 |
| 1-1-28 | 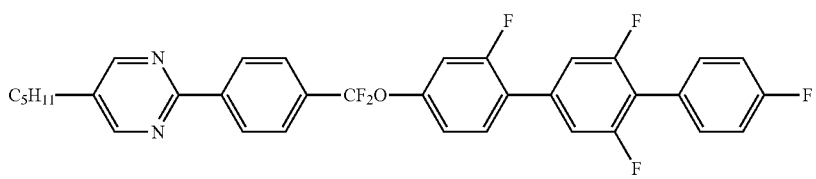 |
| 1-1-29 | 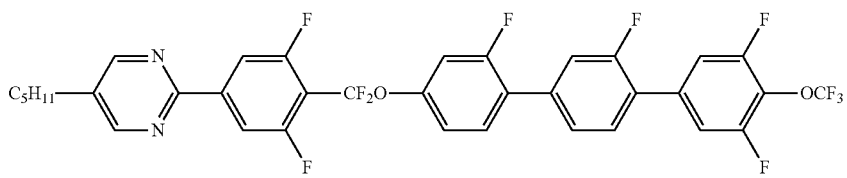 |
| 1-1-30 | 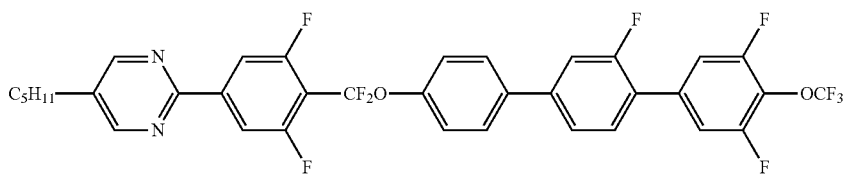 |
| 1-1-31 | 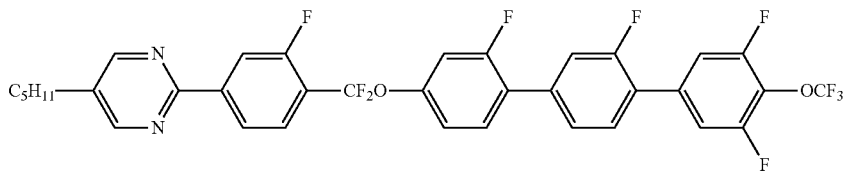 |
| 1-1-32 | 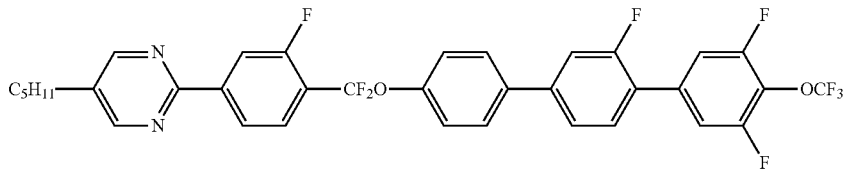 |
| 1-1-33 | 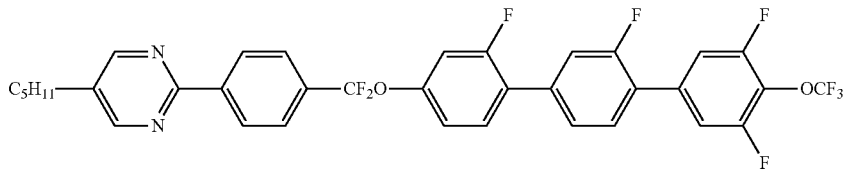 |
| 1-1-34 | 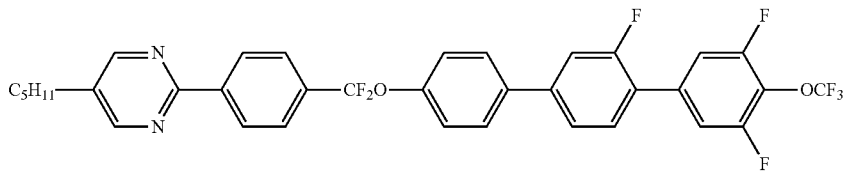 |

| No. | |
|---|---|
| 1-1-35 | 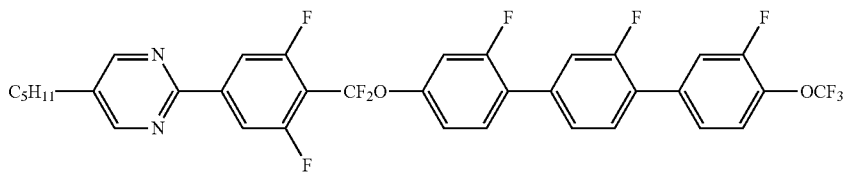 |
| 1-1-36 | 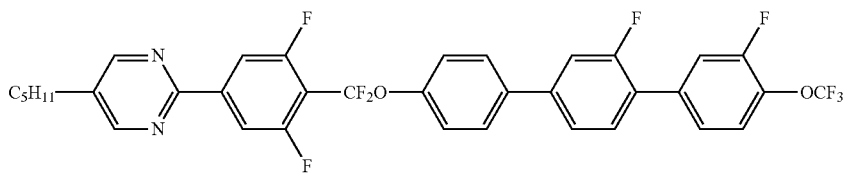 |
| 1-1-37 | 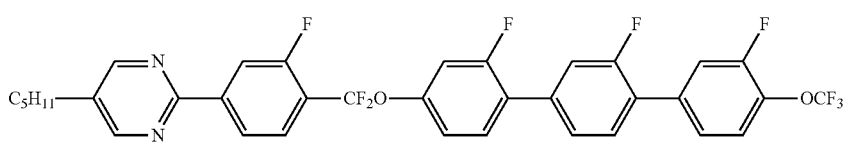 |
| 1-1-38 | 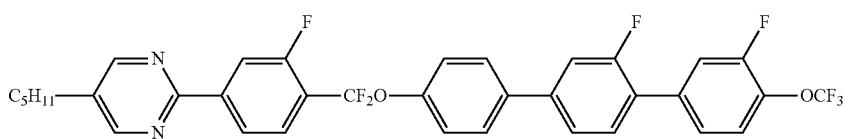 |
| 1-1-39 | 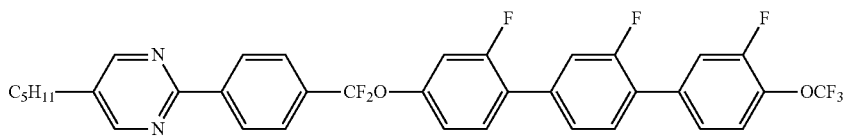 |
| 1-1-40 | 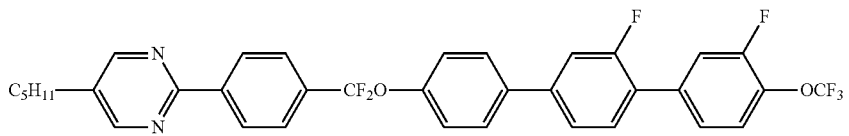 |
| 1-1-41 | 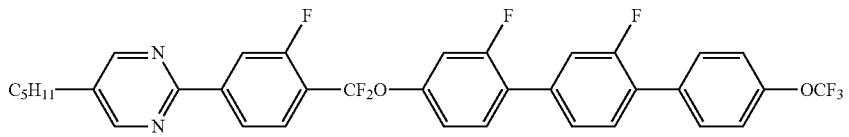 |
| 1-1-42 | 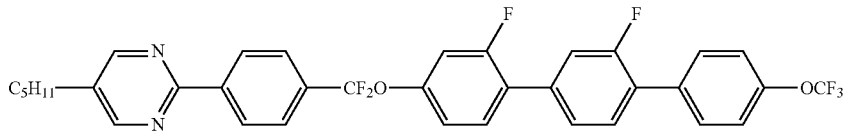 |
| 1-1-43 | 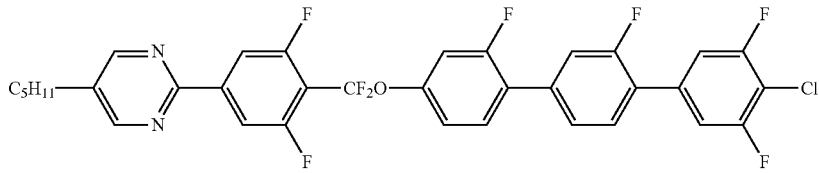 |
| 1-1-44 | 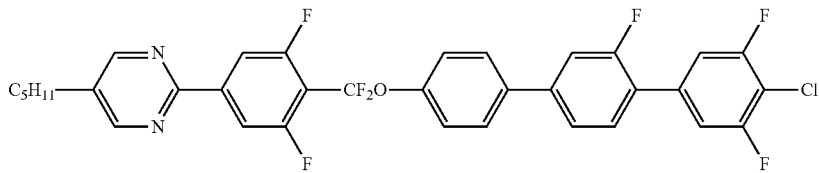 |

-continued
| No. | |
|---|---|
| 1-1-45 | 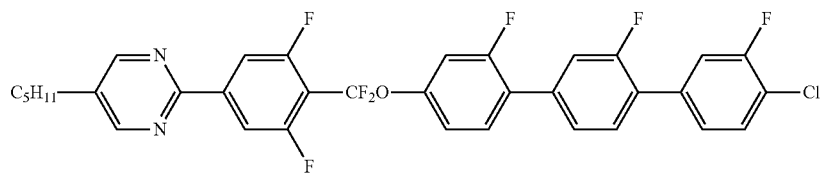 |
| 1-1-46 | 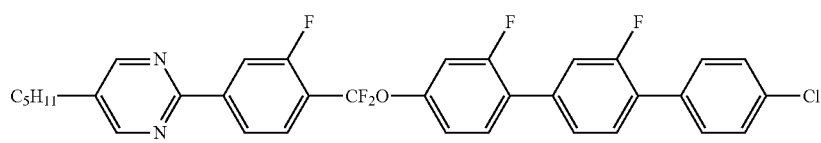 |
| 1-1-47 | 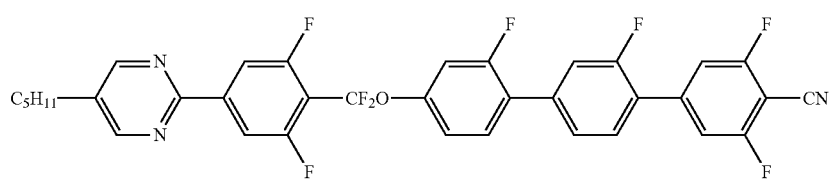 |
| 1-1-48 | 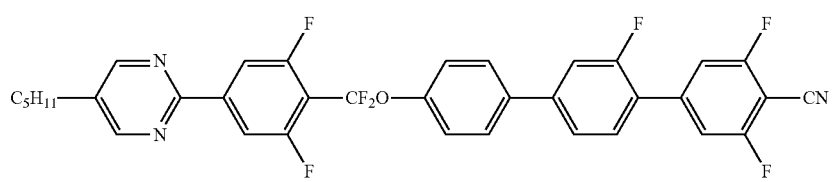 |
| 1-1-49 | 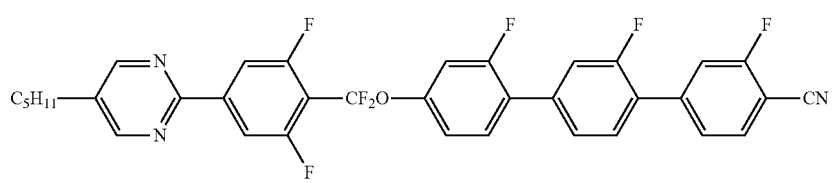 |
| 1-1-50 | 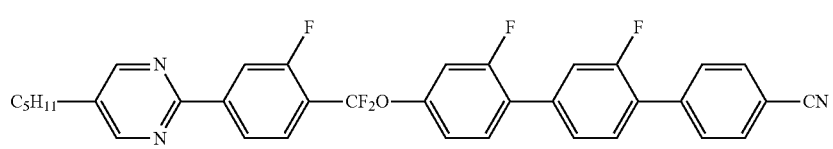 |
| 1-1-51 | 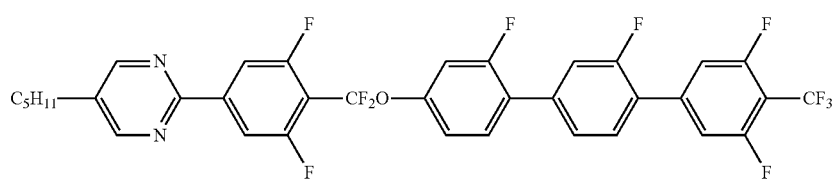 |
| 1-1-52 | 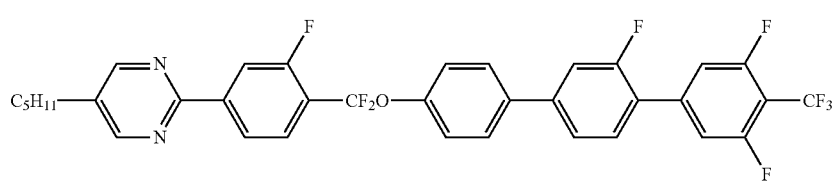 |
| 1-1-53 | 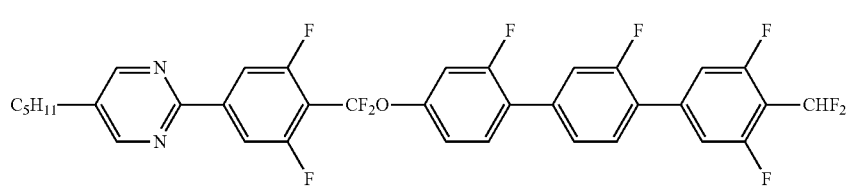 |

-continued
| No. | |
|---|---|
| 1-1-54 | 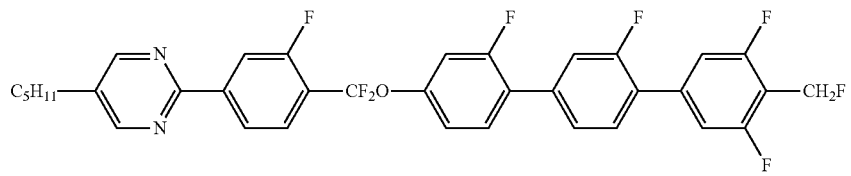 |
| 1-1-55 | 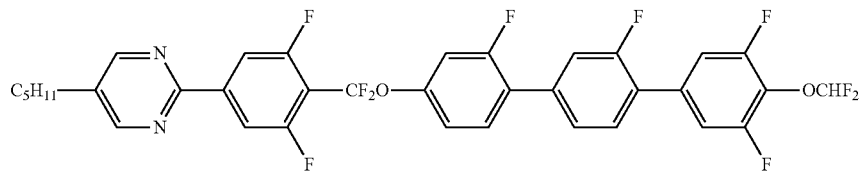 |
| 1-1-56 | 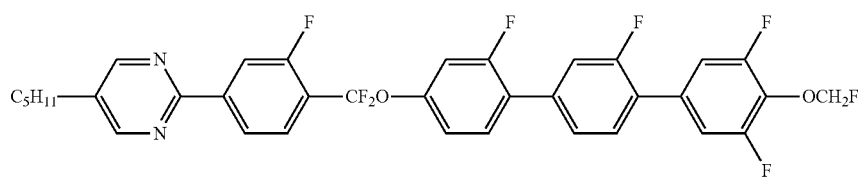 |
| 1-1-57 | 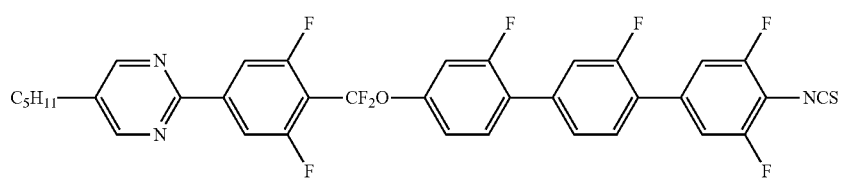 |
| 1-1-58 | 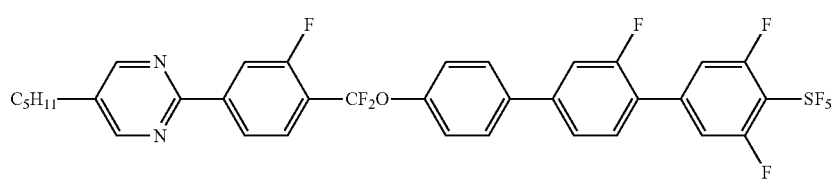 |
| 1-1-59 | 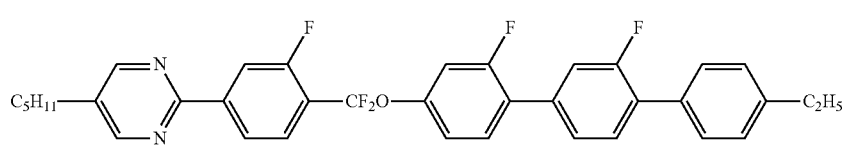 |
| 1-1-60 | 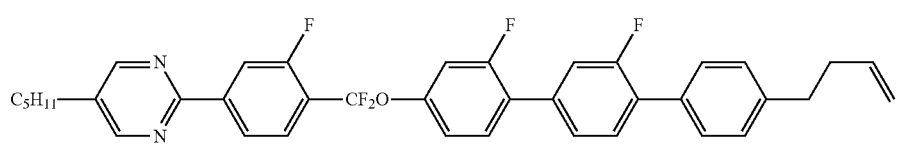 |
| 1-1-61 | 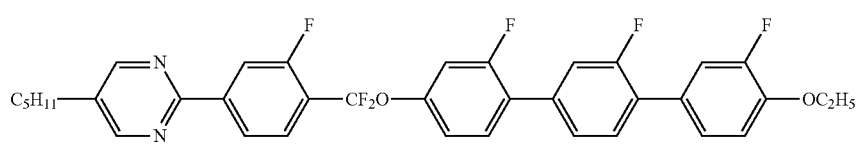 |
| 1-1-62 | 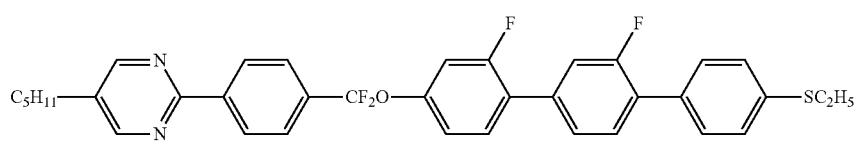 |

-continued
| No. | |
|---|---|
| 1-1-63 | 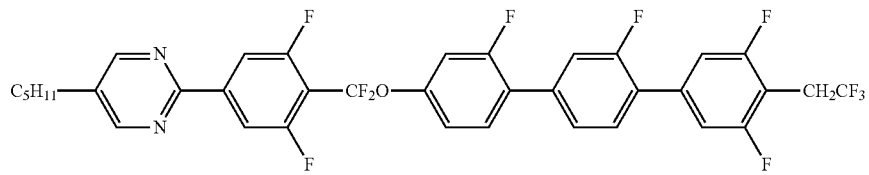 |
| 1-1-64 | 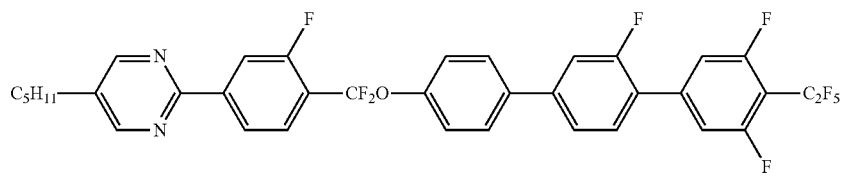 |
| 1-1-65 | 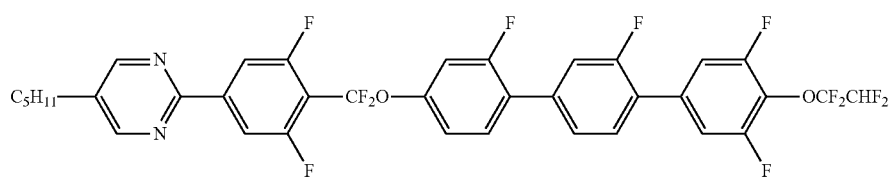 |
| 1-1-66 | 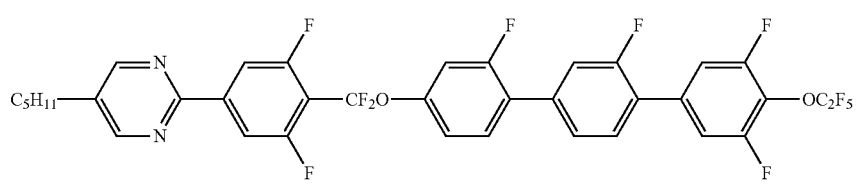 |
| 1-1-67 | 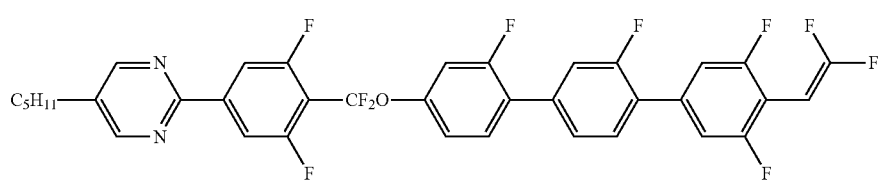 |
| 1-1-68 | 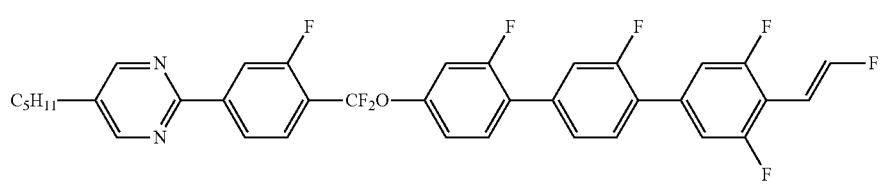 |
| 1-1-69 | 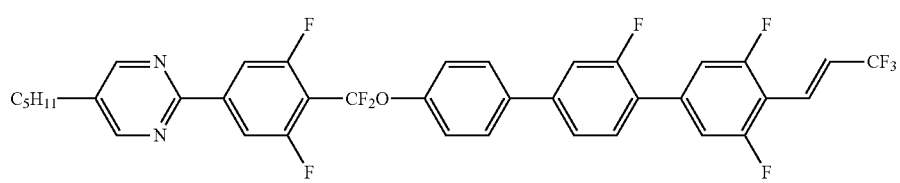 |
| 1-1-70 | 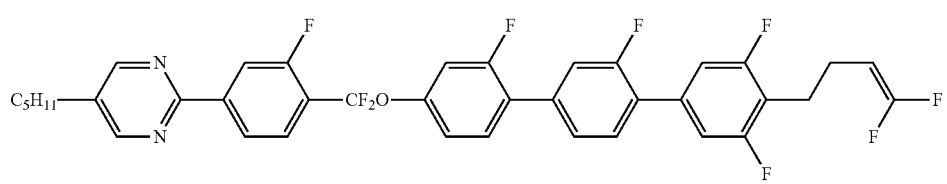 |

-continued
No.
1-1-71 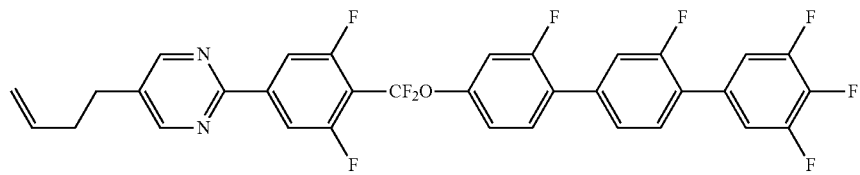
1-1-72 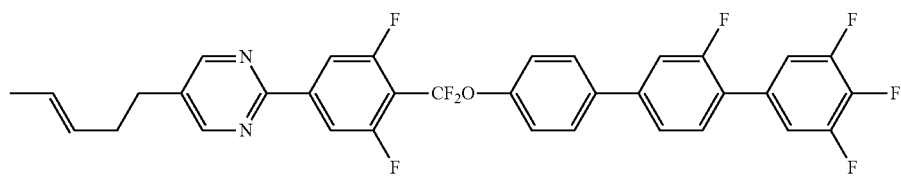
1-1-73 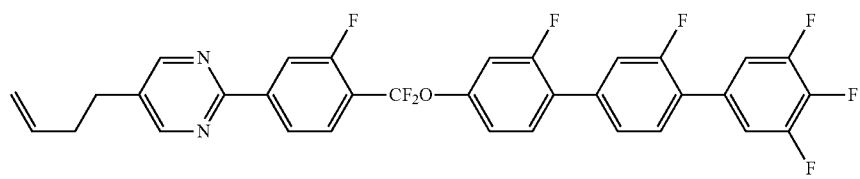
1-1-74 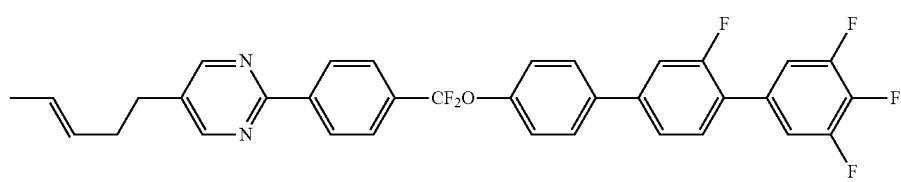
1-1-75 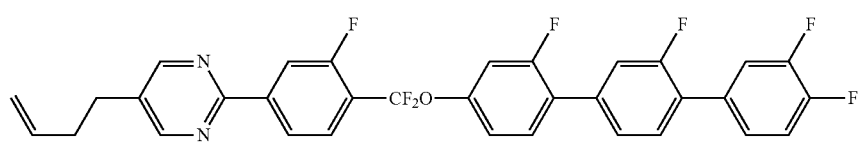
1-1-76 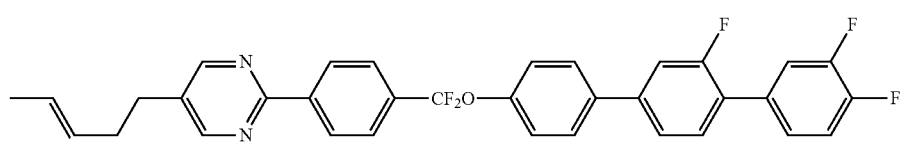
1-1-77 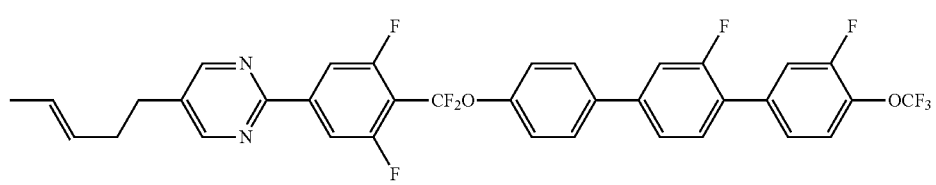
1-1-78 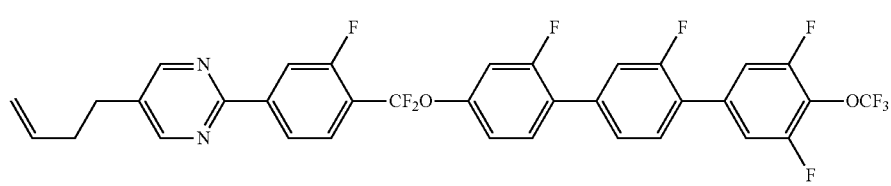
1-1-79 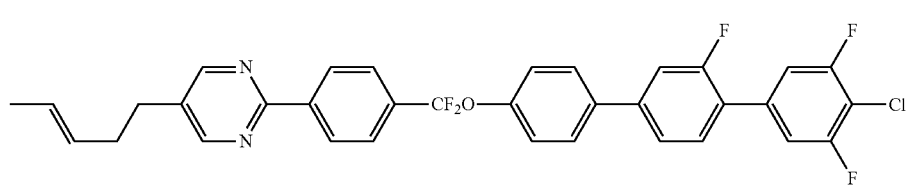

-continued
| No. | |
|---|---|
| 1-1-80 | 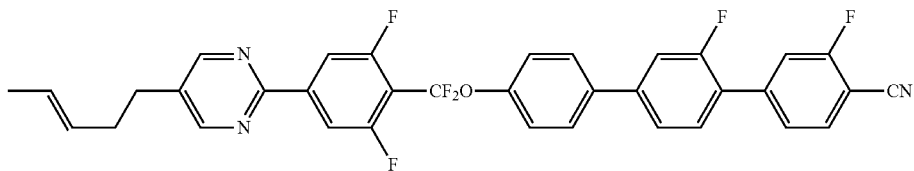 |
| 1-1-81 | 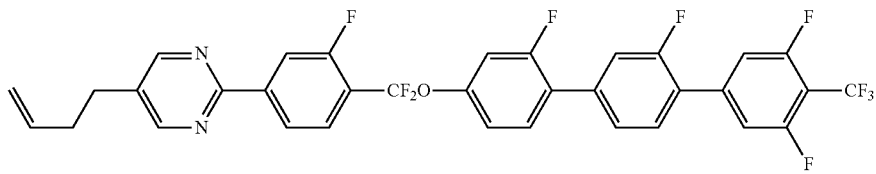 |
| 1-1-82 | 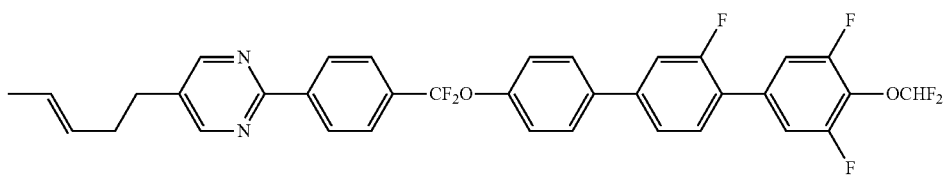 |
| 1-1-83 | 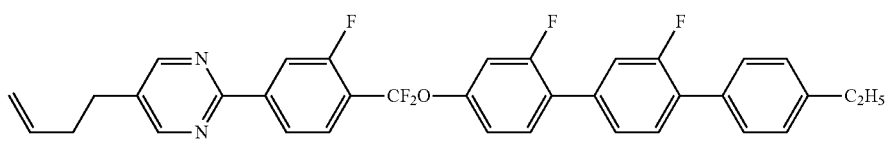 |
| 1-1-84 | 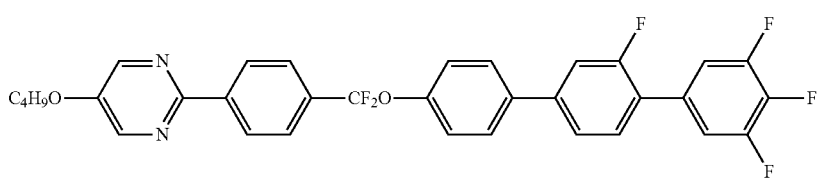 |
| 1-1-85 | 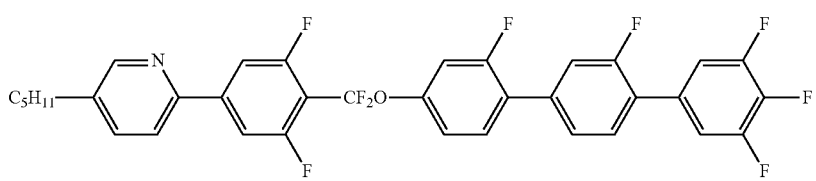 |
| 1-1-86 | 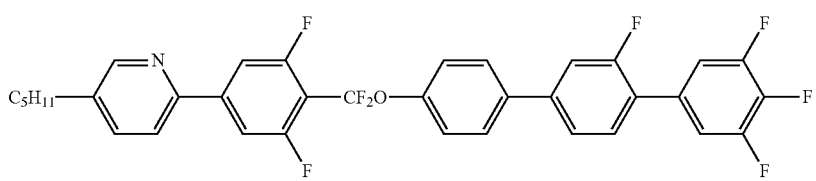 |
| 1-1-87 | 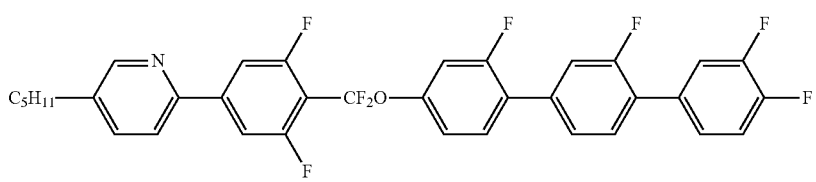 |
| 1-1-88 | 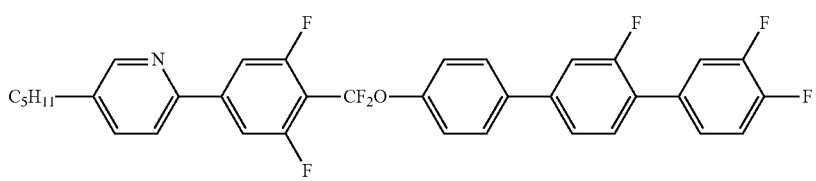 |

-continued
| No. | |
|---|---|
| 1-1-89 | 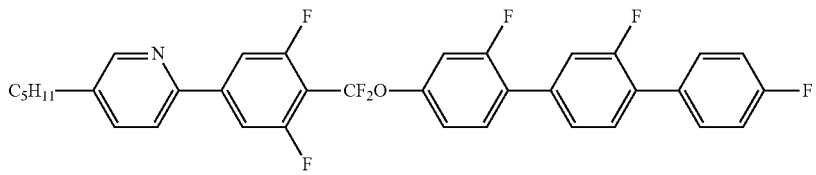 |
| 1-1-90 | 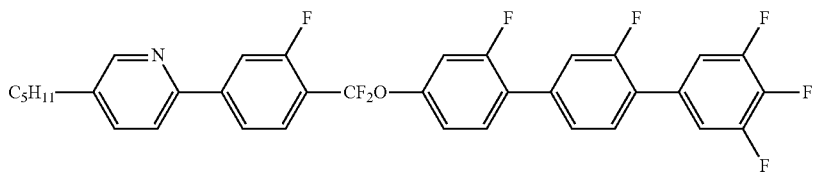 |
| 1-1-91 | 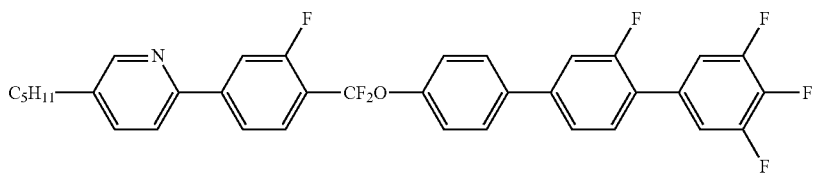 |
| 1-1-92 | 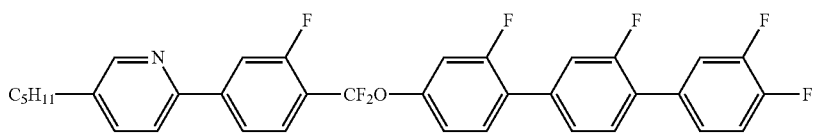 |
| 1-1-93 | 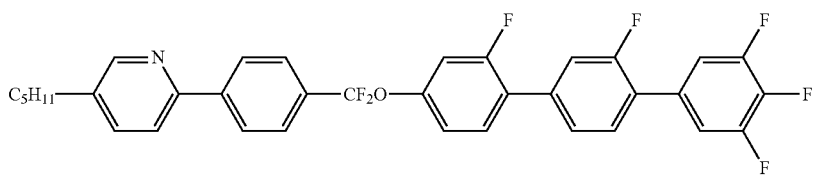 |
| 1-1-94 | 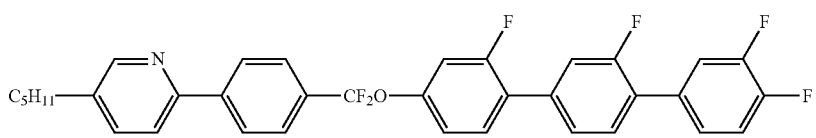 |
| 1-1-95 | 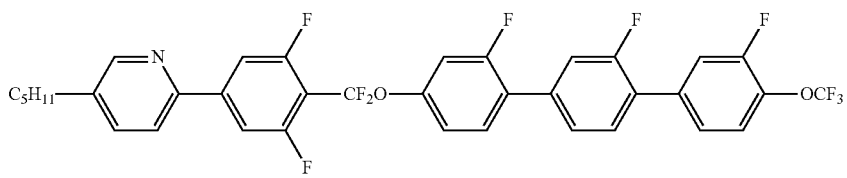 |
| 1-1-96 | 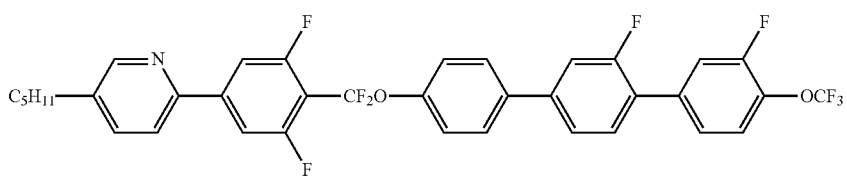 |
| 1-1-97 | 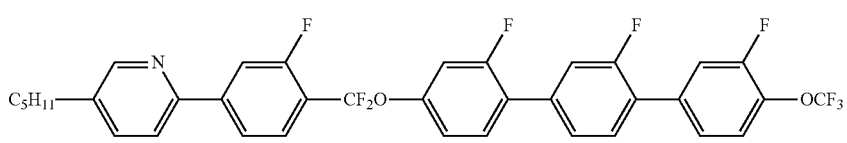 |

-continued
| No. | |
|---|---|
| 1-1-98 | 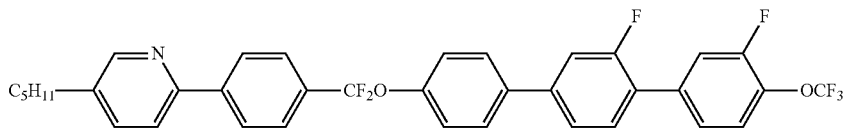 |
| 1-1-99 | 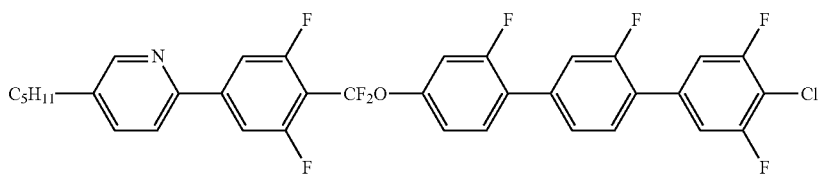 |
| 1-1-100 | 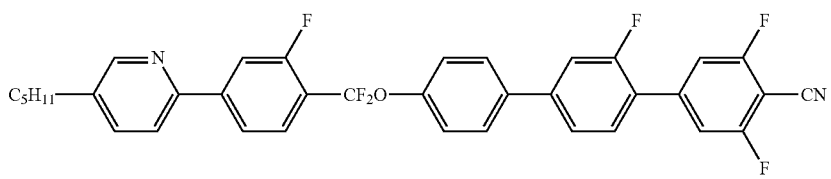 |
| 1-1-101 | 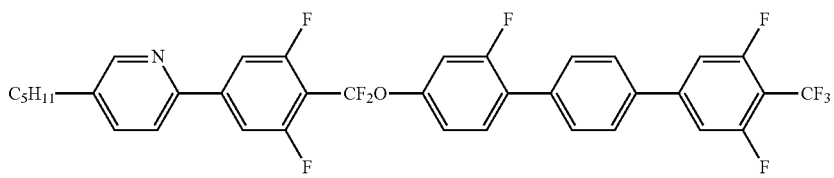 |
| 1-1-102 | 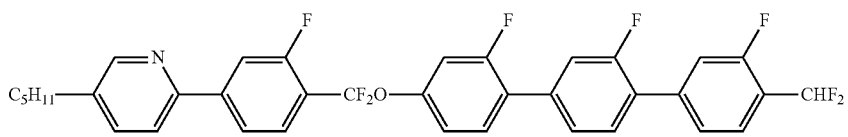 |
| 1-1-103 | 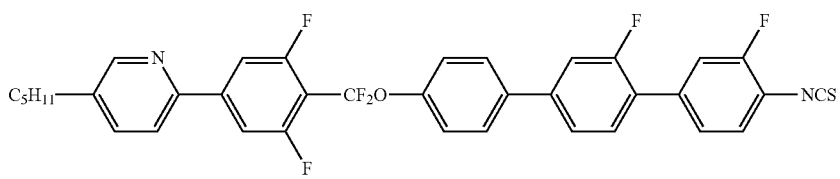 |
| 1-1-104 | 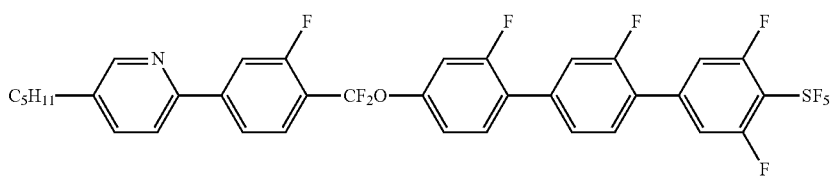 |
| 1-1-105 | 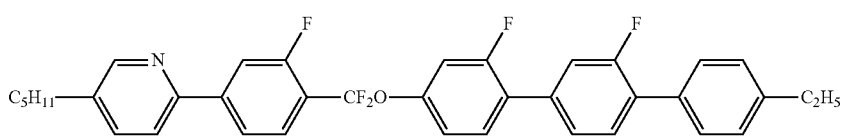 |
| 1-1-106 | 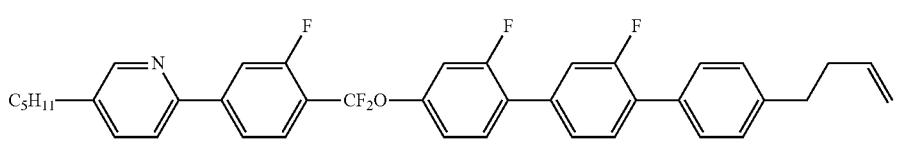 |
| 1-1-107 | 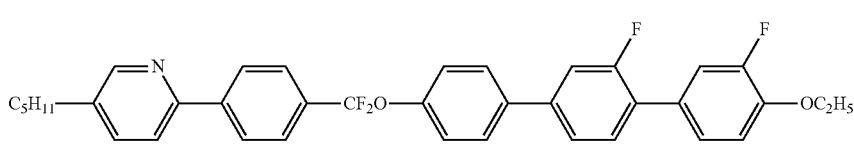 |

| No. | |
|---|---|
| 1-1-108 | 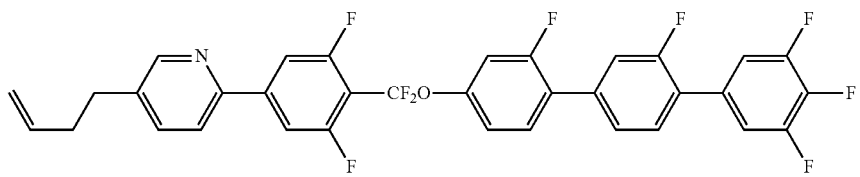 |
| 1-1-109 | 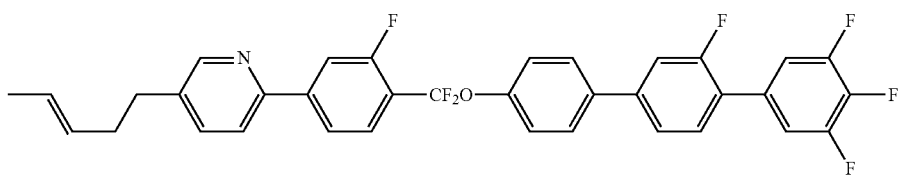 |
| 1-1-110 | 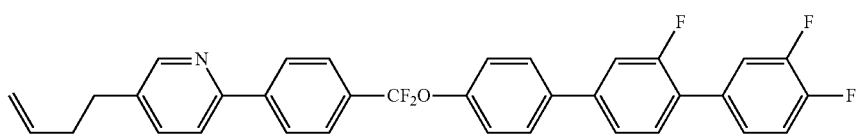 |
| 1-1-111 | 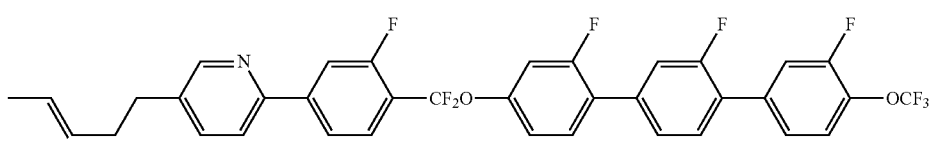 |
| 1-1-112 | 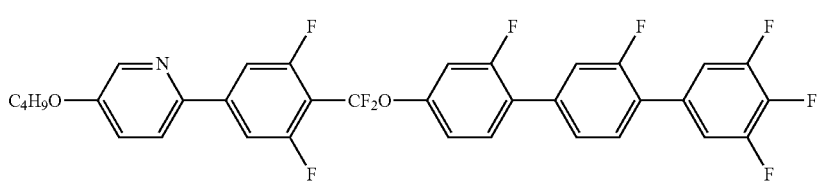 |
| 1-1-113 | 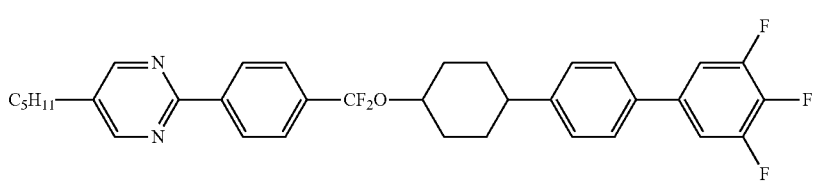 |
| 1-1-114 | 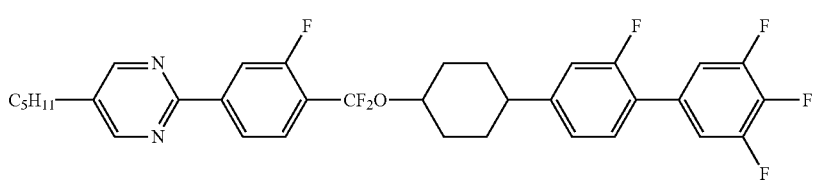 |
| 1-1-115 | 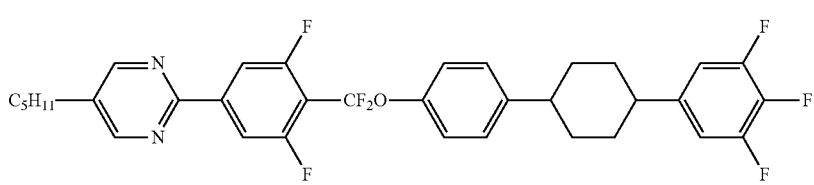 |
| 1-1-116 | 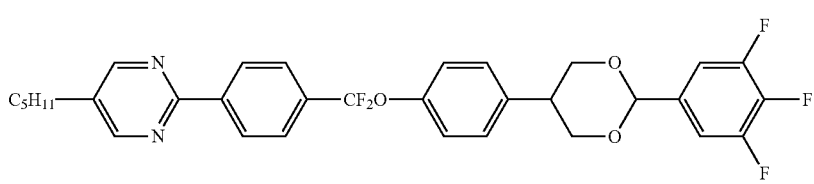 |

| No. | |
|---|---|
| 1-1-117 | 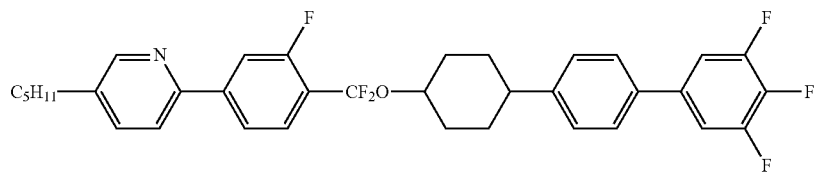 |
| 1-1-118 | 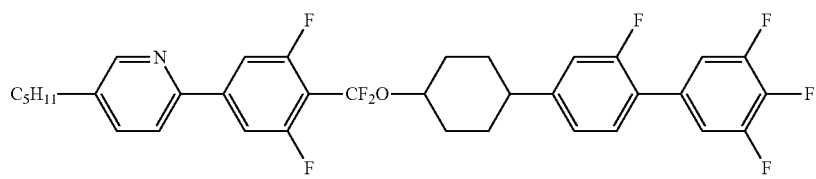 |
| 1-1-119 | 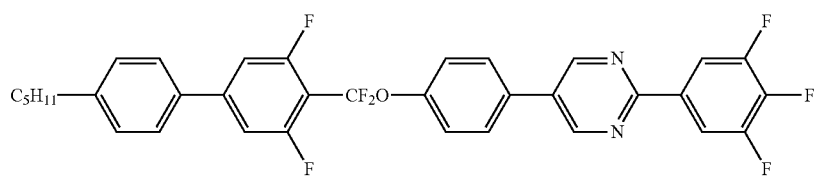 |
| 1-1-120 | 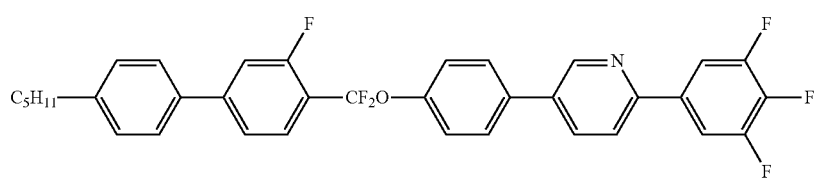 |
| 1-1-121 | 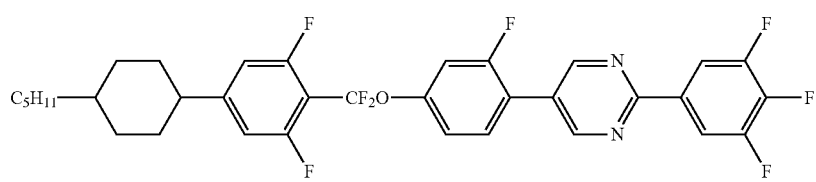 |
| 1-1-122 | 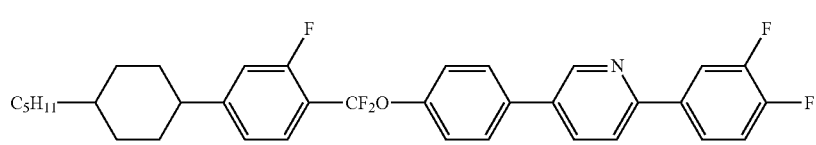 |
| 1-1-123 | 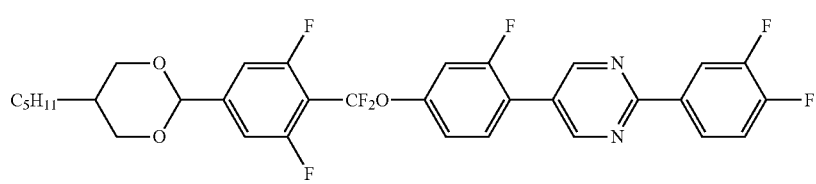 |
| 1-1-124 | 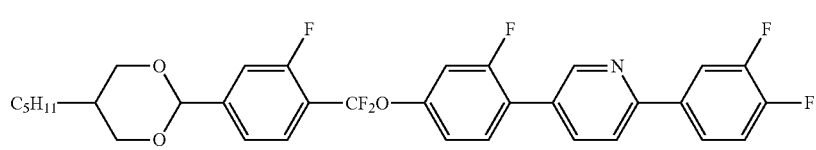 |
| 1-1-125 | 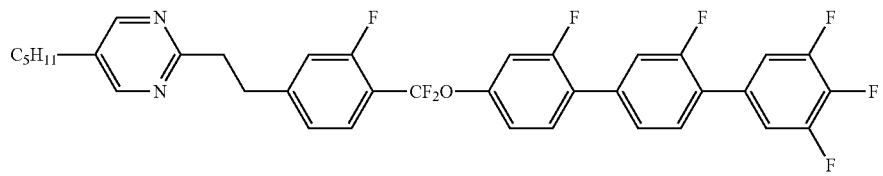 |

-continued
| No. | |
|---|---|
| 1-1-126 | 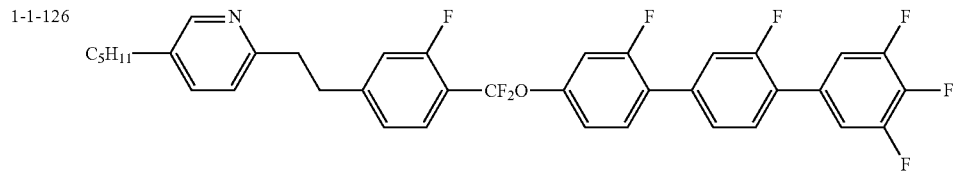 |
| 1-1-127 | 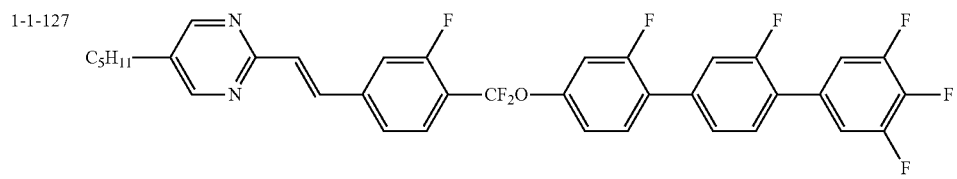 |
| 1-1-128 | 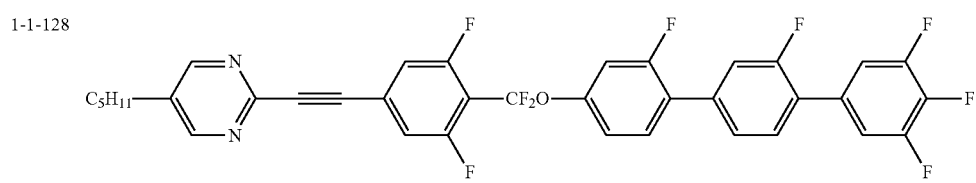 |
| 1-1-129 | 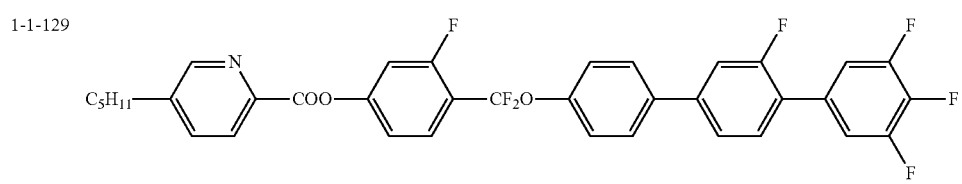 |
| 1-1-130 | 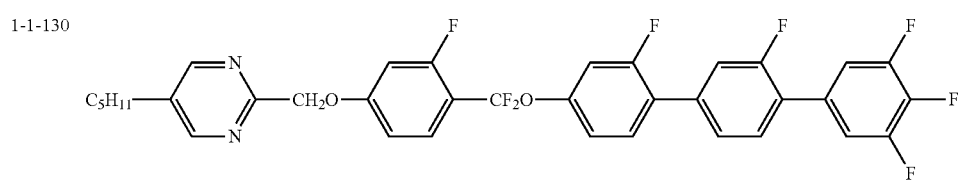 |
| 1-1-131 | 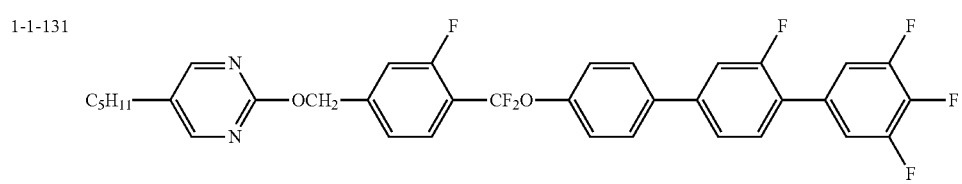 |
| 1-1-132 | 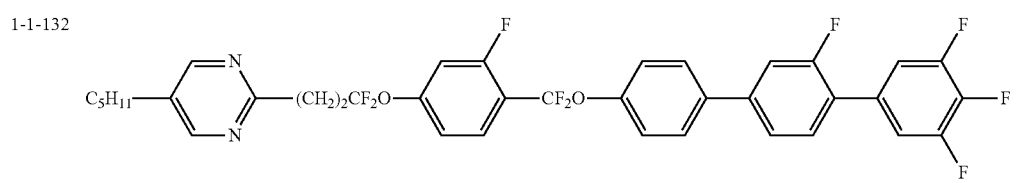 |
| 1-1-133 | 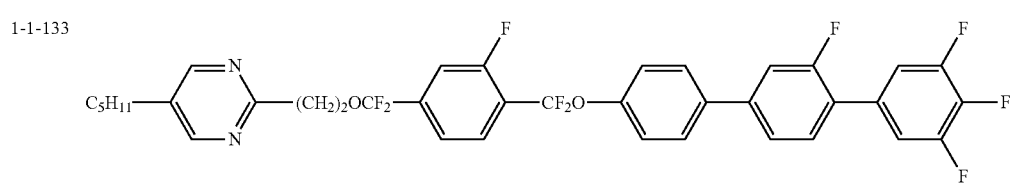 |

-continued
| No. |
|---|
| 1-1-134 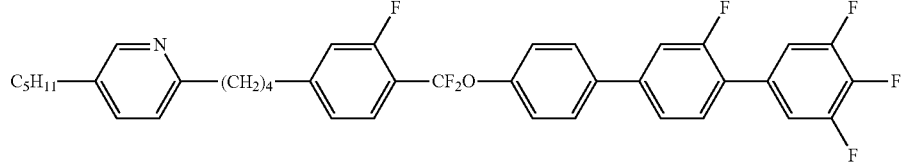 |
| 1-1-135 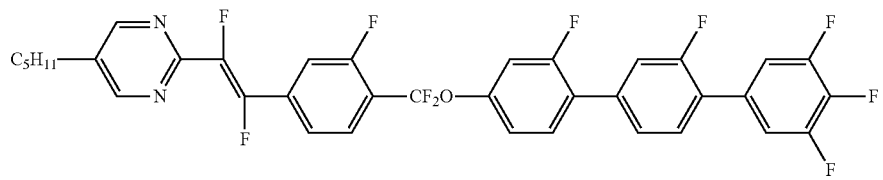 |
| 1-1-136 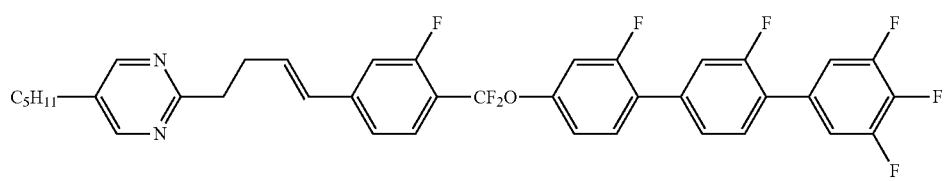 |
| 1-2-1 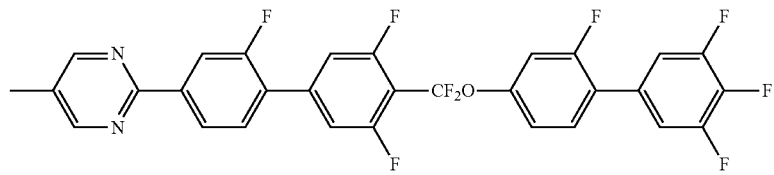 |
| 1-2-2 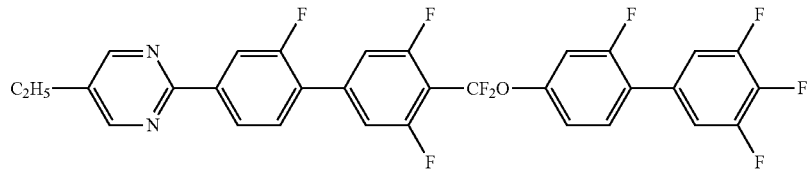 |
| 1-2-3 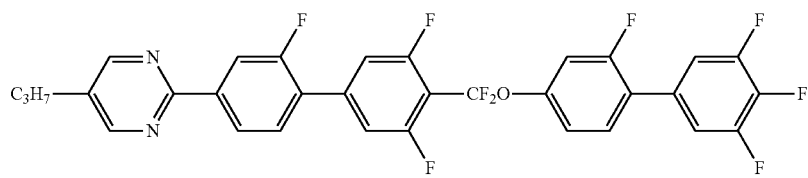 |
| 1-2-4 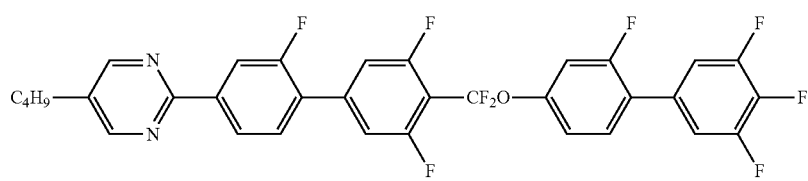 |
| 1-2-5 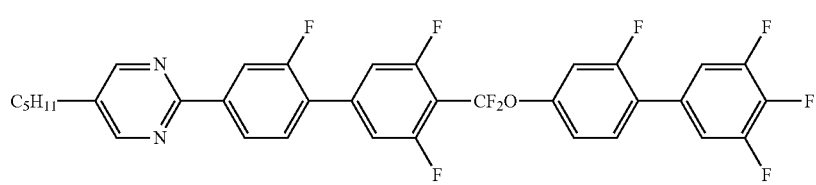 |
$T_{NI} = 154°$ C., $\Delta n = 0.237$, $\Delta \varepsilon = 56.6$ -continued
| No. | |
|---|---|
| 1-2-6 | 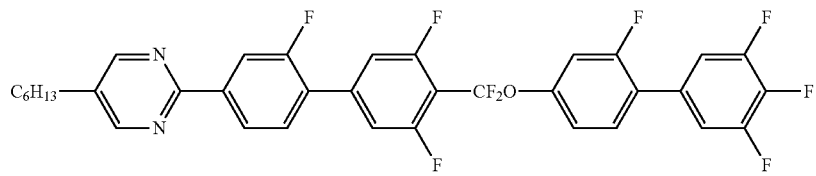 |
| 1-2-7 | 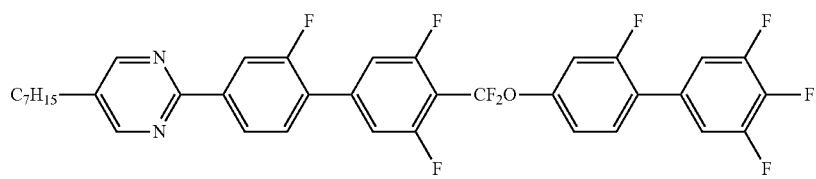 |
| 1-2-8 | 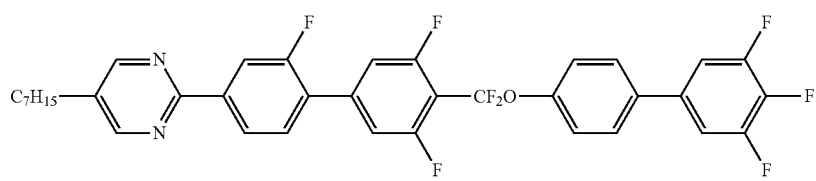 |
| 1-2-9 | 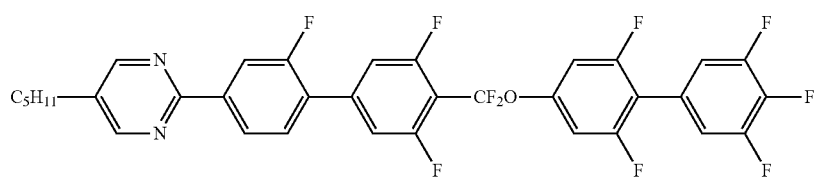 |
| 1-2-10 | 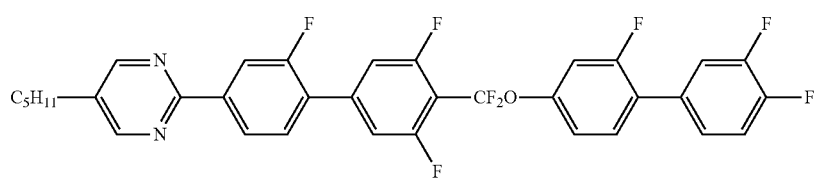 |
| 1-2-11 | 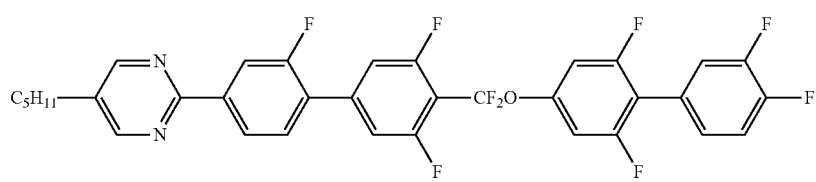 |
| 1-2-12 | 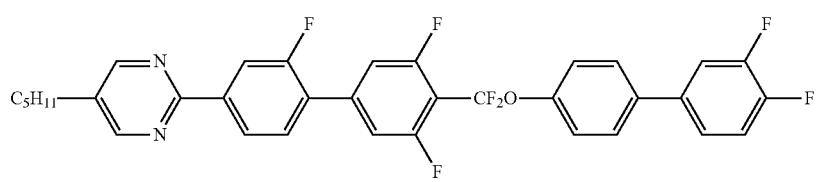 |
| 1-2-13 | 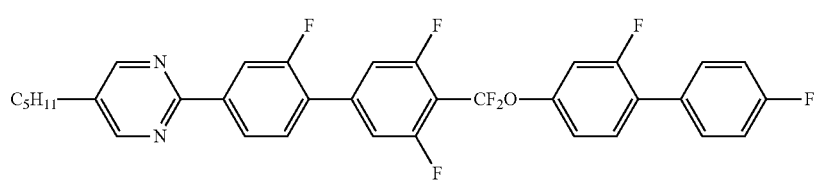 |

-continued
| No. | |
|---|---|
| 1-2-14 | 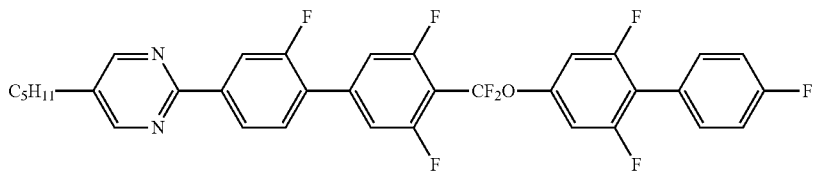 |
| 1-2-15 | 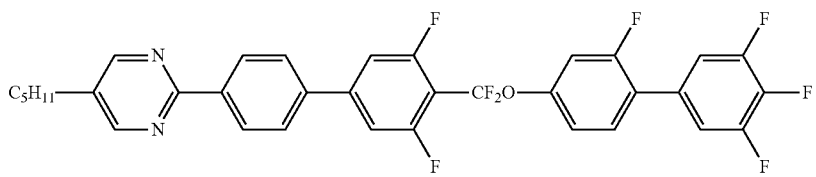 |
| 1-2-16 | 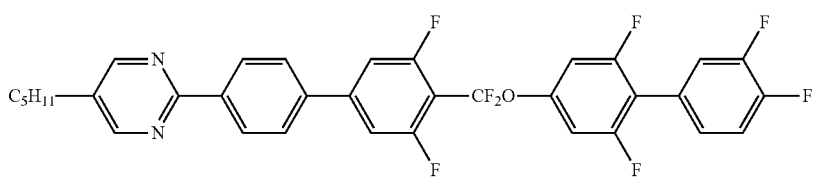 |
| 1-2-17 | 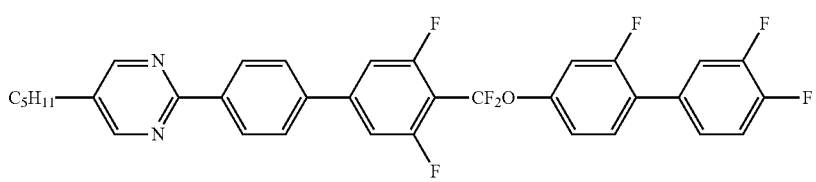 |
| 1-2-18 | 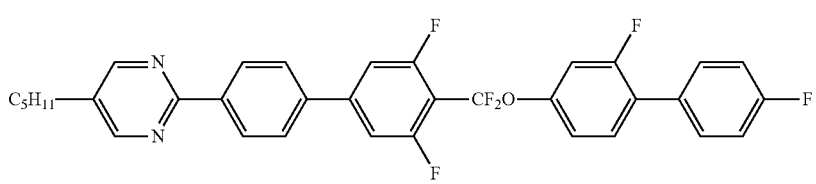 |
| 1-2-19 | 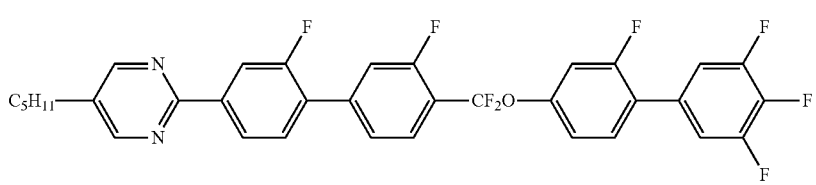 |
| 1-2-20 | 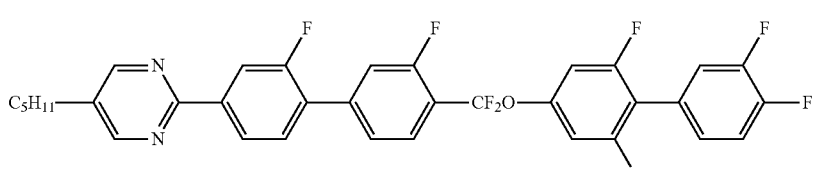 |
| 1-2-21 | 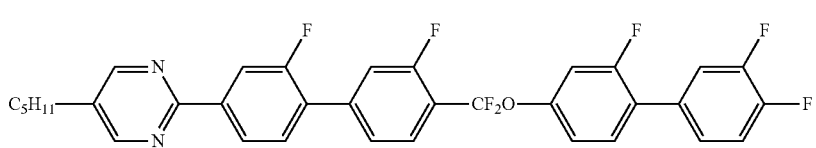 |
| 1-2-22 | 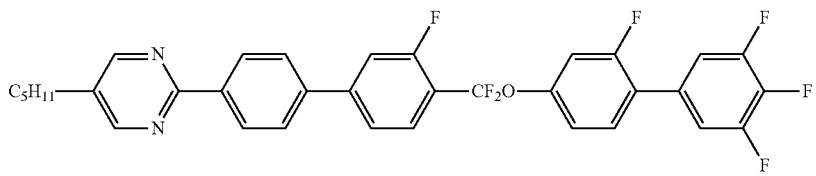 |

-continued
| No. | |
|---|---|
| 1-2-23 | 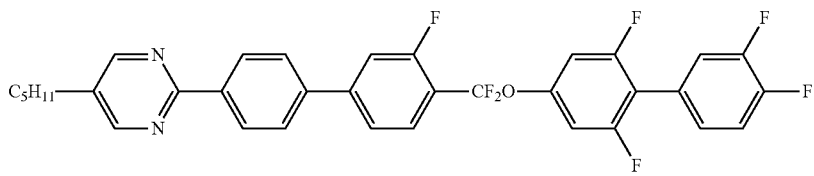 |
| 1-2-24 | 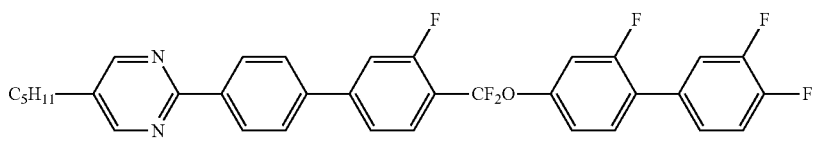 |
| 1-2-25 | 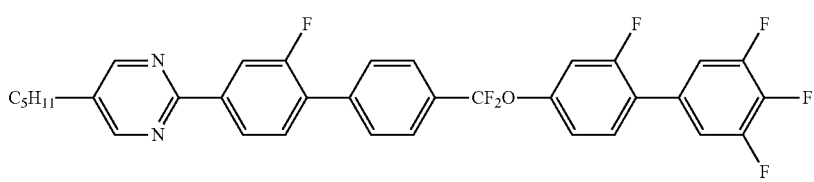 |
| 1-2-26 | 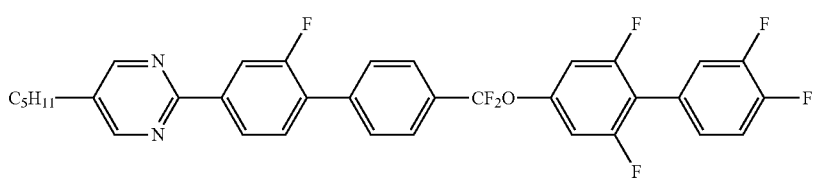 |
| 1-2-27 | 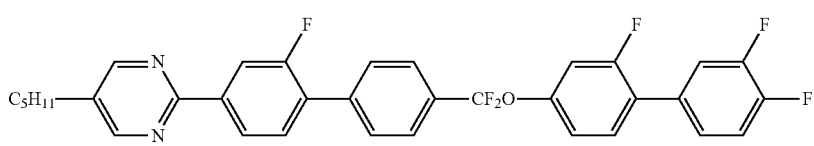 |
| 1-2-28 | 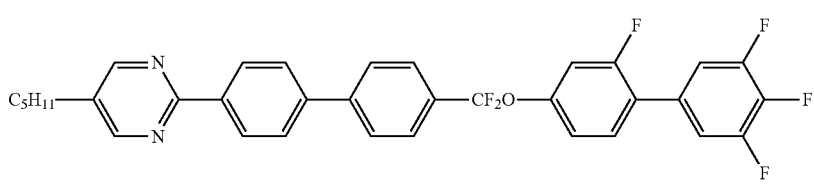 |
| 1-2-29 | 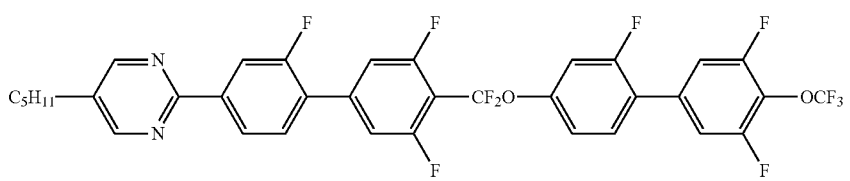 |
| 1-2-30 | 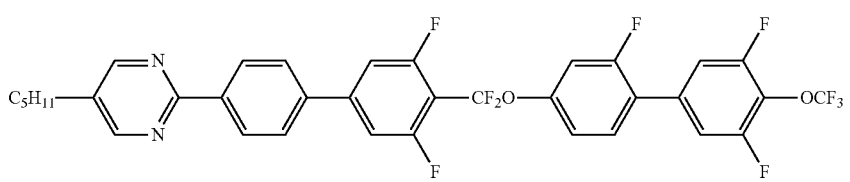 |
| 1-2-31 | 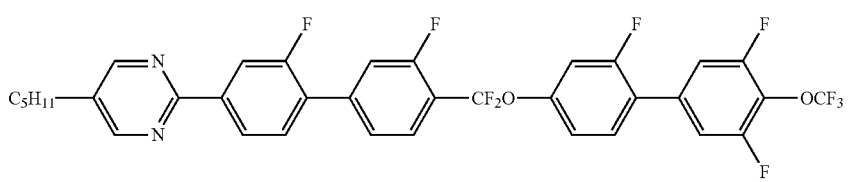 |

| No. | |
|---|---|
| 1-2-32 | 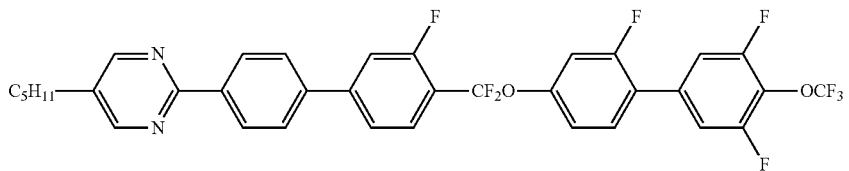 |
| 1-2-33 | 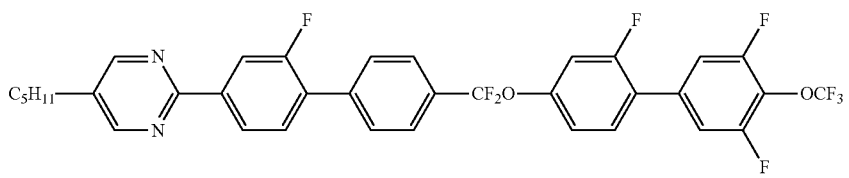 |
| 1-2-34 | 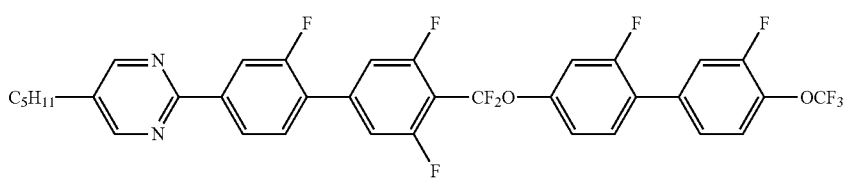 |
| 1-2-35 | 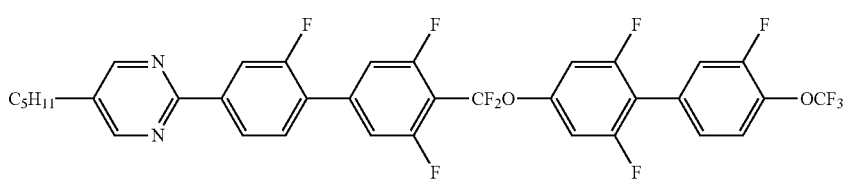 |
| 1-2-36 | 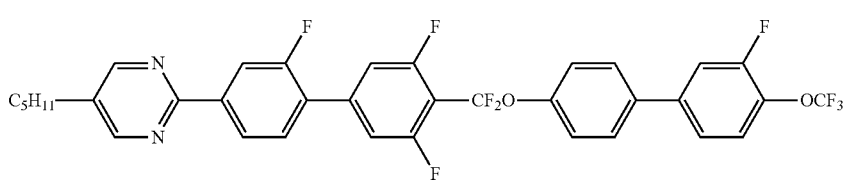 |
| 1-2-37 | 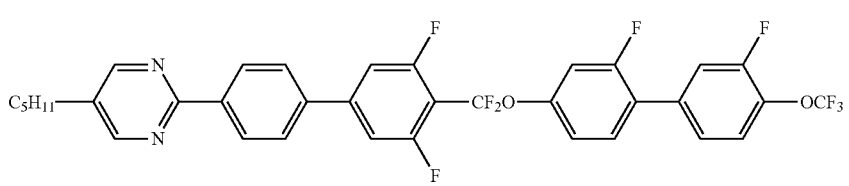 |
| 1-2-38 | 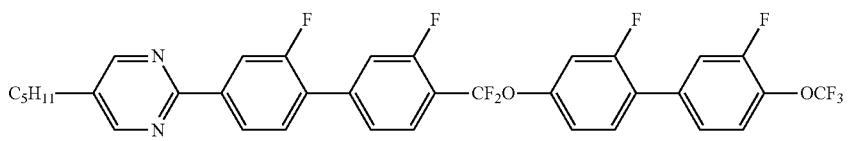 |
| 1-2-39 | 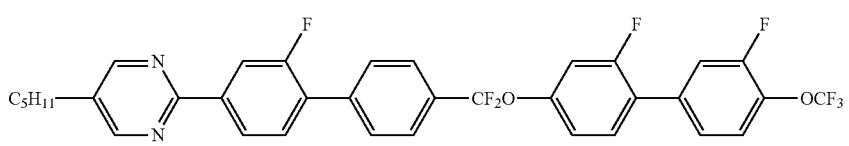 |
| 1-2-40 | 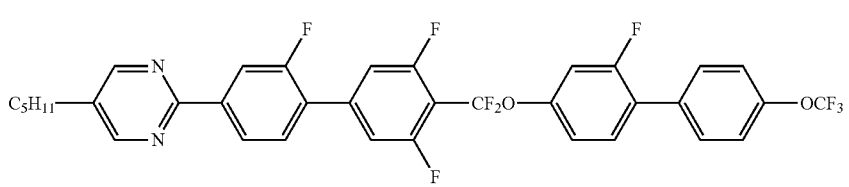 |

| No. |
|---|
| 1-2-41 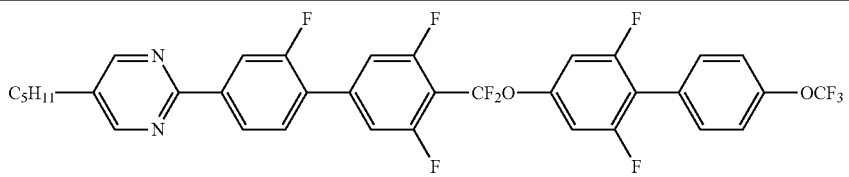 |
| 1-2-42 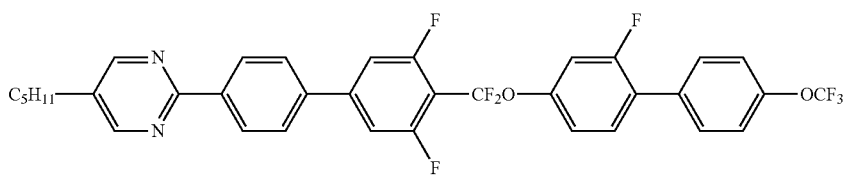 |
| 1-2-43 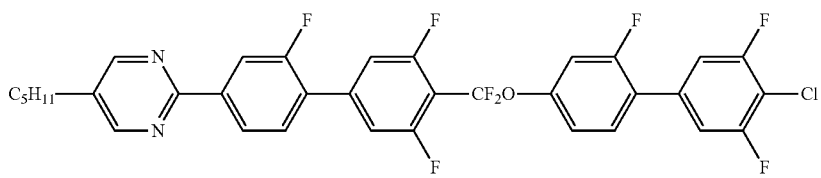 |
| 1-2-44 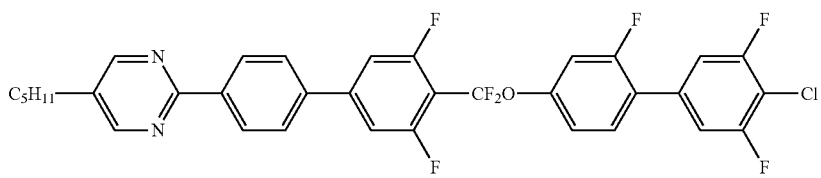 |
| 1-2-45 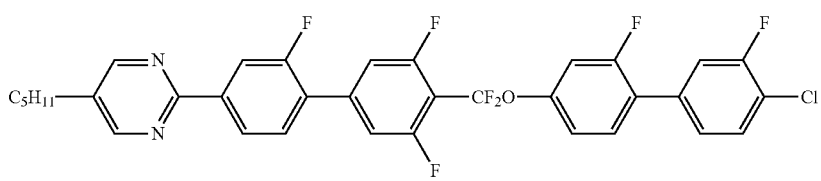 |
| 1-2-46 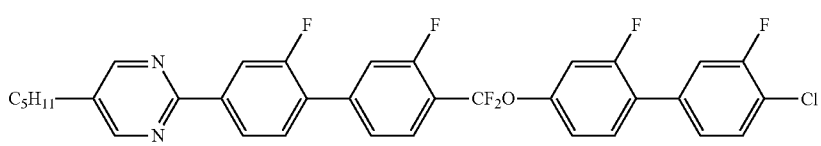 |
| 1-2-47 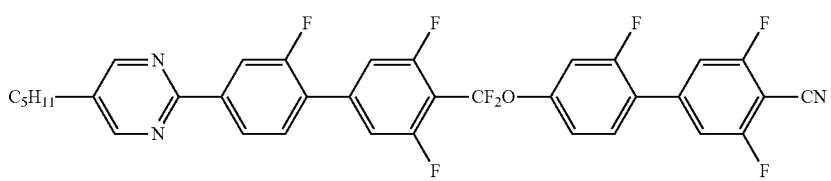 |
| 1-2-48 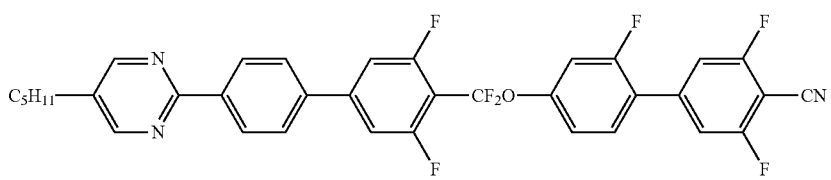 |
| 1-2-49 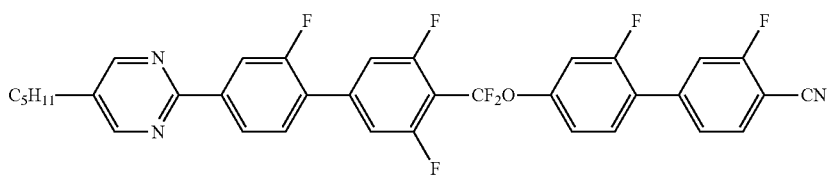 |

| No. | |
|---|---|
| 1-2-50 | 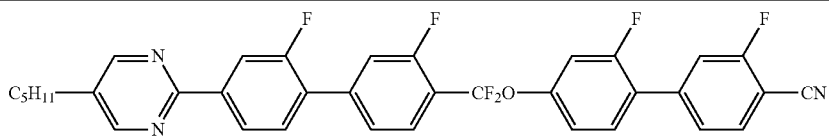 |
| 1-2-51 | 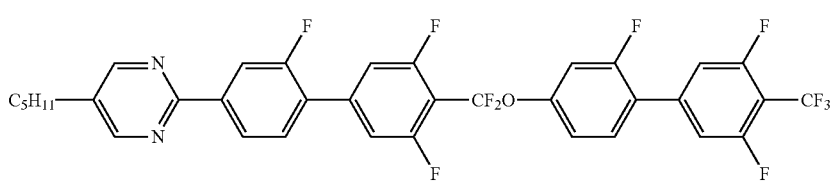 |
| 1-2-52 | 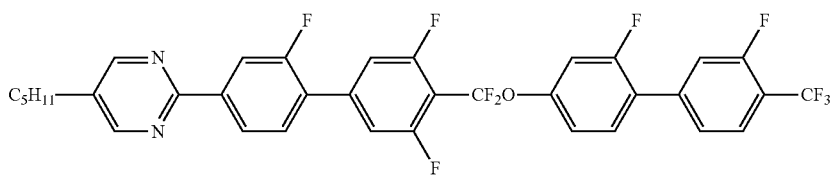 |
| 1-2-53 | 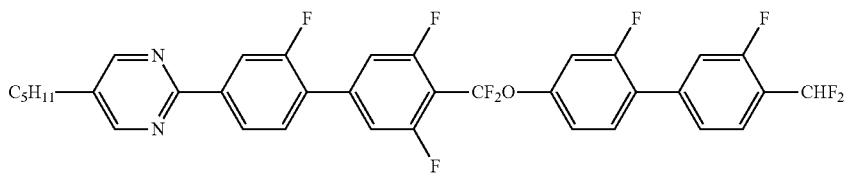 |
| 1-2-54 | 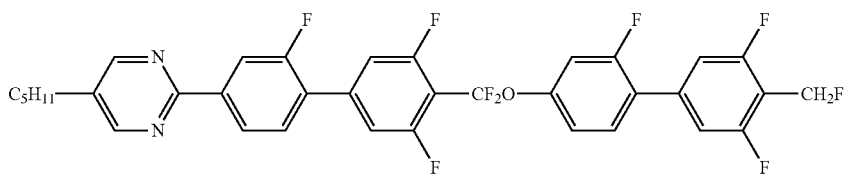 |
| 1-2-55 | 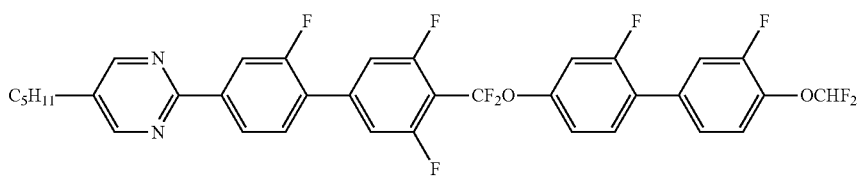 |
| 1-2-56 | 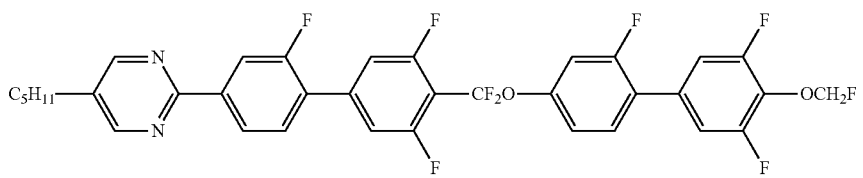 |
| 1-2-57 | 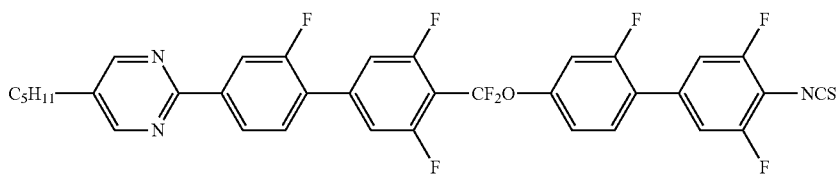 |
| 1-2-58 | 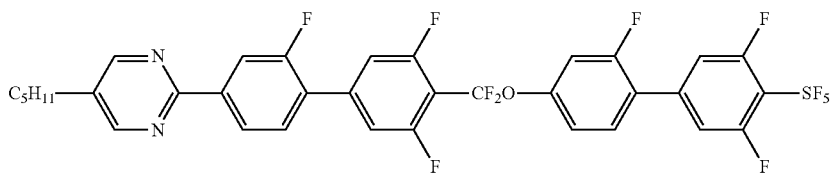 |

| No. | |
|---|---|
| 1-2-59 | 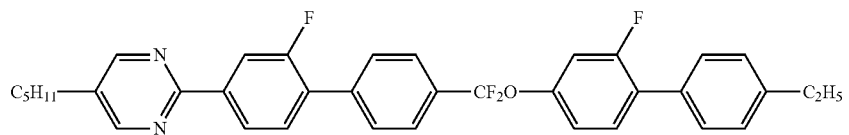 |
| 1-2-60 | 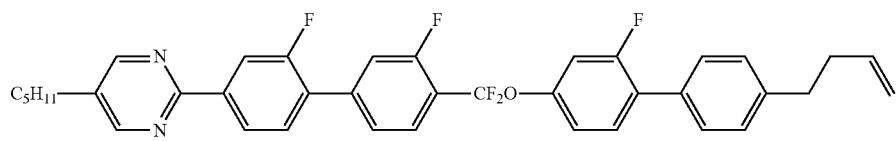 |
| 1-2-61 | 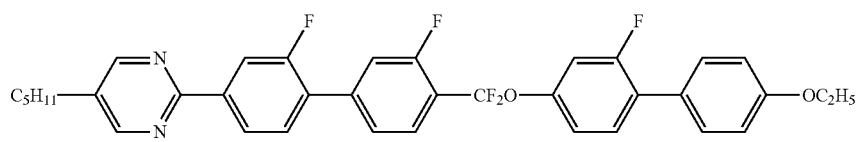 |
| 1-2-62 | 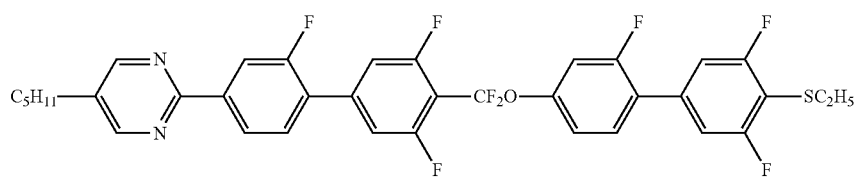 |
| 1-2-63 | 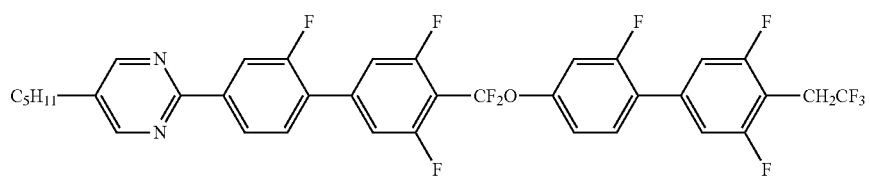 |
| 1-2-64 | 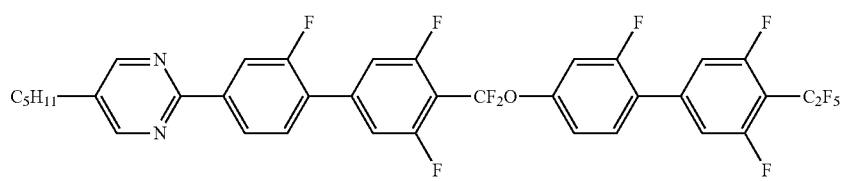 |
| 1-2-65 | 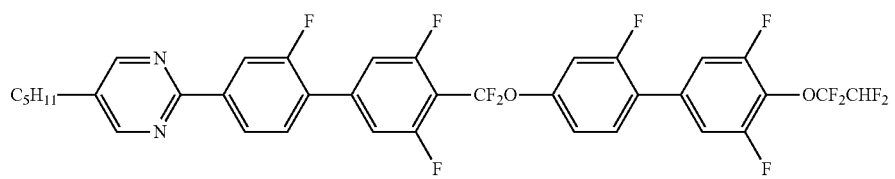 |
| 1-2-66 | 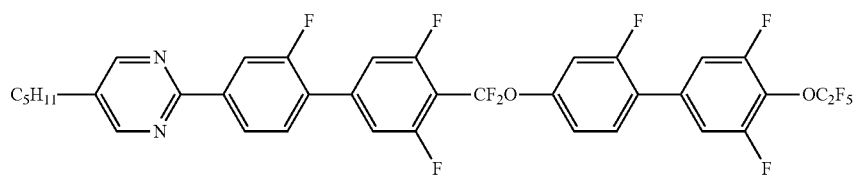 |
| 1-2-67 | 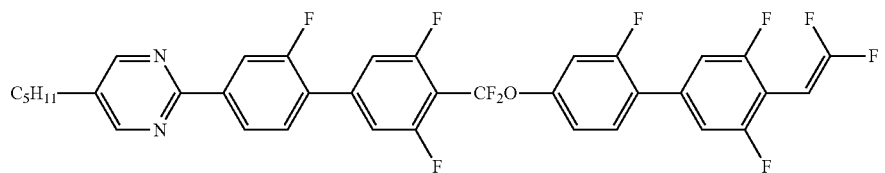 |

-continued
| No. | |
|---|---|
| 1-2-68 | 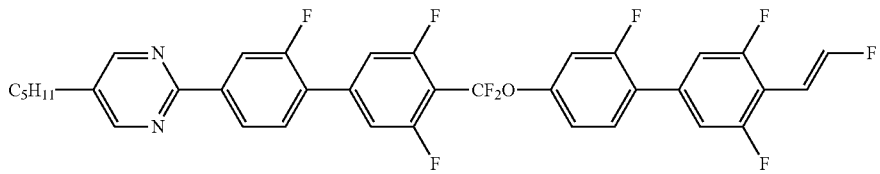 |
| 1-2-69 | 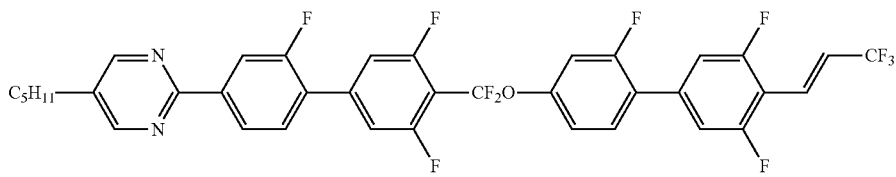 |
| 1-2-70 | 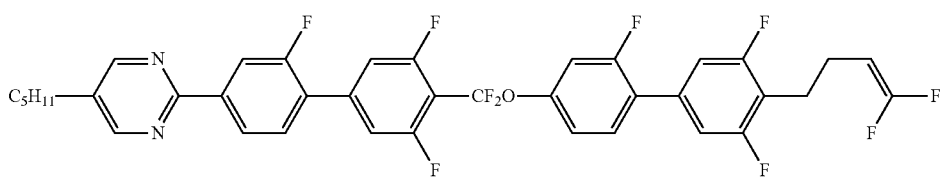 |
| 1-2-71 | 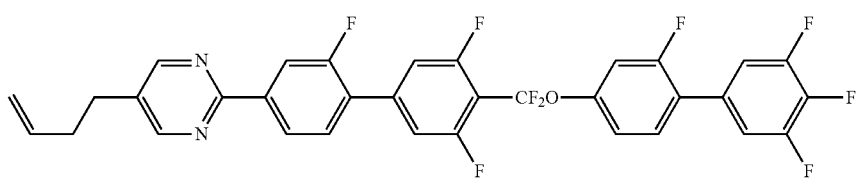 |
| 1-2-72 | 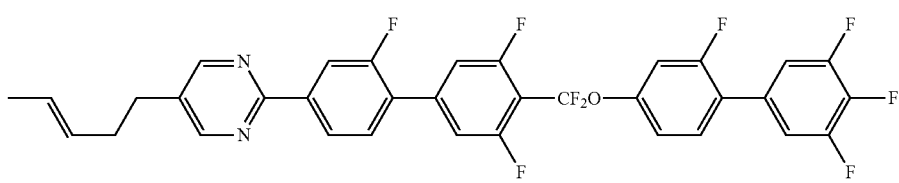 |
| 1-2-73 | 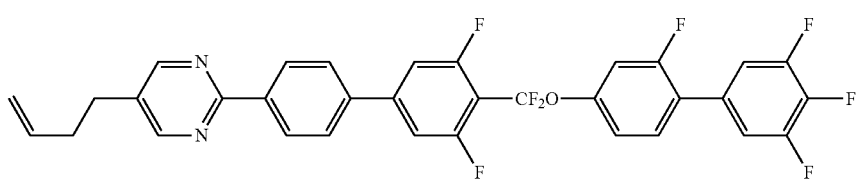 |
| 1-2-74 | 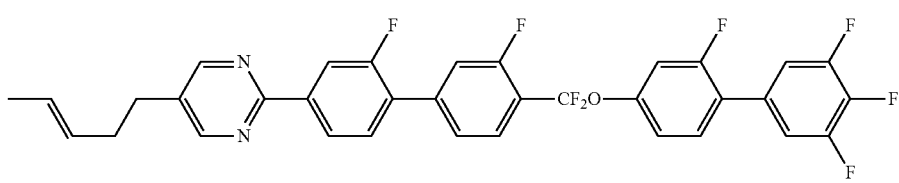 |
| 1-2-75 | 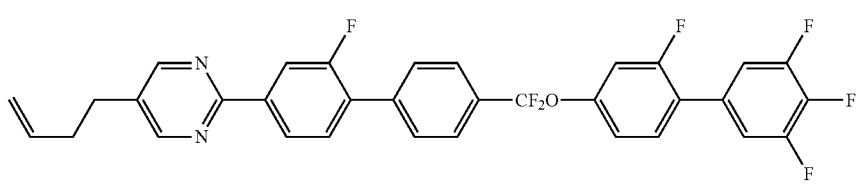 |

| No. | |
|---|---|
| 1-2-76 | 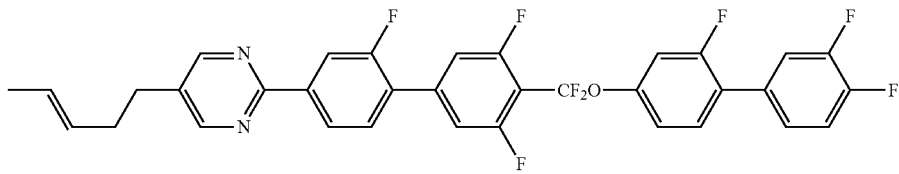 |
| 1-2-77 | 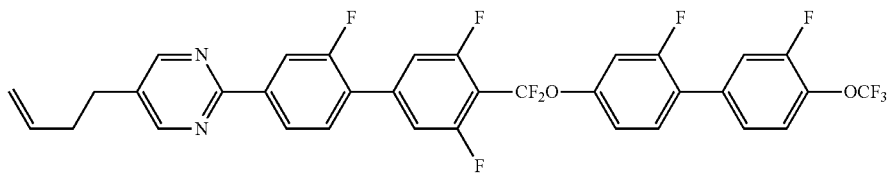 |
| 1-2-78 | 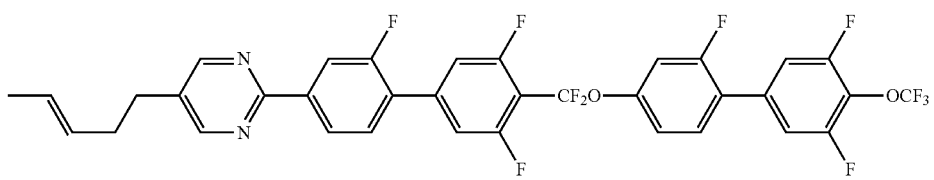 |
| 1-2-79 | 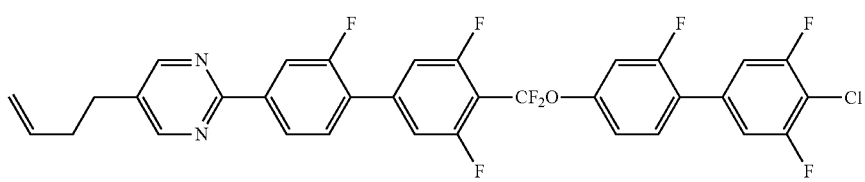 |
| 1-2-80 | 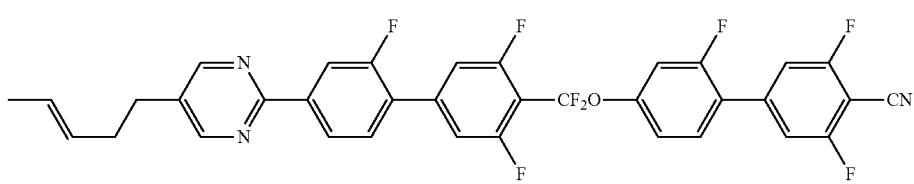 |
| 1-2-81 | 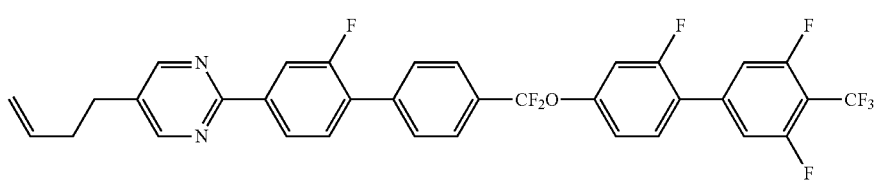 |
| 1-2-82 | 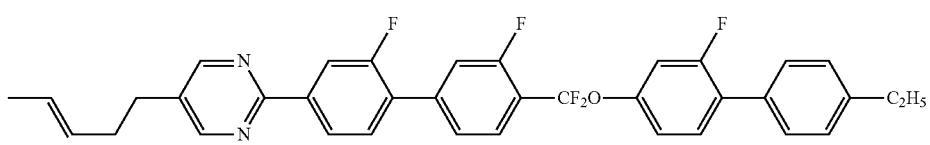 |
| 1-2-83 | 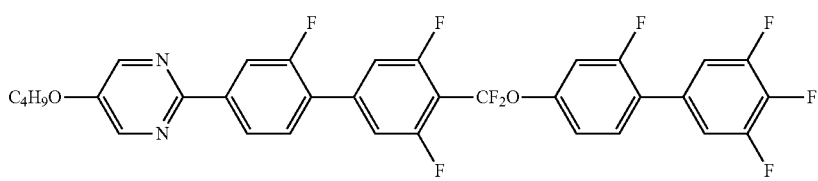 |
| 1-2-84 | 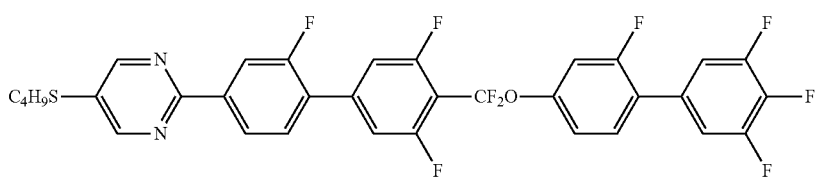 |

| No. | |
|---|---|
| 1-2-85 | 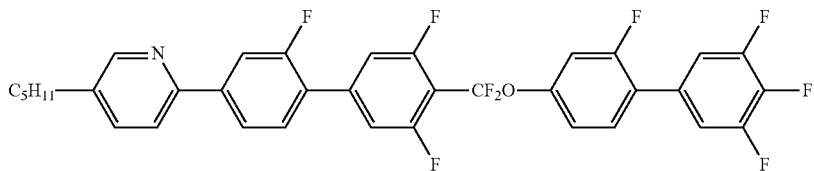<br>$T_{NI}$ = 148° C., Δn = 0.237, Δε = 48.6 |
| 1-2-86 | 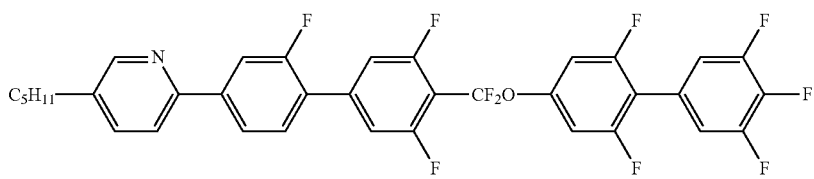 |
| 1-2-87 | 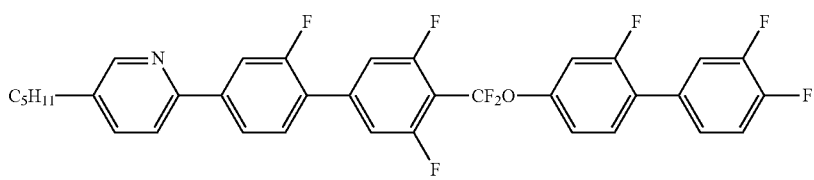 |
| 1-2-88 | 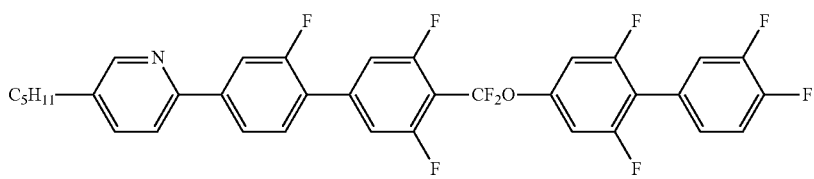 |
| 1-2-89 | 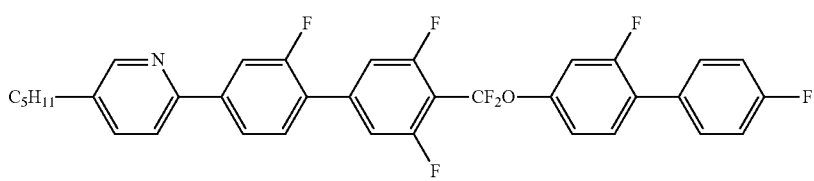 |
| 1-2-90 | 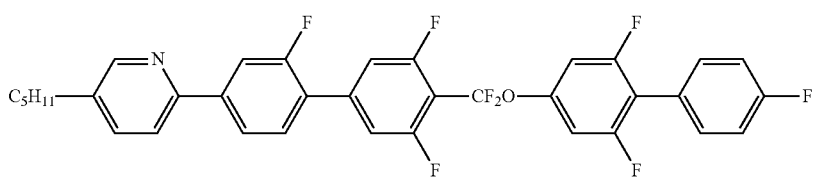 |
| 1-2-91 | 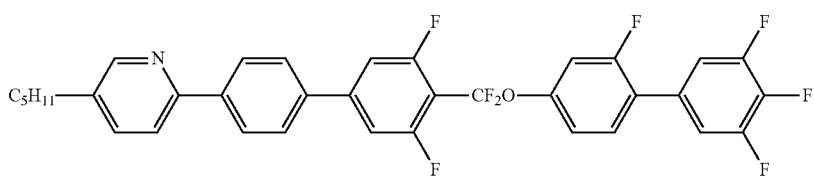 |
| 1-2-92 | 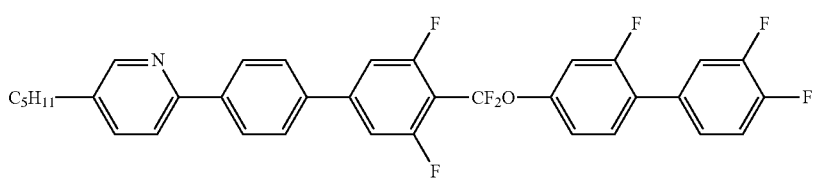 |

| No. | |
|---|---|
| 1-2-93 | 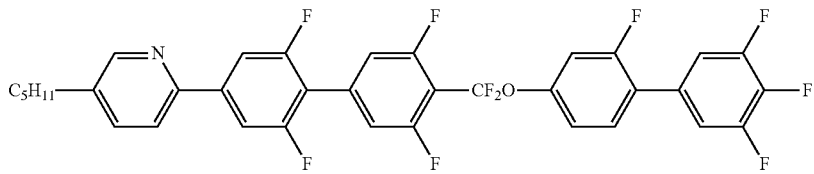 |
| 1-2-94 | 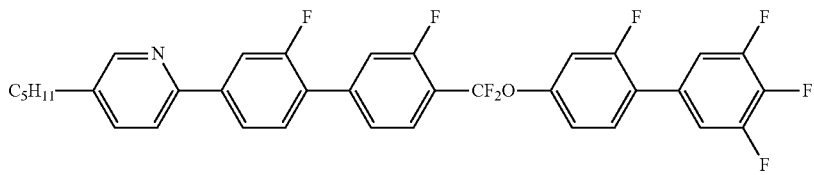 |
| 1-2-95 | 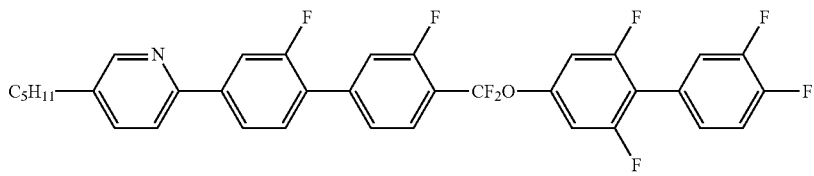 |
| 1-2-96 | 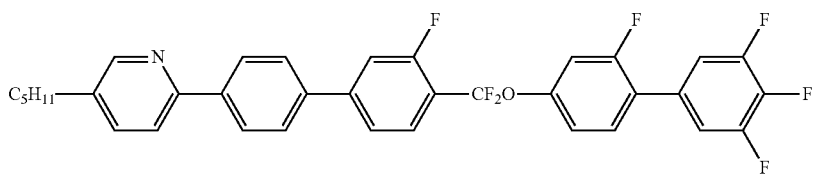 |
| 1-2-97 | 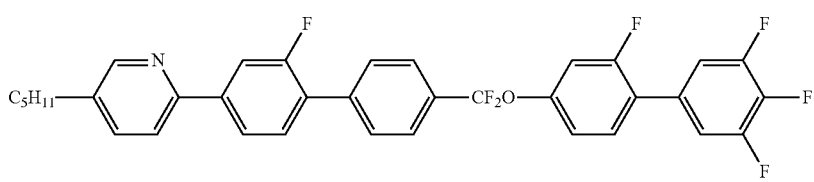 |
| 1-2-98 | 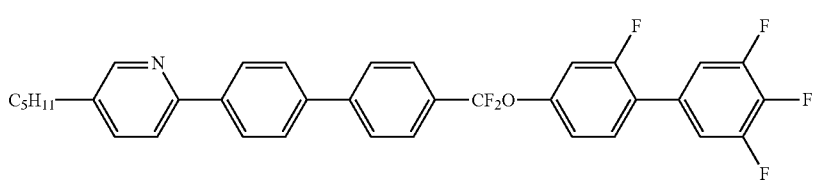 |
| 1-2-99 | 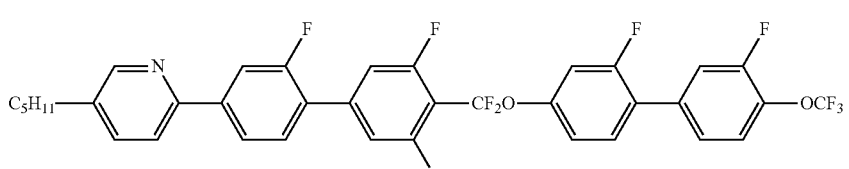 |
| 1-2-100 | 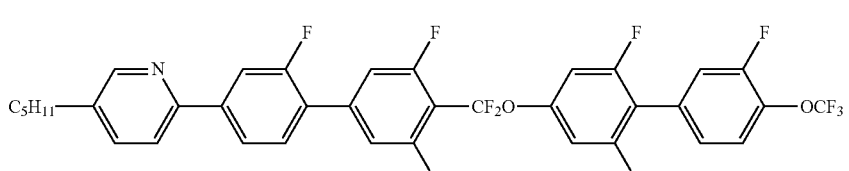 |

| No. | |
|---|---|
| 1-2-101 | 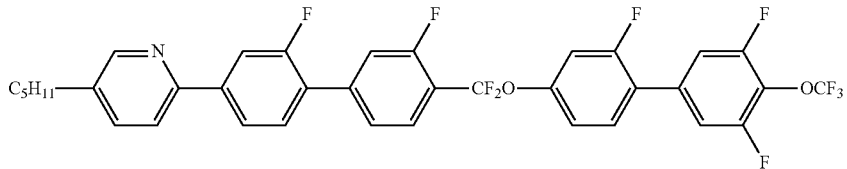 |
| 1-2-102 | 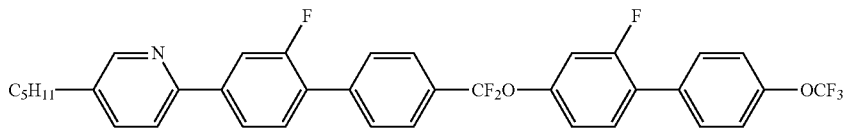 |
| 1-2-103 | 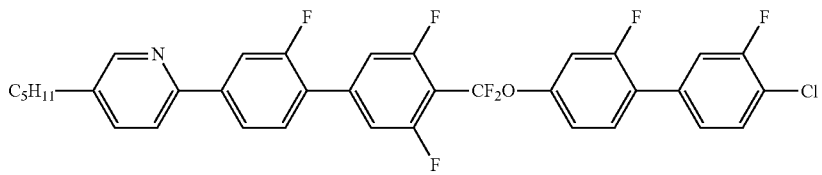 |
| 1-2-104 | 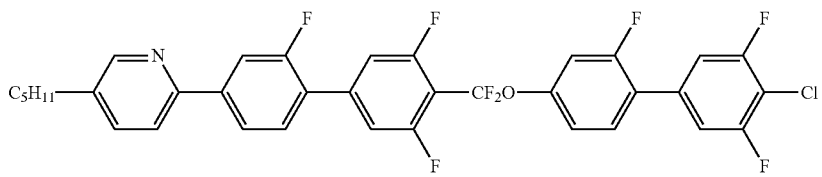 |
| 1-2-105 | 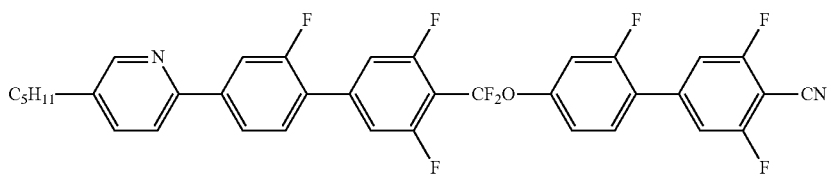 |
| 1-2-106 | 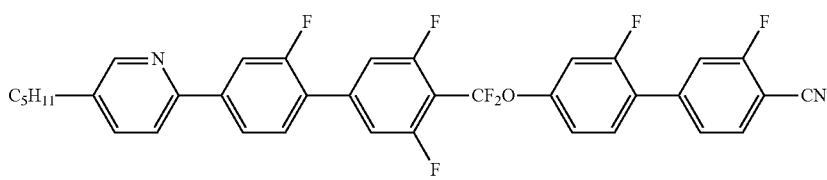 |
| 1-2-107 | 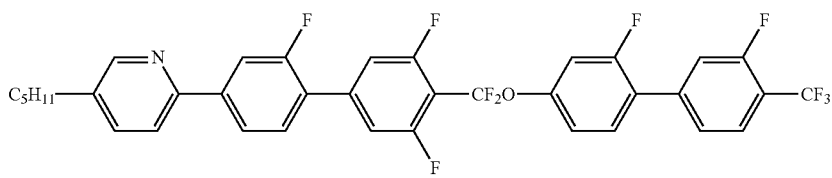 |
| 1-2-108 | 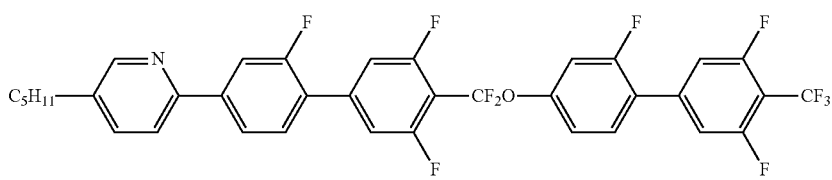 |
| 1-2-109 | 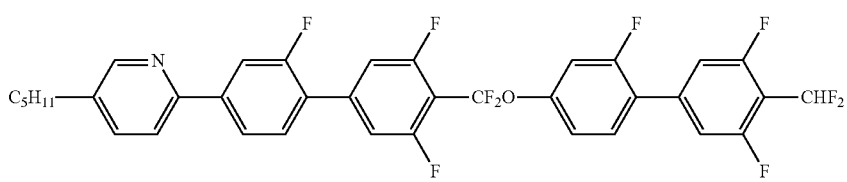 |

-continued
| No. | |
|---|---|
| 1-2-110 | 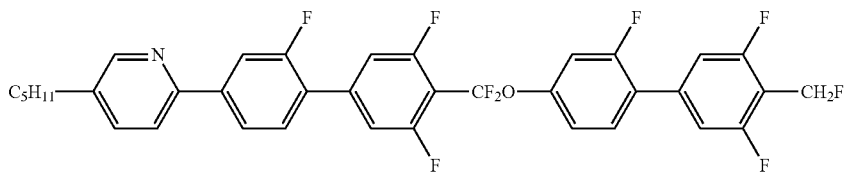 |
| 1-2-111 | 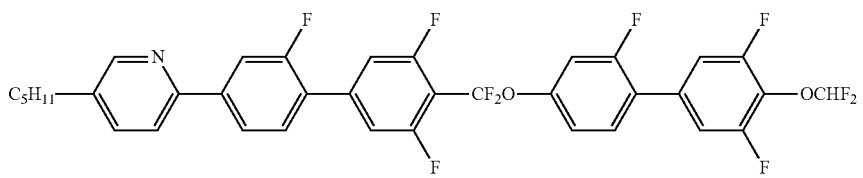 |
| 1-2-112 | 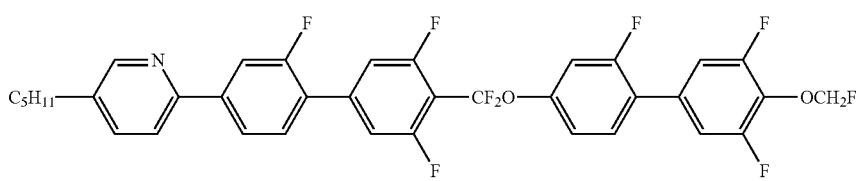 |
| 1-2-113 | 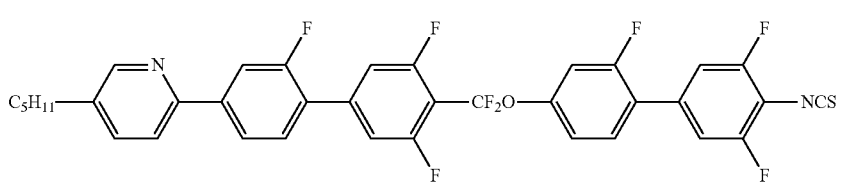 |
| 1-2-114 | 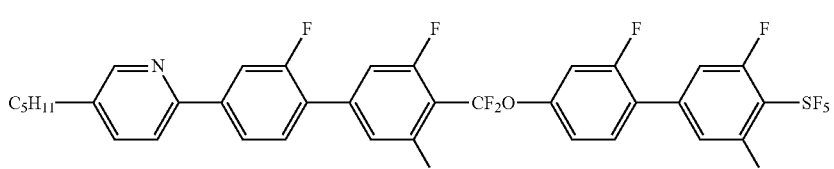 |
| 1-2-115 | 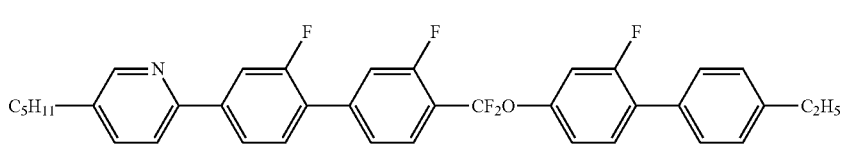 |
| 1-2-116 | 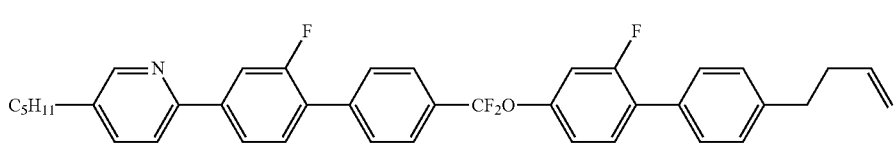 |
| 1-2-117 | 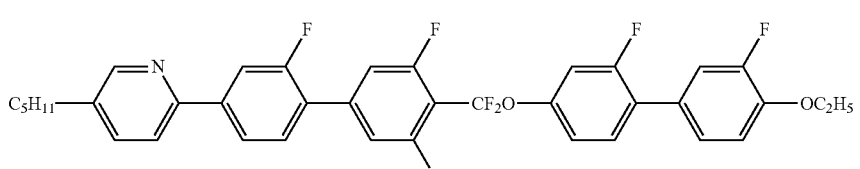 |
| 1-2-118 | 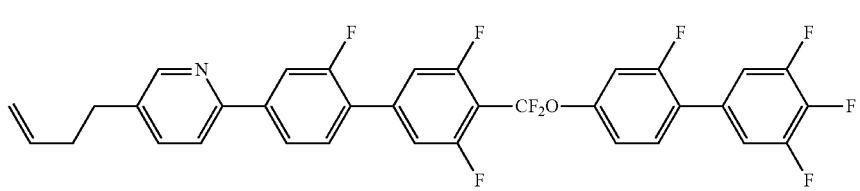 |

| No. | |
|---|---|
| 1-2-119 | 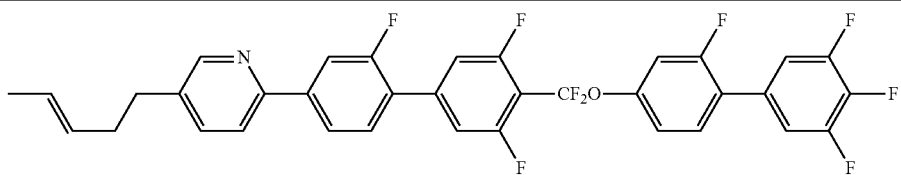 |
| 1-2-120 | 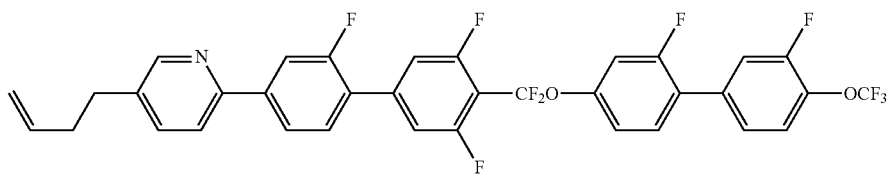 |
| 1-2-121 | 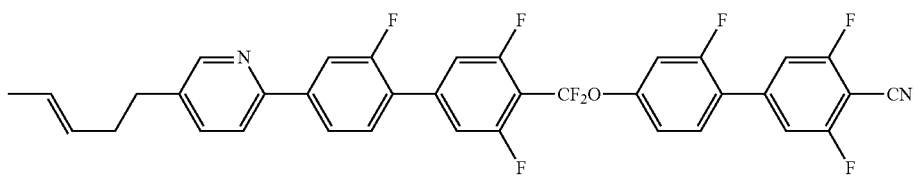 |
| 1-2-122 | 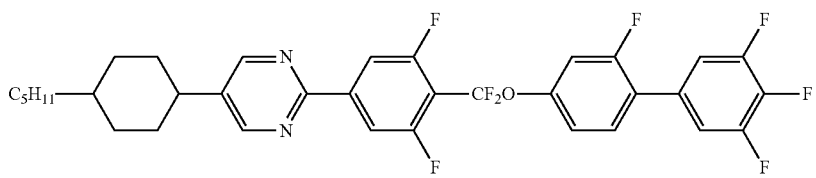 |
| 1-2-123 | 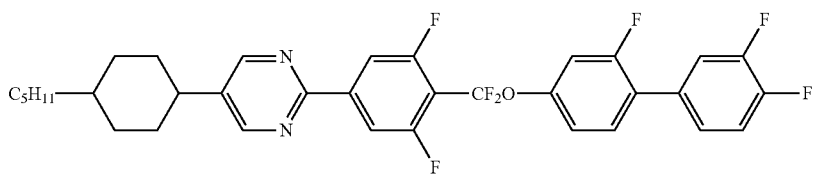 |
| 1-2-124 | 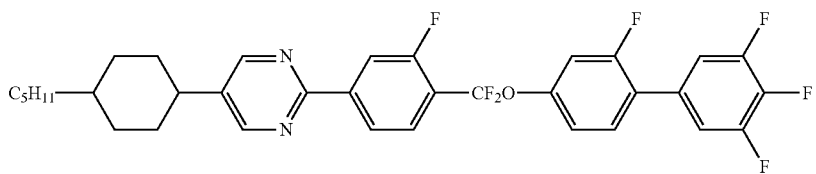 |
| 1-2-125 | 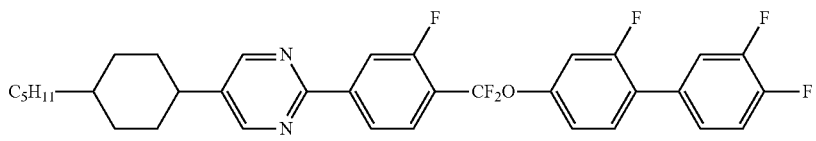 |
| 1-2-126 | 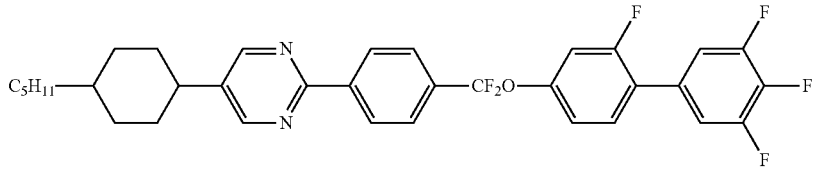 |
| 1-2-127 | 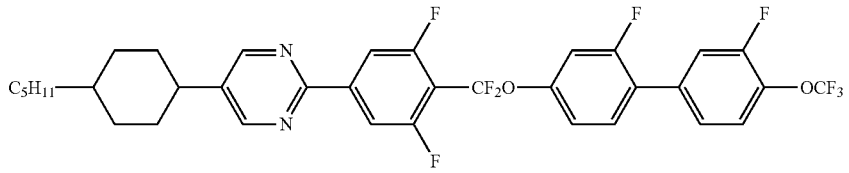 |

-continued
| No. | |
|---|---|
| 1-2-128 | 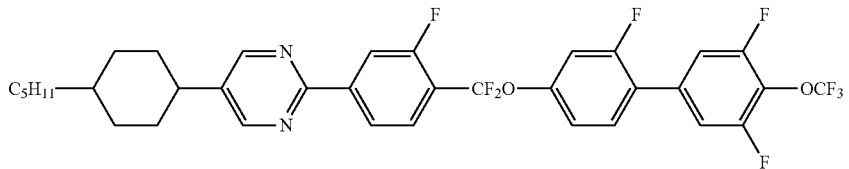 |
| 1-2-129 | 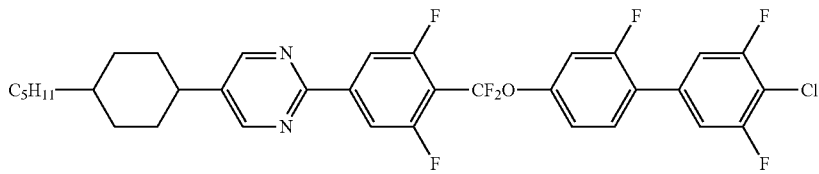 |
| 1-2-130 | 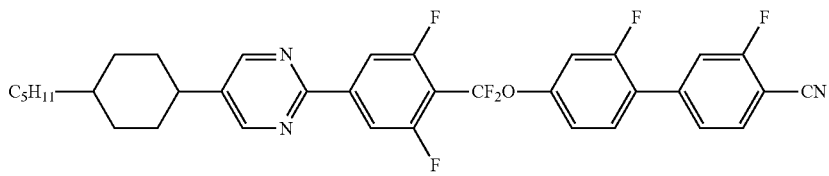 |
| 1-2-131 | 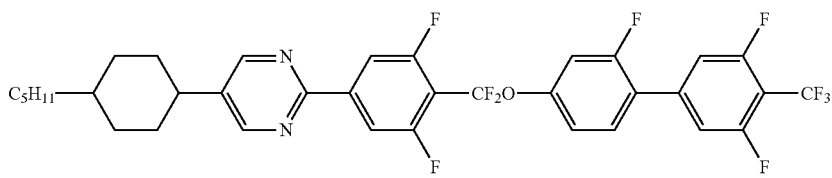 |
| 1-2-132 | 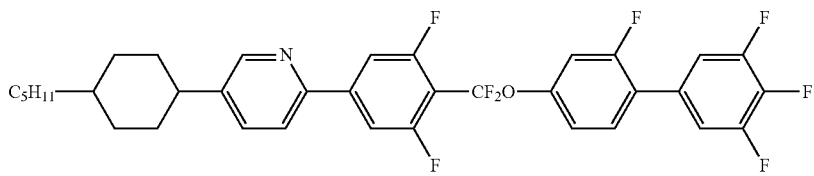 |
| 1-2-133 | 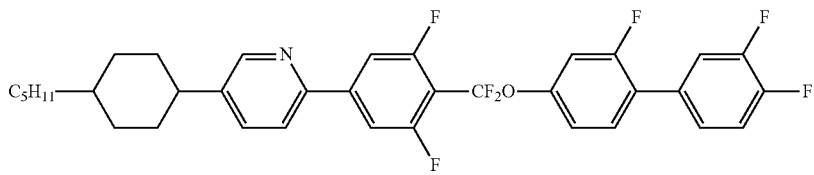 |
| 1-2-134 | 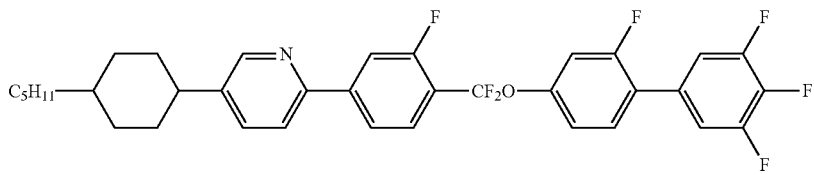 |
| 1-2-135 | 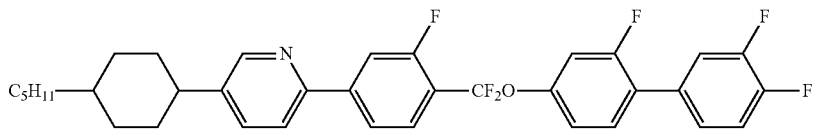 |
| 1-2-136 | 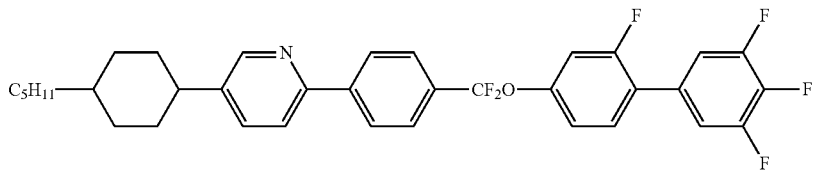 |

-continued
| No. |
|---|
| 1-2-137 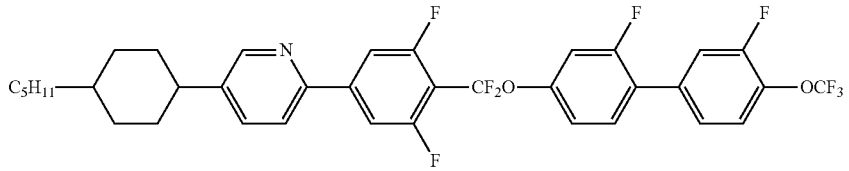 |
| 1-2-138 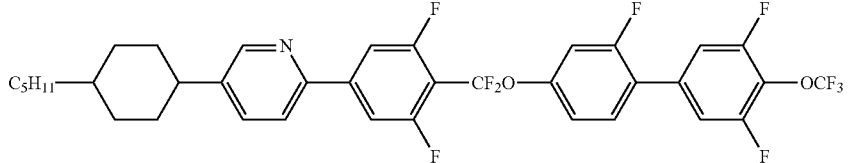 |
| 1-2-139 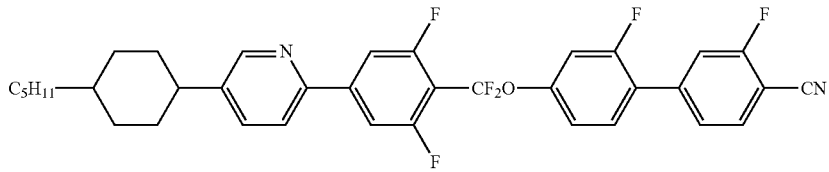 |
| 1-2-140 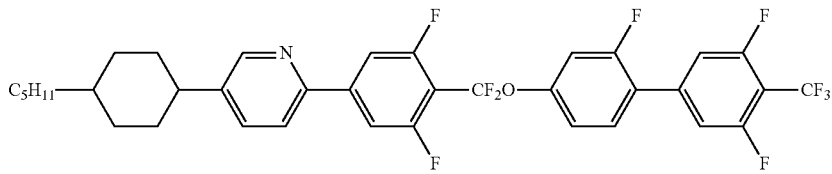 |
| 1-2-141 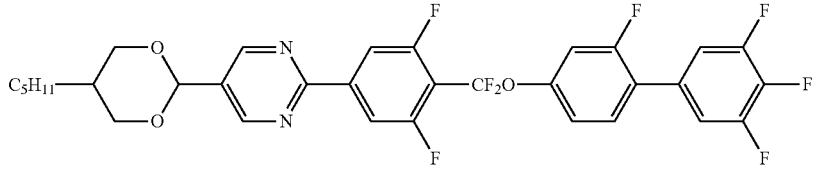 |
| 1-2-142 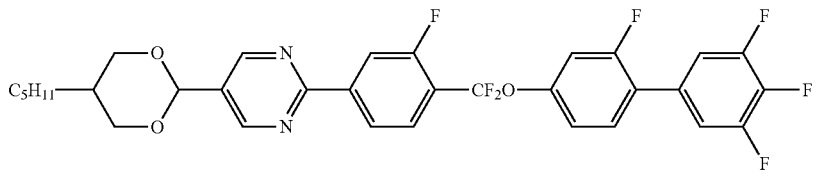 |
| 1-2-143 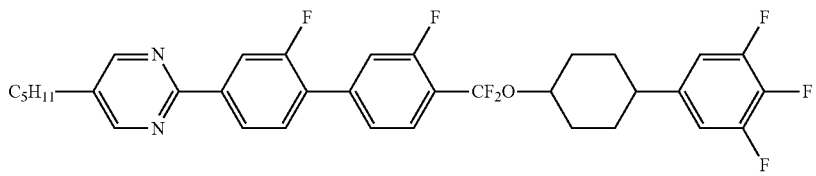 |
| 1-2-144 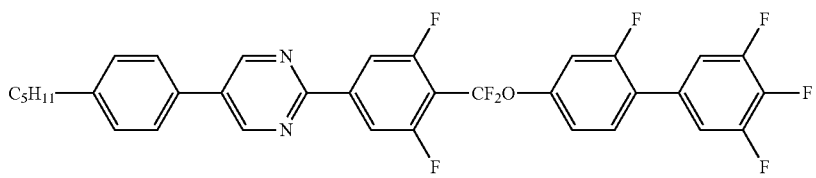 |
| 1-2-145 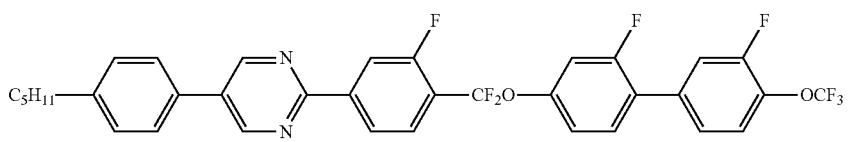 |

-continued
| No. |
|---|
| 1-2-146 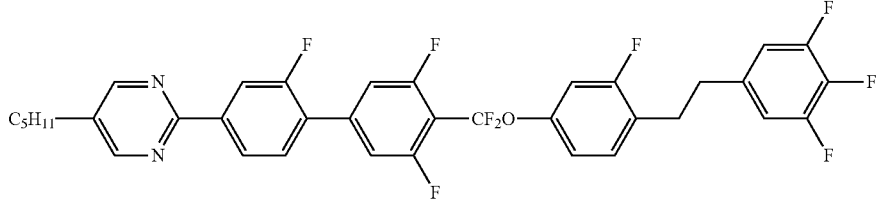 |
| 1-2-147 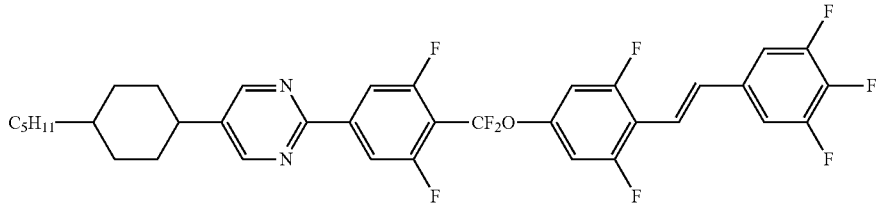 |
| 1-2-148 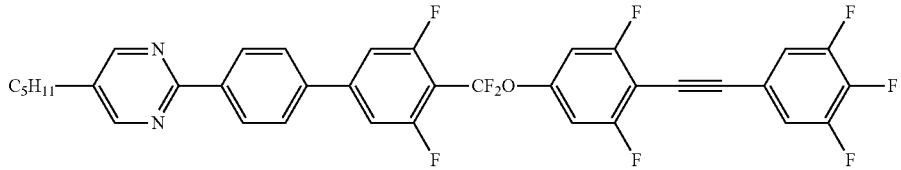 |
| 1-2-149 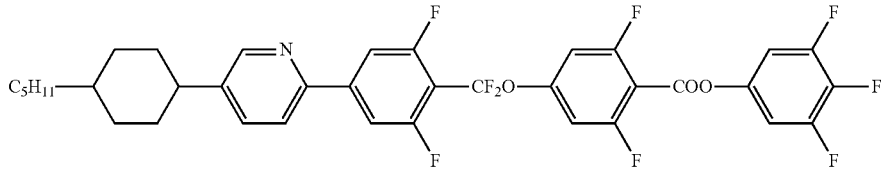 |
| 1-2-150 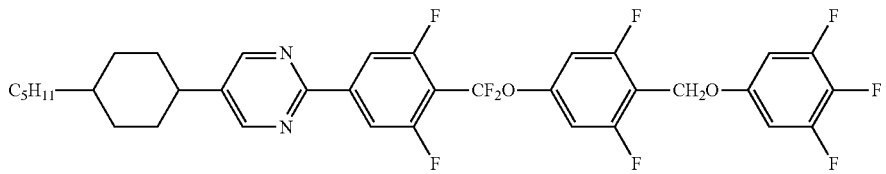 |
| 1-2-151 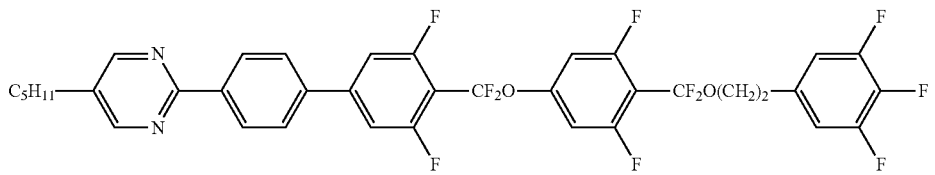 |
| 1-2-152 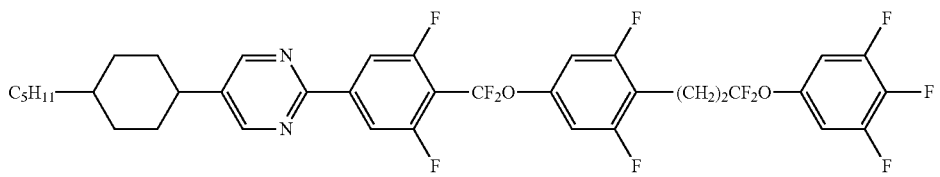 |
| 1-3-1 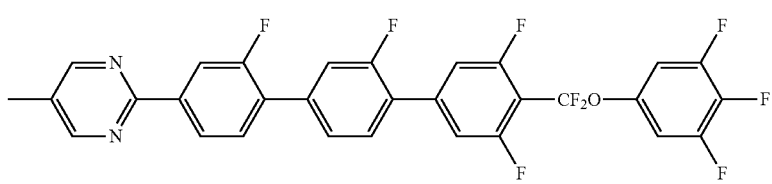 |

-continued
| No. |  |
|---|---|
| 1-3-2 | 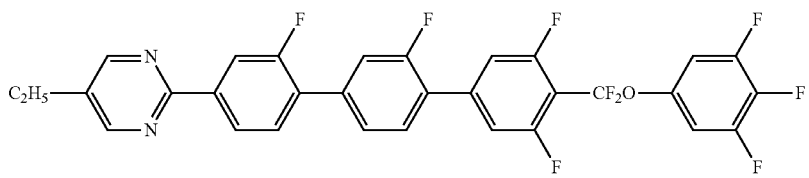 |
| 1-3-3 | 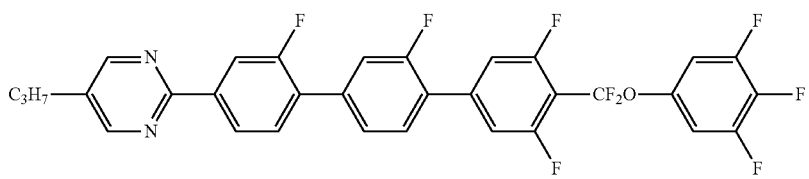 |
| 1-3-4 | 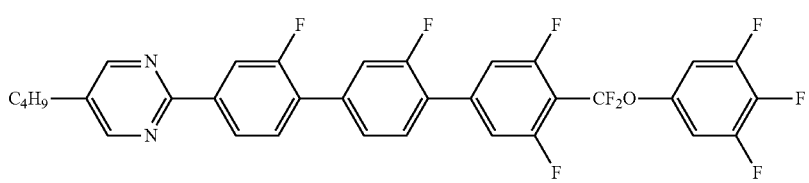 |
| 1-3-5 | 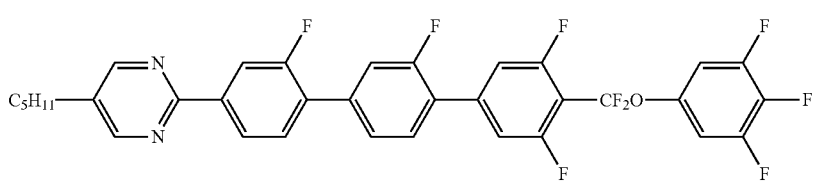<br>$T_{NI} = 172°$ C., $\Delta n = 0.257$, $\Delta \varepsilon = 49.9$ |
| 1-3-6 | 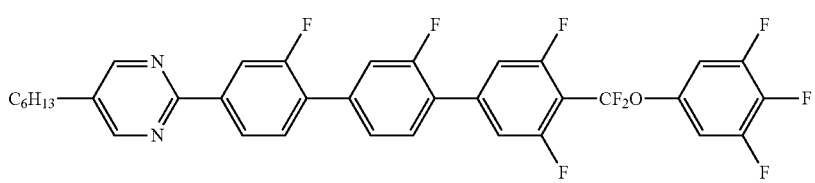 |
| 1-3-7 | 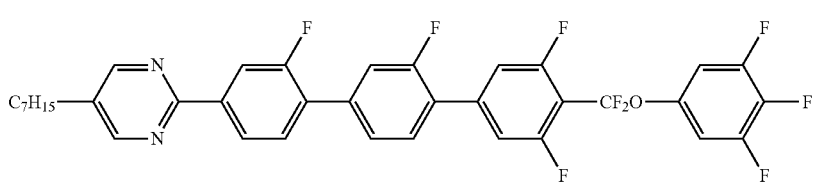 |
| 1-3-8 | 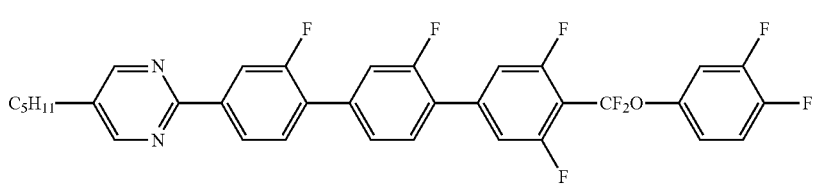 |
| 1-3-9 | 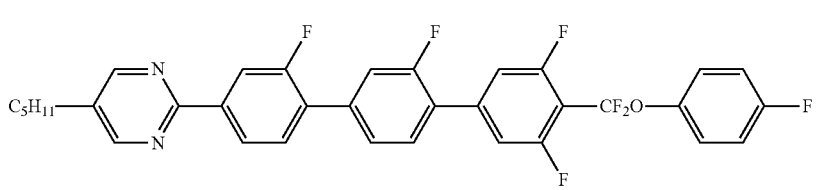 |

| No. | |
|---|---|
| 1-3-10 | 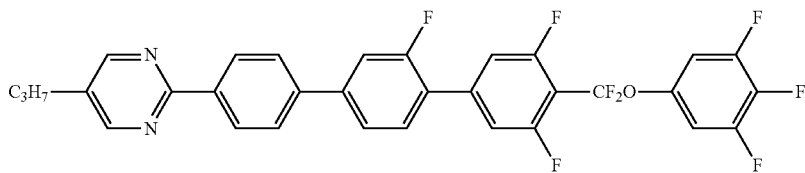 |
| 1-3-11 | 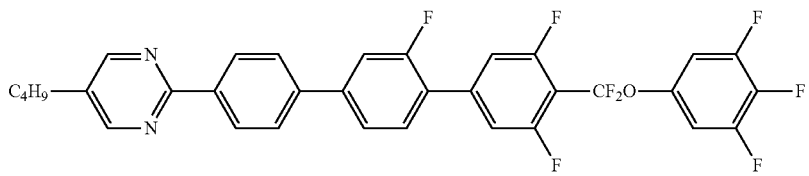 |
| 1-3-12 | 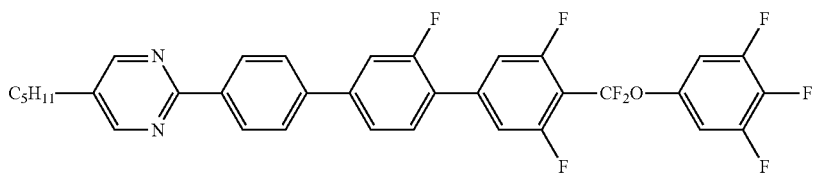 |
| 1-3-13 | 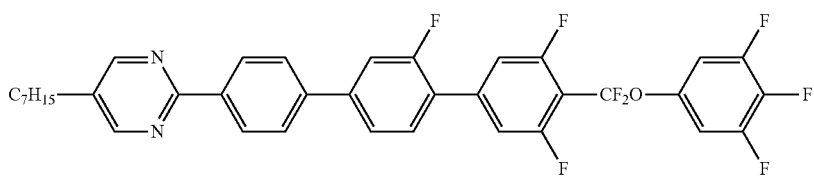 |
| 1-3-14 | 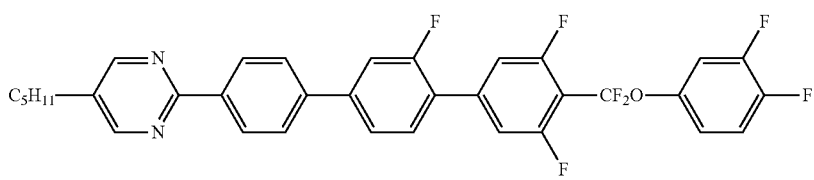 |
| 1-3-15 | 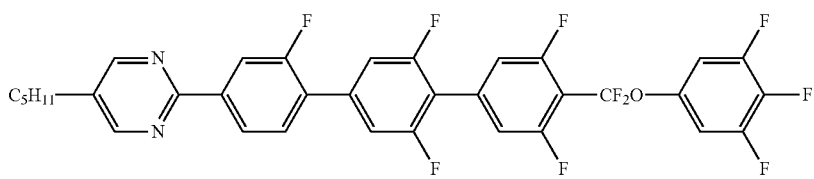 |
| 1-3-16 | 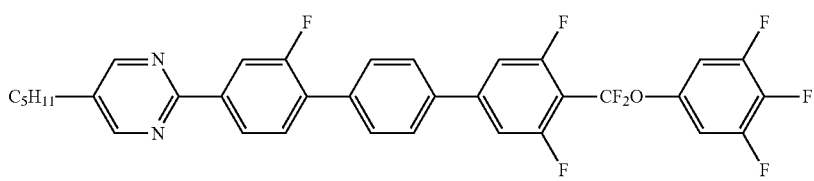 |
| 1-3-17 | 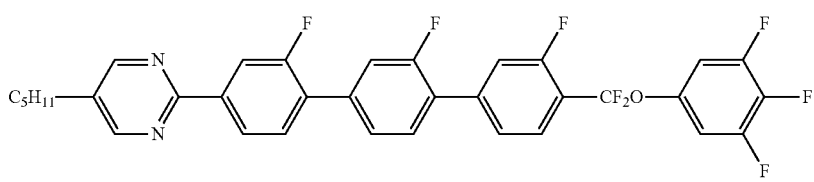 |
| 1-3-18 | 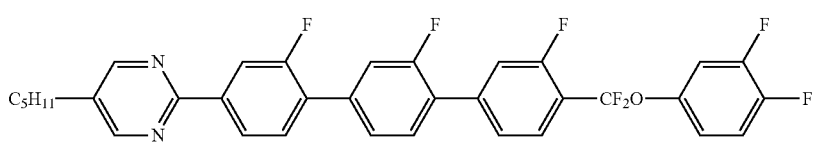 |

| No. | |
|---|---|
| 1-3-19 | 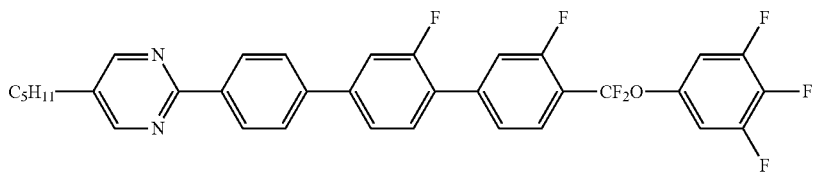 |
| 1-3-20 | 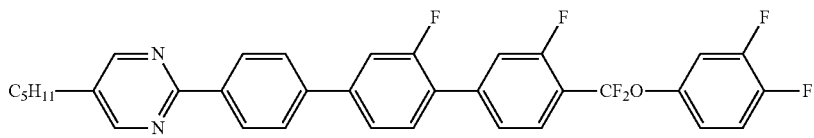 |
| 1-3-21 | 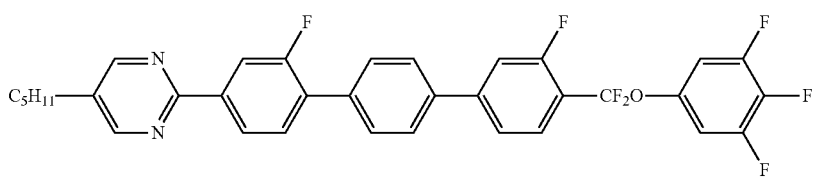 |
| 1-3-22 | 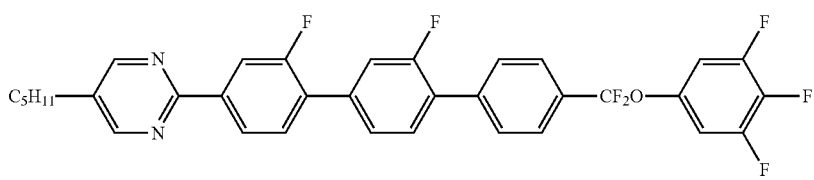 |
| 1-3-23 | 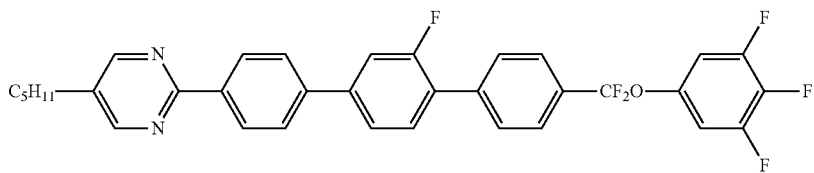 |
| 1-3-24 | 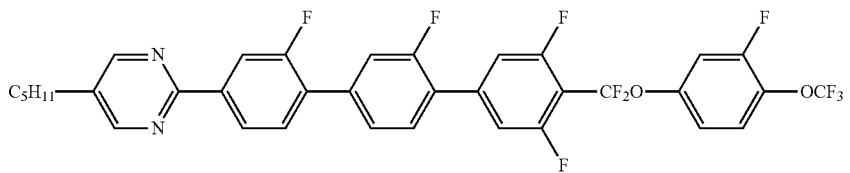 |
| 1-3-25 | 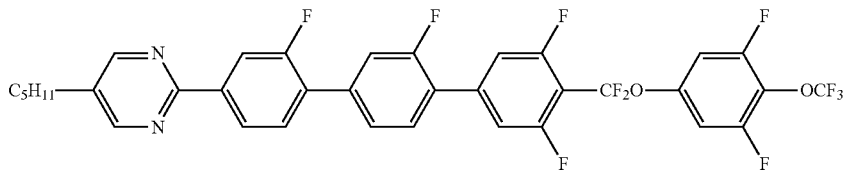 |
| 1-3-26 | 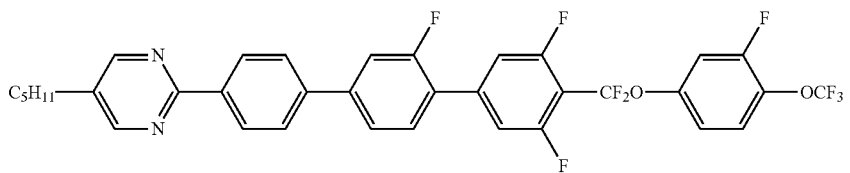 |
| 1-3-27 | 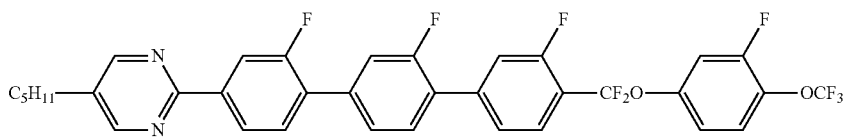 |

| No. | |
|---|---|
| 1-3-28 | 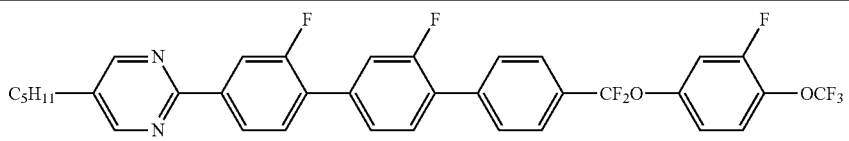 |
| 1-3-29 | 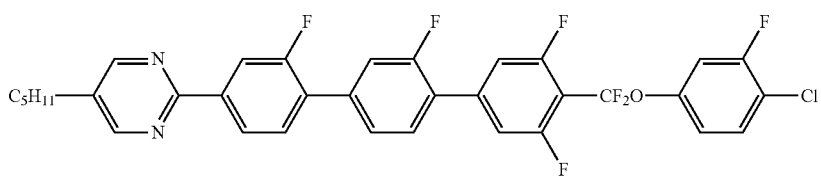 |
| 1-3-30 | 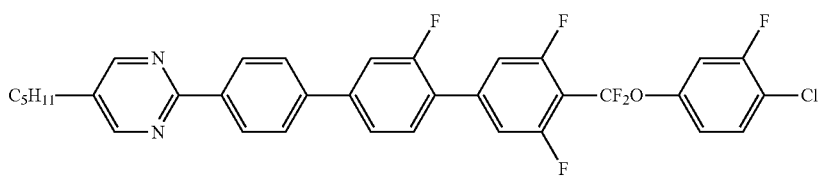 |
| 1-3-31 | 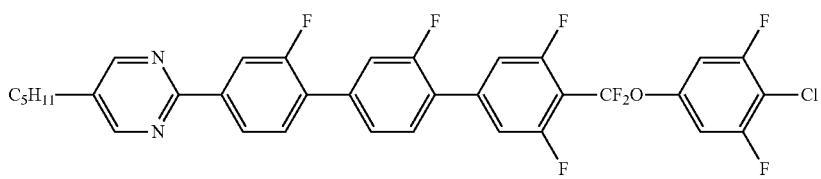 |
| 1-3-32 | 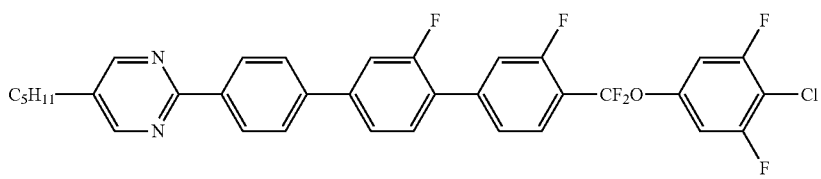 |
| 1-3-33 | 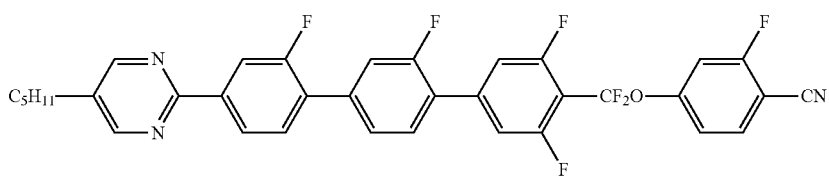 |
| 1-3-34 | 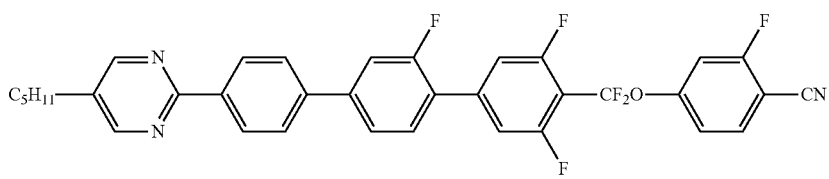 |
| 1-3-35 | 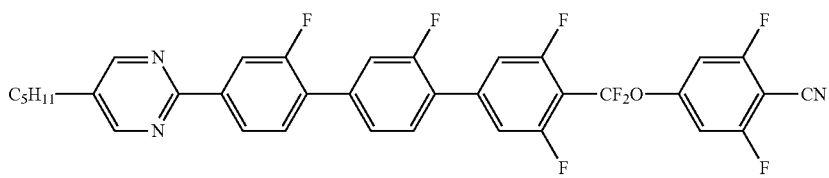 |
| 1-3-36 | 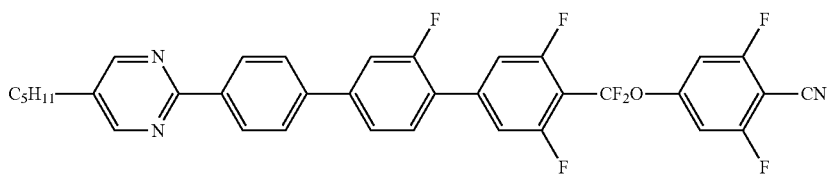 |

-continued
No.
1-3-37
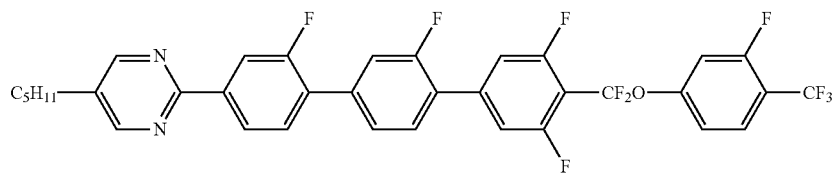
1-3-38
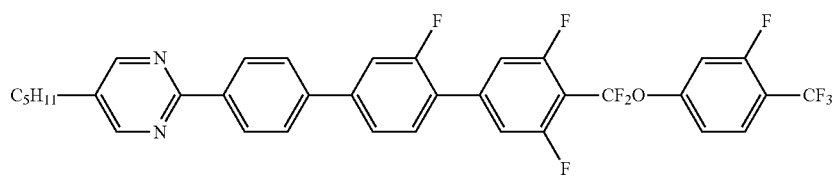
1-3-39
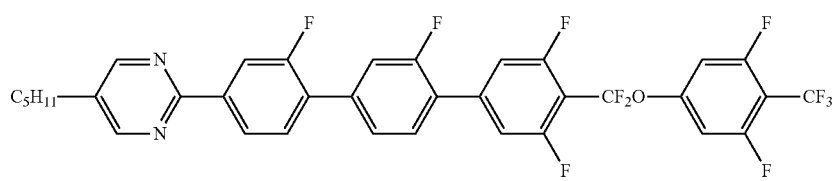
1-3-40
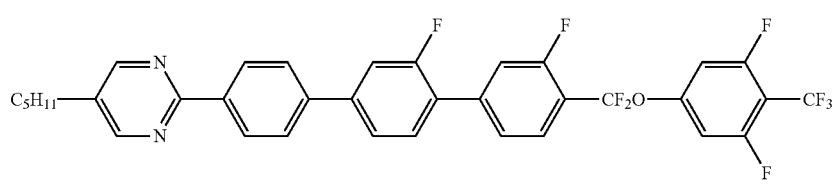
1-3-41
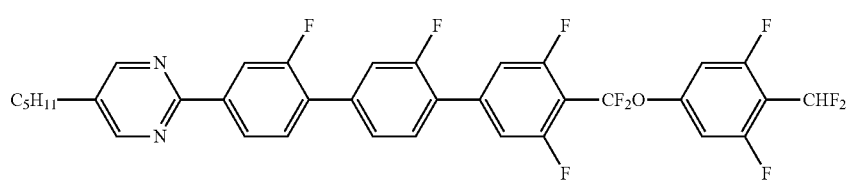
1-3-42
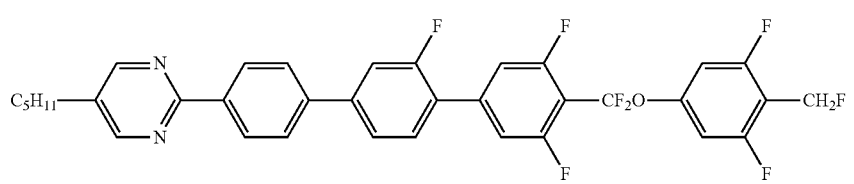
1-3-43
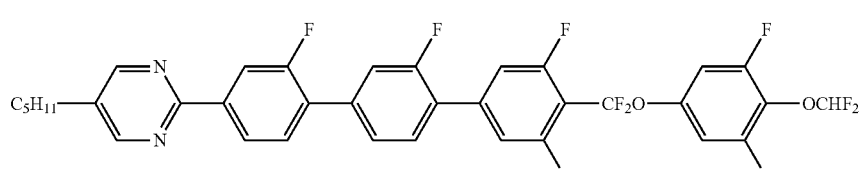
1-3-44
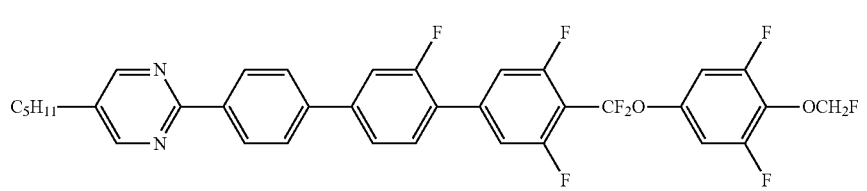

-continued
| No. | |
|---|---|
| 1-3-45 | 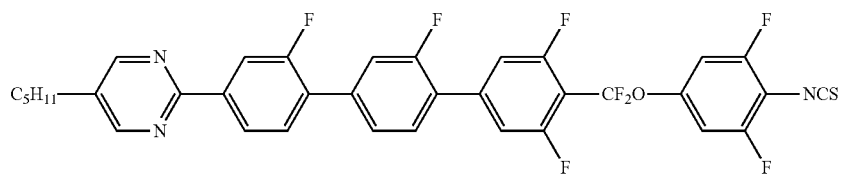 |
| 1-3-46 | 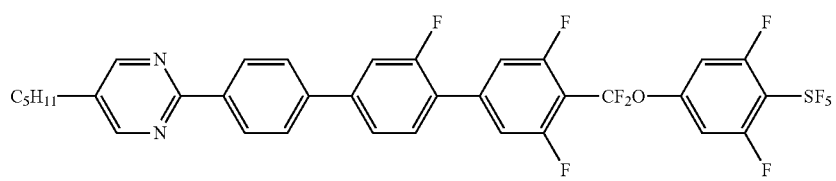 |
| 1-3-47 | 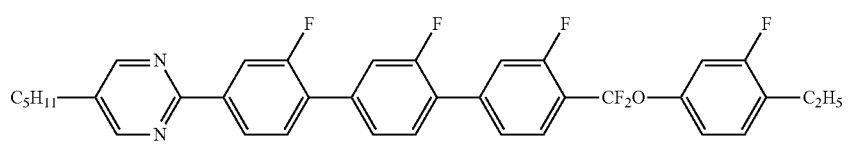 |
| 1-3-48 | 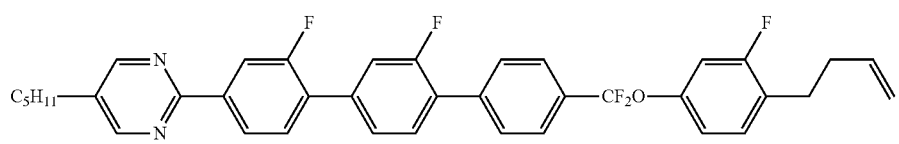 |
| 1-3-49 | 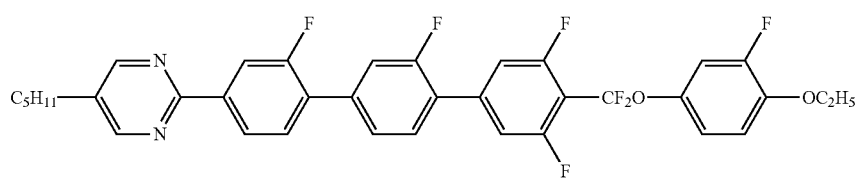 |
| 1-3-50 | 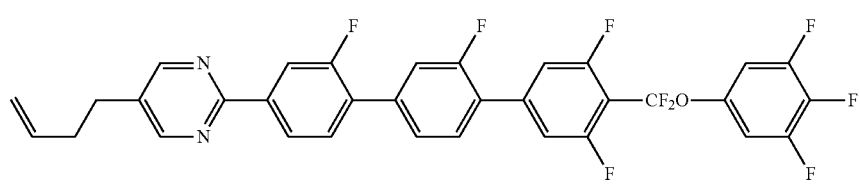 |
| 1-3-51 | 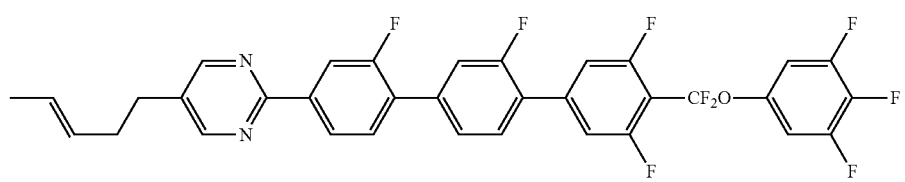 |
| 1-3-52 | 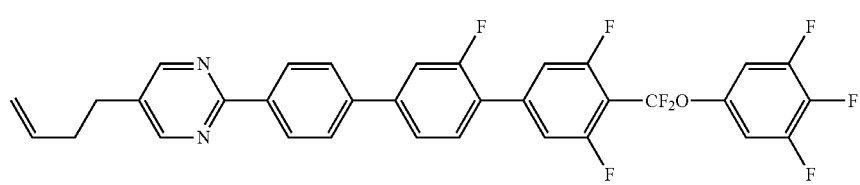 |
| 1-3-53 | 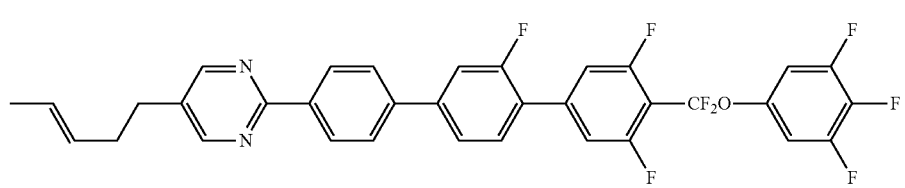 |

-continued
| No. | |
|---|---|
| 1-3-54 | 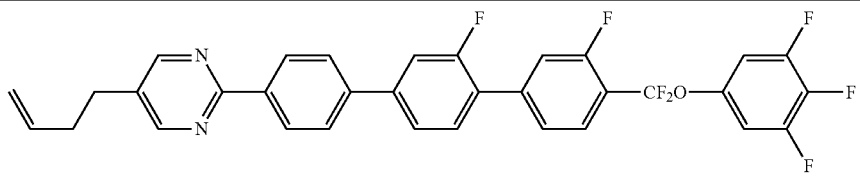 |
| 1-3-55 | 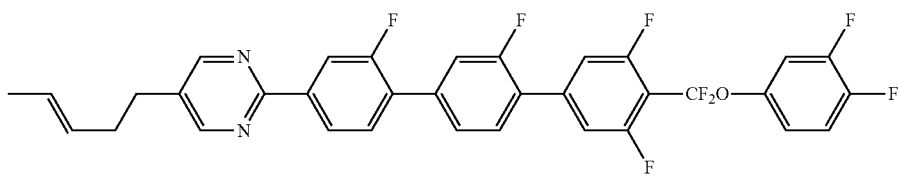 |
| 1-3-56 | 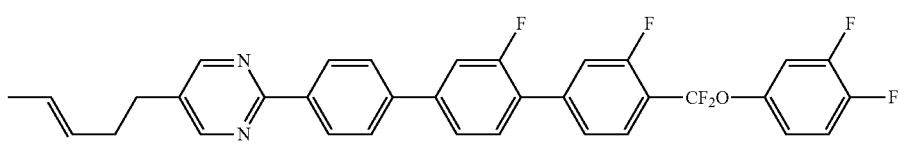 |
| 1-3-57 | 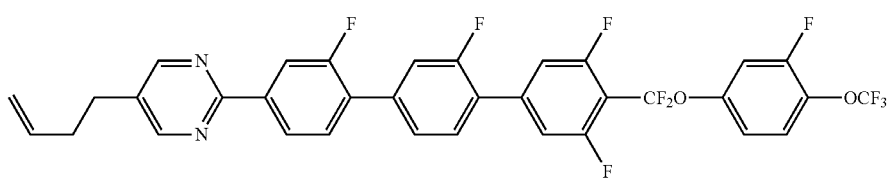 |
| 1-3-58 | 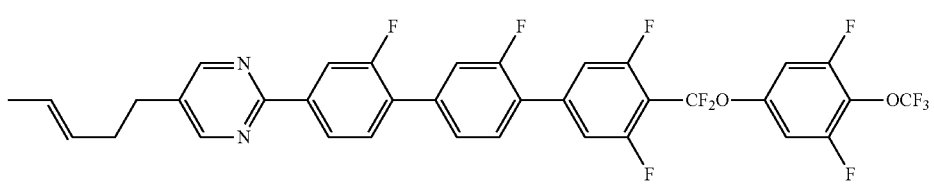 |
| 1-3-59 | 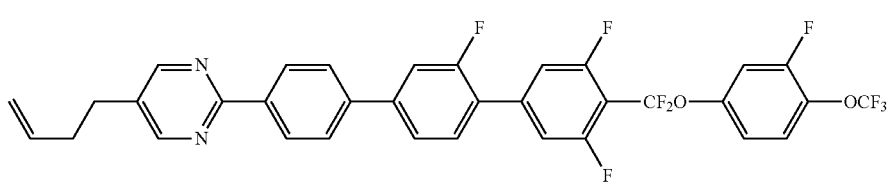 |
| 1-3-60 | 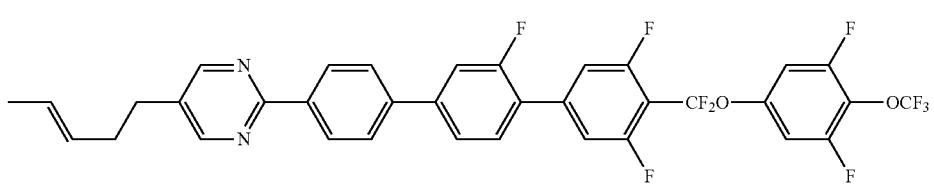 |
| 1-3-61 | 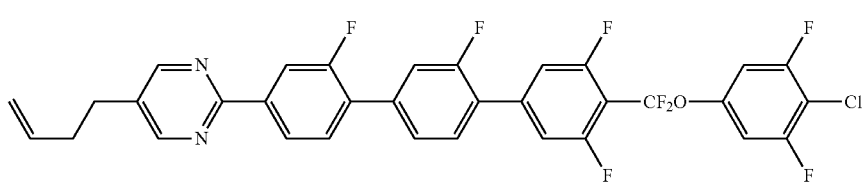 |
| 1-3-62 | 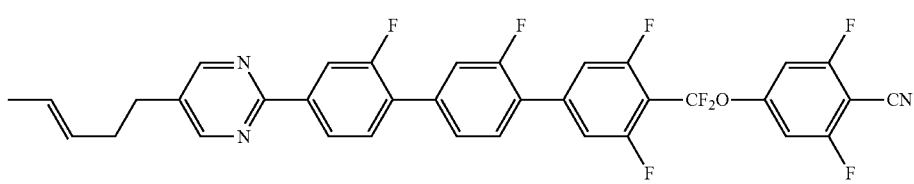 |

-continued
| No. | |
|---|---|
| 1-3-63 | 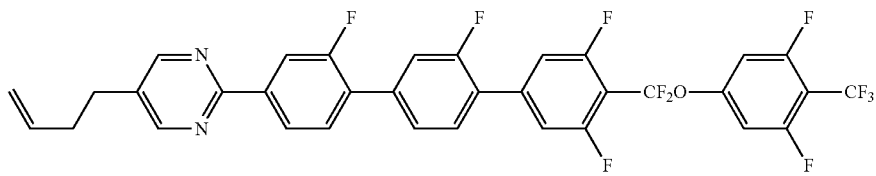 |
| 1-3-64 | 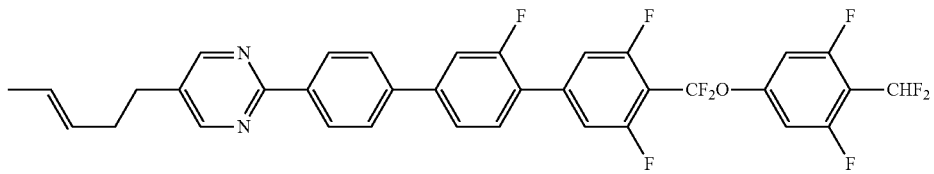 |
| 1-3-65 | 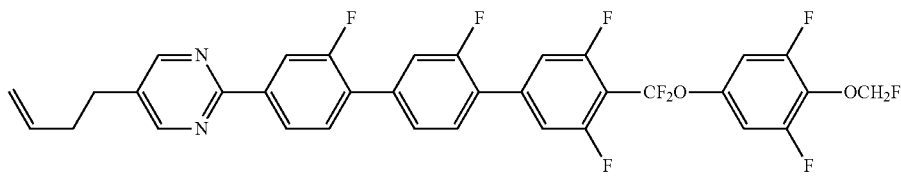 |
| 1-3-66 | 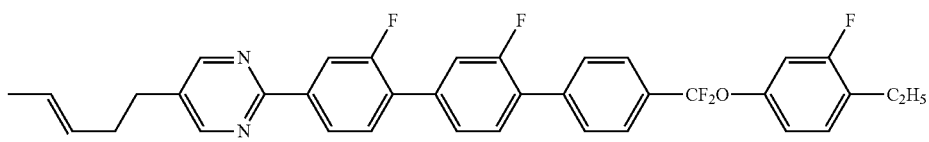 |
| 1-3-67 | 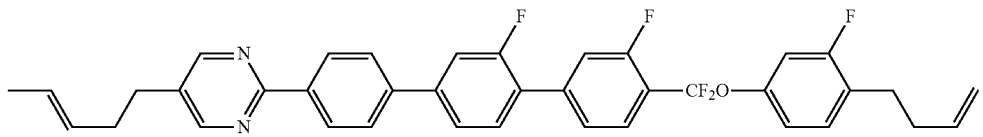 |
| 1-3-68 | 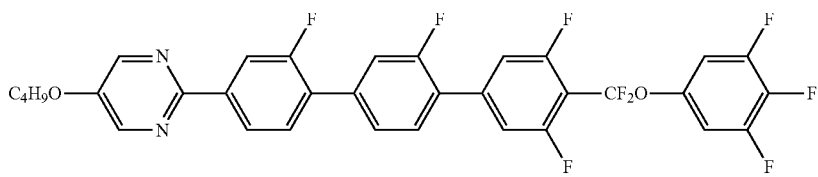 |
| 1-3-69 | 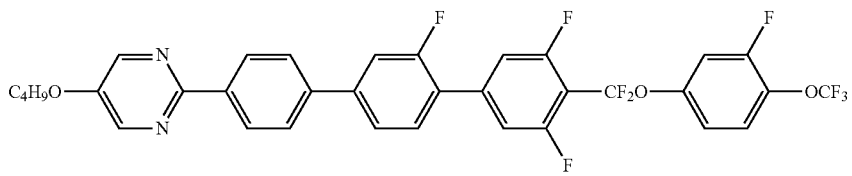 |
| 1-3-70 | 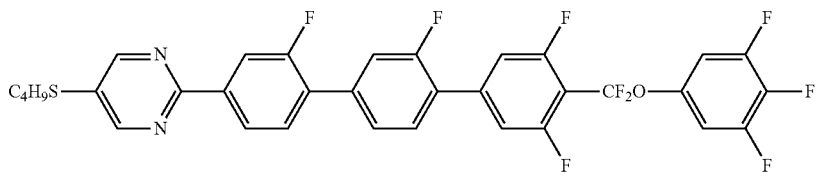 |
| 1-3-71 | 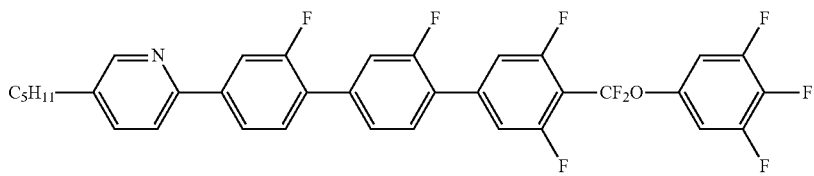 |

-continued
| No. | |
|---|---|
| 1-3-72 | 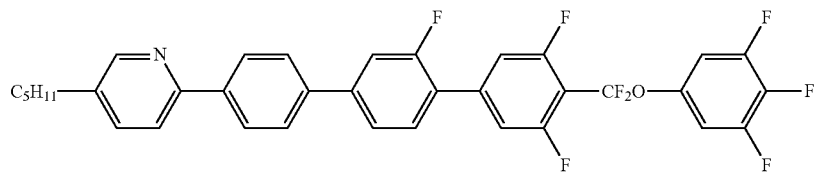 |
| 1-3-73 | 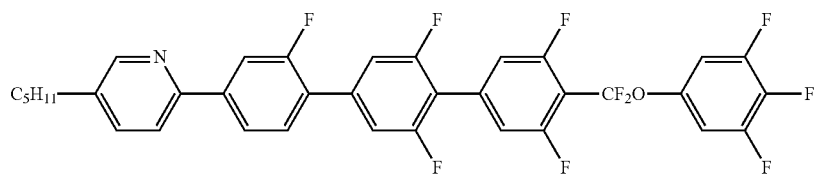 |
| 1-3-74 | 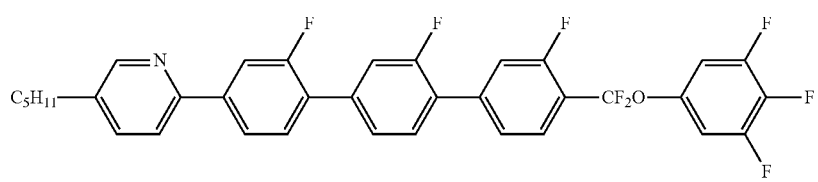 |
| 1-3-75 | 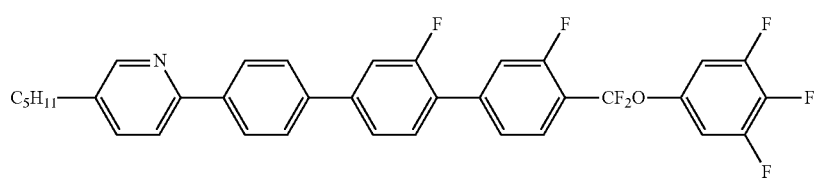 |
| 1-3-76 | 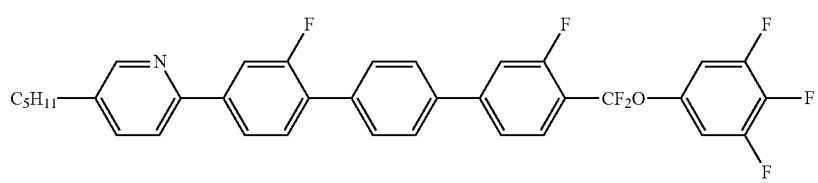 |
| 1-3-77 | 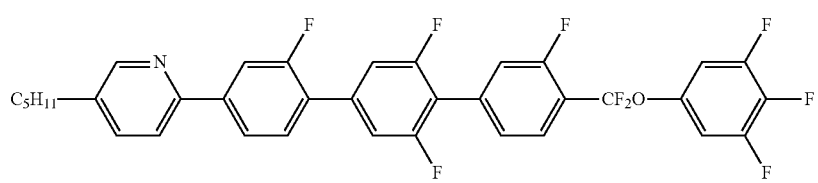 |
| 1-3-78 | 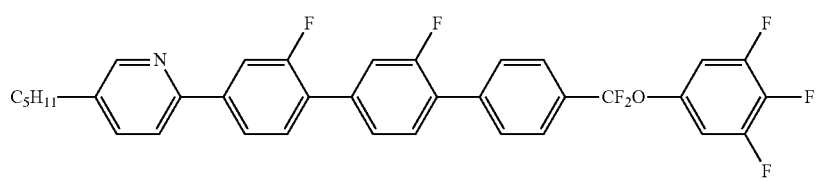 |
| 1-3-79 | 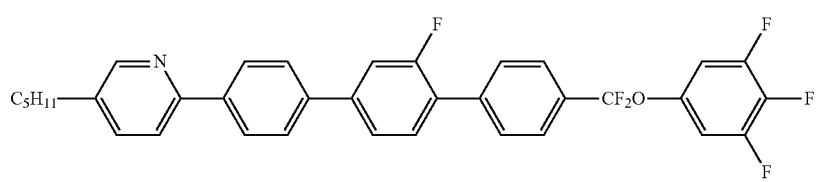 |

-continued
| No. | |
|---|---|
| 1-3-80 | 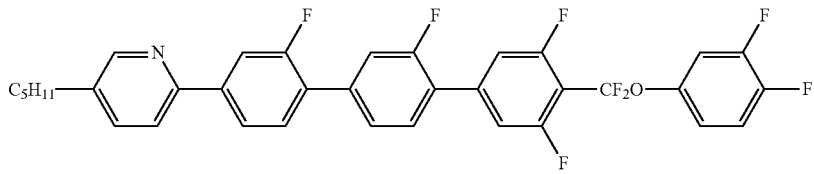 |
| 1-3-81 | 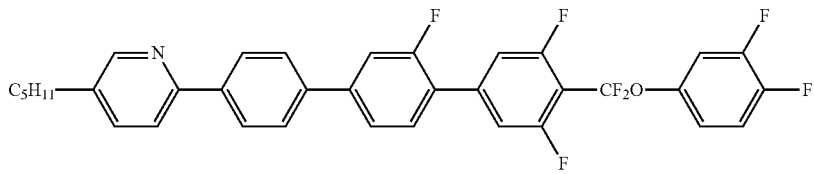 |
| 1-3-82 | 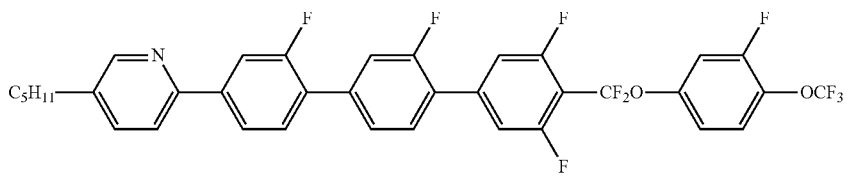 |
| 1-3-83 | 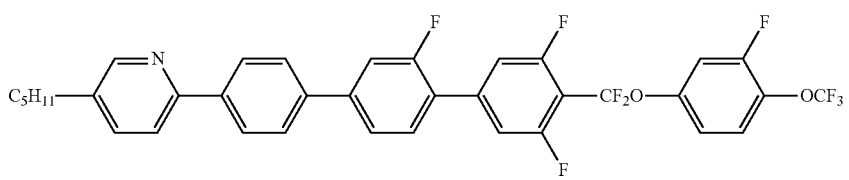 |
| 1-3-84 | 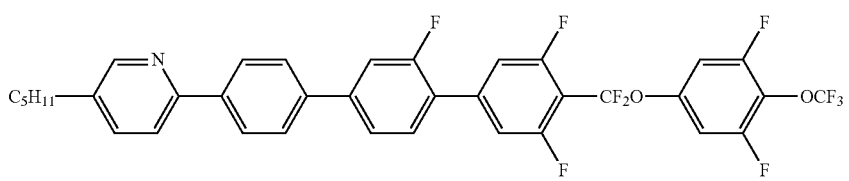 |
| 1-3-85 | 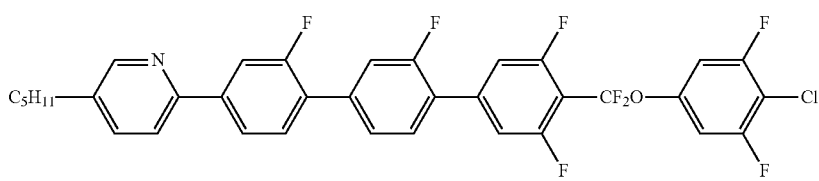 |
| 1-3-86 | 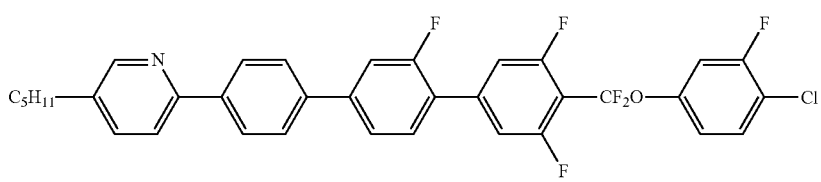 |
| 1-3-87 | 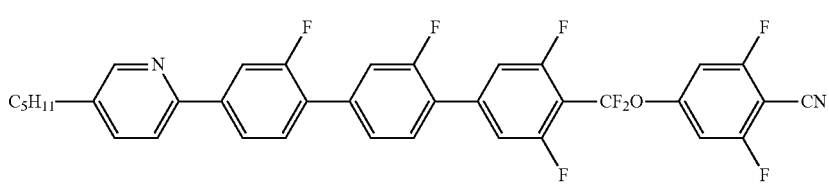 |

-continued
No.
1-3-88
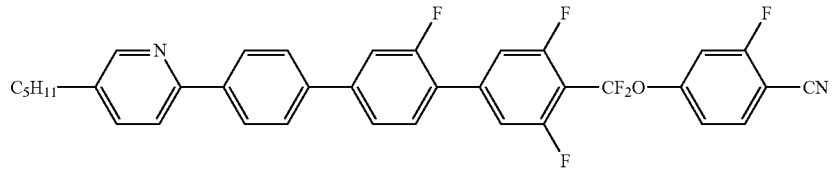
1-3-89
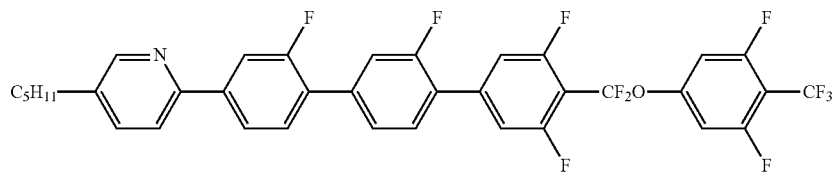
1-3-90
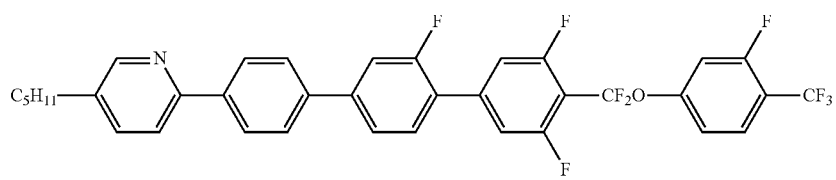
1-3-91
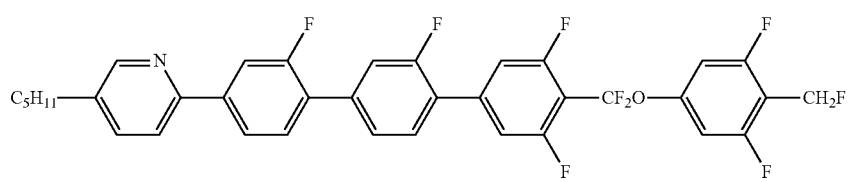
1-3-92
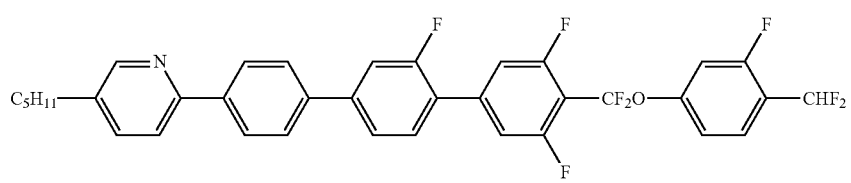
1-3-93
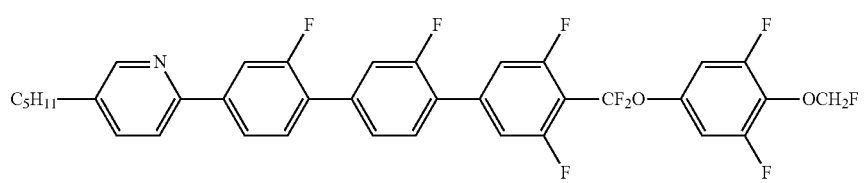
1-3-94
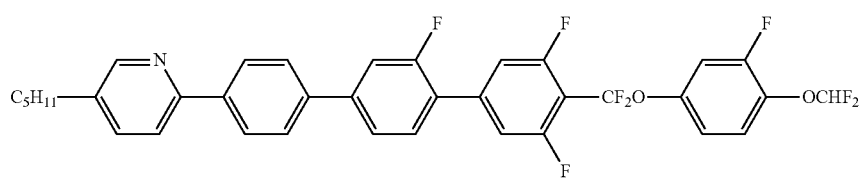
1-3-95
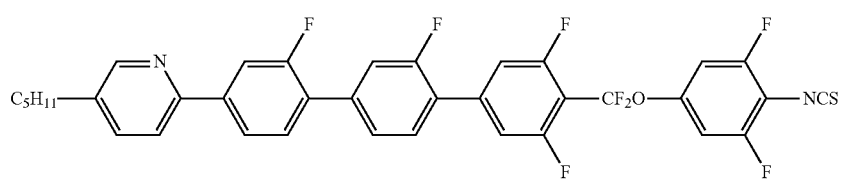

-continued
| No. | |
|---|---|
| 1-3-96 | 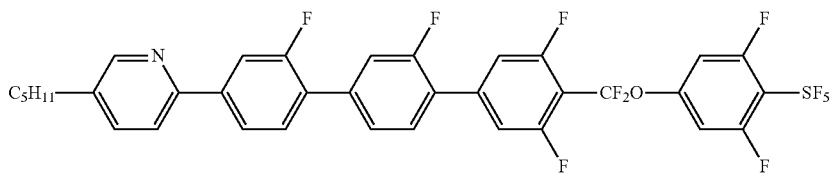 |
| 1-3-97 | 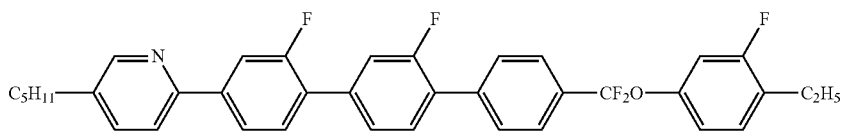 |
| 1-3-98 | 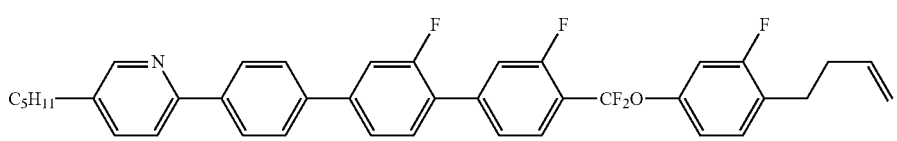 |
| 1-3-99 | 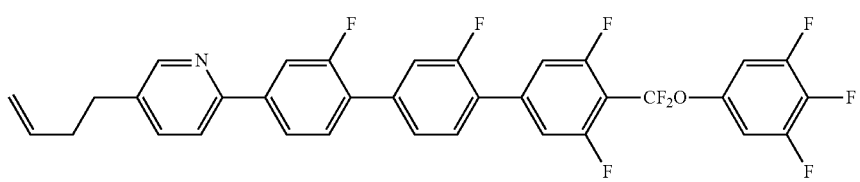 |
| 1-3-100 | 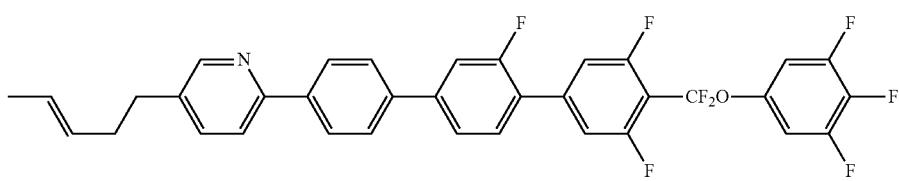 |
| 1-3-101 | 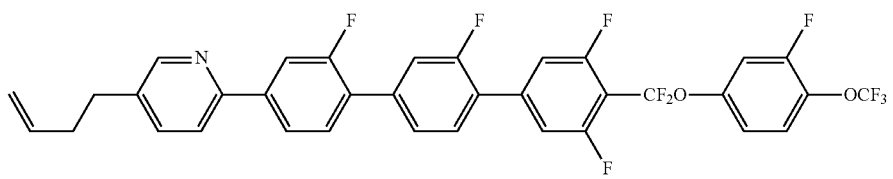 |
| 1-3-102 | 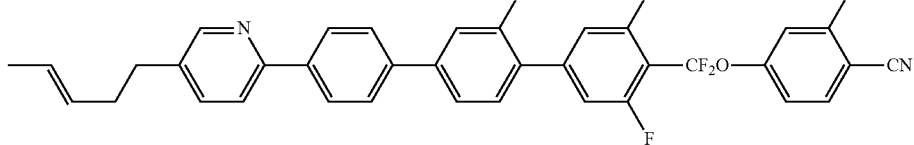 |
| 1-3-103 | 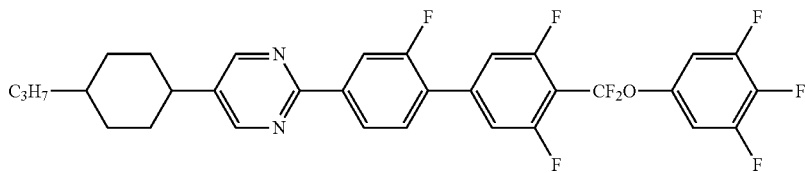 |
| 1-3-104 | 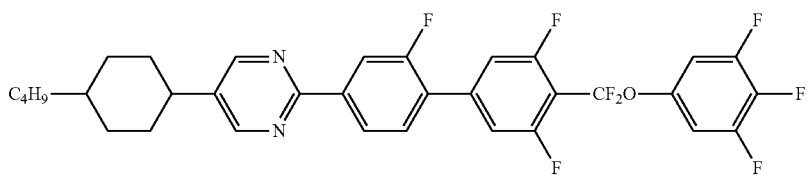 |

-continued
| No. |
|---|
| 1-3-105 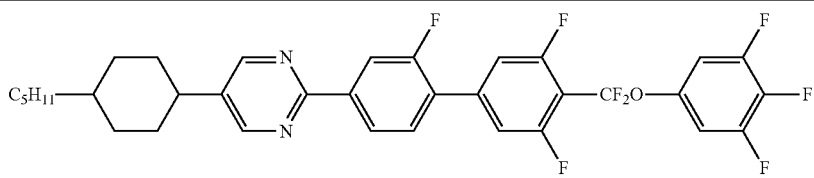 |
| 1-3-106 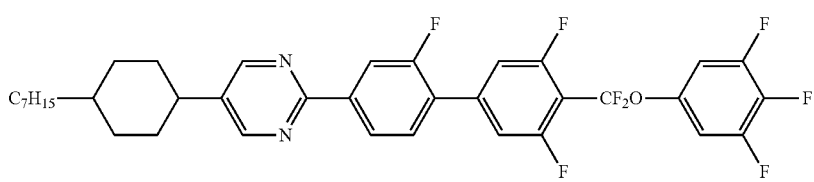 |
| 1-3-107 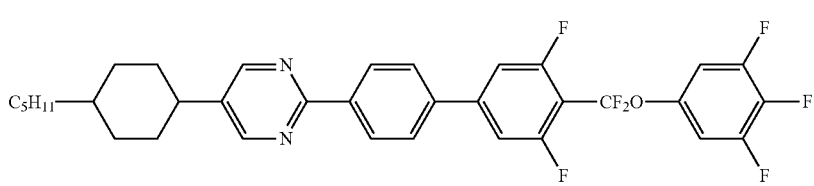 |
| 1-3-108 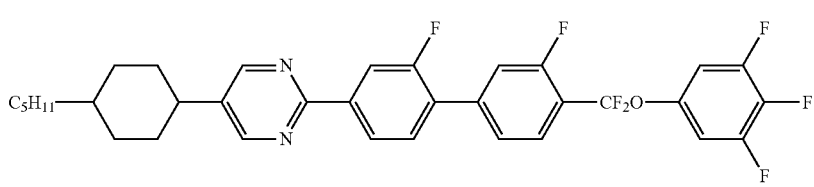 |
| 1-3-109 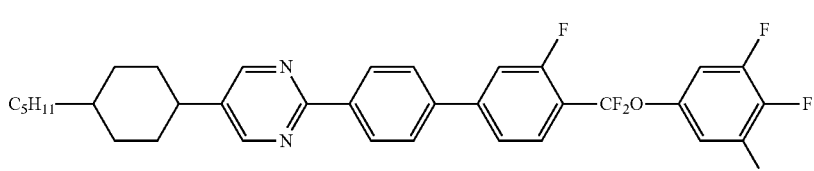 |
| 1-3-110 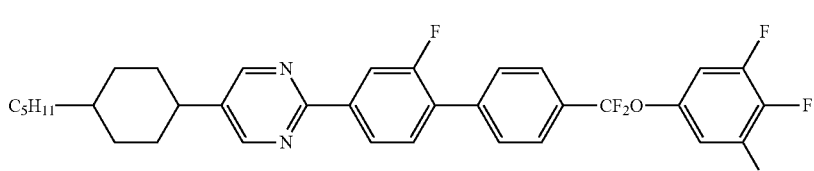 |
| 1-3-111 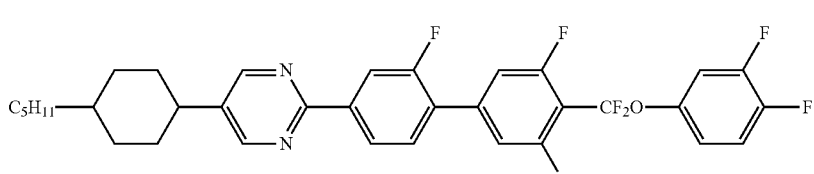 |
| 1-3-112 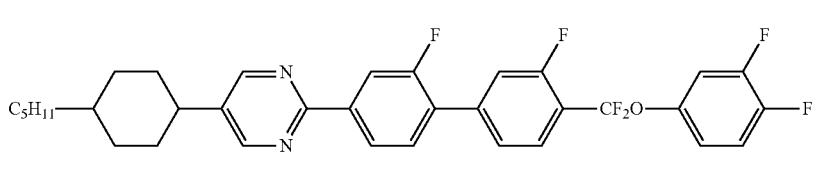 |
| 1-3-113 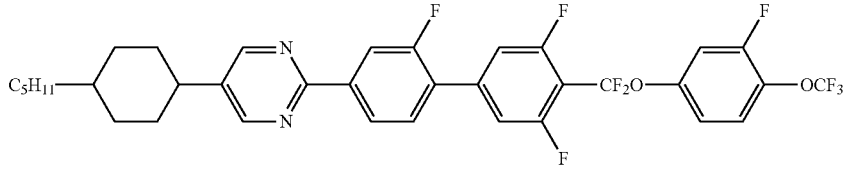 |

| No. | |
|---|---|
| 1-3-114 | 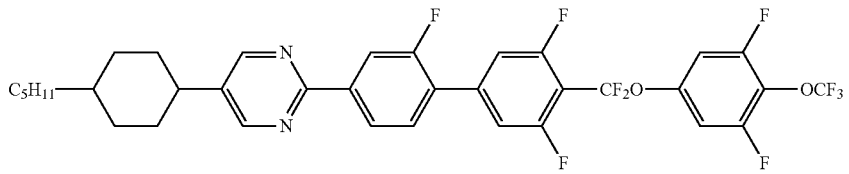 |
| 1-3-115 | 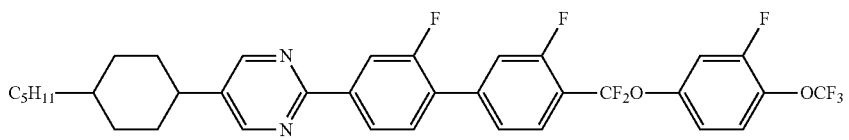 |
| 1-3-116 | 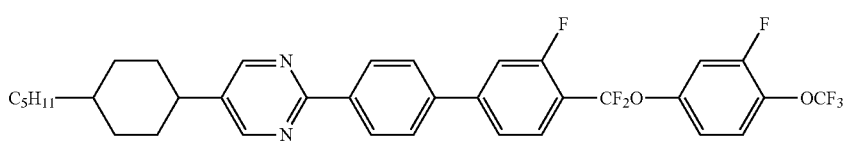 |
| 1-3-117 | 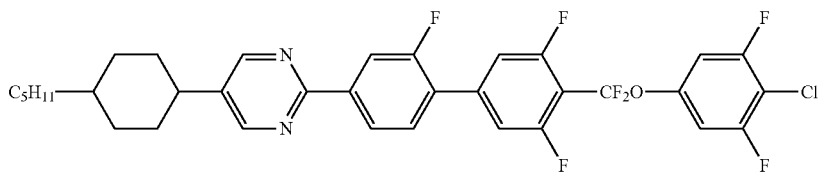 |
| 1-3-118 | 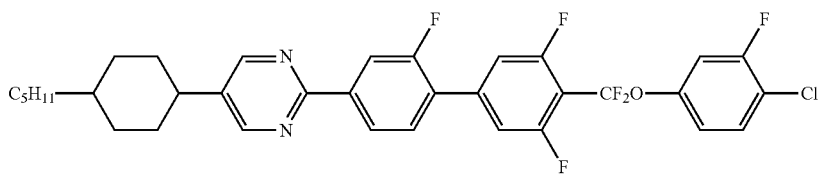 |
| 1-3-119 | 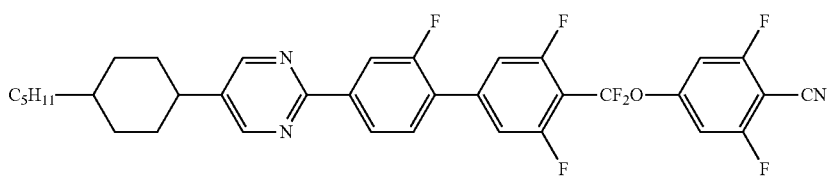 |
| 1-3-120 | 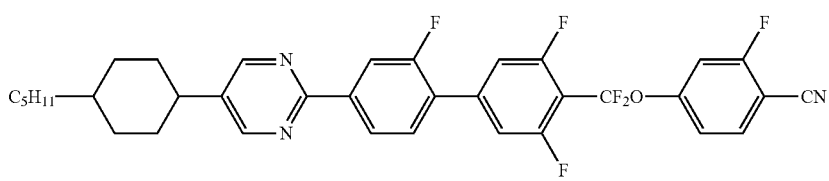 |
| 1-3-121 | 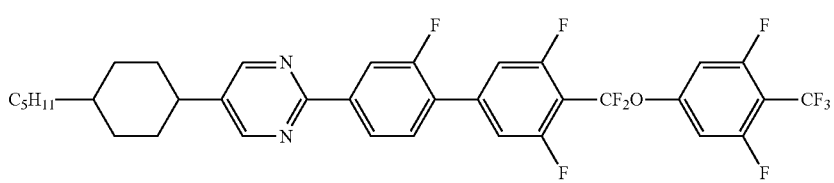 |
| 1-3-122 | 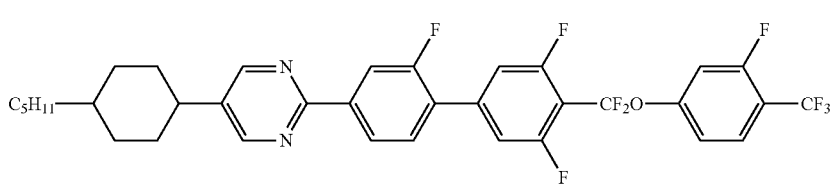 |

-continued
| No. | |
|---|---|
| 1-3-123 | 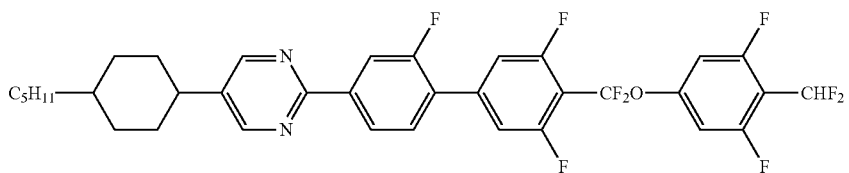 |
| 1-3-124 | 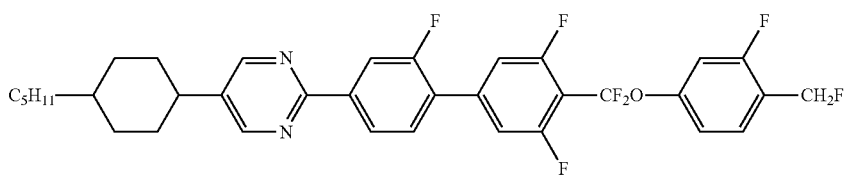 |
| 1-3-125 | 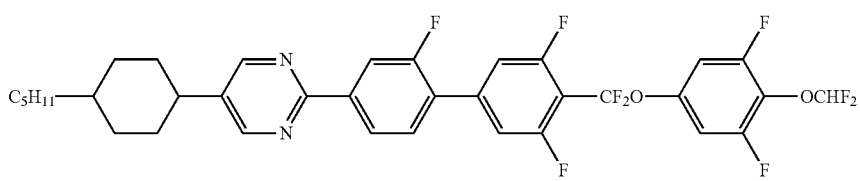 |
| 1-3-126 | 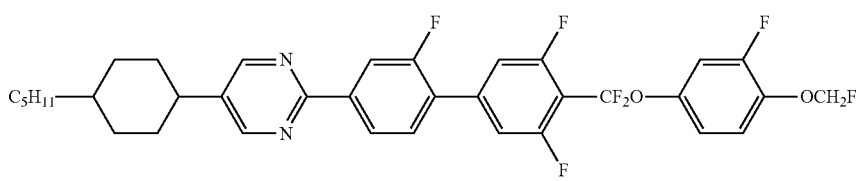 |
| 1-3-127 | 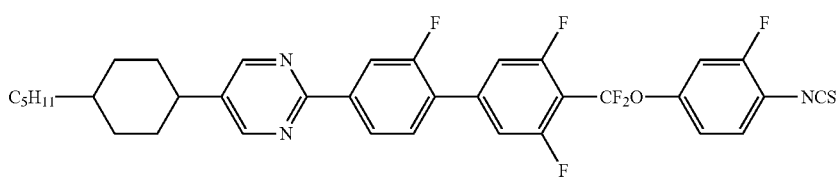 |
| 1-3-128 | 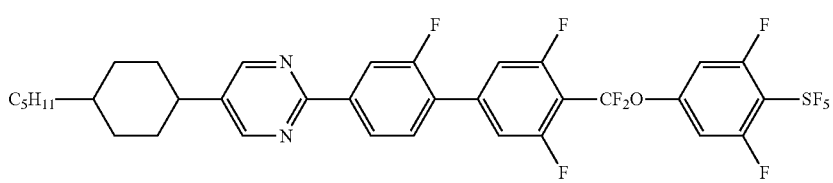 |
| 1-3-129 | 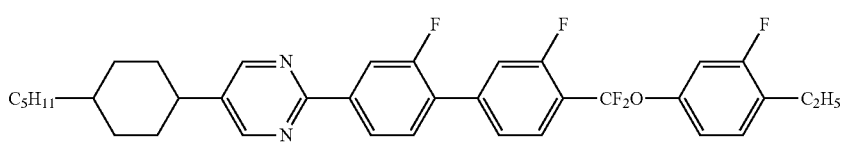 |
| 1-3-130 | 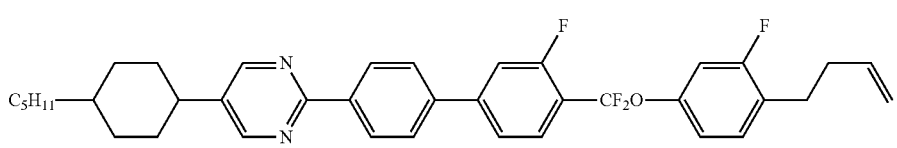 |
| 1-3-131 | 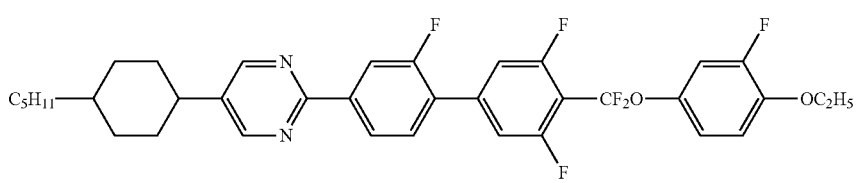 |

| No. | |
|---|---|
| 1-3-132 | 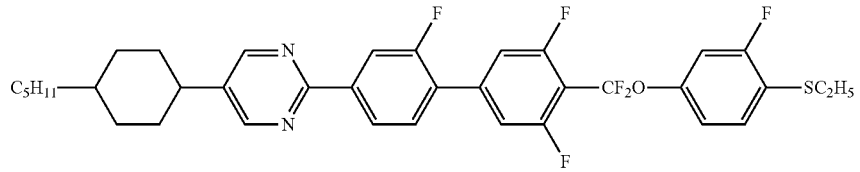 |
| 1-3-133 | 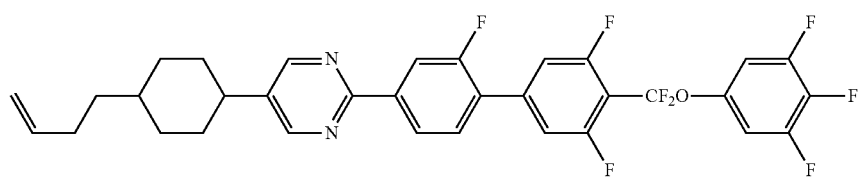 |
| 1-3-134 | 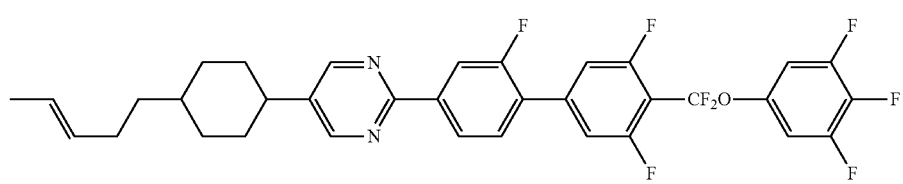 |
| 1-3-135 | 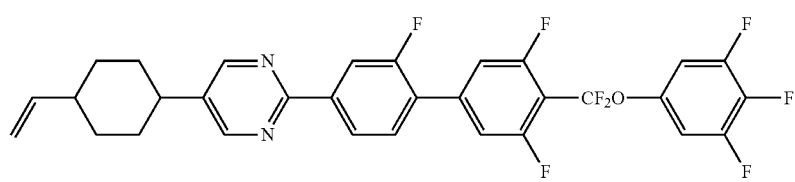 |
| 1-3-136 | 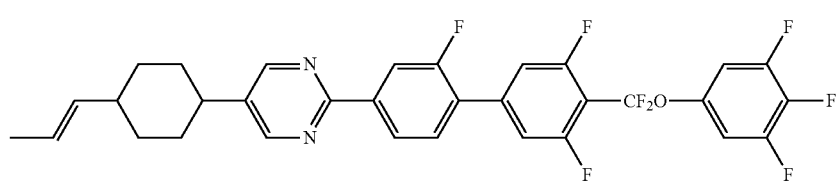 |
| 1-3-137 | 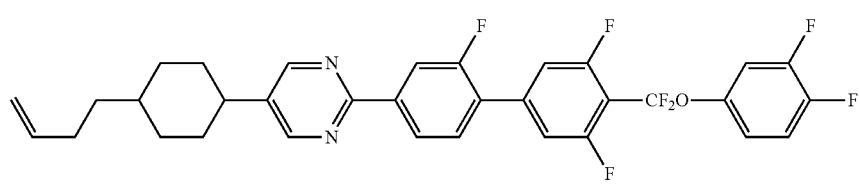 |
| 1-3-138 | 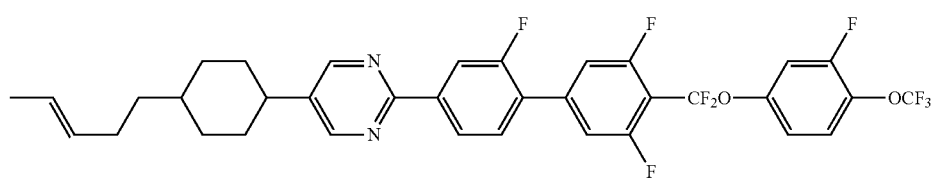 |
| 1-3-139 | 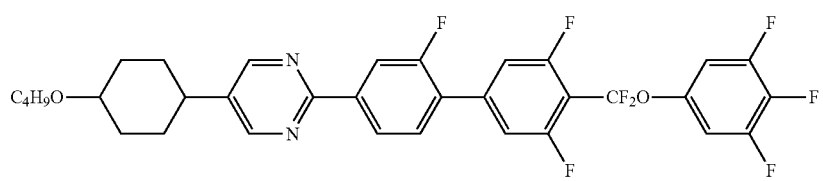 |

-continued
| No. | |
|---|---|
| 1-3-140 | 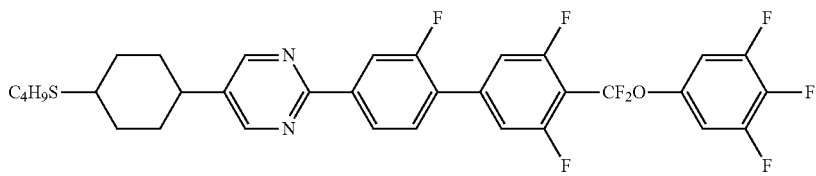 |
| 1-3-141 | 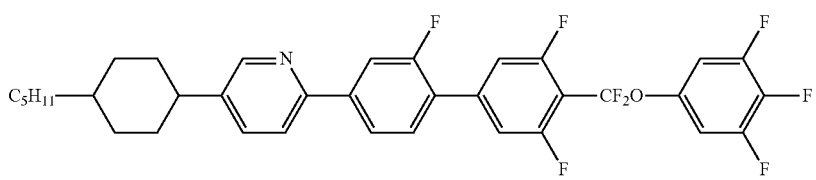 |
| 1-3-142 | 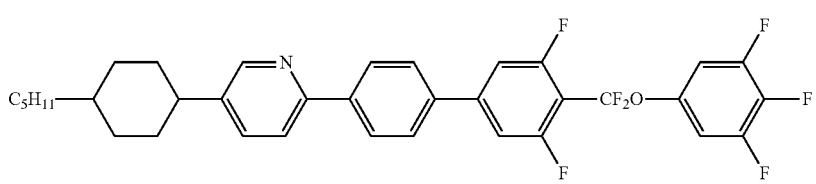 |
| 1-3-143 | 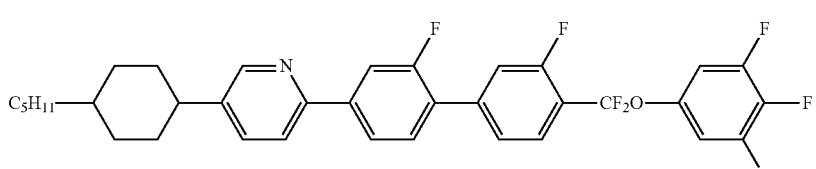 |
| 1-3-144 | 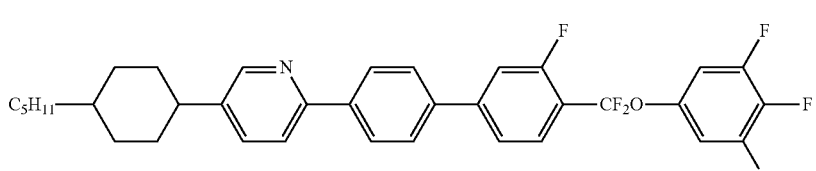 |
| 1-3-145 | 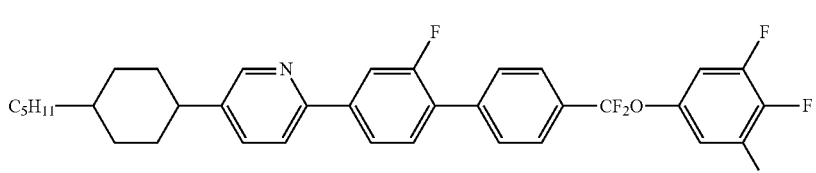 |
| 1-3-146 | 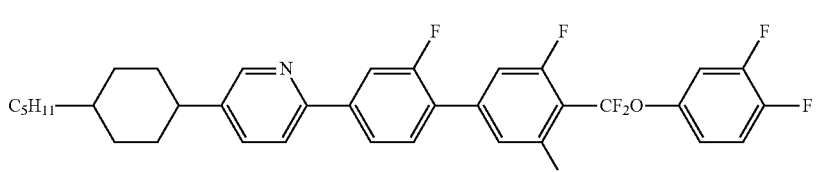 |
| 1-3-147 | 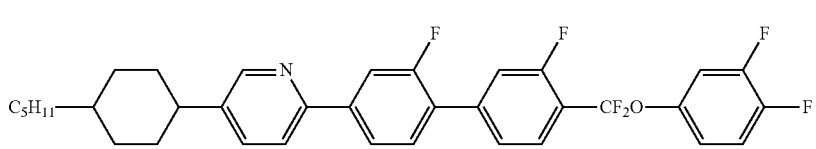 |
| 1-3-148 | 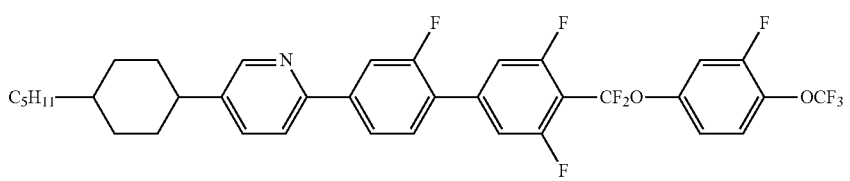 |

-continued
| No. |
|---|
| 1-3-149 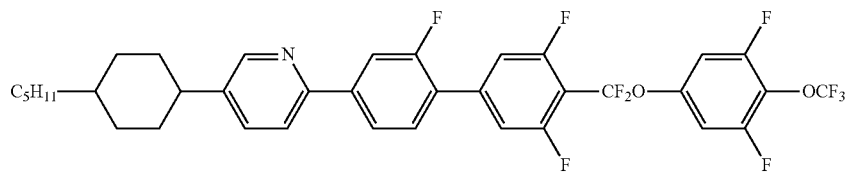 |
| 1-3-150 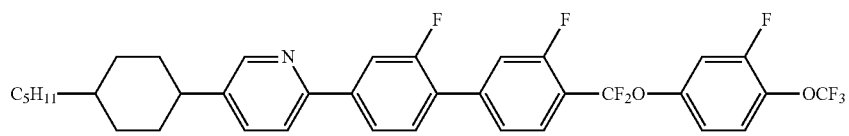 |
| 1-3-151 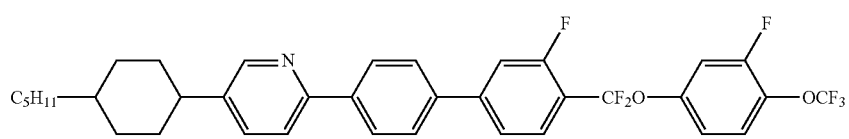 |
| 1-3-152 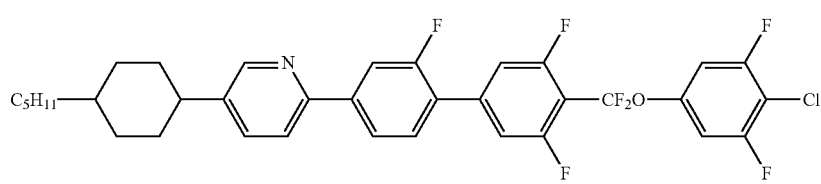 |
| 1-3-153 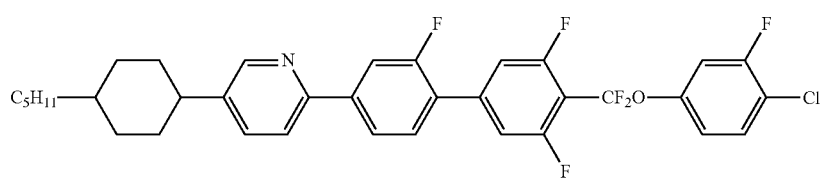 |
| 1-3-154 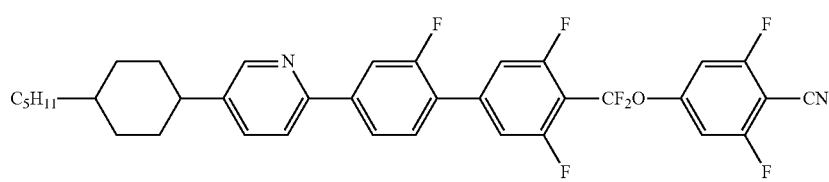 |
| 1-3-155 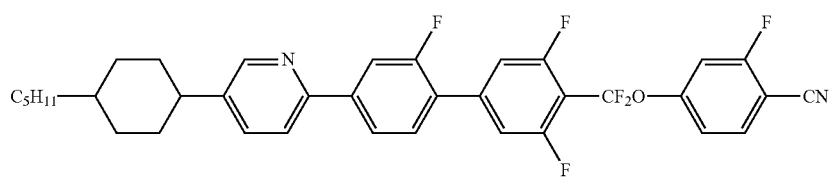 |
| 1-3-156 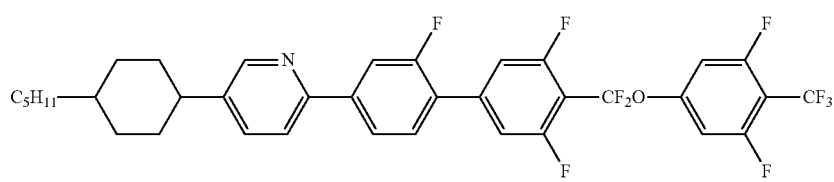 |
| 1-3-157 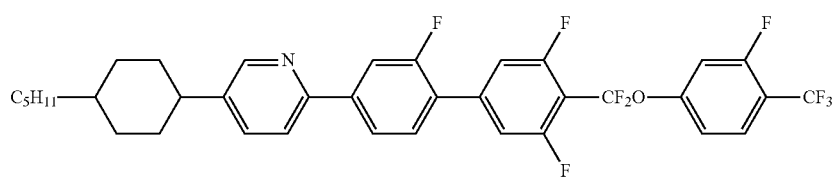 |

-continued
| No. | |
|---|---|
| 1-3-158 | 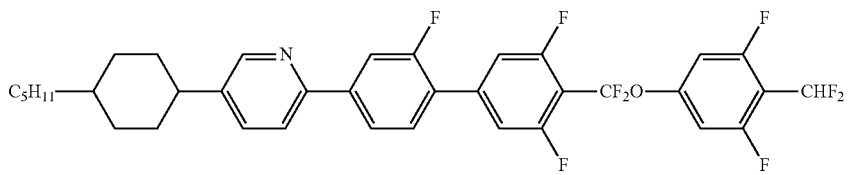 |
| 1-3-159 | 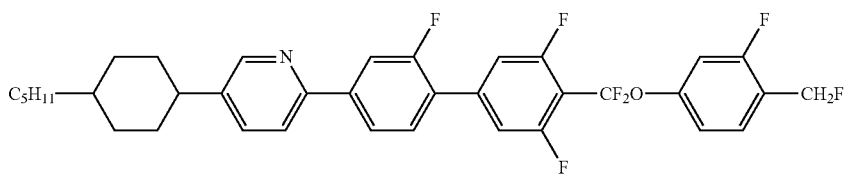 |
| 1-3-160 | 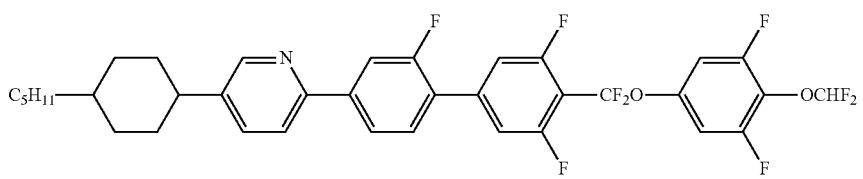 |
| 1-3-161 | 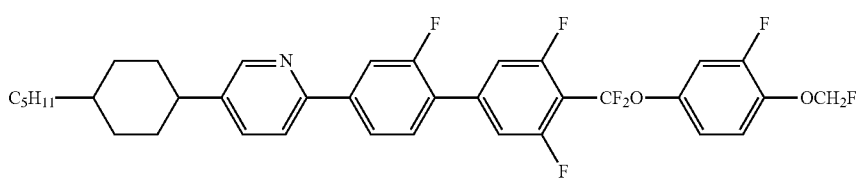 |
| 1-3-162 | 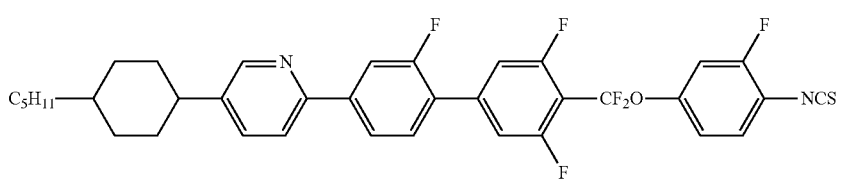 |
| 1-3-163 | 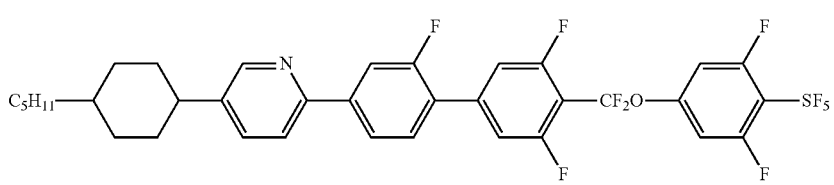 |
| 1-3-164 | 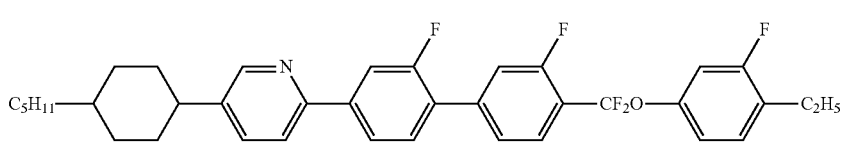 |
| 1-3-165 | 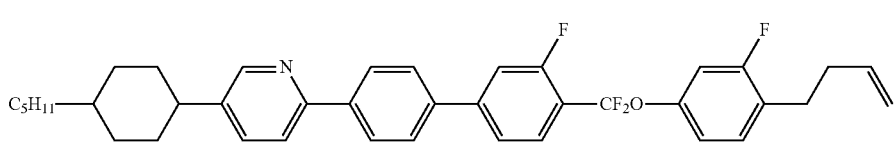 |
| 1-3-166 | 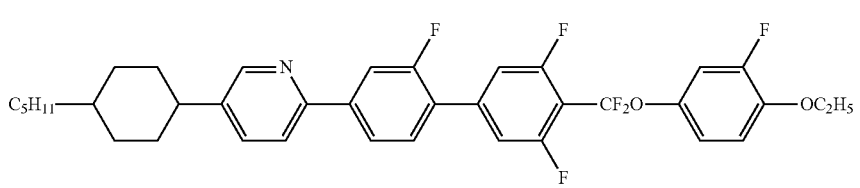 |

-continued
| No. | |
|---|---|
| 1-3-167 | 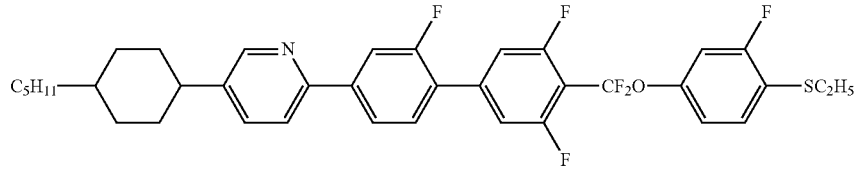 |
| 1-3-168 | 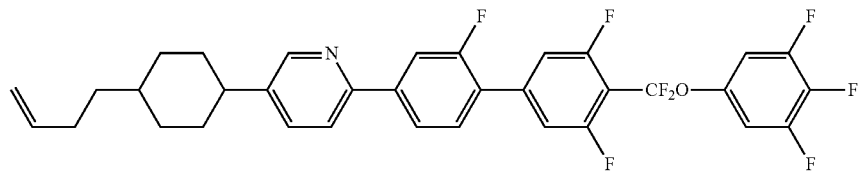 |
| 1-3-169 | 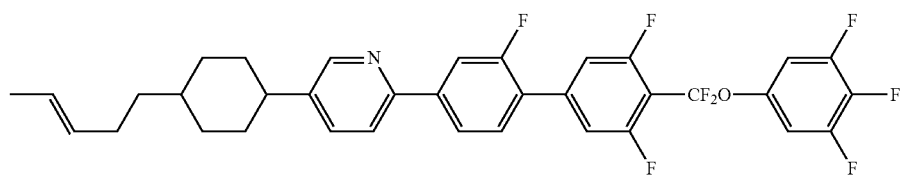 |
| 1-3-170 | 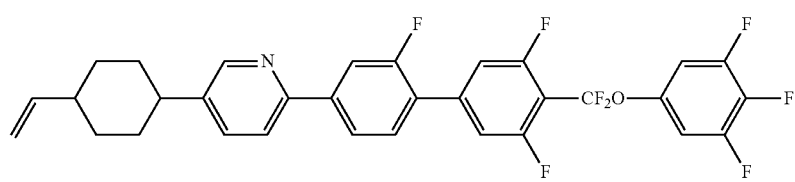 |
| 1-3-171 | 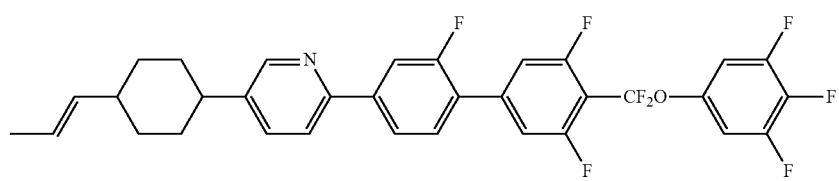 |
| 1-3-172 | 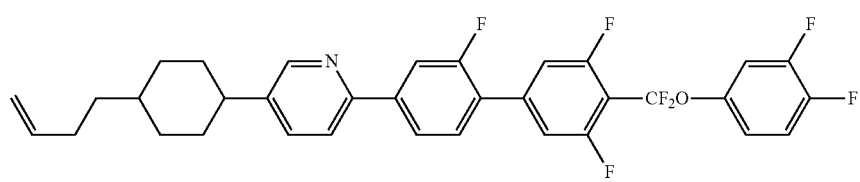 |
| 1-3-173 | 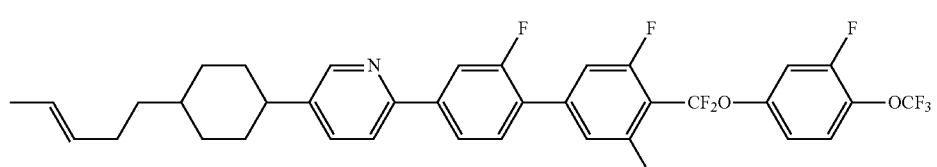 |
| 1-3-174 | 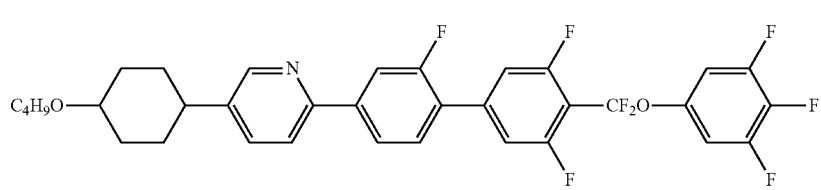 |

-continued
| No. | |
|---|---|
| 1-3-175 | 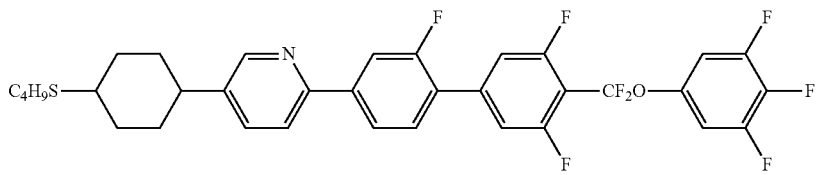 |
| 1-3-176 | 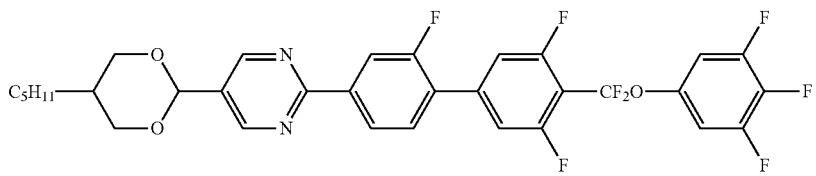 |
| 1-3-177 | 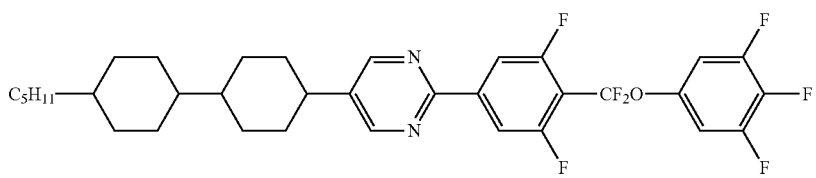 |
| 1-3-178 | 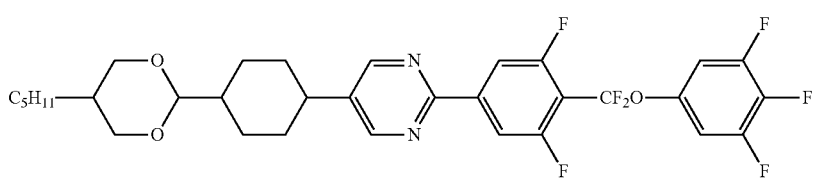 |
| 1-3-179 | 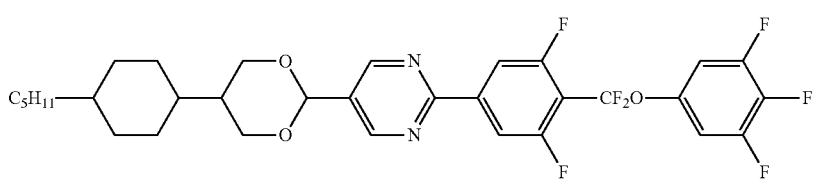 |
| 1-3-180 | 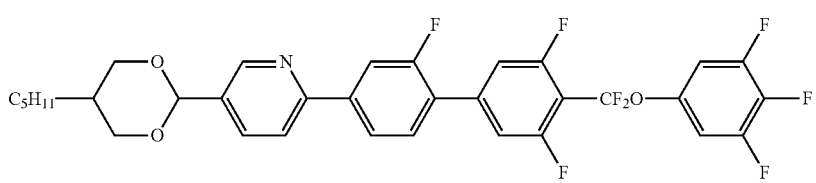 |
| 1-3-181 | 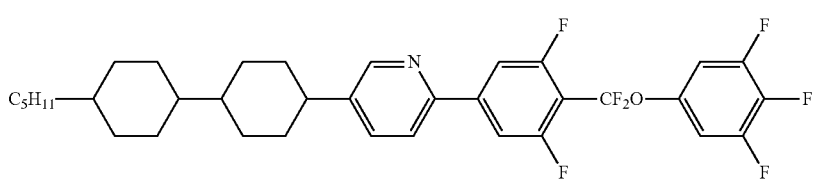 |
| 1-3-182 | 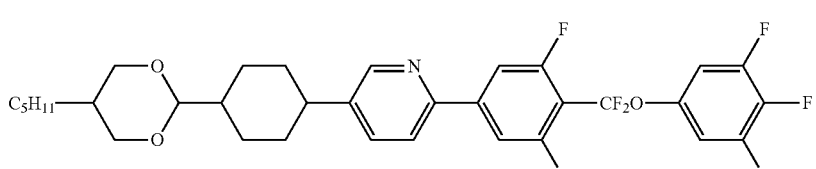 |

| No. | |
|---|---|
| 1-3-183 | 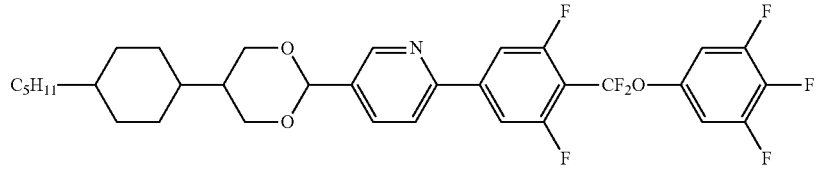 |
| 1-3-184 | 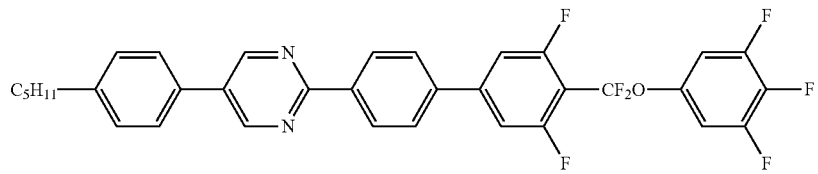 |
| 1-3-185 | 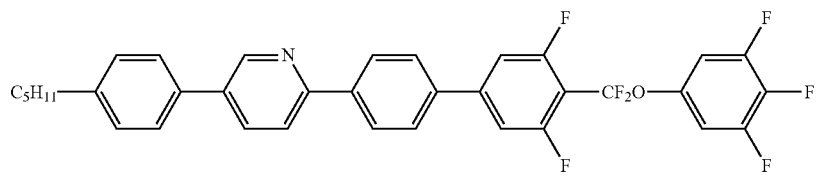 |
| 1-3-186 | 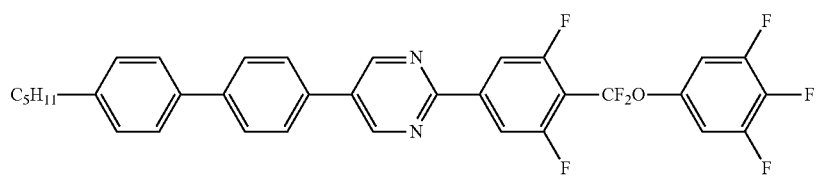 |
| 1-3-187 | 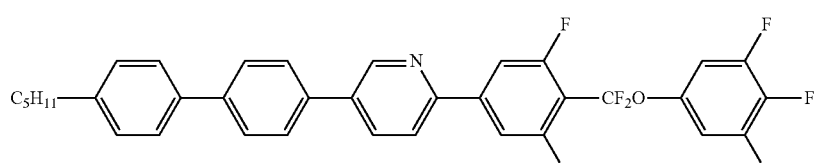 |
| 1-3-188 | 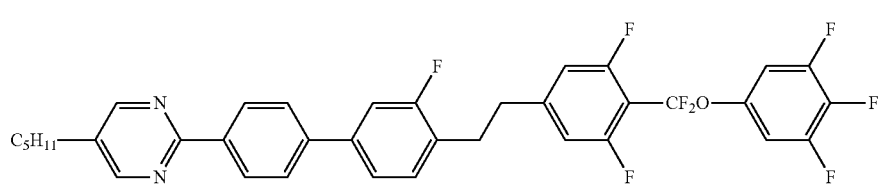 |
| 1-3-189 | 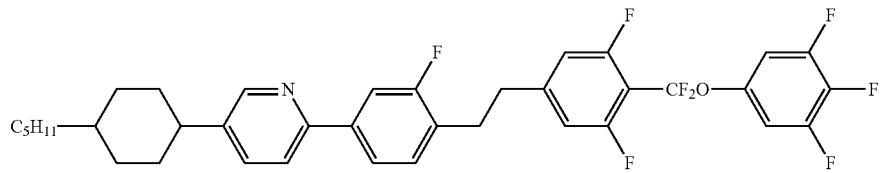 |
| 1-3-190 | 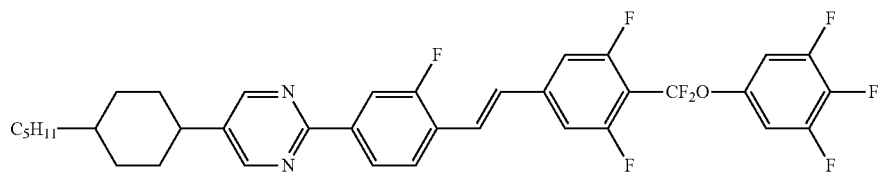 |

| No. | |
|---|---|
| 1-3-191 | 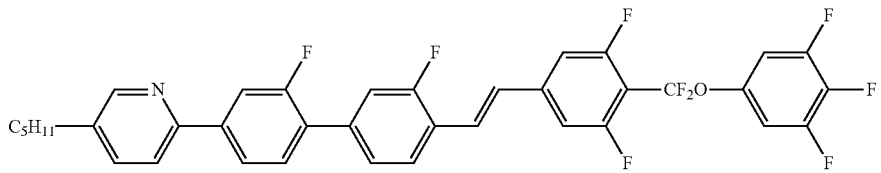 |
| 1-3-192 | 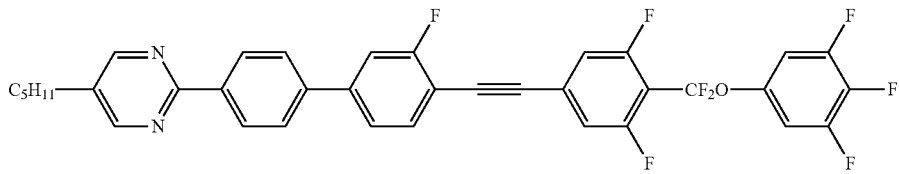 |
| 1-3-193 | 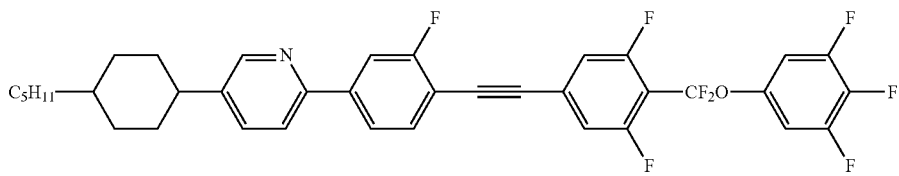 |
| 1-3-194 | 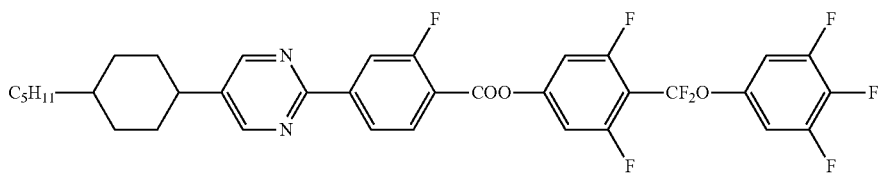 |
| 1-3-195 | 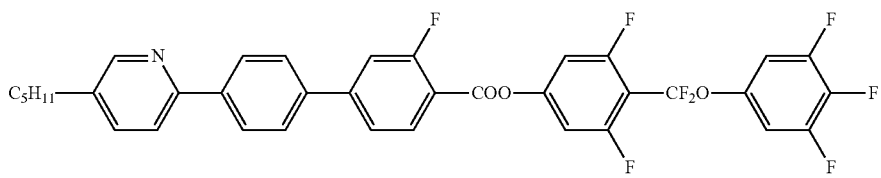 |
| 1-3-196 | 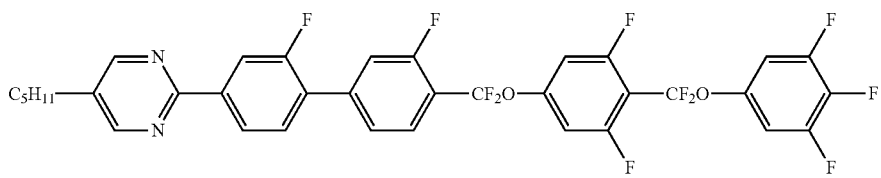 |
| 1-3-197 | 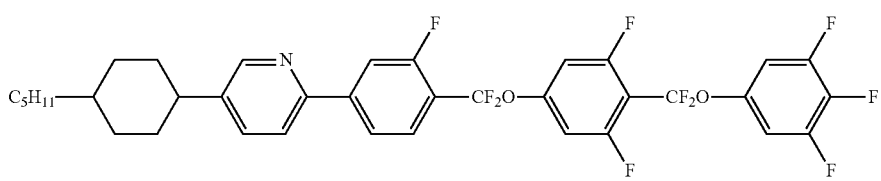 |
| 1-3-198 | 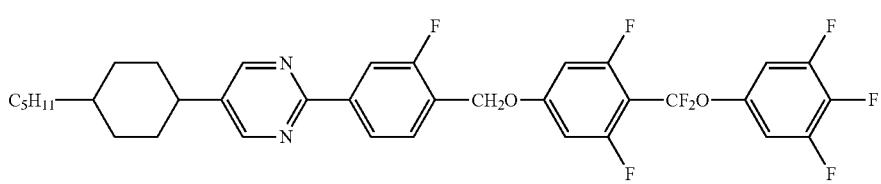 |

-continued
No.
1-3-199 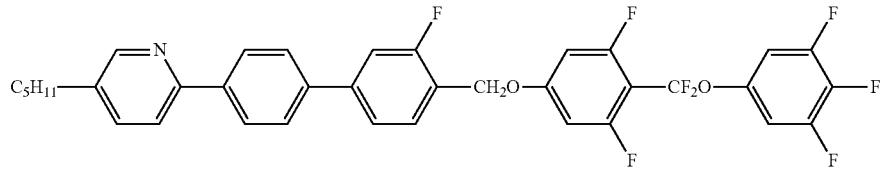
1-3-200 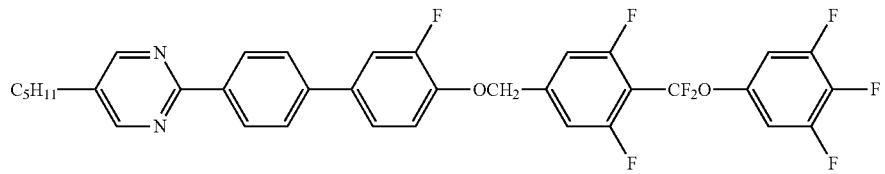
1-3-201 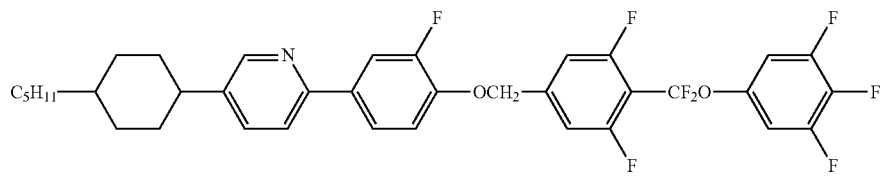
1-3-202 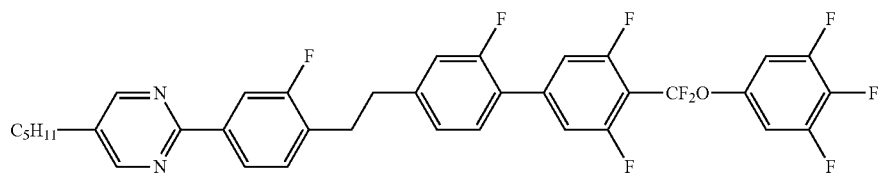
1-3-203 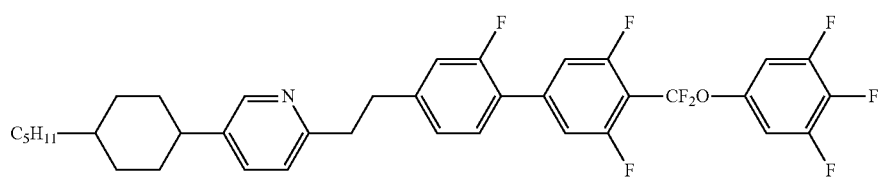
1-3-204 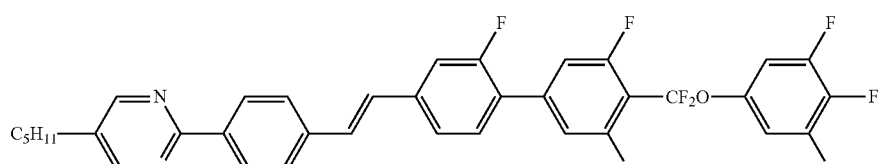
1-3-205 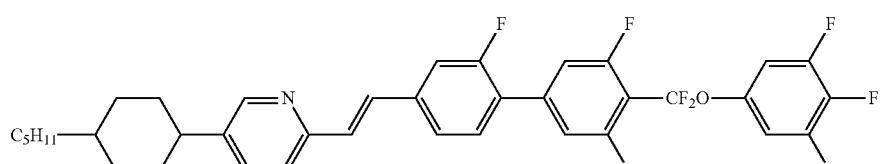
1-3-206 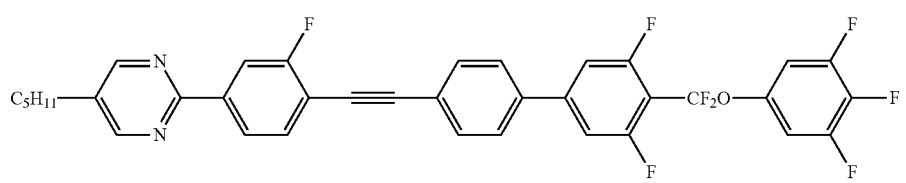

-continued
| No. | |
|---|---|
| 1-3-207 | 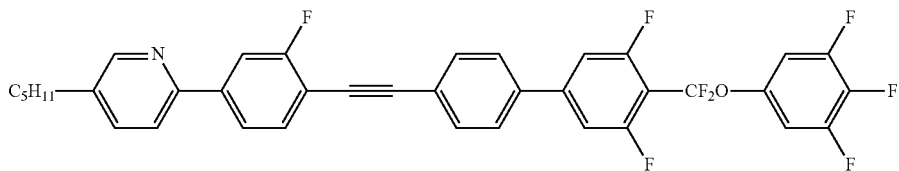 |
| 1-3-208 | 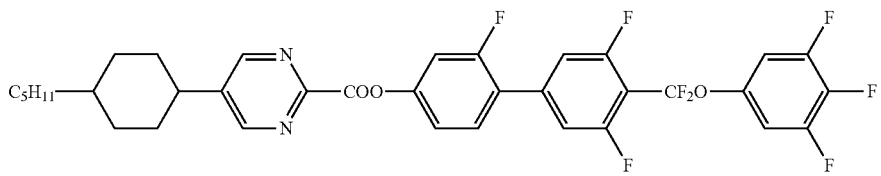 |
| 1-3-209 | 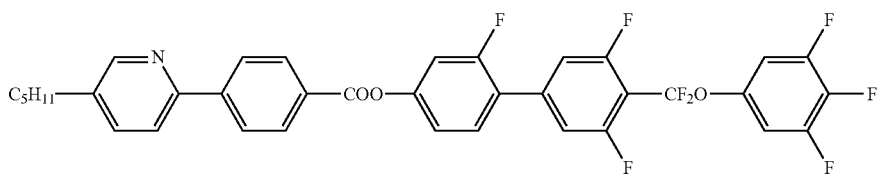 |
| 1-3-210 | 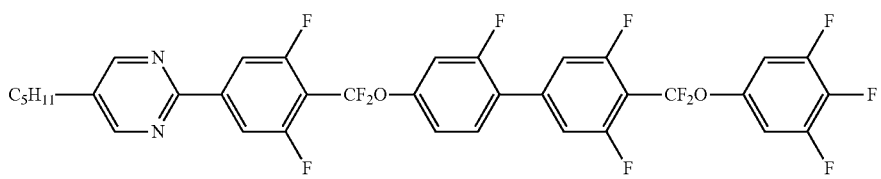 |
| 1-3-211 | 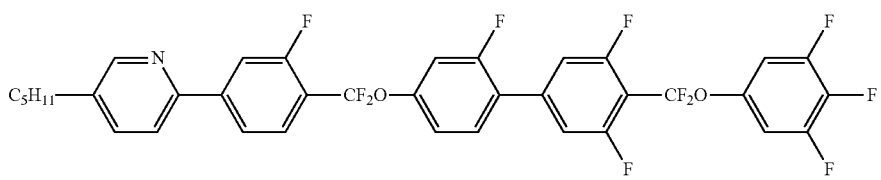 |
| 1-3-212 | 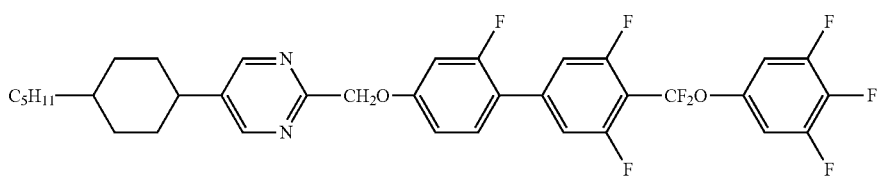 |
| 1-3-213 | 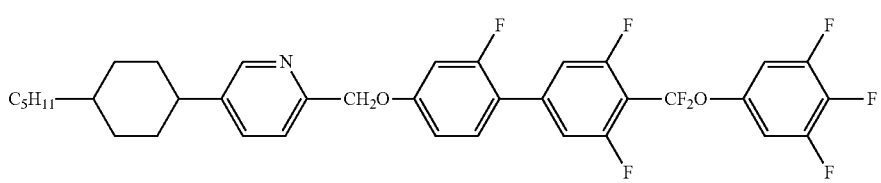 |
| 1-3-214 | 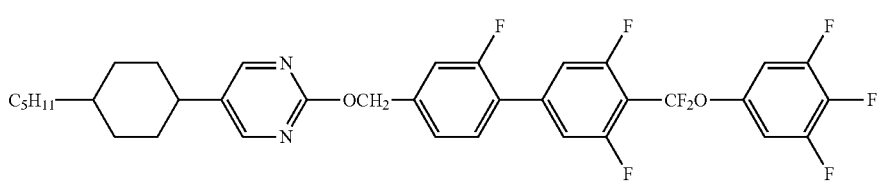 |

-continued
| No. |
|---|
| 1-3-215 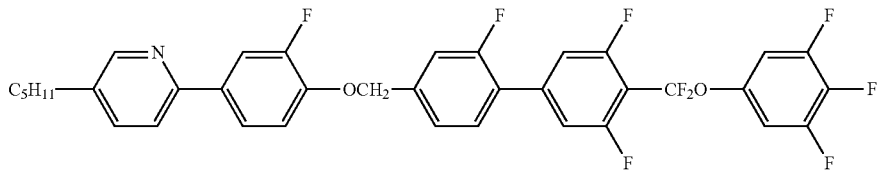 |
| 1-3-216 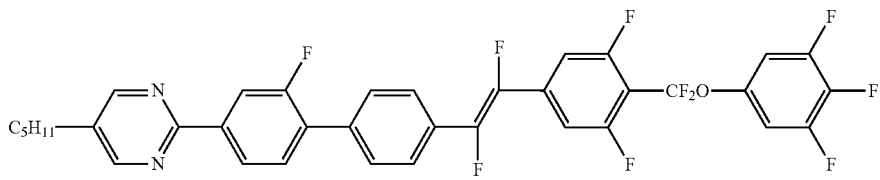 |
| 1-3-217 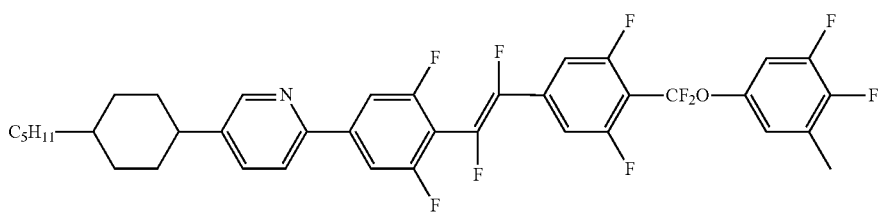 |
| 1-3-218 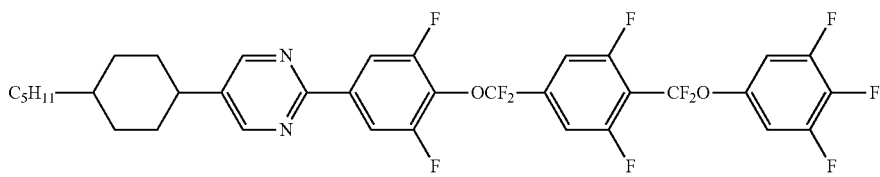 |
| 1-3-219 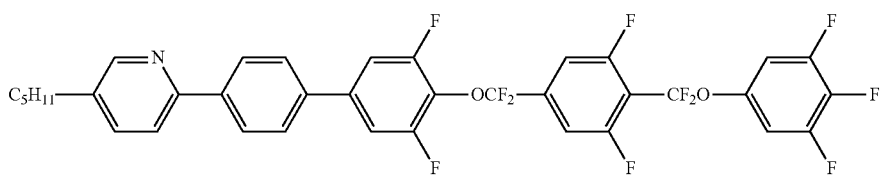 |
| 1-3-220 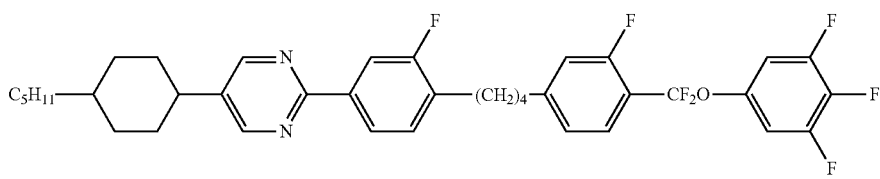 |
| 1-3-221 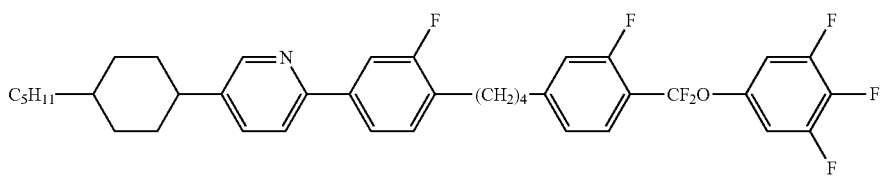 |
| 1-3-222 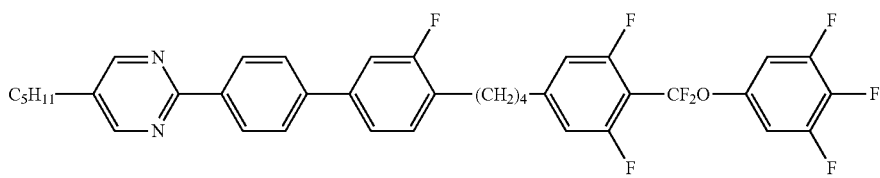 |

| No. | |
|---|---|
| 1-3-223 | 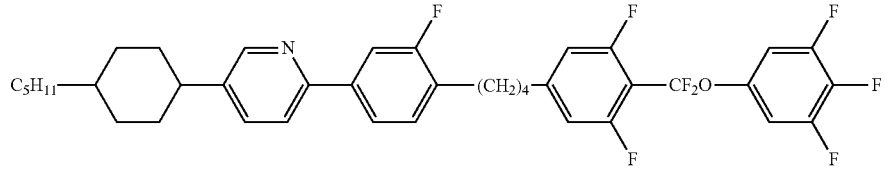 |
| 1-3-224 | 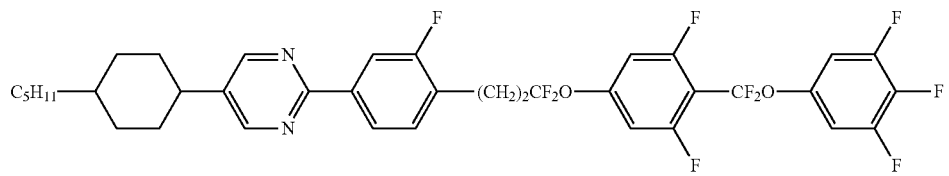 |
| 1-3-225 | 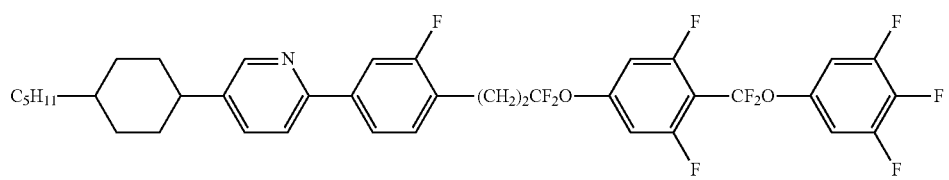 |
| 1-3-226 | 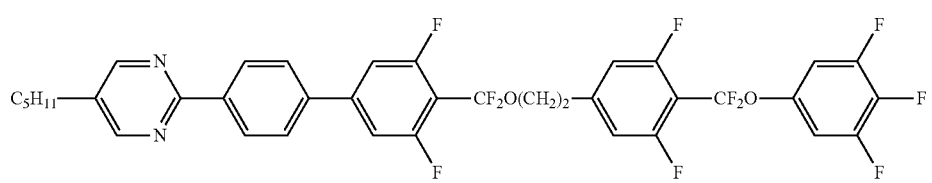 |
| 1-3-227 | 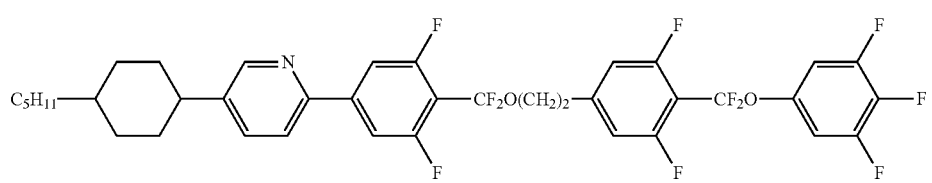 |
| 1-3-228 | 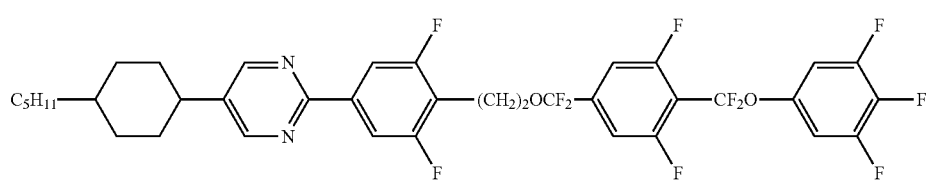 |
| 1-3-229 | 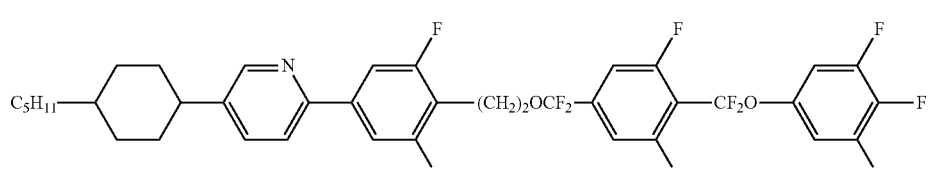 |
| 1-3-230 | 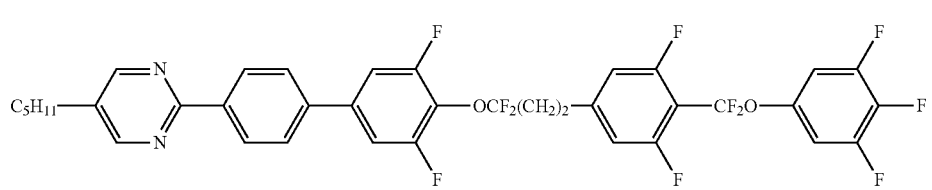 |

| No. | |
|---|---|
| 1-3-231 | 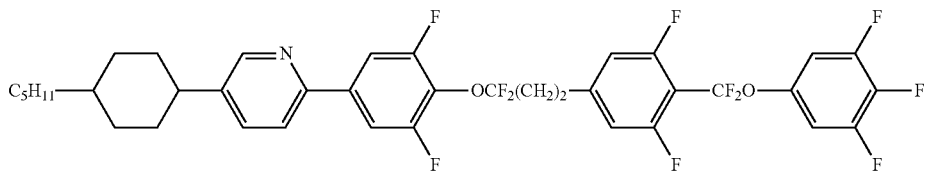 |
| 1-3-232 | 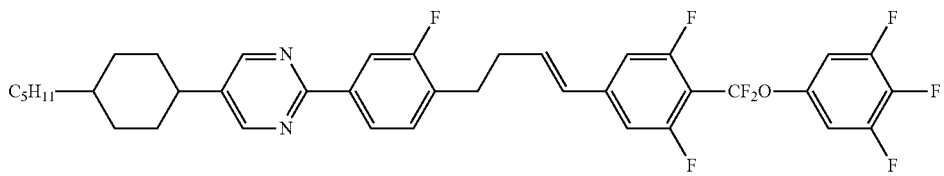 |
| 1-3-233 | 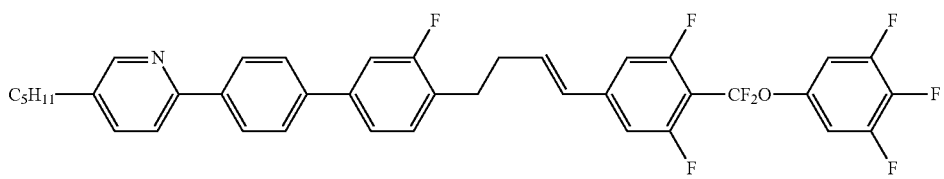 |
| 1-3-234 | 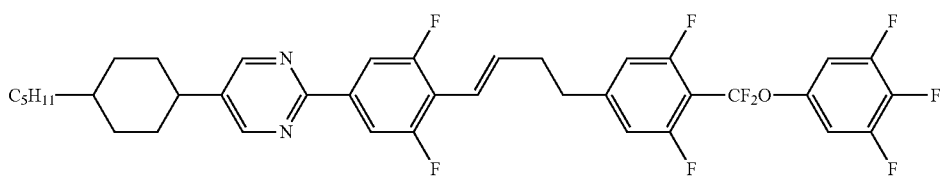 |
| 1-3-235 | 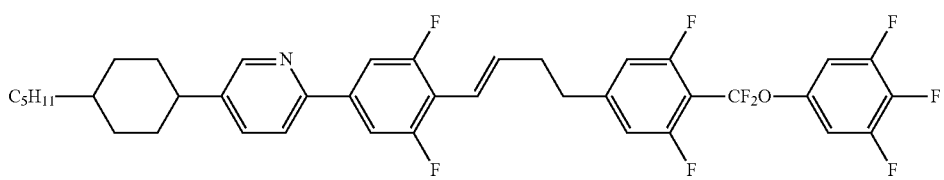 |

Comparative Example 1

A five-ring liquid crystal compound having a tetrahydropyran ring, 4-[difluoro[(2,3',4',5'-tetrafluoro[1,1'-biphenyl]-4-yl)oxy]methyl]-4'-(5-pentyltetrahydropyran-2-yl)-2',3,5,6'-tetrafluoro-1,1'-biphenyl (S-1-1) that was described in WO 2005-019378 A1 was prepared for comparison.

The chemical shift (δ, ppm) in $^1$H-NMR analysis was described below, and the compound obtained was identified as 4-[difluoro[(2,3',4',5'-tetrafluoro [1,1'-biphenyl]-4-yl)oxy] methyl]-4'-(5-pentyltetrahydropyran-2-yl)-2',3,5,6'-tetrafluoro-1,1'-biphenyl. The solvent for measurement was CDCl$_3$.

Chemical shift δ (ppm): 7.38 (dd, J=8.65 Hz, J=8.40 Hz, 1H), 7.23-7.11 (m, 6H), 7.08-7.00 (m, 2H), 4.28 (dd, J=11.8 Hz, J=1.95 Hz, 1H), 4.10 (dq, J=11.2 Hz, J=2.00 Hz, 1H), 3.21 (t, J=11.2 Hz, 1H), 2.05-1.98 (m, 1H), 1.95-1.88 (m, 1H), 1.73-1.62 (m, 1H), 1.60-1.48 (m, 1H), 1.45-1.09 (m, 5H) and 0.92 (t, J=6.80 Hz, 3H).

The phase transition temperature of the resulting comparative compound (S-1-1) was as follows.

Phase transition temperature: C 101 N 198 I.

(S-1-1)

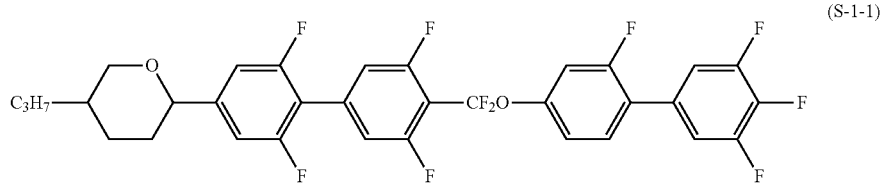

The liquid crystal composition E consisting of the mother liquid crystals A (85% by weight) and the comparative compound (S-1-1) (15% by weight) was prepared. The physical properties of the resulting liquid crystal composition E were measured, and the extrapolated values of the physical properties of the comparative compound (S-1-1) were calculated. The values were as follows.

Maximum temperature $(T_{NI})$=118° C.; refractive index anisotropy (Δn)=0.177; dielectric anisotropy (Δ∈)=52.3.

The compounds (No. 1-2-5), (No. 1-2-85) and (No. 1-3-5) of the invention, all of these are shown in Examples, will be compared with the comparative compound (S-1-1). First, in a comparison of each of the phase transition temperature, the compounds (No. 1-2-5), (No. 1-2-85) and (No. 1-3-5) have a wider temperature range of a liquid crystal phase. In particular, the compounds (No. 1-2-5) and (No. 1-2-85) of the invention have a lower minimum temperature and a higher compatibility with other compounds.

Next, in a comparison of the extrapolated values of physical properties of the compound of the invention with those of the comparative compound (S-1-1), the compounds (No. 1-2-5), (No. 1-2-85) and (No. 1-3-5) have a higher clearing point and a larger refractive index anisotropy. Thus, it is concluded that the compounds (No. 1-2-5), (No. 1-2-85) and (No. 1-3-5) are superior in view of usability in a wider temperature range and a larger refractive index anisotropy.

Comparative Example 2

For further comparison, a four ring-liquid crystal compound having a $CF_2O$ bonding group, 4-[difluoro(3,4,5-trifluorophenoxy)methyl]-3,5-difluoro-4'-(4-propylcyclohexyl)-1,1'-biphenyl (S-6) described in WO 96-11897 A1 was prepared.

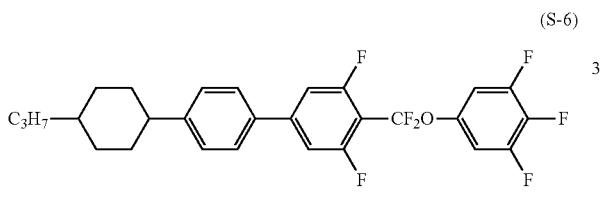

(S-6)

The chemical shift (δ, ppm) in $^1$H-NMR analysis was described below, and the compound obtained was identified as 4-[difluoro(3,4,5-trifluorophenoxy)methyl]-3,5-difluoro-4'-(4-propylcyclohexyl)-1,1'-biphenyl. The solvent for measurement was $CDCl_3$.

Chemical shift δ (ppm); 7.49 (d, J=8.23 Hz, 2H), 7.32 (d, J=8.23 Hz, 2H), 7.20 (d, J=10.6 Hz, 2H), 7.03-6.90 (m, 2H), 2.53 (tt, J=12.1 Hz, J=3.00 Hz, 1H), 1.97-1.86 (m, 4H), 1.51-1.40 (m, 2H), 1.40-1.18 (m, 4H), 1.13-1.01 (m, 2H) and 0.91 (t, J=7.20 Hz, 3H).

The phase transition temperature of the resulting comparative compound (S-6) was as follows.

Phase transition temperature: C 82.1 N 141 I.

The liquid crystal composition F consisting of the mother liquid crystals A (85% by weight) and the comparative compound (S-6) (15% by weight) were prepared. The physical properties of the resulting liquid crystal composition F were measured, and the extrapolated values of the physical properties of the comparative compound (S-6) were calculated. The values were as follows.

Maximum temperature $(T_{NI})$=110° C.; dielectric anisotropy $(\Delta\varepsilon)$=23.4; refractive index anisotropy $(\Delta n)$=0.157.

The compound (No. 1-2-5), (No. 1-2-85) and (No. 1-3-5) of the invention, those of which are shown in Examples, will be compared with the comparative compound (S-6). First, in a comparison of each of the phase transition temperature, the compounds (No. 1-2-5), (No. 1-2-85) and (No. 1-3-5) have a wider temperature range of a liquid crystal phase.

Next, in a comparison of the extrapolated values of physical properties of the compound of the invention with the comparative compound (S-6), the compounds (No. 1-2-5), (No. 1-2-85) and (No. 1-3-5) have a higher clearing points, a larger dielectric anisotropy and a larger refractive index anisotropy. Thus, it is concluded that the compounds (No. 1-2-5), (No. 1-2-85) and (No. 1-3-5) are superior in view of usability in a wider temperature range, a larger dielectric anisotropy and a larger refractive index anisotropy.

Comparative Example 3

The compound of the invention will be compared with a five ring-liquid crystal compound having a tetrahydropyran ring and a dioxane ring, 4-[difluoro(3,4,5-trifluorophenoxy)methyl]-3,5-difluoro-4'-(4-propylcyclohexyl)-1,1'-biphenyl (S-4) described in WO 2006-12551 A1.

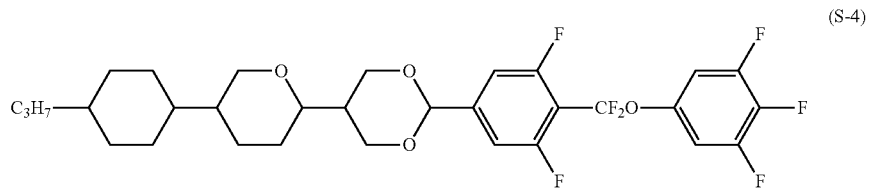

(S-4)

The phase transition temperature of the compound (S-4) described in WO 2006-12551 A1 are as follows.

The phase transition temperature: C 95 N 251 I.

In a comparison of the phase transition temperature of the compounds (No. 1-2-5) and (No. 1-2-85) of the invention, these of which are shown in Examples, with that of the comparative compound (S-4), the compounds (No. 1-2-5) and (No. 1-2-85) have a lower minimum temperature of a liquid crystal phase. Thus, it is concluded that the compound (No. 1-2-5) is superior in view of an excellent compatibility with other compounds and usability at lower temperature. In a comparison of the phase transition temperature of the compound (No. 1-3-5) of the invention that is shown in Example with that of the comparative compound (S-4), the compound (No. 1-3-5) has a higher maximum temperature. Thus, it is concluded that the compound (No. 1-3-5) is superior in view of usability at a higher temperature.

Example 8

Furthermore, typical compositions of the invention were summarized in Composition Example 1 to Composition Example 15. First, compounds that are a component of the composition and their amounts (% by weight) are shown. The compounds were expressed with the symbols of a left-terminal group, a bonding group, a ring structure and a right-terminal group according to the definition in the table below.

The configuration of 1,4-cyclohexylene and 1,3-dioxane-2,5-diyl is trans. The absence of the symbol of the terminal group means that the terminal group is hydrogen. The number written next to a liquid crystal compound used in each example corresponds to that of formula showing the liquid crystal compound of the invention. Next, the values of physical properties of the composition are shown. Values of physical properties here mean measured values as it is.

TABLE

Method of Description of Compounds using Symbols
$R-(A_1)-Z_1-\ldots-Z_n-(A_n)-R'$

| 1) Left-terminal Group R— | Symbol |
|---|---|
| $C_nH_{2n+1}-$ | n- |
| $C_nH_{2n+1}O-$ | nO— |
| $C_mH_{2m+1}OC_nH_{2n}-$ | mOn- |
| $CH_2=CH-$ | V— |
| $C_nH_{2n+1}-CH=CH-$ | nV— |
| $CH_2=CH-C_nH_{2n}-$ | Vn- |
| $C_mH_{2m+1}-CH=CH-C_nH_{2n}-$ | mVn- |
| $CF_2=CH-$ | VFF— |
| $CF_2=CH-C_nH_{2n}-$ | VFFn- |

| 2) Right-terminal Group —R' | Symbol |
|---|---|
| $-C_nH_{2n+1}$ | -n |
| $-OC_nH_{2n+1}$ | —On |
| $-CH=CH_2$ | —V |
| $-CH=CH-C_nH_{2n+1}$ | —Vn |
| $-C_nH_{2n}-CH=CH_2$ | -nV |
| $-C_mH_{2m}-CH=CH-C_nH_{2n+1}$ | -mVn |
| $-CH=CF_2$ | —VFF |
| $-COOCH_3$ | —EMe |
| —F | —F |
| —Cl | —CL |
| —CN | —C |
| $-OCF_3$ | —OCF3 |

| 3) Bonding Group —$Z_n$— | Symbol |
|---|---|
| $-C_nH_{2n}-$ | n |
| —COO— | E |
| —CH=CH— | V |
| $-CH_2O-$ | 1O |
| $-OCH_2-$ | O1 |
| $-CF_2O-$ | X |
| —C≡C— | T |

| 4) Ring Structure —$A_n$— | Symbol |
|---|---|
| 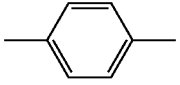 | B |
| 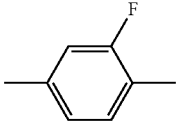 | B(F) |
| 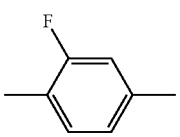 | B(2F) |
| 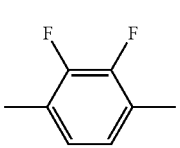 | B(2F,3F) |

TABLE-continued
Method of Description of Compounds using Symbols
R—(A₁)—Z₁— ... —Zₙ—(Aₙ)—R'
| Structure | Symbol |
|---|---|
| | B(F,F) |
| | B(2F,5F) |
| | Pr |
| | Py |
| | H |
| | G |
5) Examples of Description
Example 1. 5-PyB(F)B(F,F)XB(F)B(F,F)-F
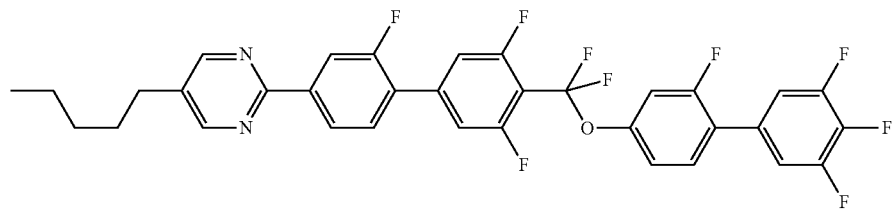
Example 2. 5-PrB(F)B(F,F)XB(F)B(F,F)-F
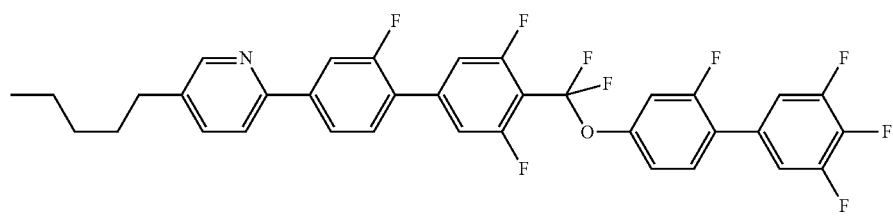
Example 3. 5-HBB(F)B-3
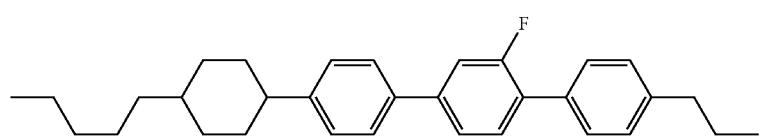

TABLE-continued

Method of Description of Compounds using Symbols
R—(A$_1$)—Z$_1$— ... —Z$_n$—(A$_n$)—R'

Example 4. 3-HH-4

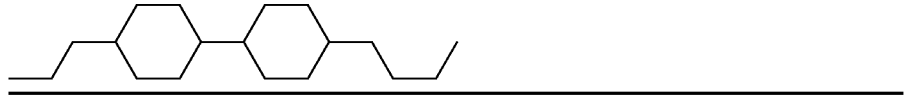

Characteristics can be measured according to the following methods. Most methods are described in the Standards of Electronic Industries Association of Japan, EIAJ•ED-2521A or those with some modifications. A TN device used for measurement was not equipped with a TFT.

Maximum Temperature of a Nematic Phase (NI; ° C.)

A sample was placed on a hot plate in a melting point apparatus equipped with a polarizing microscope and was heated at the rate of 1° C. per minute. The temperature was measured when part of the sample began to change from a nematic phase to an isotropic liquid. A higher limit of the temperature range of a nematic phase may be abbreviated to "the maximum temperature."

Minimum Temperature of a Nematic Phase (Tc; ° C.)

A sample having a nematic phase was kept in freezers at temperatures of 0° C., -10° C., -20° C. -30° C. and -40° C. for 10 days, and then the liquid crystal phases were observed. For example, when the sample maintained the nematic phase at -20° C. and changed to crystals or a smectic phase at -30° C., Tc was expressed as ≦-20° C. A lower limit of the temperature range of a nematic phase may be abbreviated to "the minimum temperature."

Viscosity (Bulk Viscosity; η; Measured at 20° C.; mPa·s)

An E-type viscometer was used for measurement.

Viscosity (Rotational Viscosity; γ1; Measured at 25° C.; mPa·s)

(1) Sample Having Positive Dielectric Anisotropy

Measurement was carried out according to the method described in M. Imai, et al., Molecular Crystals and Liquid Crystals, Vol. 259, 37 (1995). A sample was poured into a TN device in which the twist angle was 0 degrees and the distance between two glass substrates (the cell gap) was 5 micrometers. A voltage with an increment of 0.5 volt in the range of 16 to 19.5 volts was applied stepwise to the TN device. After a period of 0.2 second with no voltage, a voltage was applied repeatedly under the conditions of only one rectangular wave (rectangular pulse; 0.2 second) and of no voltage (2 seconds). The peak current and the peak time of the transient current generated by the applied voltage were measured. The value of rotational viscosity was obtained from the measured values and the calculating equation (8) on page 40 of the paper presented by M. Imai, et al. The value of dielectric anisotropy necessary for this calculation was obtained by use of the device that had been used for the measurement of this rotational viscosity, according to the method for measurement of dielectric anisotropy that will be described below.

(2) Sample Having Negative Dielectric Anisotropy

Measurement was carried out according to the method described in M. Imai et al., Molecular Crystals and Liquid Crystals, Vol. 259, 37 (1995). A sample was poured into a VA device, in which the distance of two glass substrates (the cell gap) was 20 micrometers. A voltage with an increment of 1 volt in the range of 30 to 50 volts was applied stepwise to the device. After a period of 0.2 second with no voltage, a voltage was applied repeatedly under the conditions of only one rectangular wave (rectangular pulse; 0.2 second) and of no voltage (2 seconds). The peak current and the peak time of the transient current generated by the applied voltage were measured. The value of rotational viscosity was obtained from the measured values and the calculating equation (8) on page 40 of the paper presented by M. Imai, et al. The value of dielectric anisotropy necessary for this calculation was supplied by measurement of dielectric anisotropy that will be described below.

Optical Anisotropy (Refractive Index Anisotropy; Δn; Measured at 25° C.)

Measurement was carried out by use of an Abbe refractometer with a polarizing plate mounted on the ocular, using light at a wavelength of 589 nanometers. The surface of the main prism was rubbed in one direction, and then a sample was dropped on the main prism. A refractive index (n∥) was measured when the direction of polarized light was parallel to that of the rubbing. A refractive index (n⊥) was measured when the direction of polarized light was perpendicular to that of the rubbing. The value of optical anisotropy was calculated from the equation: Δn=n∥-n⊥. When a sample was a composition, the optical anisotropy was measured according to this method. When the sample was a compound, the optical anisotropy was measured after the compound had been mixed with a suitable composition. The optical anisotropy of the compound was expressed as an extrapolated value.

Dielectric Anisotropy (Δ∈; Measured at 25° C.)

When the sample was a compound, the optical anisotropy was measured after the compound had been mixed with a suitable composition. The dielectric anisotropy of the compound was expressed as an extrapolated value.

(1) Composition Having Positive Dielectric Anisotropy

A sample was poured into a liquid crystal cell in which the distance between two glass substrates (the cell gap) were about 9 micrometers and the twist angel was 80 degrees. A voltage of 20 V was applied to the cell and a dielectric constant (∈∥) in the major axis direction of liquid crystal molecules was measured. A voltage of 0.5 V was applied and a dielectric constant (∈⊥) in the minor axis direction of liquid crystal molecules was measured. The value of dielectric anisotropy was calculated from the equation: Δ∈=∈∥-∈⊥.

(2) Composition Having Negative Dielectric Anisotropy

A sample was poured into a liquid crystal cell having homeotropic orientation, and a dielectric constant (∈∥) was measured while 0.5 V was applied. A sample was poured into a liquid crystal cell having homogeneous orientation, and a dielectric constant (∈⊥) was measured. The value of dielectric anisotropy was calculated from the equation: Δ∈=∈∥-∈⊥.

Threshold Voltage (Vth; Measured at 25° C.;

When the sample was a compound, the threshold voltage was measured after the compound had been mixed with a suitable composition. The threshold voltage of the compound was expressed as an extrapolated value.

(1) Composition Having Positive Dielectric Anisotropy

A sample was poured into a liquid crystal display device having a normally white mode, in which the distance between two glass substrates (the cell gap) was (0.5/Δn) micrometers and the twist angle was 80 degrees. Δn is the value of optical anisotropy measured by the method described above. Rectangular waves at a frequency of 32 Hz were applied to the device. The voltage of the rectangular waves was increased, and the value of voltage was measured when the transmittance of light that had passed through the device became 90%.

(2) Composition Having Negative Dielectric Anisotropy

A sample was poured into a liquid crystal display device having a normally black mode and having homeotropic orientation, in which the distance between two glass substrates (the cell gap) was about 9 micrometers. Rectangular waves at a frequency of 32 Hz were applied to the device. The voltage of the rectangular waves was increased, and the value of voltage was measured when the transmittance of light that had passed through the device became 10%.

Voltage Holding Ratio (VHR-1; Measured at 25° C.; %)

A TN device used for measurement had a polyimide-alignment film, and the distance between the two glass substrates (the cell gap) was 6 micrometers. A sample was poured into the device, and then the device was sealed with a UV-polymerizable adhesive. A pulse voltage (60 microseconds at 5 V) was applied to the TN device and the device was charged. A decreasing voltage was measured for 16.7 milliseconds with a high-speed voltmeter, and the area A between a voltage curve and a horizontal axis in a unit cycle was obtained. The area B was an area without the decrease. The voltage holding ratio was the percentage of the area A to the area B.

Helical Pitch (Measured at 20° C.; Micrometer)

The helical pitch was measured according to the Cano's wedge method. After a sample had been poured into a Cano's wedge-shaped cell, the interval (a; micrometer) of disclination lines was measured. The helical pitch (P) was calculated from the following equation, wherein θ was the angle between two glass plates in the wedge cell:

$$P = 2 \times a \times \tan \theta.$$

The ratio (percentage) of components or liquid crystal compounds is expressed as a percentage by weight (% by weight) based on the total weight of liquid crystal compounds. Components such as liquid crystal compounds are weighed and then mixed to prepare a composition. Accordingly, it is easy to calculate weight percentage of the components.

Composition Example 1

| | | |
|---|---|---|
| 5-PyB(F)B(F,F)XB(F)B(F,F)-F | (1-2-5) | 10% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 11% |
| 3-HB-O2 | (11-5) | 10% |
| 3-HH-4 | (11-1) | 3% |
| 3-HHB-F | (3-1) | 3% |
| 3-HHB-1 | (12-1) | 3% |
| 3-HHB-O1 | (12-1) | 4% |
| 3-HBEB-F | (3-37) | 4% |
| 3-HHEB-F | (3-10) | 7% |
| 5-HHEB-F | (3-10) | 7% |
| 3-H2BTB-2 | (12-16) | 4% |
| 3-H2BTB-3 | (12-16) | 4% |
| 3-H2BTB-4 | (12-16) | 4% |
| 3-HB(F)TB-2 | (12-17) | 5% |

NI = 96.1° C.; Δn = 0.154; Δε = 30.2; Vth = 1.03 V.

Composition Example 2

| | | |
|---|---|---|
| 5-PrB(F)B(F,F)XB(F)B(F,F)-F | (1-2-85) | 4% |
| 5-PyB(F)B(F)B(F,F)XB(F,F)-F | (1-3-5) | 4% |
| 2-HB-C | (5-1) | 5% |
| 3-HB-C | (5-1) | 12% |
| 3-HB-O2 | (11-5) | 15% |
| 2-BTB-1 | (11-10) | 3% |
| 3-HHB-1 | (12-1) | 8% |
| 3-HHB-F | (3-1) | 4% |
| 3-HHB-O1 | (12-1) | 5% |
| 3-HHB-3 | (12-1) | 10% |
| 3-HHEB-F | (3-10) | 2% |
| 5-HHEB-F | (3-10) | 4% |
| 2-HHB(F)-F | (3-2) | 7% |
| 3-HHB(F)-F | (3-2) | 5% |
| 5-HHB(F)-F | (3-2) | 7% |
| 3-HHB(F,F)-F | (3-3) | 5% |

NI = 100.5° C.; Δn = 0.111; Δε = 8.1; Vth = 1.90 V.

Composition Example 3

| | | |
|---|---|---|
| 5-HPyB(F)B(F,F)XB(F,F)-F | (1-3-105) | 4% |
| 5-PrB(F)B(F)B(F,F)XB(F,F)-F | (1-3-71) | 4% |
| 3-BEB(F)-C | (5-14) | 8% |
| 3-HB-C | (5-1) | 8% |
| V-HB-C | (5-1) | 8% |
| 1V-HB-C | (5-1) | 8% |
| 3-HB-O2 | (11-5) | 3% |
| 3-HH-2V | (11-1) | 14% |
| 3-HH-2V1 | (11-1) | 7% |
| V2-HHB-1 | (12-1) | 15% |
| 3-HHB-1 | (12-1) | 5% |
| 3-HHEB-F | (3-10) | 3% |
| 3-H2BTB-2 | (12-16) | 2% |
| 3-H2BTB-3 | (12-16) | 6% |
| 3-H2BTB-4 | (12-16) | 5% |

Composition Example 4

| | | |
|---|---|---|
| 5-PyB(F)B(F,F)XB(F)B(F,F)-F | (1-2-5) | 5% |
| 5-PrB(F)B(F,F)XB(F)B(F,F)-F | (1-2-85) | 5% |
| 5-BEB(F)-C | (5-14) | 5% |
| V-HB-C | (5-1) | 11% |
| 5-PyB-C | (5-9) | 6% |
| 4-BB-3 | (11-8) | 11% |
| 3-HH-2V | (11-1) | 10% |
| 5-HH-V | (11-1) | 11% |
| V-HHB-1 | (12-1) | 7% |
| V2-HHB-1 | (12-1) | 10% |
| 3-HHB-1 | (12-1) | 9% |
| 1V2-HBB-2 | (12-4) | 5% |
| 3-HHEBH-3 | (13-6) | 5% |

NI = 90.4° C.; Δn = 0.124; Δε = 9.6; Vth = 1.64 V.

Composition Example 5

| | | |
|---|---|---|
| 5-PyB(F)B(F)B(F,F)XB(F,F)-F | (1-3-5) | 4% |
| 5-HPyB(F)B(F,F)XB(F,F)-F | (1-3-105) | 4% |
| 1V2-BEB(F,F)-C | (5-15) | 6% |
| 3-HB-C | (5-1) | 18% |

-continued

| | | |
|---|---|---|
| 2-BTB-1 | (11-10) | 10% |
| 5-HH-VFF | (11-1) | 26% |
| VFF-HHB-1 | (12-1) | 8% |
| VFF2-HHB-1 | (12-1) | 7% |
| 3-H2BTB-2 | (12-16) | 5% |
| 3-H2BTB-3 | (12-16) | 4% |
| 3-H2BTB-4 | (12-16) | 4% |
| 3-HHB-1 | (12-1) | 4% |

Composition Example 6

| | | |
|---|---|---|
| 5-PyB(F)B(F,F)XB(F)B(F,F)-F | (1-2-5) | 5% |
| 5-PrB(F)B(F,F)XB(F)B(F,F)-F | (1-2-85) | 4% |
| 5-HB-CL | (2-2) | 16% |
| 3-HH-4 | (11-1) | 12% |
| 3-HH-5 | (11-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 5% |
| 4-HHB(F)-F | (3-2) | 5% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (13-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 119.4° C.; Δn = 0.105; Δε = 7.9; Vth = 1.87 V.

Composition Example 7

| | | |
|---|---|---|
| 5-PyB(F)B(F,F)XB(F)B(F,F)-F | (1-2-5) | 8% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 21% |
| 5-HBB(F,F)-F | (3-24) | 20% |
| 3-H2BB(F,F)-F | (3-27) | 6% |
| 5-HHBB(F,F)-F | (4-6) | 3% |
| 5-HH2BB-F | (4-13) | 2% |
| 3-HH2BB(F,F)-F | (4-15) | 3% |
| 1O1-HBBH-4 | (13-1) | 2% |
| 1O1-HBBH-5 | (13-1) | 2% |

NI = 98.1° C.; Δn = 0.123; Δε = 12.9; Vth = 1.47 V.

The helical pitch was 63.5 micrometers when the optically active compound (Op-5) (0.25 parts by weight) was added to the preceding composition (100 parts by weight).

Composition Example 8

| | | |
|---|---|---|
| 5-PrB(F)B(F,F)XB(F)B(F,F)-F | (1-2-85) | 5% |
| 5-PyB(F)B(F)B(F,F)XB(F,F)-F | (1-3-5) | 5% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF3 | (3-3) | 5% |
| 3-HBB(F)-F | (3-23) | 5% |
| 5-HBB(F)-F | (3-23) | 5% |
| 3-HH2B(F)-F | (3-5) | 3% |
| 3-HB(F)BH-3 | (13-2) | 3% |
| 5-HBBH-3 | (13-1) | 3% |
| 3-HHB(F,F)-OCF2H | (3-3) | 4% |

NI = 92.5° C.; Δn = 0.103; Δε = 8.6; Vth = 1.89 V.

Composition Example 9

| | | |
|---|---|---|
| 5-HPyB(F)B(F,F)XB(F,F)-F | (1-3-105) | 3% |
| 5-PrB(F)B(F)B(F,F)XB(F,F)-F | (1-3-71) | 5% |
| 5-HB-CL | (2-2) | 11% |
| 3-HH-4 | (11-1) | 8% |
| 3-HBB(F,F)-F | (3-24) | 20% |
| 5-HBB(F,F)-F | (3-24) | 12% |
| 3-HHB(F,F)-F | (3-3) | 8% |
| 3-HHEB(F,F)-F | (3-12) | 5% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |
| 3-HHB-1 | (12-1) | 5% |

Composition Example 10

| | | |
|---|---|---|
| 5-PyB(F)B(F,F)XB(F)B(F,F)-F | (1-2-5) | 5% |
| 5-PyB(F)B(F)B(F,F)XB(F,F)-F | (1-3-5) | 3% |
| 5-H4HB(F,F)-F | (3-21) | 7% |
| 5-H4HB-OCF3 | (3-19) | 15% |
| 3-H4HB(F,F)-CF3 | (3-21) | 8% |
| 5-H4HB(F,F)-CF3 | (3-21) | 10% |
| 3-HB-CL | (2-2) | 3% |
| 5-HB-CL | (2-2) | 4% |
| 2-H2BB(F)-F | (3-26) | 5% |
| 3-H2BB(F)-F | (3-26) | 5% |
| 5-H2HB(F,F)-F | (3-15) | 5% |
| 3-HHB-OCF3 | (3-1) | 5% |
| 3-H2HB-OCF3 | (3-13) | 5% |
| V-HHB(F)-F | (3-2) | 5% |
| 3-HHB(F)-F | (3-2) | 5% |
| 5-HHB(F)-F | (3-2) | 5% |
| 3-HBEB(F,F)-F | (3-39) | 5% |

NI = 78.5° C.; Δn = 0.108; Δε = 12.1; Vth = 1.63 V.

Composition Example 11

| | | |
|---|---|---|
| 5-PyB(F)B(F,F)XB(F)B(F,F)-F | (1-2-5) | 5% |
| 5-PrB(F)B(F,F)XB(F)B(F,F)-F | (1-2-85) | 5% |
| 5-HB-CL | (2-2) | 12% |
| 7-HB(F,F)-F | (2-4) | 3% |
| 3-HH-4 | (11-1) | 10% |
| 3-HH-5 | (11-1) | 5% |
| 3-HB-O2 | (11-5) | 10% |
| 3-H2HB(F,F)-F | (3-15) | 5% |

-continued

| | | |
|---|---|---|
| 4-H2HB(F,F)-F | (3-15) | 5% |
| 3-HHB(F,F)-F | (3-3) | 6% |
| 2-HHB(F)-F | (3-2) | 7% |
| 3-HHB(F)-F | (3-2) | 7% |
| 5-HHB(F)-F | (3-2) | 7% |
| 3-HHB-1 | (12-1) | 8% |
| 3-HHB-O1 | (12-1) | 5% |

NI = 85.1° C.; Δn = 0.090; Δε = 7.7; Vth = 1.50 V.

Composition Example 12

| | | |
|---|---|---|
| 5-PyB(F)B(F)B(F,F)XB(F,F)-F | (1-3-5) | 5% |
| 5-PrB(F)B(F)B(F,F)XB(F,F)-F | (1-3-71) | 5% |
| 7-HB(F)-F | (2-3) | 7% |
| 5-HB-CL | (2-2) | 3% |
| 3-HH-4 | (11-1) | 9% |
| 3-HH-EMe | (11-2) | 18% |
| 3-HHEB(F,F)-F | (3-12) | 5% |
| 4-HHEB(F,F)-F | (3-12) | 5% |
| 3-HHEB-F | (3-10) | 8% |
| 5-HHEB-F | (3-10) | 8% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

Composition Example 13

| | | |
|---|---|---|
| 5-PyB(F)B(F,F)XB(F)B(F,F)-F | (1-2-5) | 10% |
| 3-BB(F,F)XB(F,F)-F | (3-97) | 28% |
| 3-HH-4 | (11-1) | 8% |
| 3-HHB(F,F)-F | (3-3) | 10% |
| 3-H2HB(F,F)-F | (3-15) | 9% |
| 3-HBB(F,F)-F | (3-24) | 15% |
| 2-HHBB(F,F)-F | (4-6) | 3% |
| 3-HHBB(F,F)-F | (4-6) | 3% |
| 3-HH2BB(F,F)-F | (4-15) | 4% |
| 3-HHB-1 | (12-1) | 3% |
| 1O1-HBBH-5 | (13-1) | 7% |

NI = 91.5° C.; Δn = 0.128; Δε = 12.6; Vth = 1.17 V.

Composition Example 14

| | | |
|---|---|---|
| 5-PyB(F)B(F,F)XB(F)B(F,F)-F | (1-2-5) | 5% |
| 5-PrB(F)B(F,F)XB(F)B(F,F)-F | (1-2-85) | 5% |
| 5-HPyB(F)B(F,F)XB(F,F)-F | (1-3-105) | 5% |
| 5-HB-CL | (2-2) | 13% |
| 3-PyB(F)-F | (2-15) | 10% |
| 5-PyB(F)-F | (2-15) | 10% |
| 3-HBB(F,F)-F | (3-24) | 7% |
| 3-PyBB-F | (3-80) | 6% |
| 4-PyBB-F | (3-80) | 7% |
| 5-PyBB-F | (3-80) | 7% |
| 3-HB-O2 | (11-5) | 5% |
| 5-HBB(F)B-2 | (13-5) | 10% |
| 5-HBB(F)B-3 | (13-5) | 10% |

Composition Example 15

| | | |
|---|---|---|
| 5-PyB(F)B(F,F)XB(F)B(F,F)-F | (1-2-5) | 10% |
| 3-HH-V | (11-1) | 30% |
| 3-BB(F,F)XB(F,F)-F | (3-97) | 18% |

-continued

| | | |
|---|---|---|
| 3-HHB-1 | (12-1) | 2% |
| 2-HBB-F | (3-22) | 3% |
| 3-HBB-F | (3-22) | 4% |
| 3-HHB-CL | (3-1) | 2% |
| 1-BB(F)B-2V | (12-6) | 6% |
| 2-BB(F)B-2V | (12-6) | 6% |
| 3-BB(F)B-2V | (12-6) | 3% |
| 2-HHB(F,F)-F | (3-3) | 2% |
| 3-HHB(F,F)-F | (3-3) | 4% |
| 4-BB(F)B(F,F)XB(F,F)-F | (4-46) | 10% |

NI = 91.2° C.; Δn = 0.146; Δε = 12.3; Vth = 1.45 V; η = 25.8 mPa · sec.

INDUSTRIAL APPLICABILITY

The invention provides a liquid crystal compound having general physical properties necessary for a compound, stability to heat, light or the like, a wide temperature range of a liquid crystal phase, a high clearing point, an excellent compatibility with other liquid crystal compounds, a large refractive index anisotropy and a large dielectric anisotropy. The invention provides a liquid crystal composition including this liquid crystal compound. Since a liquid crystal display device contains the liquid crystal composition, it has a wide operating temperature range, a short response time, small electric power consumption, a large contrast and a low driving voltage, and thus it can be utilized for a display of a watch, a calculator, a word processor and so forth.

What is claimed is:

1. A compound represented by any one of formulas (1-1) to (1-3):

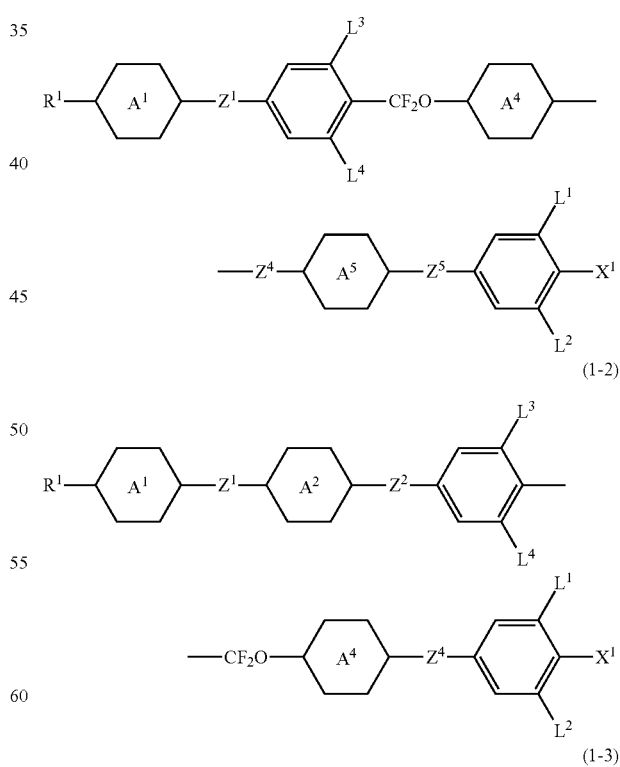

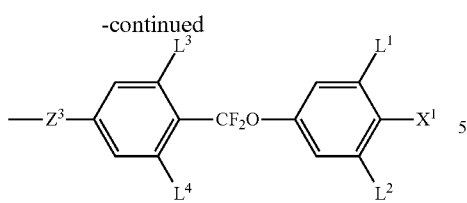

wherein $R^1$ is alkyl having 1 to 15 carbons, alkenyl having 2 to 15 carbons, alkoxy having 1 to 15 carbons or alkenyloxy having 2 to 15 carbons; the ring $A^1$ is pyrimidine-2,5-diyl; the ring $A^2$, the ring $A^3$, the ring $A^4$ and the ring $A^5$ are independently 1,4-cyclohexylene, 1,3-dioxane-2,5-diyl, 1,4-phenylene, or 1,4-phenylene in which arbitrary hydrogen is replaced by halogen; $Z^1, Z^2, Z^3, Z^4$ and $Z^5$ are independently a single bond, —CH$_2$CH$_2$—, —CH=CH—, —C≡C—, —COO—, —CF$_2$O—, —CH$_2$O— or —OCH$_2$—; $L^1, L^2, L^3$ and $L^4$ are independently hydrogen or fluorine; and $X^1$ is fluorine, chlorine, —C≡N, —CF$_3$, —CHF$_2$, —CH$_2$F, —OCF$_3$, —OCHF$_2$ or —OCH$_2$F.

2. A compound represented by any one of formulas (1-4) to (1-6):

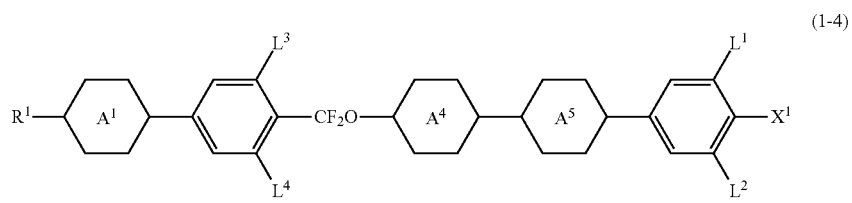

(1-4)

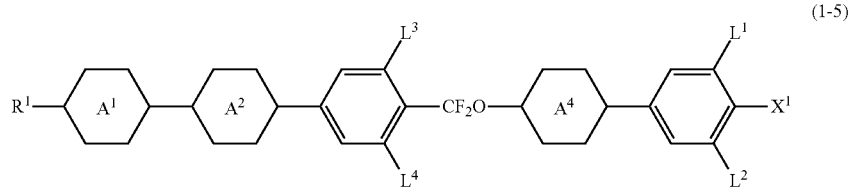

(1-5)

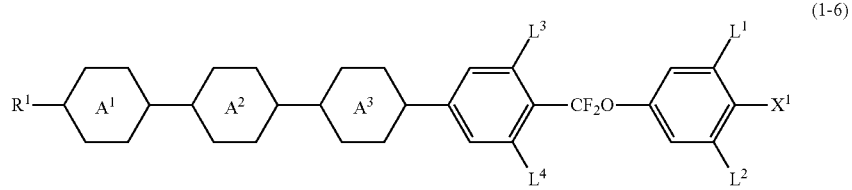

(1-6)

wherein $R^1$ is alkyl having 1 to 15 carbons or alkenyl having 2 to 15 carbons; the ring $A^1$ is pyrimidine-2,5-diyl; the ring $A^2$, the ring $A^3$, the ring $A^4$ and the ring $A^5$ are independently 1,4-cyclohexylene, 1,3-dioxane-2,5-diyl, 1,4-phenylene, or 1,4-phenylene in which arbitrary hydrogen is replaced by halogen; $L^1, L^2, L^3$ and $L^4$ are independently hydrogen or fluorine; and $X^1$ is fluorine, chlorine, —C≡N, —CF$_3$, —CHF$_2$, —CH$_2$F, —OCF$_3$, —OCHF$_2$ or —OCH$_2$F.

3. The compound according to claim 1, wherein the compound is represented by any one of formulas (1-7), (1-9), and (1-13):

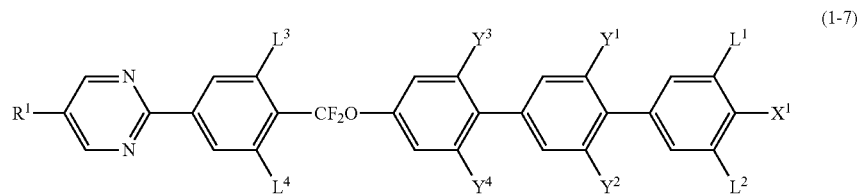

(1-7)

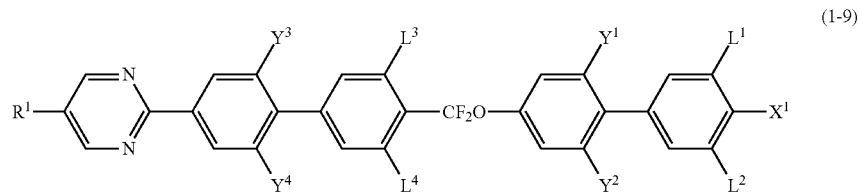

(1-9)

(1-13)

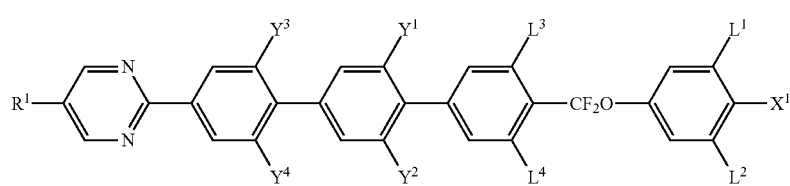

wherein $R^1$ is alkyl having 1 to 15 carbons; $L^1, L^2, L^3, L^4$, $Y^1, Y^2, Y^3$, and $Y^4$ are independently hydrogen or fluorine; and $X^1$ is fluorine or —$OCF_3$.

4. The compound according to claim 1, wherein the compound is represented by any one of formulas (1-17), (1-18) and (1-20):

(1-17)

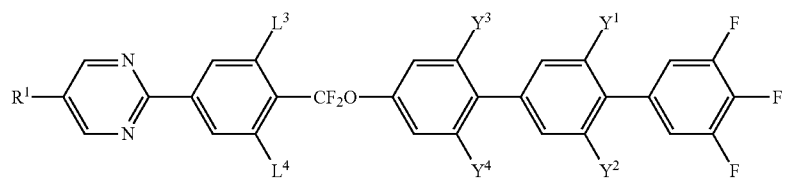

(1-18)

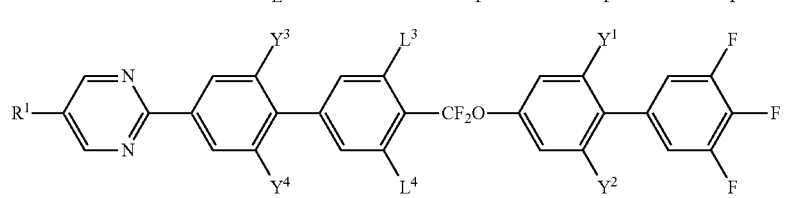

(1-20)

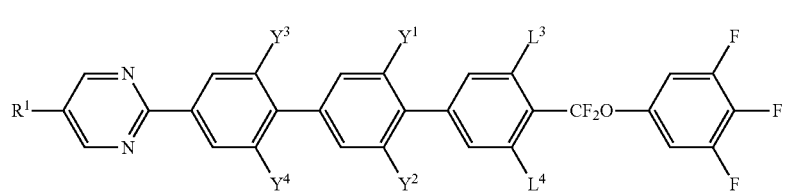

wherein $R^1$ is alkyl having 1 to 15 carbons; and $L^3, L^4, Y^1, Y^2, Y^3$, and $Y^4$ are independently hydrogen or fluorine.

5. A liquid crystal composition including two or more components, wherein one component is at least one compound according to claim 1 as one component.

6. The liquid crystal composition according to claim 5, including at least one compound selected from the group of compounds represented by the general formulas (2), (3) and (4) as one component:

(2)

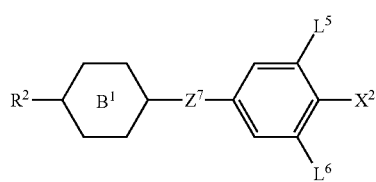

(3)

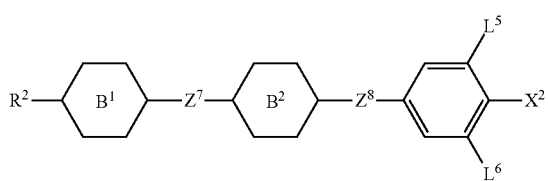

(4)

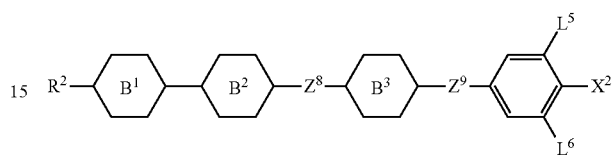

wherein $R^2$ is alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—; $X^2$ is fluorine, chlorine, —$OCF_3$, —$OCHF_2$, —$CF_3$, —$CHF_2$, —$CH_2F$, —$OCF_2CHF_2$ or —$OCF_2CHFCF_3$; the ring $B^1$, the ring $B^2$ and the ring $B^3$ are independently 1,4-cyclohexylene, 1,3-dioxane-2,5-diyl, pyrimidine-2,5-diyl, tetrahydropyran-2,5-diyl, 1,4-phenylene, or 1,4-phenylene in which arbitrary hydrogen is replaced by fluorine; $Z^7, Z^8$ and $Z^9$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^5$ and $L^6$ are independently hydrogen or fluorine.

7. The liquid crystal composition according to claim 5, including at least one compound selected from the group of compounds represented by the general formula (5) as one component:

(5)

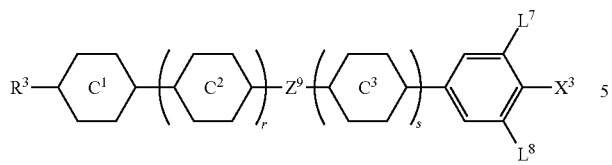

wherein $R^3$ is alkyl having 1 to 10 carbons or alkenyl having 2 to 10 carbons, and in the alkyl and the alkenyl, arbitrary hydrogen may be replaced by fluorine, arbitrary —$CH_2$— may be replaced by —O—; $X^3$ is —C≡N or —C≡C—C≡N; the ring $C^1$, the ring $C^2$ and the ring $C^3$ are independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl or pyrimidine-2,5-diyl; $Z^9$ is —$(CH_2)_2$—, —COO—, —$CF_2O$—, —$OCF_2$—, —C≡C—, —$CH_2O$— or a single bond; $L^7$ and $L^8$ are independently hydrogen or fluorine; and r is 0 or 1, s is 0 or 1, and r+s is 0, 1 or 2.

8. The liquid crystal composition according to claim 5, including at least one compound selected from the group of compounds represented by the general formulas (6), (7), (8), (9) and (10) as one component:

(6)

(7)

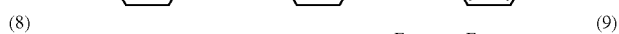

(8)

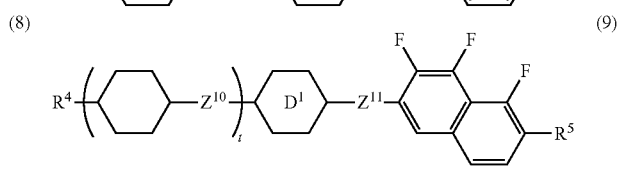

(9)

(10)

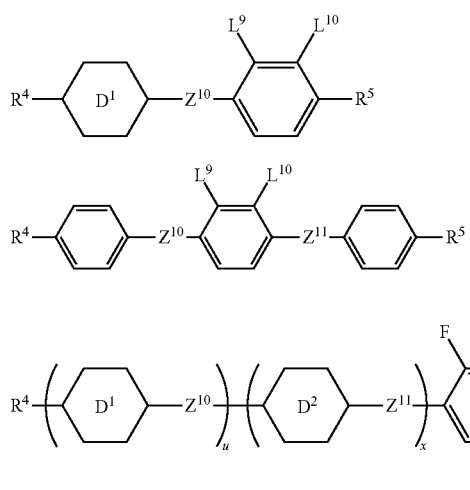

wherein $R^4$ and $R^5$ are independently alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—; the ring $D^1$, the ring $D^2$, the ring $D^3$ and the ring $D^4$ are independently 1,4-cyclohexylene, 1,4-cyclohexenylene, 1,4-phenylene, 1,4-phenylene in which arbitrary hydrogen is replaced by fluorine, tetrahydropyran-2,5-diyl or decahydronaphthalene-2,6-diyl; $Z^{10}$, $Z^{11}$, $Z^{12}$ and $Z^{13}$ are independently —$(CH_2)_2$—, —COO—, —$CH_2O$—, —$OCF_2$—, —$OCF_2$—$(CH_2)_2$— or a single bond; $L^9$ and $L^{10}$ are independently fluorine or chlorine; and t, u, x, y and z are independently 0 or 1, and u+x+y+z is 1 or 2.

9. The liquid crystal composition according to claim 5, including at least one compound selected from the group of compounds represented by the general formulas (11), (12) and (13) as one component:

(11)

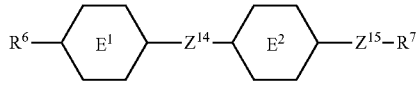

(12)

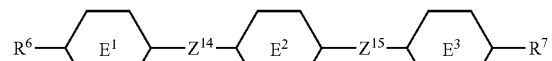

(13)

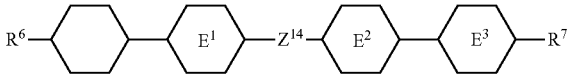

wherein $R^6$ and $R^7$ are independently alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—; the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene;

and $Z^{14}$ and $Z^{15}$ are independently —C≡C—, —COO—, —$(CH_2)_2$—, —C=H=CH— or a single bond.

10. The liquid crystal composition according to claim 6, further including at least one compound selected from the group of compounds represented by the general formula (5) as one component:

(5)

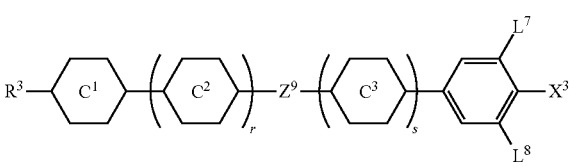

wherein $R^3$ is alkyl having 1 to 10 carbons or alkenyl having 2 to 10 carbons, and in the alkyl and the alkenyl, arbitrary hydrogen may be replaced by fluorine, arbitrary —CH$_2$— may be replaced by —O—; X$^3$ is —C≡N or —C≡C—C≡N; the ring C$^1$, the ring C$^2$ and the ring C$^3$ are independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl or pyrimidine-2,5-diyl; Z$^9$ is —(CH$_2$)$_2$—, —COO—, —CF$_2$O—, —OCF$_2$—, —C≡C—, —CH$_2$O— or a single bond; L$^7$ and L$^8$ are independently hydrogen or fluorine; and r is 0 or 1, s is 0 or 1, and r+s is 0, 1 or 2.

11. The liquid crystal composition according to claim 6, further including at least one compound selected from the group of compounds represented by the general formulas (11), (12) and (13) as one component:

(11)

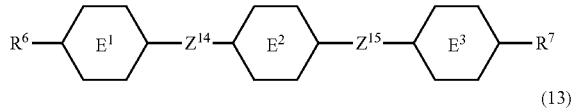
(12)

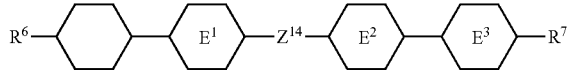
(13)

wherein R$^6$ and R$^7$ are independently alkyl having 1 to 10 carbons or alkenyl having 2 to 10 carbons, and in the alkyl and the alkenyl, arbitrary hydrogen may be replaced by fluorine and arbitrary —CH$_2$— may be replaced by —O—; the ring E$^1$, the ring E$^2$ and the ring E$^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z$^{14}$ and Z$^{15}$ are independently —C≡C—, —COO—, —(CH$_2$)$_2$—, —CH=CH— or a single bond.

12. The liquid crystal composition according to claim 7, further including at least one compound selected from the group of compounds represented by the general formulas (11), (12) and (13) as one component:

(11)

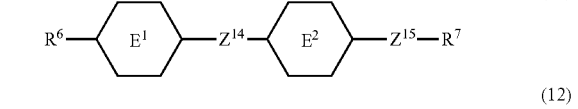
(12)

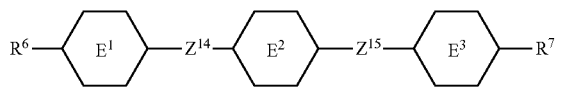
(13)

wherein R$^6$ and R$^7$ are independently alkyl having 1 to 10 carbons or alkenyl having 2 to 10 carbons, and in the alkyl and the alkenyl, arbitrary hydrogen may be replaced by fluorine and arbitrary —CH$_2$— may be replaced by —O—; the ring E$^1$, the ring E$^2$ and the ring E$^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z$^{14}$ and Z$^{15}$ are independently —C≡C—, —COO—, —(CH$_2$)$_2$—, —CH=CH— or a single bond.

13. The liquid crystal composition according to claim 8, further including at least one compound selected from the group of compounds represented by the general formulas (11), (12) and (13) as one component:

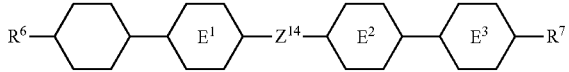
(11)

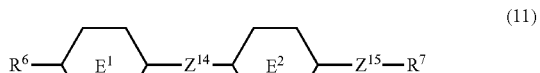
(12)

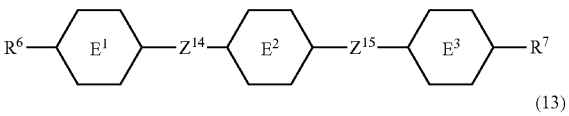
(13)

wherein R$^6$ and R$^7$ are independently alkyl having 1 to 10 carbons or alkenyl having 2 to 10 carbons, and in the alkyl and the alkenyl, arbitrary hydrogen may be replaced by fluorine and arbitrary —CH$_2$— may be replaced by —O—; the ring E$^1$, the ring E$^2$ and the ring E$^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z$^{14}$ and Z$^{15}$ are independently —C≡C—, —COO—, —(CH$_2$)$_2$—, —CH=CH— or a single bond.

14. The liquid crystal composition according to claim 5, further including at least one optically active compound.

15. The liquid crystal composition according to claim 5, including at least one antioxidant and/or ultraviolet light absorber.

16. A liquid crystal display device containing the liquid crystal composition according to claim 5.

* * * * *